(12) United States Patent
Frendéus et al.

(10) Patent No.: US 12,291,569 B2
(45) Date of Patent: May 6, 2025

(54) ANTIBODIES AND NUCLEOTIDE SEQUENCES, AND USES THEREOF

(71) Applicant: BIOINVENT INTERNATIONAL AB, Lund (SE)

(72) Inventors: Björn Frendéus, Lund (SE); Ingrid Teige, Lund (SE); Monika Semmrich, Malmö (SE); Linda Mårtensson, Bjärred (SE); Petra Holmkvist, Kävlinge (SE)

(73) Assignee: BIOINVENT INTERNATIONAL AB, Lund (SE)

( * ) Notice: Subject to any disclaimer, the term of this patent is extended or adjusted under 35 U.S.C. 154(b) by 959 days.

(21) Appl. No.: 17/272,740

(22) PCT Filed: Sep. 3, 2019

(86) PCT No.: PCT/EP2019/073488
§ 371 (c)(1),
(2) Date: Mar. 2, 2021

(87) PCT Pub. No.: WO2020/049001
PCT Pub. Date: Mar. 12, 2020

(65) Prior Publication Data
US 2022/0041723 A1  Feb. 10, 2022

(30) Foreign Application Priority Data
Sep. 3, 2018 (EP) .................................... 18192311

(51) Int. Cl.
  *C07K 16/28* (2006.01)
  *A61P 35/00* (2006.01)
  *C12N 7/00* (2006.01)
  *C12N 15/86* (2006.01)
  *A61K 39/00* (2006.01)

(52) U.S. Cl.
  CPC .......... *C07K 16/2818* (2013.01); *A61P 35/00* (2018.01); *C12N 7/00* (2013.01); *C12N 15/86* (2013.01); *A61K 2039/505* (2013.01); *C07K 2317/33* (2013.01); *C07K 2317/565* (2013.01); *C07K 2317/732* (2013.01); *C07K 2317/76* (2013.01); *C12N 2710/24143* (2013.01)

(58) Field of Classification Search
None
See application file for complete search history.

(56) References Cited

U.S. PATENT DOCUMENTS

| | | | |
|---|---|---|---|
| 10,196,445 B1* | 2/2019 | Engelhardt | A61K 39/39558 |
| 2017/0157188 A1 | 6/2017 | Silvestre et al. | |
| 2018/0037654 A1 | 2/2018 | Eenennaam et al. | |

FOREIGN PATENT DOCUMENTS

| | | |
|---|---|---|
| WO | WO 1993/00431 | 1/1993 |
| WO | WO 1997/20574 | 6/1997 |
| WO | WO 2000/37504 | 6/2000 |
| WO | WO 2001/14424 | 3/2001 |
| WO | WO 2005/042728 | 5/2005 |
| WO | WO 2006/108846 | 10/2006 |
| WO | WO 2007/147528 | 12/2007 |
| WO | WO 2008/129058 | 10/2008 |
| WO | WO 2008/138533 | 11/2008 |
| WO | WO 2009/065546 | 5/2009 |
| WO | WO 2009/100521 | 8/2009 |
| WO | WO 2010/130753 | 11/2010 |
| WO | WO 2010/130756 | 11/2010 |
| WO | WO 2012/001075 | 1/2012 |
| WO | WO 2013/022764 | 2/2013 |
| WO | WO 2017/106372 A1 | 6/2017 |
| WO | WO 2018/106862 A1 | 6/2018 |
| WO | WO 2018/209701 A1 | 11/2018 |

OTHER PUBLICATIONS

Beatty, G. L., et al., "CD40 agonists alter tumor stroma and show efficacy against pancreatic carcinoma in mice and humans", Science, 331(6024): 1612-1616, 2011.
Bianchi et al., "High level expression and rational mutagenesis of a designed protein, the minibody. From an insoluble to a soluble molecule", J. Mol. Biol., 236: 649-59, 1994.
Binyamin, L., et al., "Blocking NK cell inhibitory self-recognition promotes antibody-dependent cellular cytotoxicity in a model of anti-lymphoma therapy." Journal of immunology 180, 6392-6401, 2008.
Blank et al., "Therapeutic use of anti-CTLA-4 antibodies. International Immunology," 27(1): 3-10, 2015.
Bommareddy, P. K., et al. "Integrating oncolytic viruses in combination cancer immunotherapy", Nat Rev Immunol 18(8): 498-513, 2018.
Bosma GC et al., 'A severe combined immunodeficiency mutation in the mouse' Nature. 301(5900):527-30, 1983.
Brahmer, J. R., et al. "Safety and activity of anti-PD-L1 antibody in patients with advanced cancer," N Engl J Med, 366(26): 2455-2465, 2012.
Bulliard, Jolicoeur et al., "Activating Fc γ receptors contribute to the antitumor activities of immunoregulatory receptor-targeting antibodies," J Exp Med, 210(9):1685-93, 2013.

(Continued)

*Primary Examiner* — Anand U Desai
*Assistant Examiner* — Cheom-Gil Cheong
(74) *Attorney, Agent, or Firm* — Parker Highlander PLLC

(57) ABSTRACT

Described are novel anti-CTLA-4 antibody molecules and nucleotide sequences and expression vectors, such as viruses, encoding such antibody molecules. The novel antibody molecules are Treg depleting antibody molecules, and they have an improved depleting effect on CTLA-4 positive cells, such as Tregs, compared to ipilimumab. Described is also the use of such antibody molecules or nucleotide sequences or viruses in medicine, such as in the treatment of cancer, such as solid tumours.

8 Claims, 53 Drawing Sheets
Specification includes a Sequence Listing.

(56) References Cited

OTHER PUBLICATIONS

Callahan et al, "Anti-CTLA-4 Antibody Therapy: Immune Monitoring During Clinical Development of a Novel Immunotherapy." Semin Oncol. 37(5): 473-484, 2010.
Chakrabarti et al., "Compact, synthetic, vaccinia virus early/late promoter for protein expression" Biotechniques 23: 1094-7, 1997.
Chambers et al., "Comparison of genetically engineered herpes simplex viruses for the treatment of brain tumors in a scid mouse model of human malignant glioma," Proc. Natl. Acad. Sci. USA, 92(5): 1411-5, 1995.
Chan, W. M. et al., "Oncolytic poxviruses" Annu Rev Virol 1(1): 119-141, 2014.
Cox J H et al., "Antibody-mediated targeting of the Orai1 calcium channel inhibits T cell function", PLoS One, 8(12):e82944. doi: 10.1371/journal.pone.0082944. eCollection 2013.
Dahan et al, "Therapeutic Activity of Agonistic, Human Anti-CD40 Monoclonal Antibodies Requires Selective FcγR Engagement." Cancer Cell. 29(6):820-31, 2016.
Erbs et al., "Modified vaccinia virus Ankara as a vector for suicide gene therapy," Cancer Gene Ther. 15(1): 18-28, 2008.
Foloppe et al., "Targeted delivery of a suicide gene to human colorectal tumors by a conditionally replicating vaccinia virus," Gene Ther., 15: 1361-71, 2008.
Gao et al., "Molecular cloning of a proteolytic antibody light chain,", J. Biol. Chem., 269: 32389-93, 1994.
Geevarghese et al., "Phase I/II study of oncolytic herpes simplex virus NV1020 in patients with extensively pretreated refractory colorectal cancer metastatic to the liver." Hum. Gene Ther. 21(9): 1119-28, 2010.
Guse et al., "Oncolytic vaccinia virus for the treatment of cancer" Expert Opinion Biol. Ther.11(5): 595-608, 2011.
Hammond et al, "A synthetic vaccinia virus promoter with enhanced early and late activity" J. Virol Methods 66: 135-8, 1997.
Harrington et al., "Clinical development of talimogene laherparepvec (T-VEC): a modified herpes simplex virus type-1-derived oncolytic immunotherapy" Expert Rev. Anticancer Ther. 15(12):1389-1403, 2015.
Heap et al., "Analysis of a 17-amino acid residue, virus-neutralizing microantibody.", J. Gen. Virol., 86: 1791-1800, 2005.
Hodi, F. S., et al. " Improved survival with ipilimumab in patients with metastatic melanoma," N Engl J Med 363(8): 711-723, 2010.
Ito M et al, "NOD/SCID/$\gamma^{null}$ mouse: an excellent recipient mouse model for engraftment of human cells." Blood 100(9):3175-3182, 2002.
Khuri et al., "A controlled trial of intratumoral ONYX-015, a selectively-replicating adenovirus, in combination with cisplatin and 5-fluorouracil in patients with recurrent head and neck cancer" Nat. Med 6(8): 879-85, 2000.
Kleinpeter, P., et al. "Vectorization in an oncolytic vaccinia virus of an antibody, a Fab and a scFv against programmed cell death-1 (PD-1) allows their intratumoral delivery and an improved tumor-growth inhibition" Oncoimmunology 5(10): e1220467, 2016.
Korman et al, "Checkpoint blockade in cancer immunotherapy," Adv Immunol. 90:297-339, 2006.
Kumar and Boyle, "A poxvirus bidirectional promoter element with early/late and late functions." Virology 179: 151-8, 1990.
Ladner, "Antibodies cut down to size" Nature Biotechnology, 25:875-7, 2007.
Laune et al., "Systematic exploration of the antigen binding activity of synthetic peptides isolated from the variable regions of immunoglobulins." JBC, 272: 30937-44, 1997.
Marabelle, A., et al. "Depleting tumor-specific Tregs at a single site eradicates disseminated tumors", J Clin Invest 123(6): 2447-2463, 2013.
Marino, N., et al., "Development of a versatile oncolytic virus platform for local intra-tumoural expression of therapeutic transgenes" PLoS One 12(5): e0177810, 2017.
Martuza et al., "Experimental therapy of human glioma by means of a genetically engineered virus mutant." Science 252: 854-6, 1991.
Mineta et al., "Treatment of malignant gliomas using ganciclovir-hypersensitive, ribonucleotide reductase-deficient herpes simplex viral mutant." Cancer Res. 54: 3963-66, 1994.
Monnet et al., "Synthetic Peptides Derived from the Variable Regions of an Anti-CD4 Monoclonal Antibody Bind to CD4 and Inhibit HIV-1 Promoter Activation in Virus-infected Cells", JBC, 274: 3789-96, 1999.
Nicaise et al., "Affinity transfer by CDR grafting on a nonimmunoglobulin scaffold", Protein Science, 13:1882-91, 2004.
Orubu et al. "Expression and Cellular Immunogenicity of a Transgenic Antigen Driven by Endogenous Poxviral Early Promoters at Their Authentic Loci in MVA" 2012, PloS One 7: e40167, 2012.
Pessi et al., "A designed metal-binding protein with a novel fold" Nature, 362: 367-9, 1993.
Pyles et al., "Evidence that the herpes simplex virus type 1 uracil DNA glycosylase is required for efficient viral replication and latency in the murine nervous system.", J. Virol. 68: 4963-72, 1994.
Qiu et al., "Small antibody mimetics comprising two complementarity-determining regions and a framework region for tumor targeting", Nature Biotechnology, 25:921-9, 2007.
Quiocho "Protein engineering. Making of the minibody", Nature, 362: 293-4, 1993.
Ribas, "Overcoming immunologic tolerance to melanoma: targeting CTLA-4 with tremelimumab (CP-675,206)" Oncologist, 13 (Suppl 4):10-5, 2008.
Simpson, T. R., et al. "Fc-dependent depletion of tumor-infiltrating regulatory T cells co-defines the efficacy of anti-CTLA-4 therapy against melanoma" J Exp Med 210(9): 1695-1710, 2013.
Söderlind E, et al Recombining germline-derived CDR sequences for creating diverse single-framework antibody libraries, Nat Biotechnol. 2000;18(8):852-6, 2000.
Søndergaard H. et al., "Human T cells depend on functional calcineurin, tumour necrosis factor-α and CD80/CD86 for expansion and activation in mice" Clin Exp Immunol., 172(2):300-10. doi: 10.1111/cei.12051, 2013.
Topalian, S. L., et al. "Safety, activity, and immune correlates of anti-PD-1 antibody in cancer" N Engl J Med 366(26): 2443-2454, 2012.
Vaughan & Sollazzo, "Of minibody, camel and bacteriophage." Combinatorial Chemistry & High Throughput Screening, 4: 417-430, 2001.
Weber, "Overcoming immunologic tolerance to melanoma: targeting CTLA-4 with ipilimumab (MDX-010)" Oncologist, 13 (Suppl 4):16-25, 2008.
Wong et al., "Oncolytic Viruses for Cancer Therapy: Overcoming the Obstacles." Viruses 2: 78-106, 2010.
Xia et al., "[Phase III randomized clinical trial of intratumoral injection of E1B gene-deleted adenovirus (H101) combined with cisplatin-based chemotherapy in treating squamous cell cancer of head and neck or esophagus]" Ai Zheng 23(12): 1666-70 (English abstract), 2004.
Semmrich, M. et al., "Vectorized Treg-depleting αCTLA-4 elicits antigen cross-presentation and CD8⁺ T cell immunity to reject 'cold' tumors," *Journal of Immunotherapy of Cancer*, 10 (2022): e003488, 1-36.
"BioInvent and Transgene report positive Phase 1a data on oncolytic virus BT-001 in solid tumors," *Press Release*, (2023): 1-4.
Kipps, T. J. et al., "Importance of Immunoglobulin Isotype in Human Antibody-Dependent, Cell-Mediated Cytotoxicity Directed by Murine Monoclonal Antibodies," *J. Exp. Med.*, 161 (1985): 1-17.
Office Action issued in Korean Patent Application No. 10-2021-7009505, issued on Dec. 4, 2024.

* cited by examiner

A
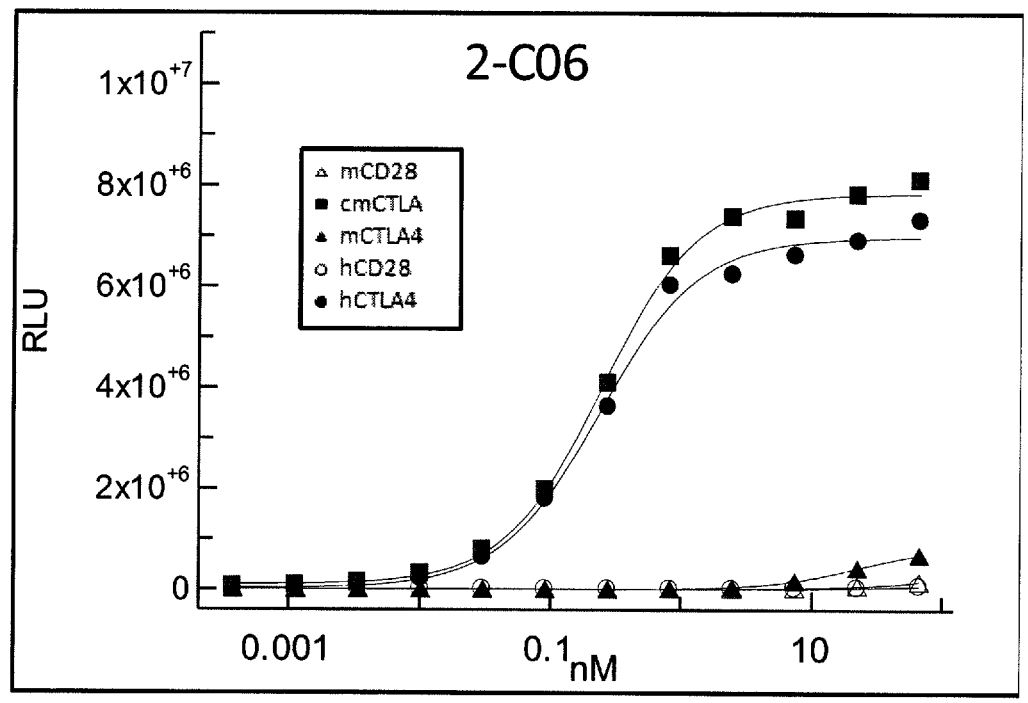
B
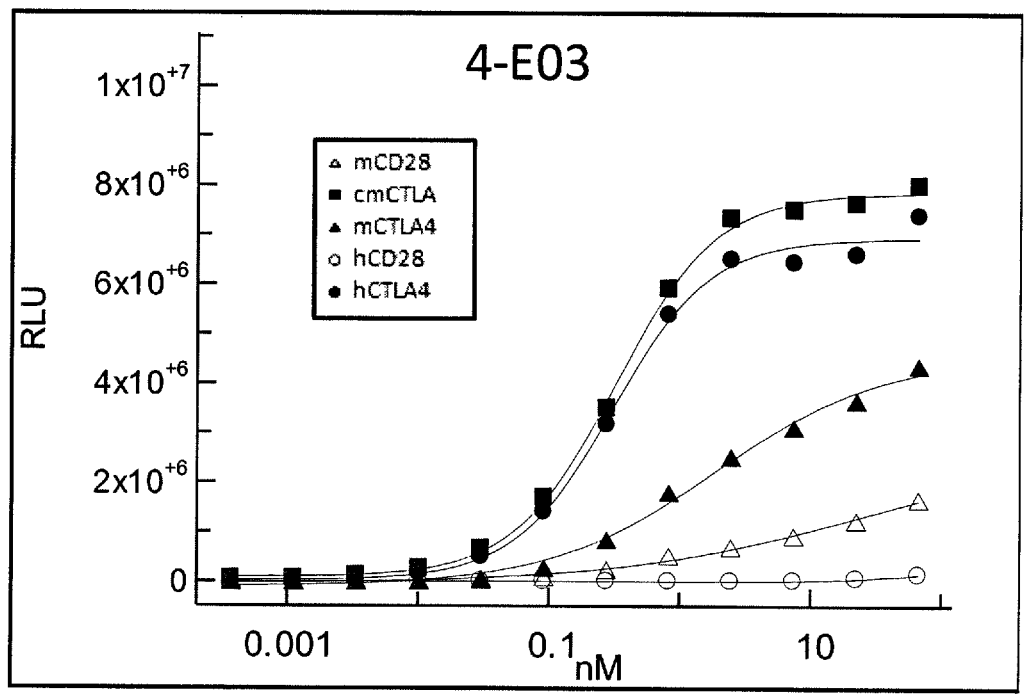
Fig. 1

C
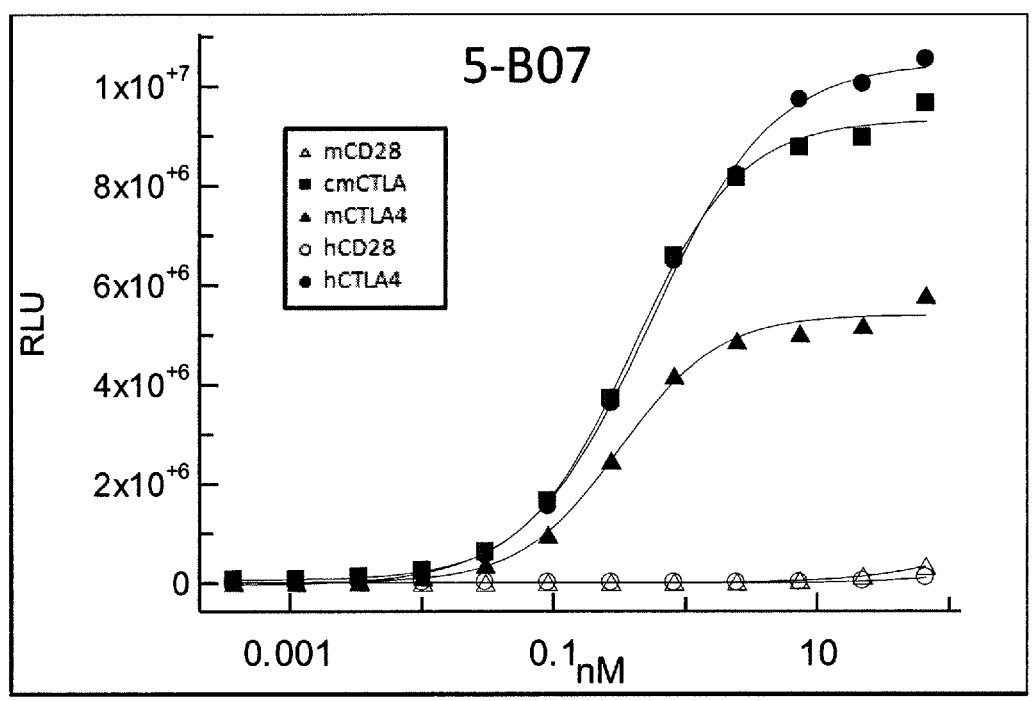
D
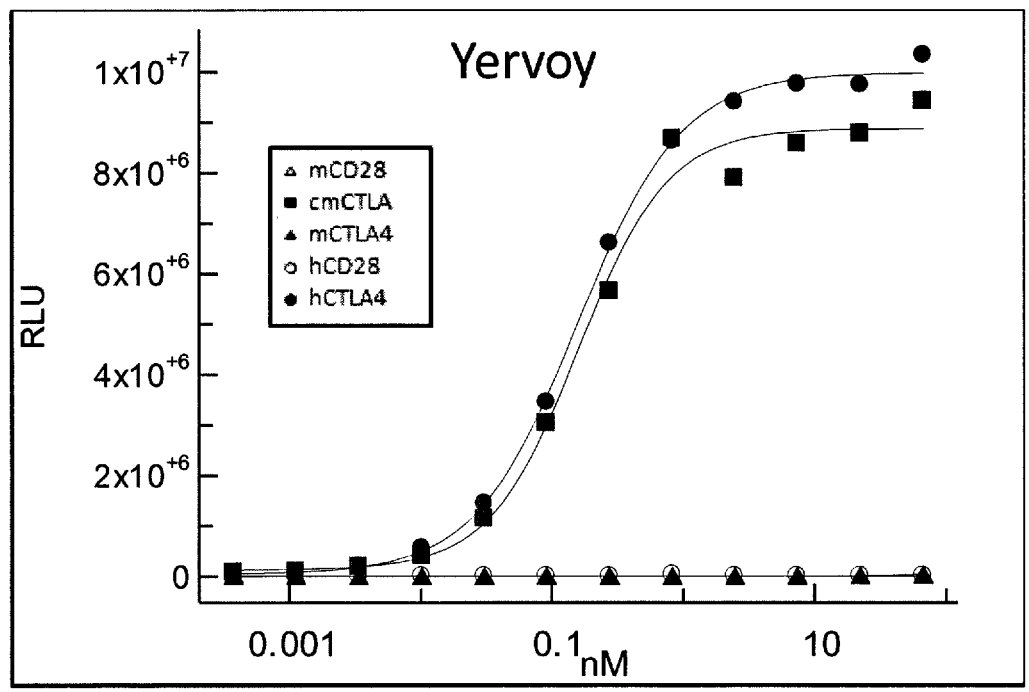
*Fig. 1, cont.*

A
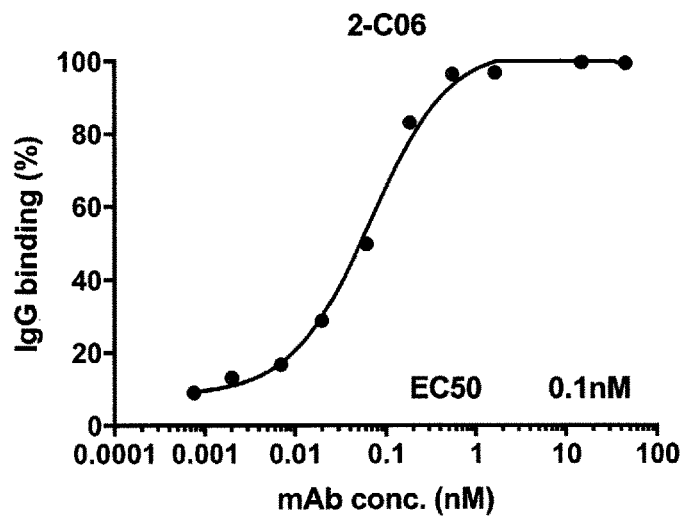
B
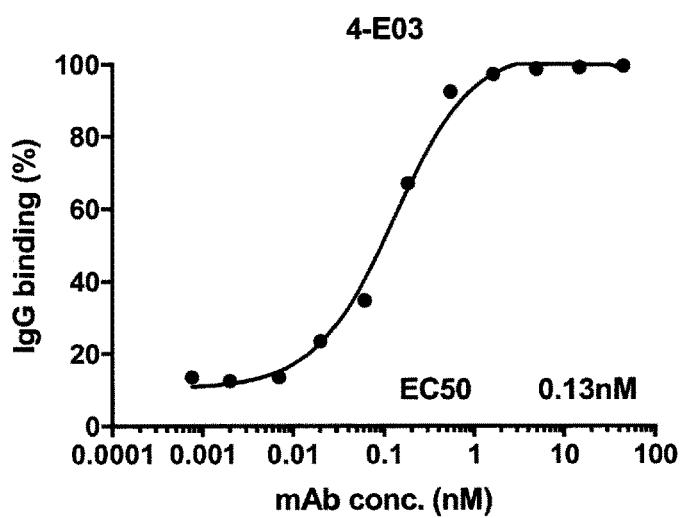
C
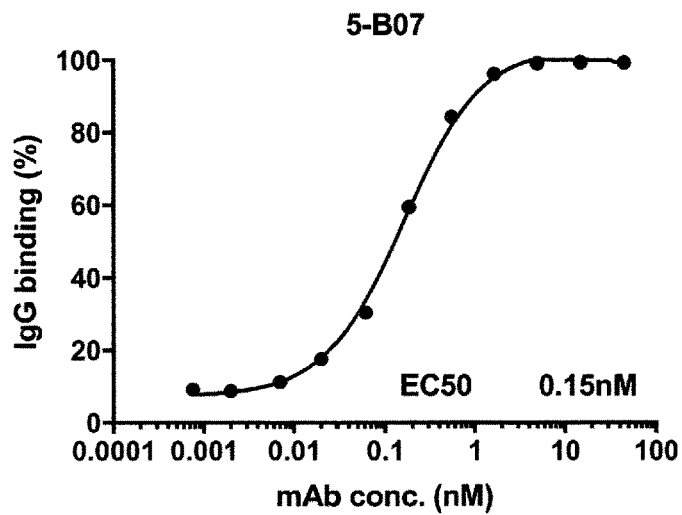
*Fig. 2*

D
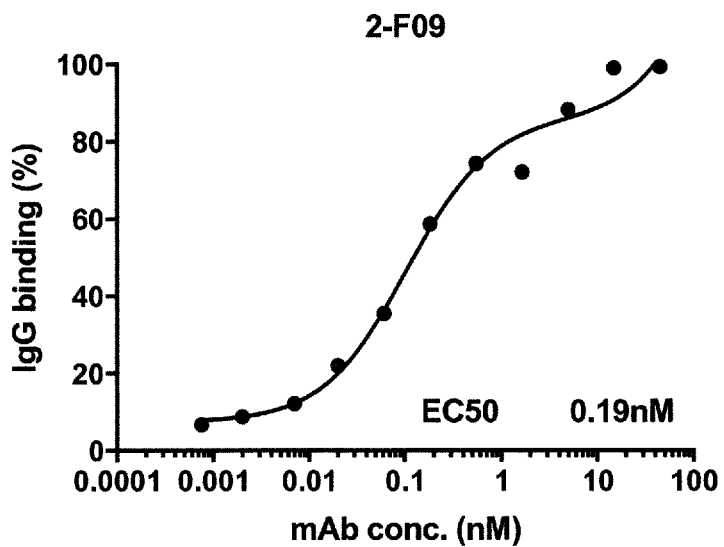
E
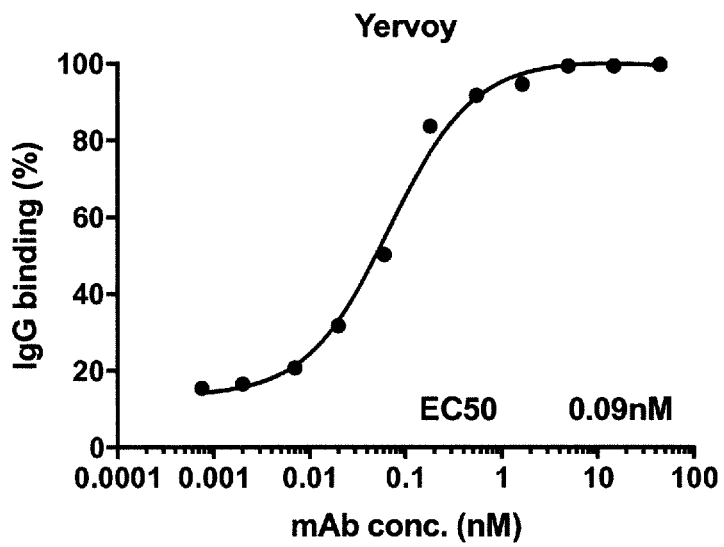
*Fig. 2, cont.*

B
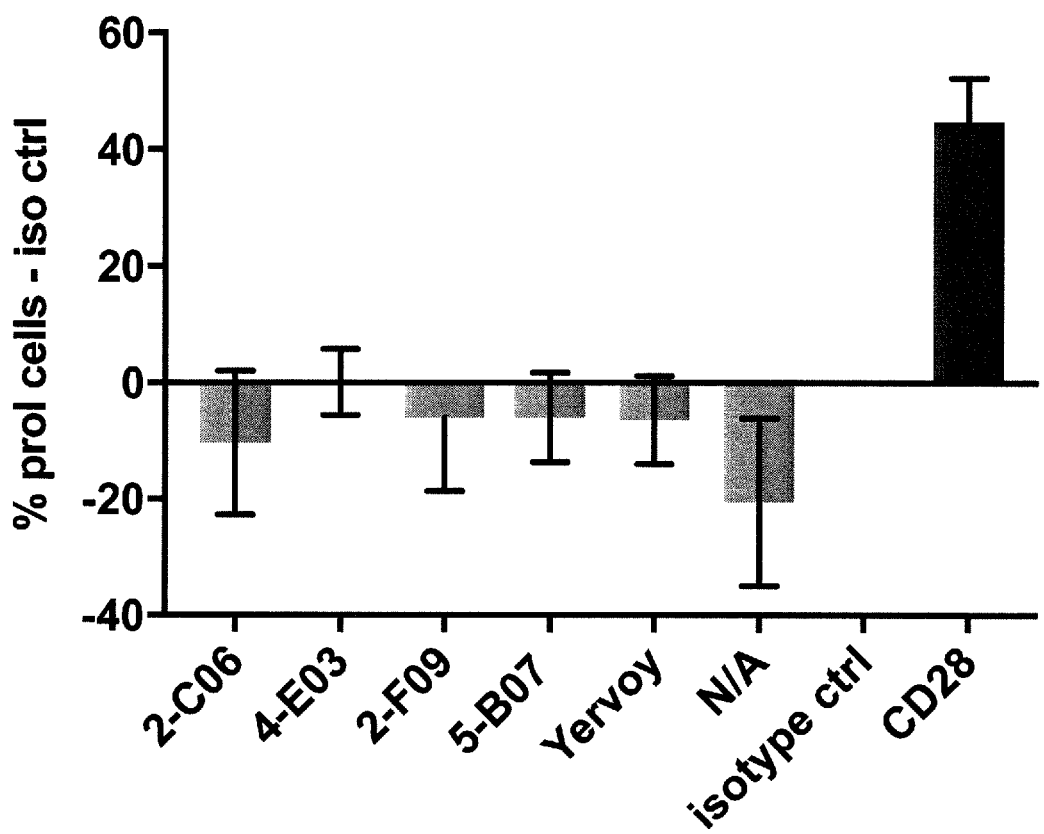
*Fig. 9, cont.*

A
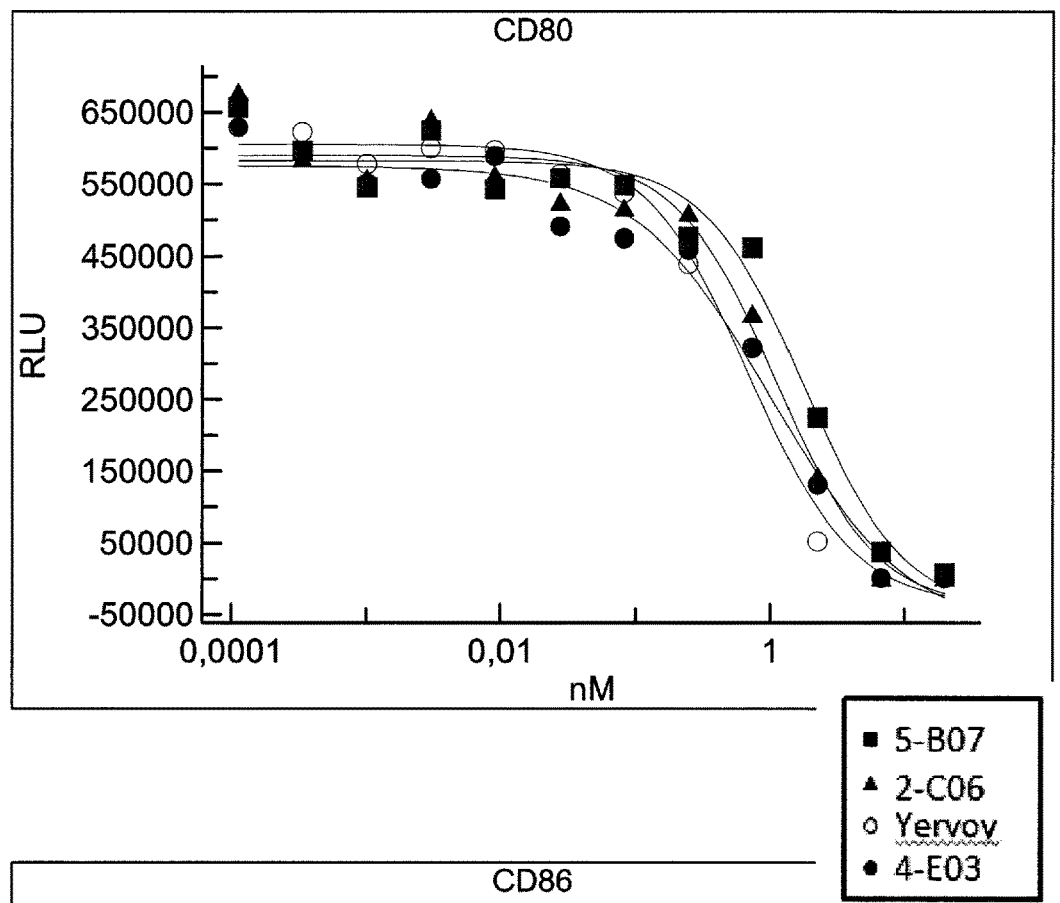
B
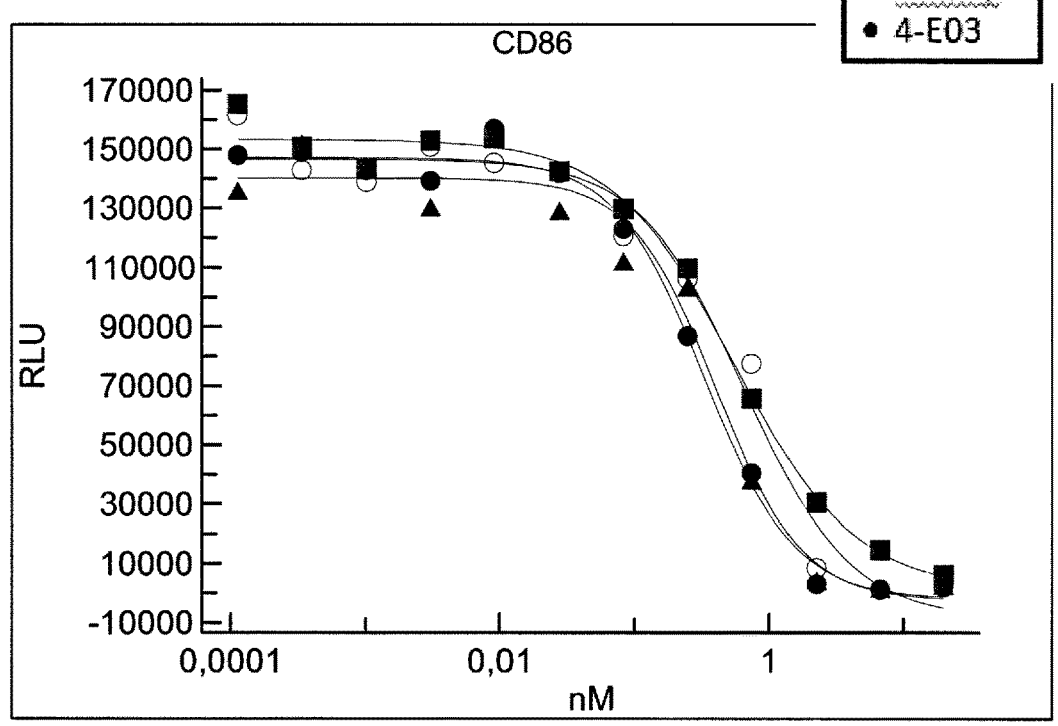
*Fig. 10*

A
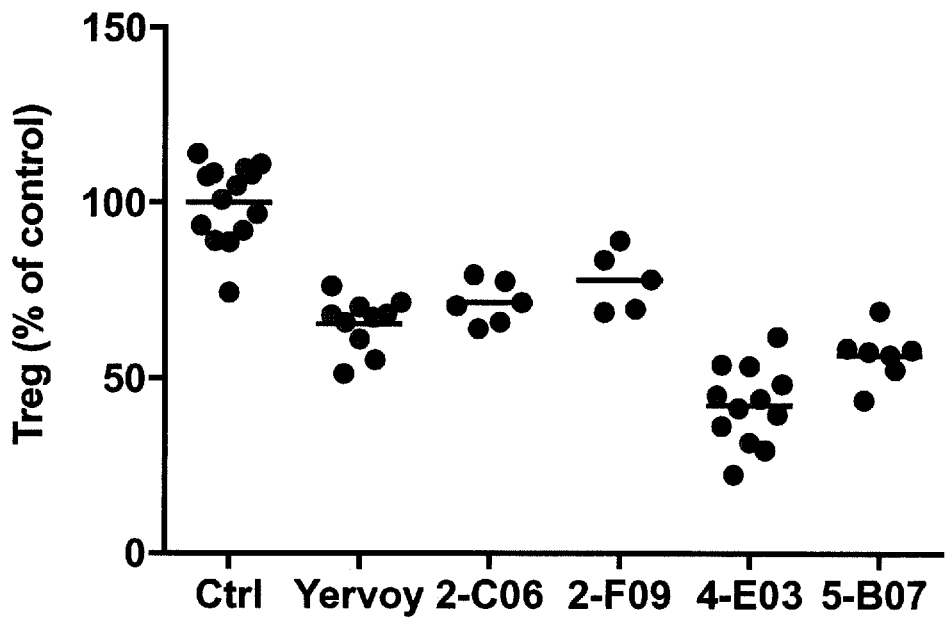
B
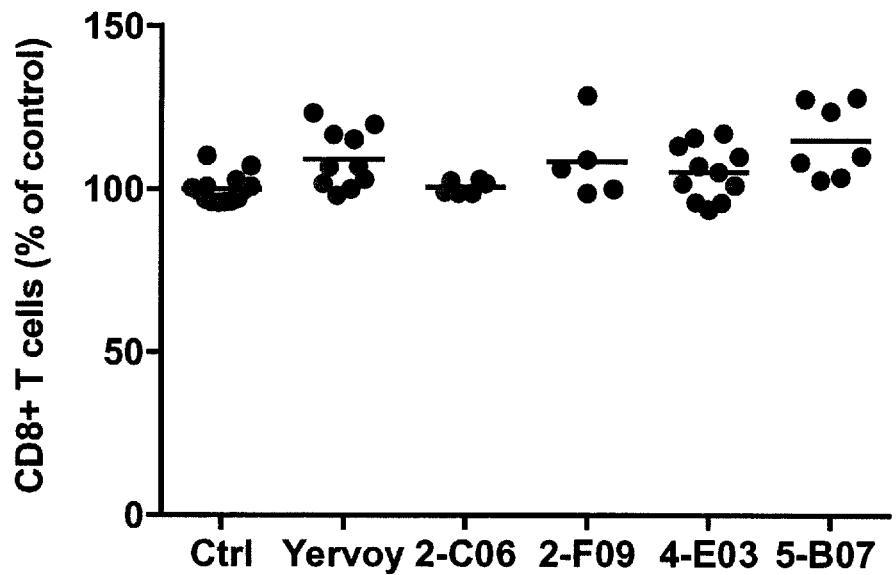
*Fig. 14*

| Clone | Cell binding | Cyno cell binding | Binding block by cm protein | Protein binding | | | | | Blocking | | | | ADCC |
|---|---|---|---|---|---|---|---|---|---|---|---|---|---|
| | EC50 | | | hCTLA4 | hCD28 | cmCTLA4 | mCTLA4 | mCD28 | hCD80 | hCD86 | mCD80 | mCD86 | (% of CTLA4+) |
| 002-C06 | 0.2 | weak | YES | 0.2 | no binding | 0.2 | no binding | no binding | complete | complete | N/A | N/A | 25.6 |
| 004-E03 | 0.1 | YES | YES | 0.3 | no binding | 0.2 | 3.1 | 7.1 | complete | complete | N/A | N/A | 68.5 |
| 002-F09 | 0.19 | no | YES | 0.3 | no binding | 0.2 | no binding | no binding | complete | complete | N/A | N/A | 42.8 |
| 5-B07 | 0.15 | no | YES | 0.5 | no binding | 0.4 | 0.3 | no binding | complete | complete | N/A | N/A | 15.1 |
| Yervoy | 0.13 | YES | YES | 0.2 | no binding | 0.2 | no binding | no binding | complete | complete | N/A | N/A | 46.3 |

Fig. 15

A
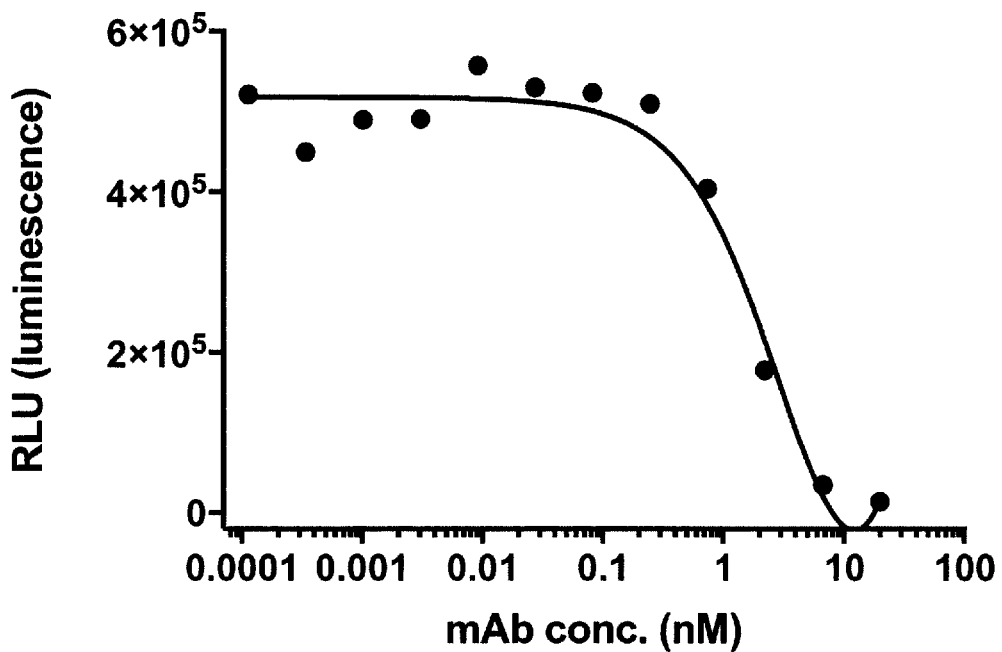
B
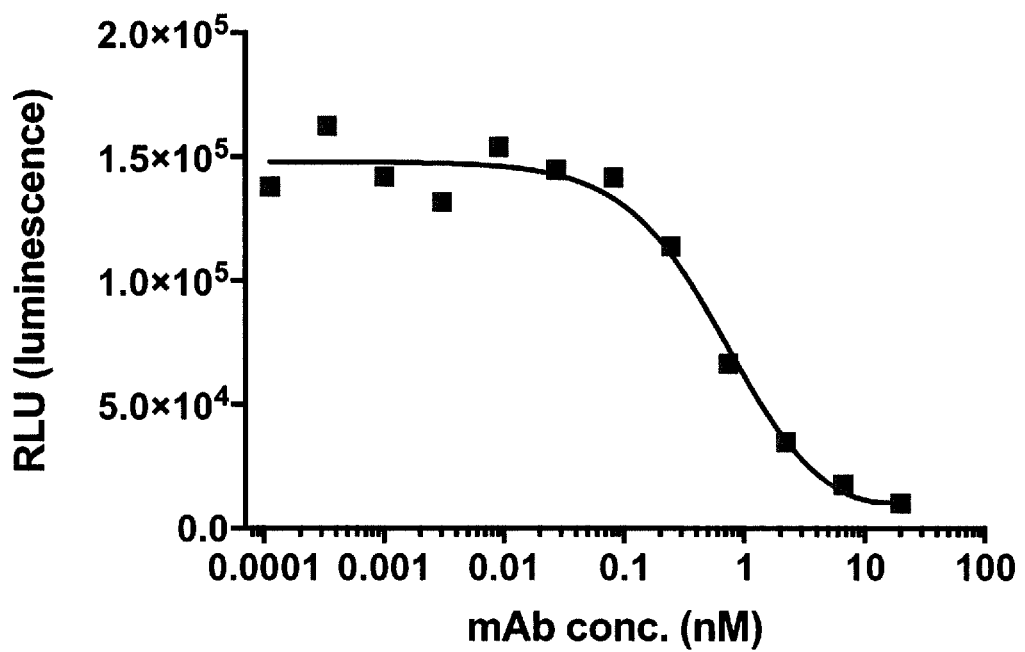
*Fig. 16*

C
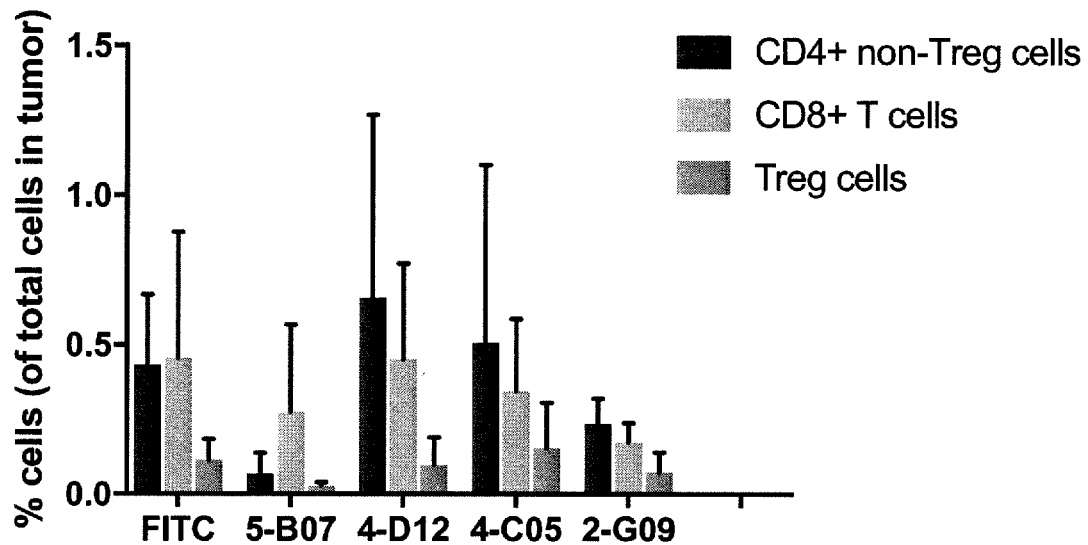
D
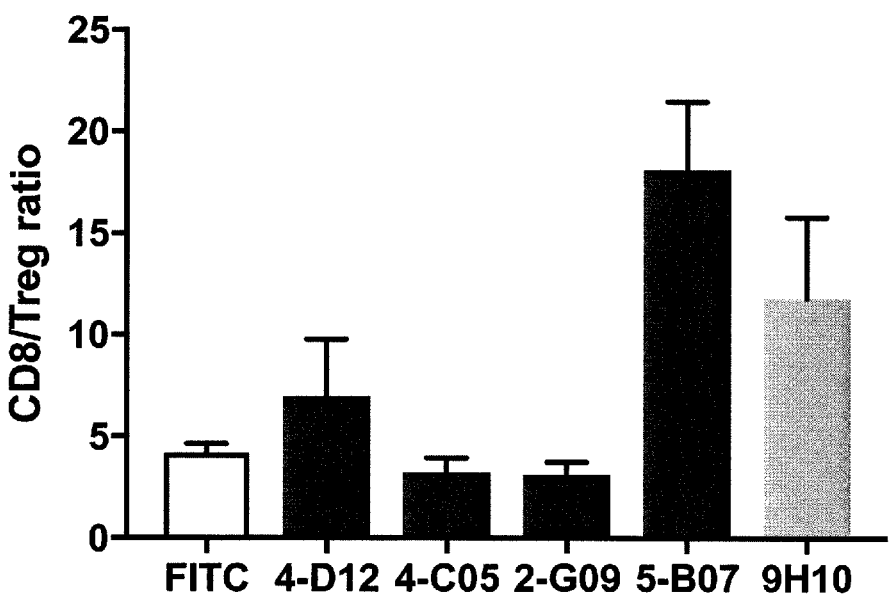
*Fig. 16, cont.*

COPTG19384
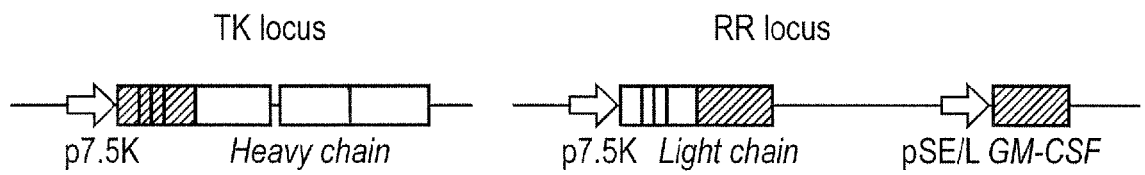
COPTG19385
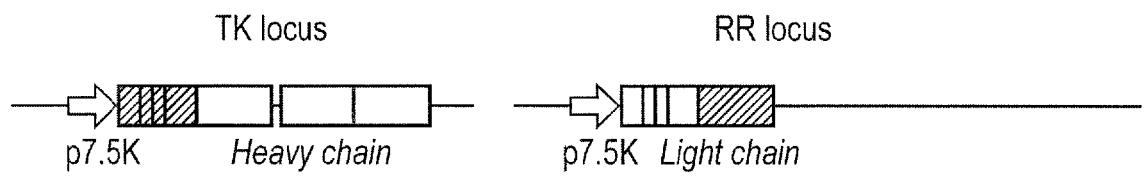
FIG. 17

A
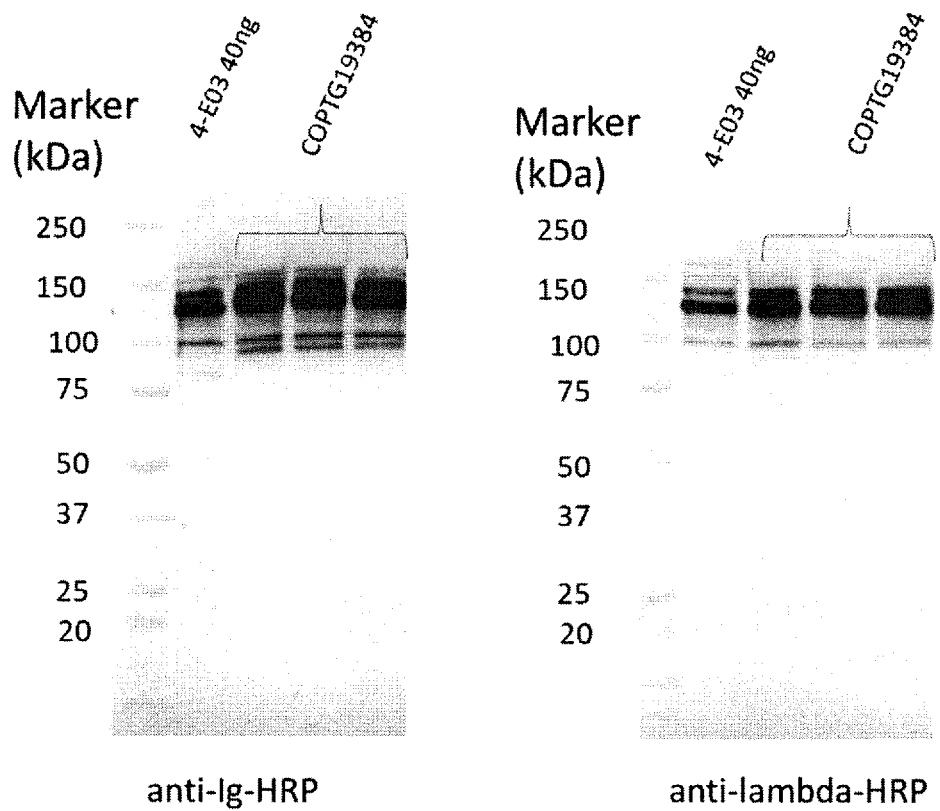
B
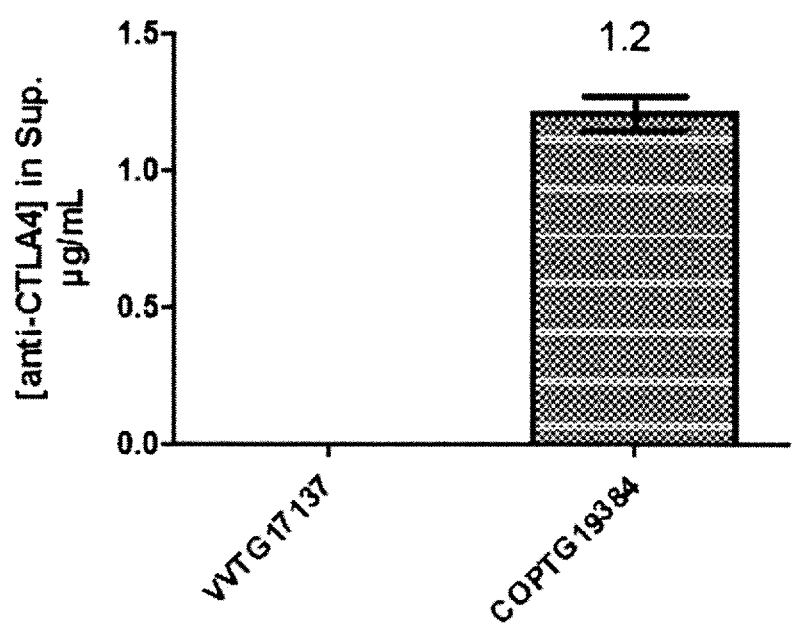
Fig. 18

A
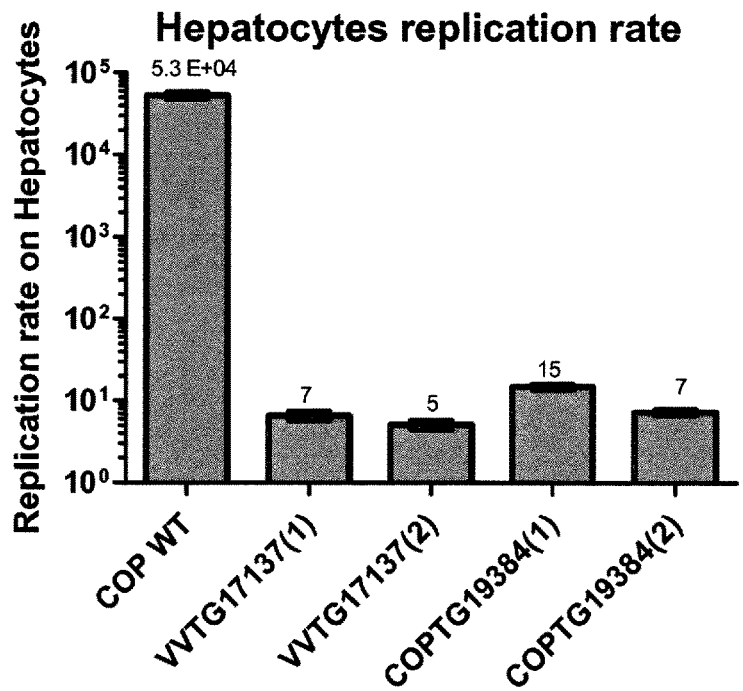
B
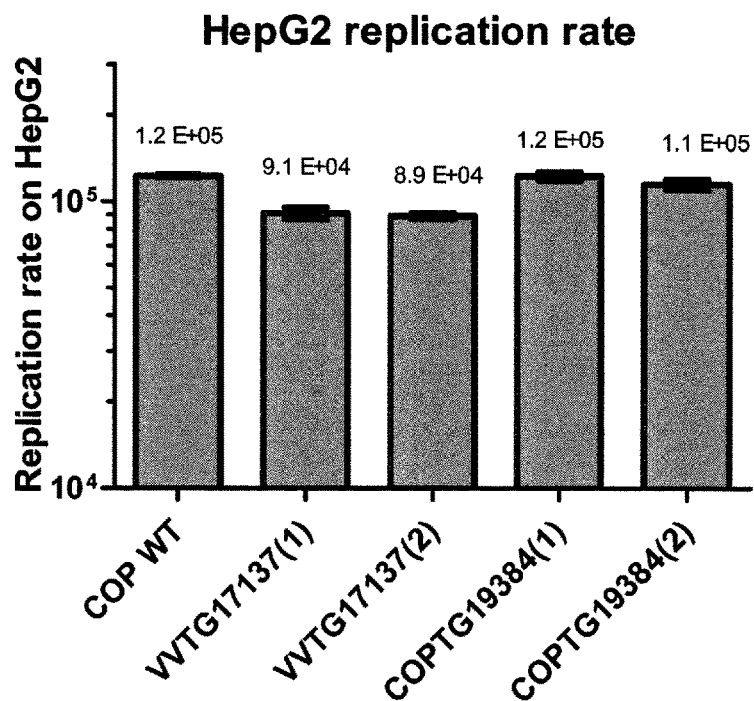
Fig. 20

C
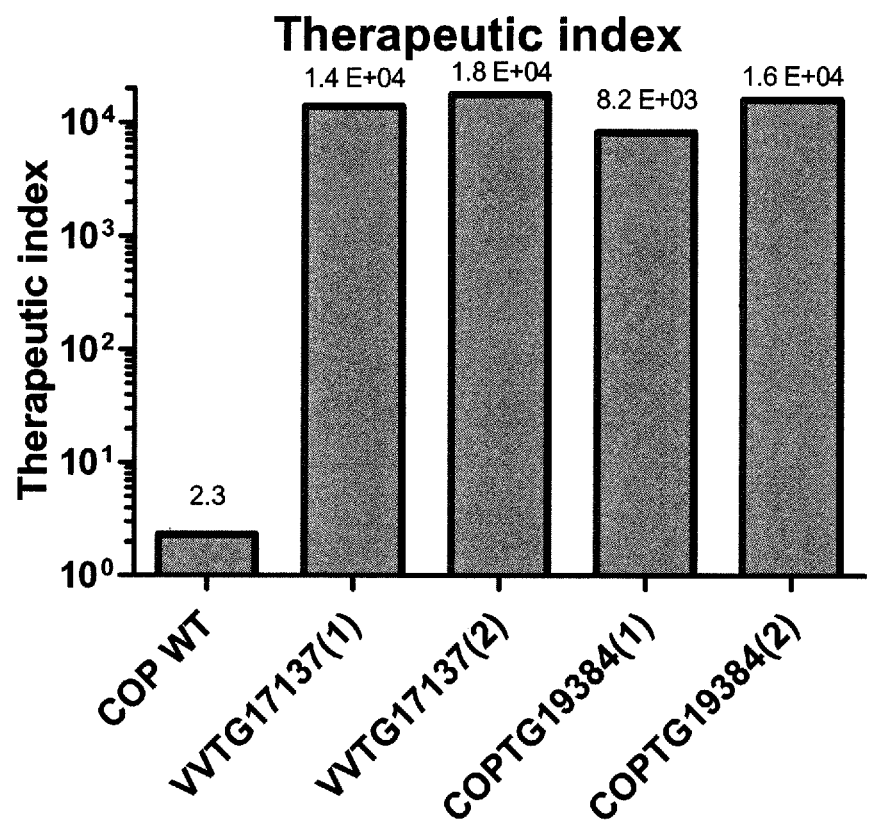
Fig. 20, cont.

A
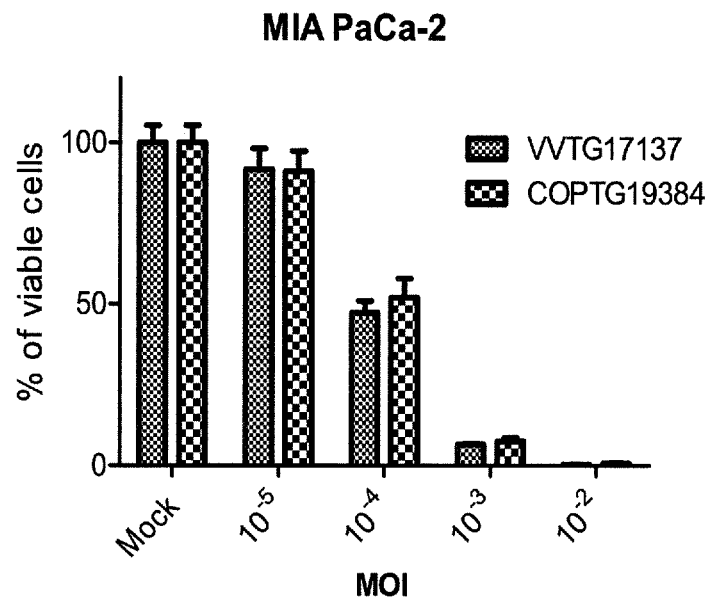
B
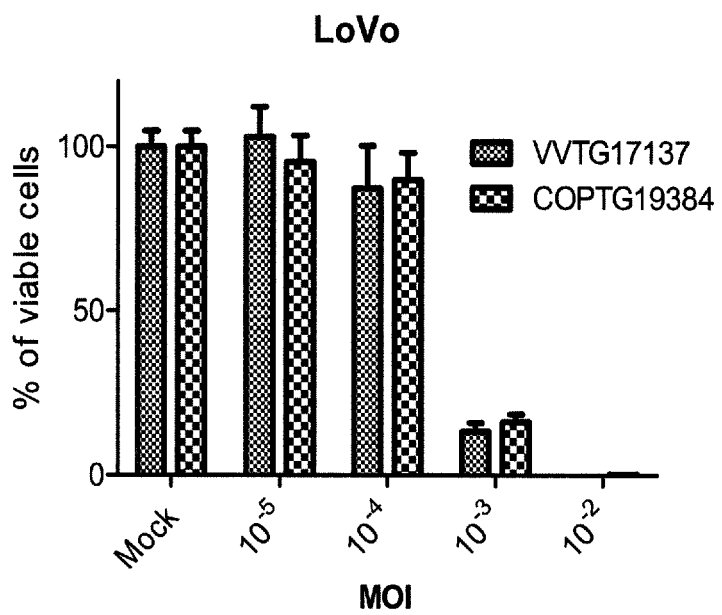
Fig. 22

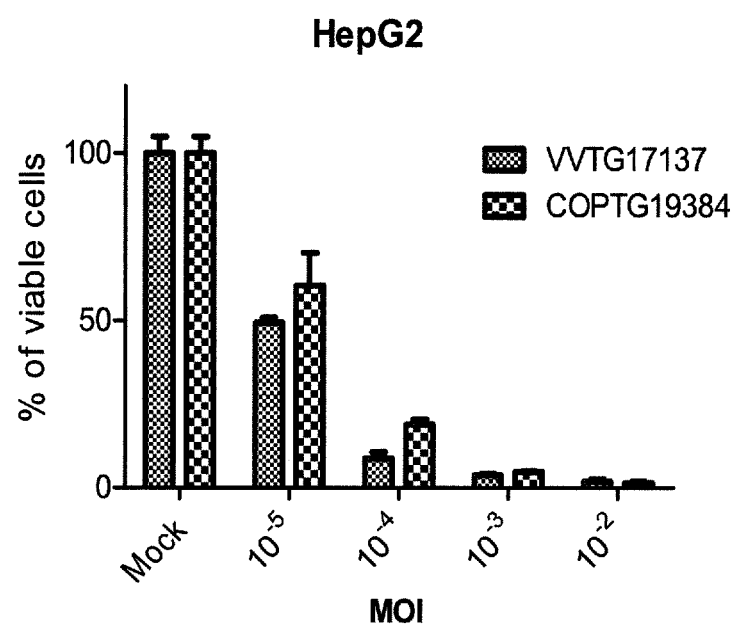
*Fig. 22, cont.*

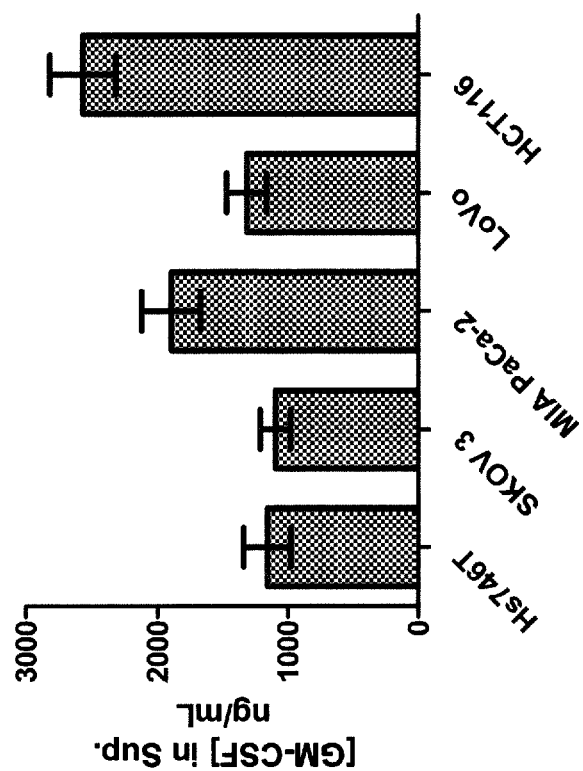
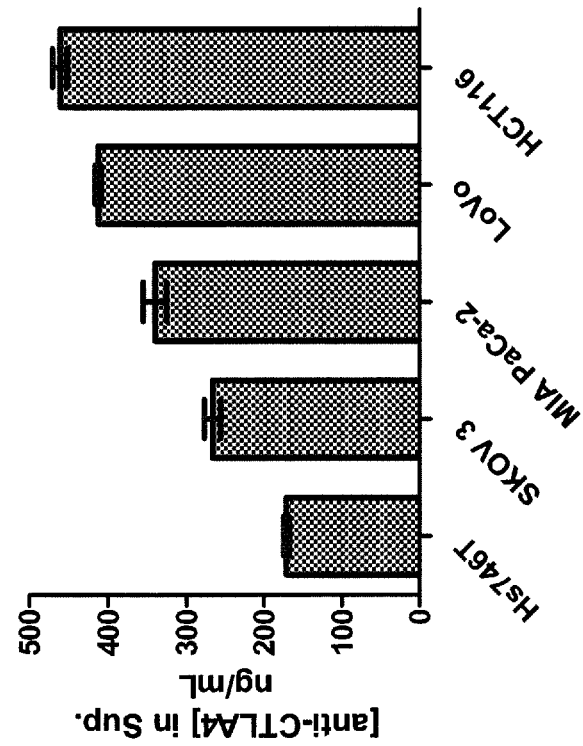
Fig. 23, cont.

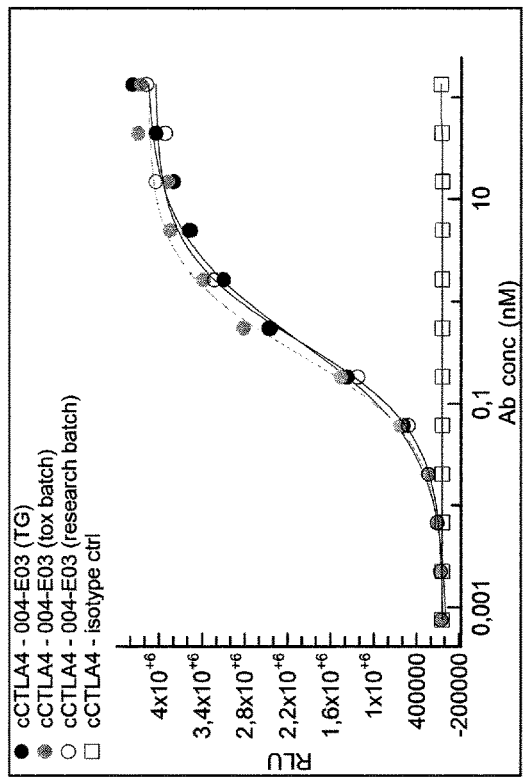
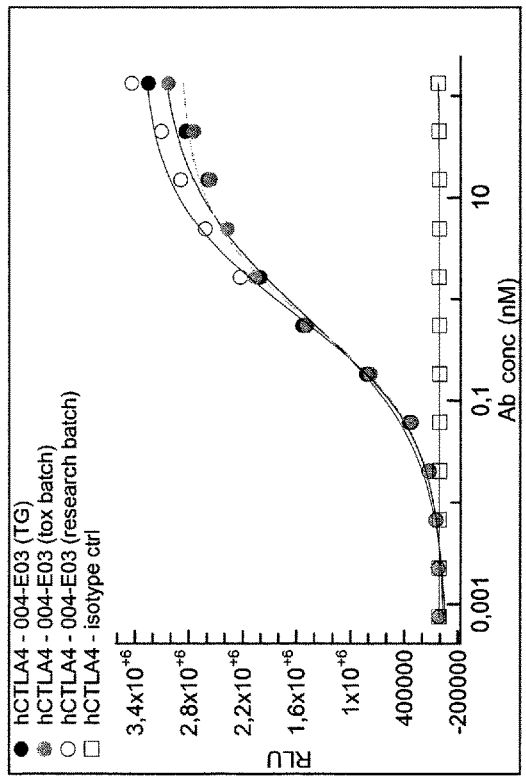
Fig. 24

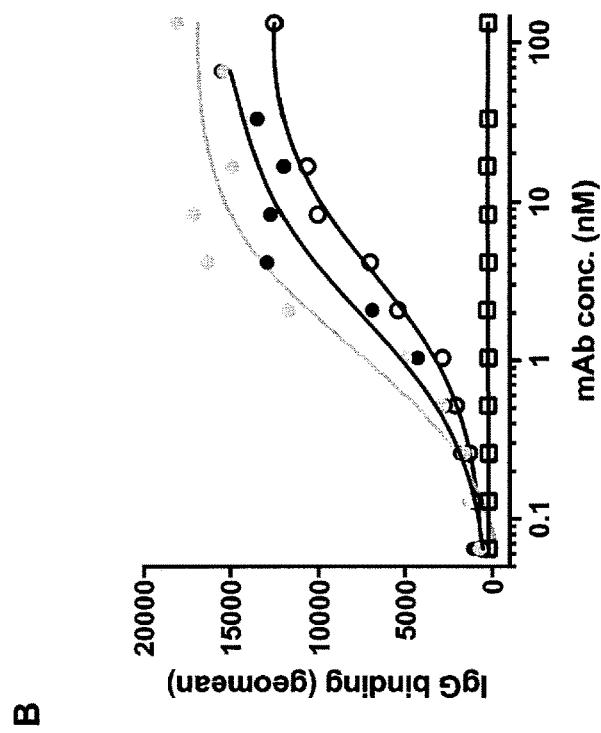
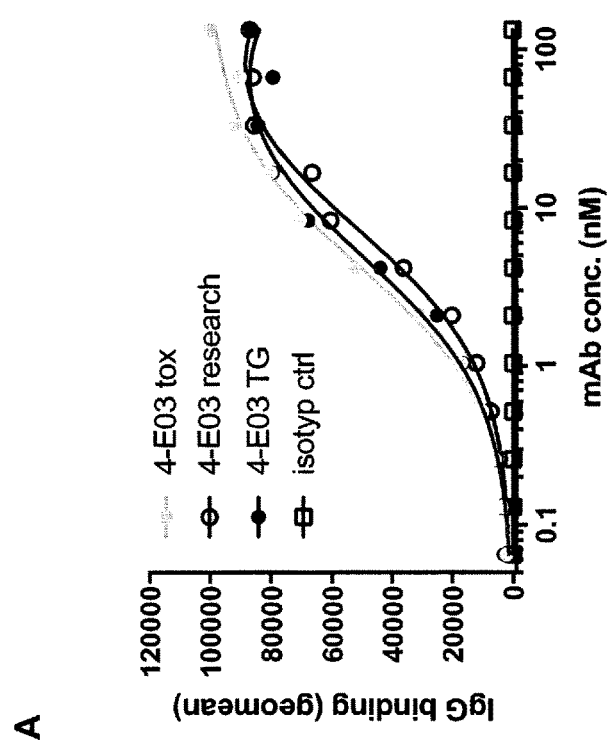
*Fig. 25*

A
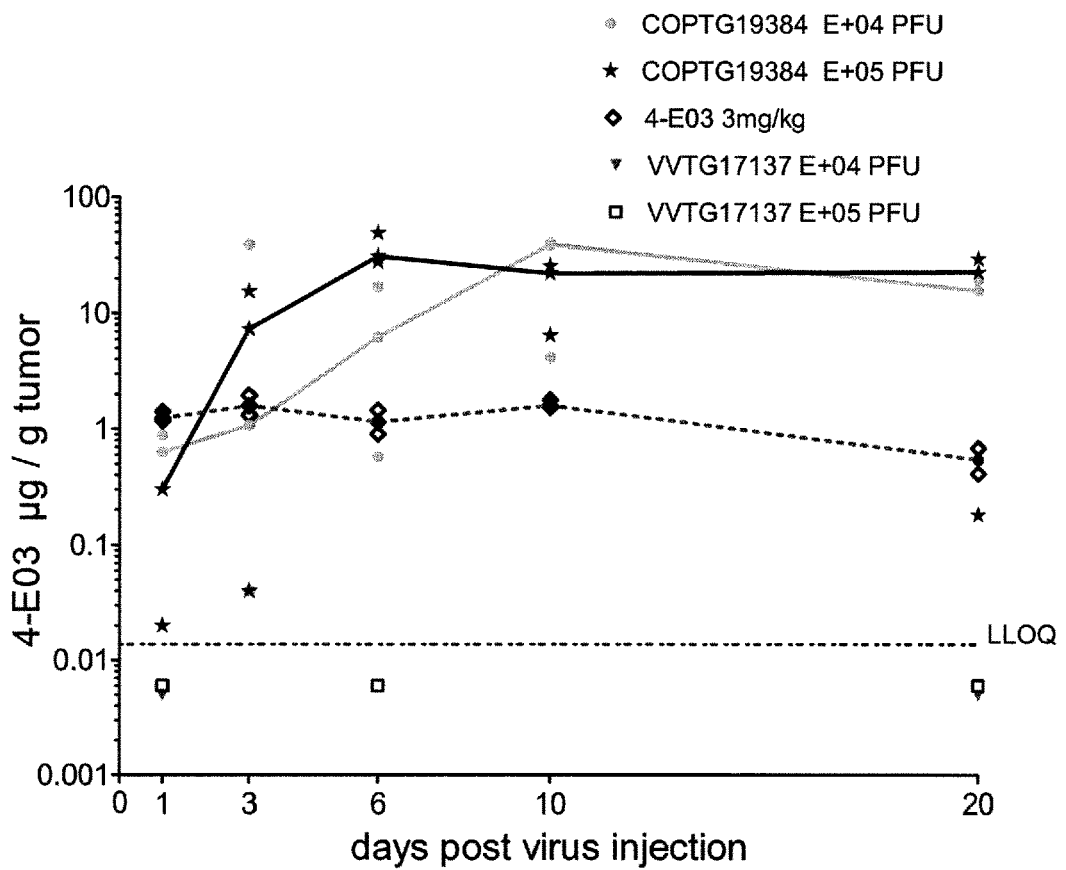
B
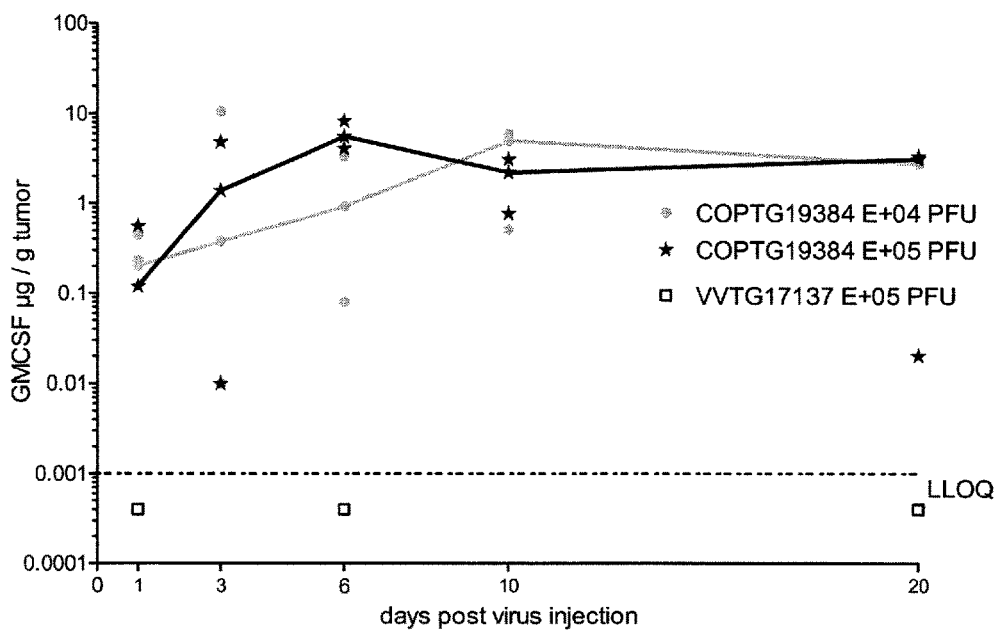
*Fig. 27*

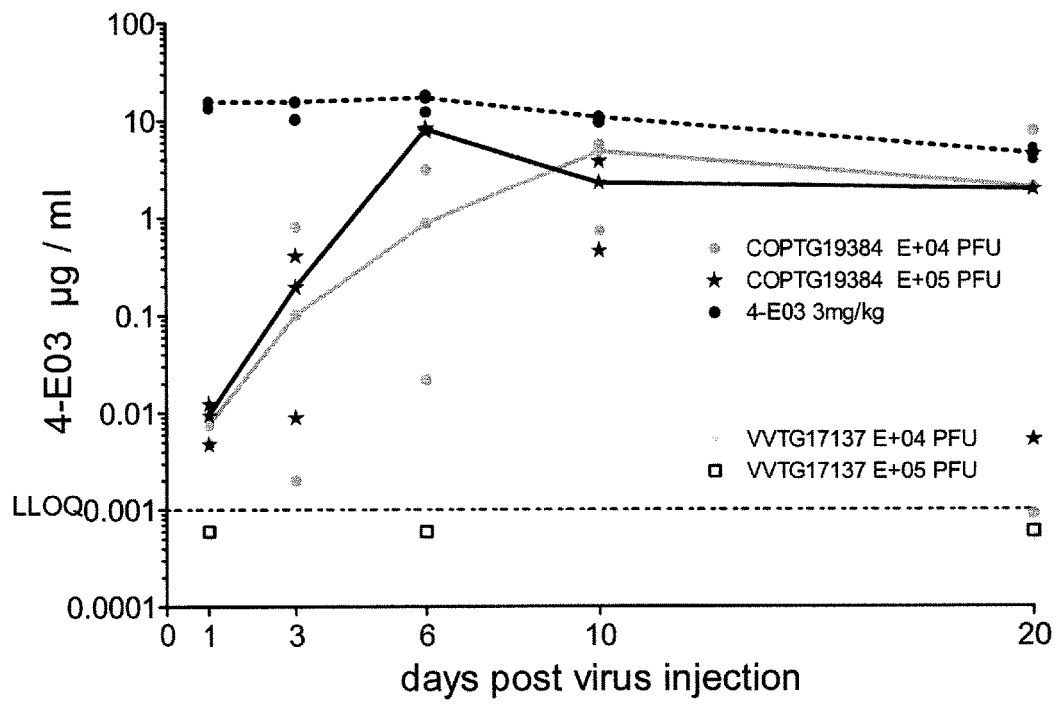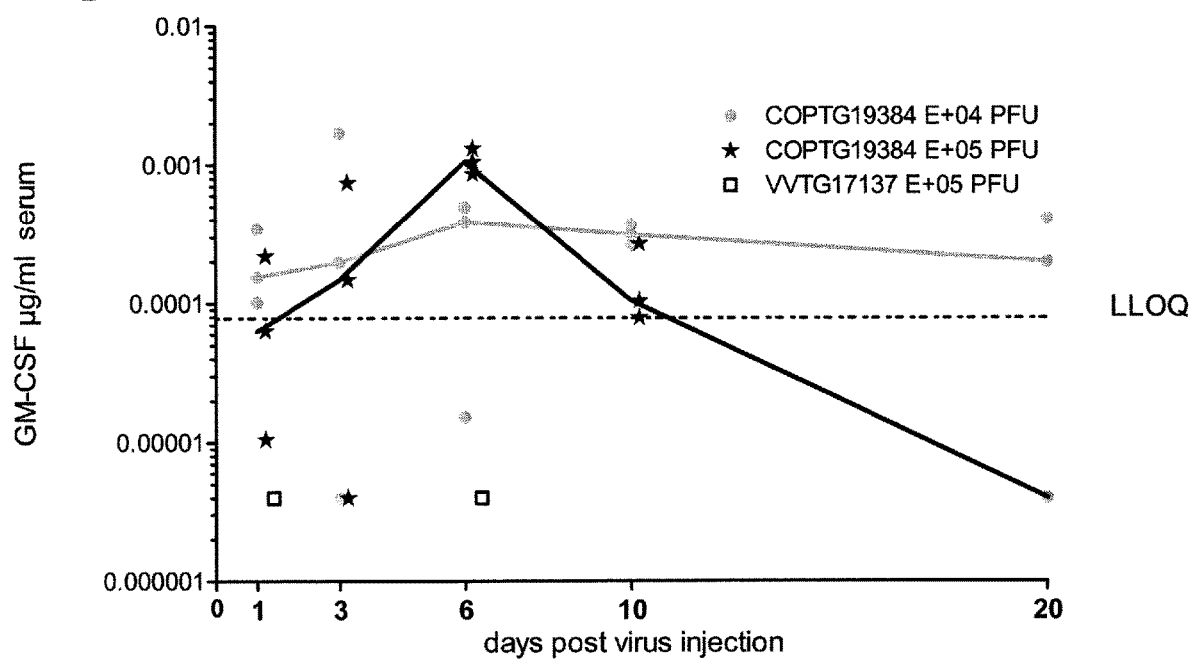
Fig. 28

A
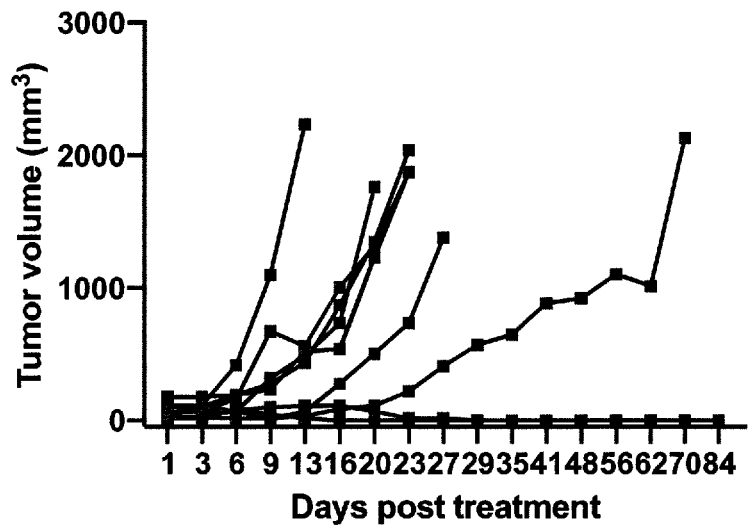
B
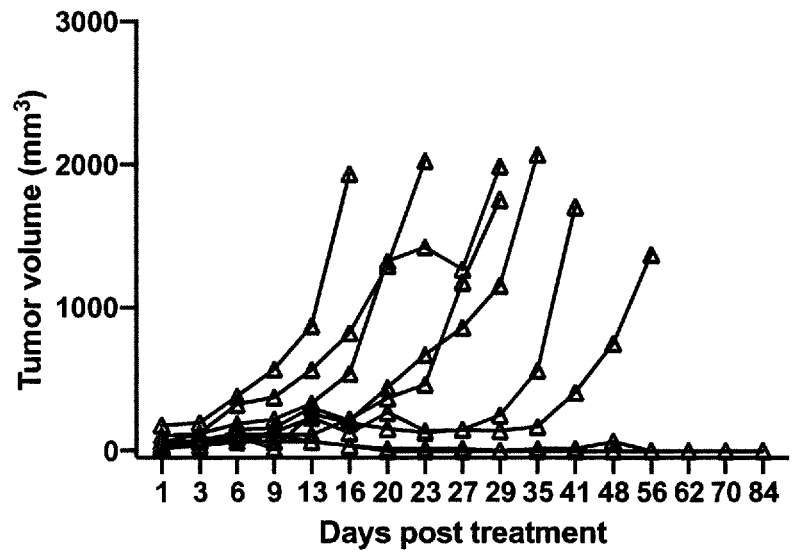
Fig. 34

C
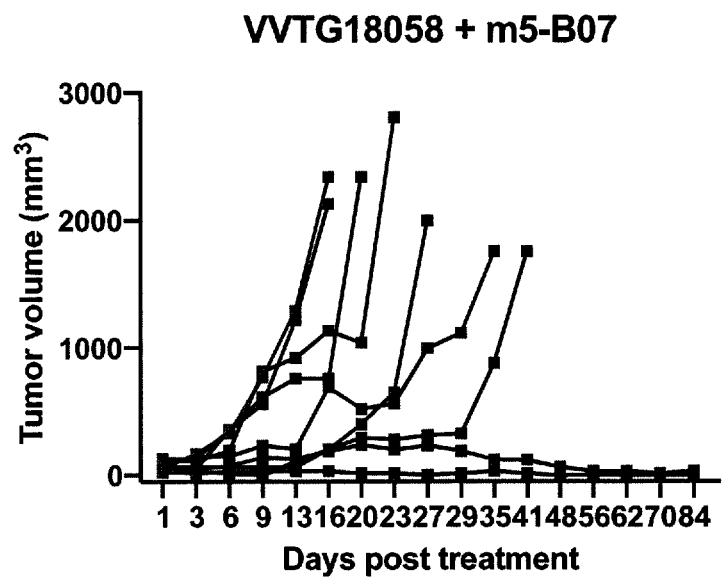
D
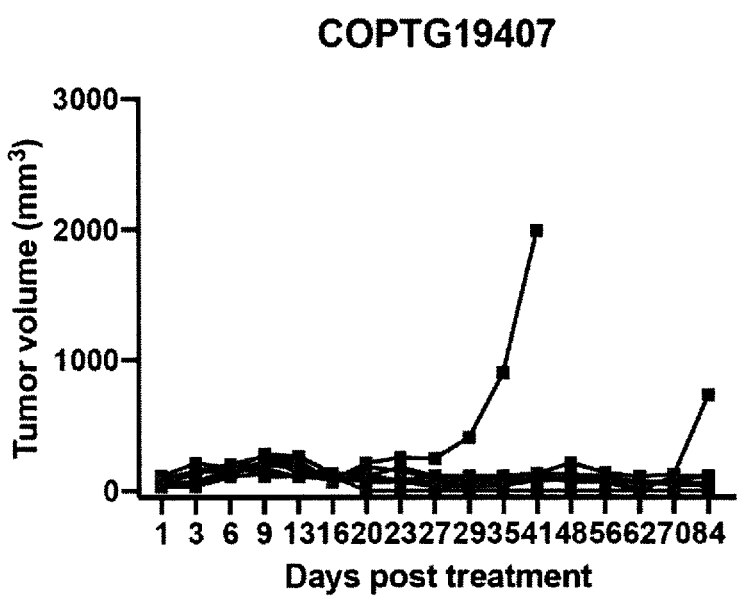
*Fig. 34, cont.*

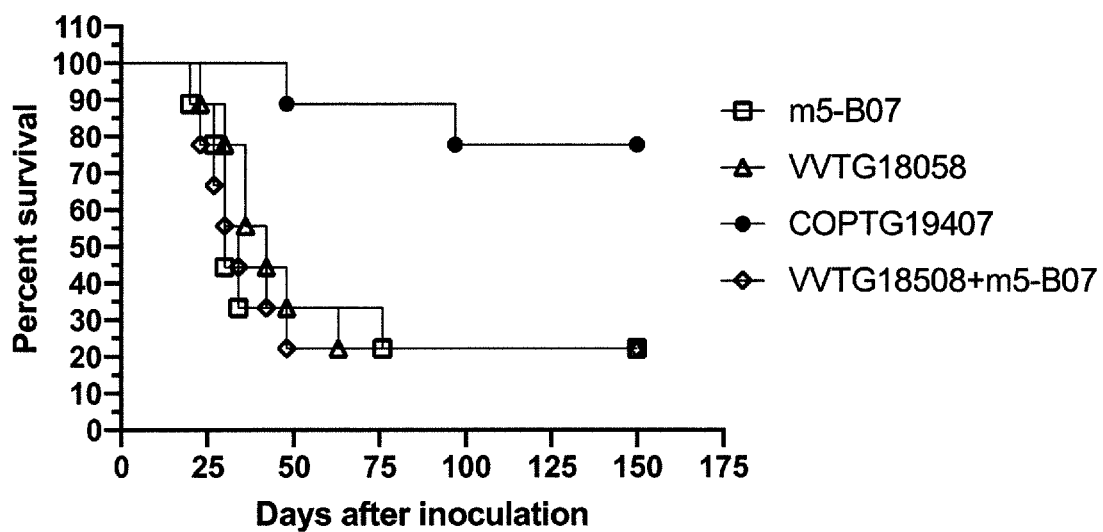
*Fig. 34, cont.*

A
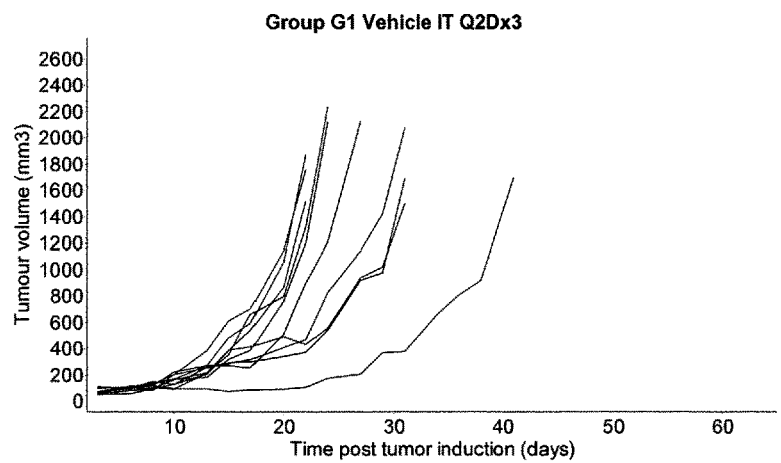
B
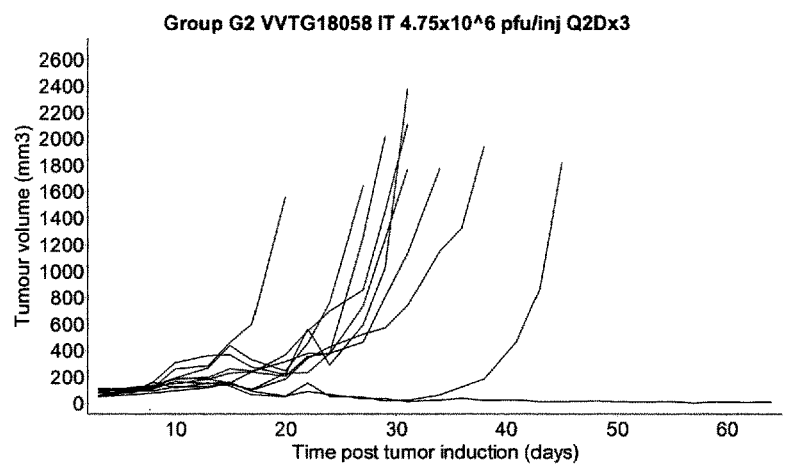
C
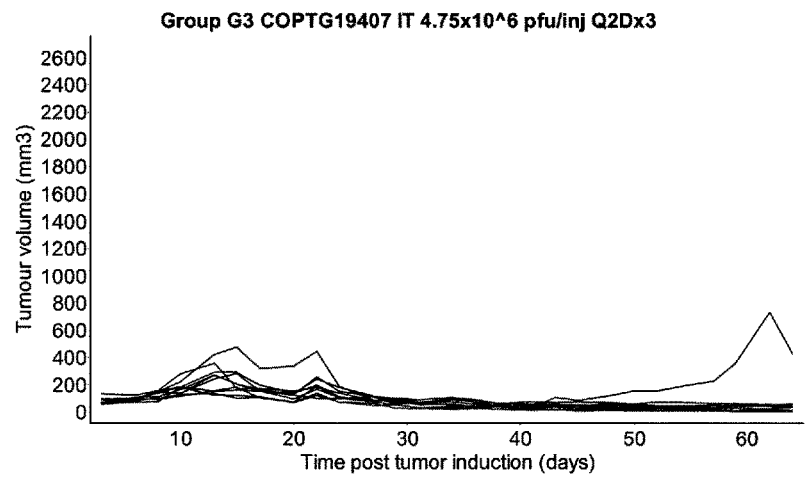
*Fig. 35*

D
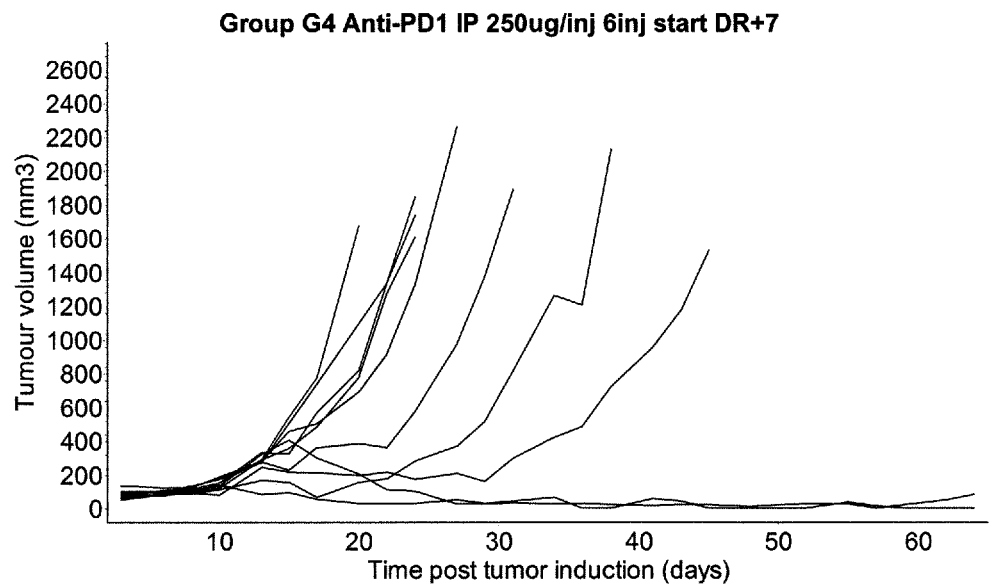
E
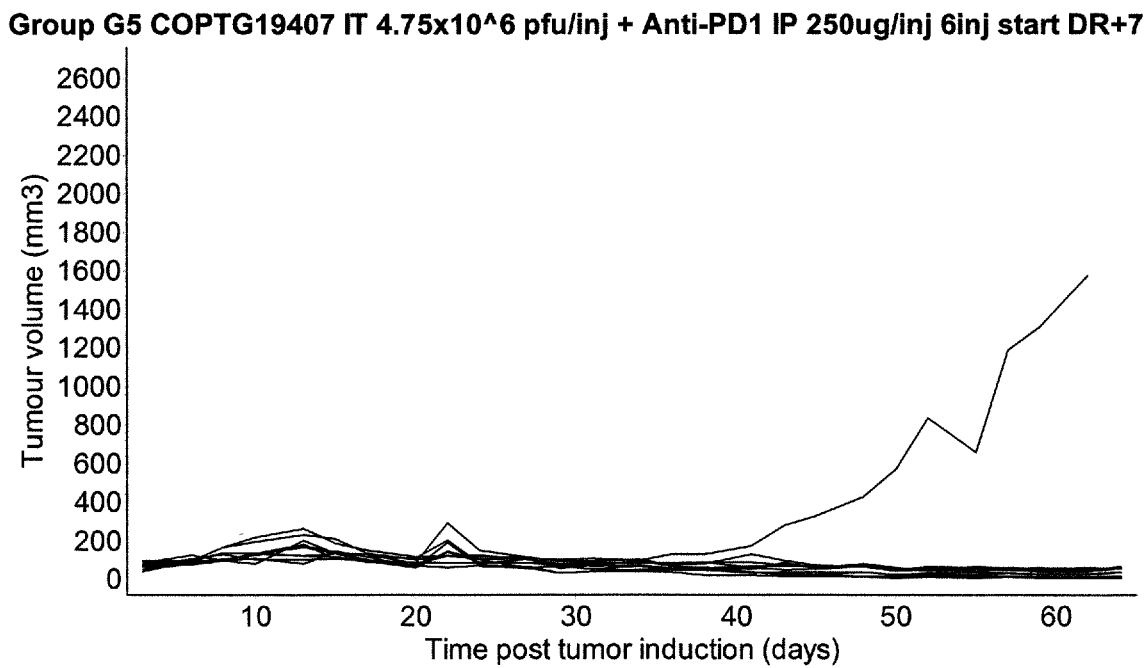
*Fig. 35, cont.*

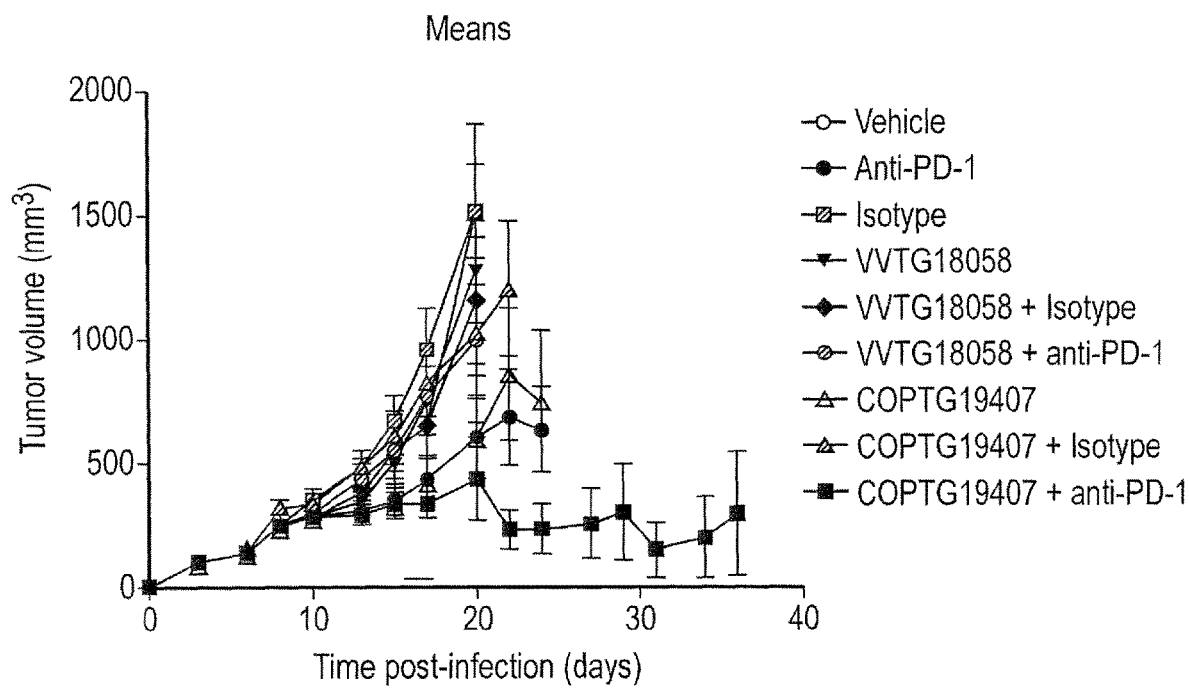
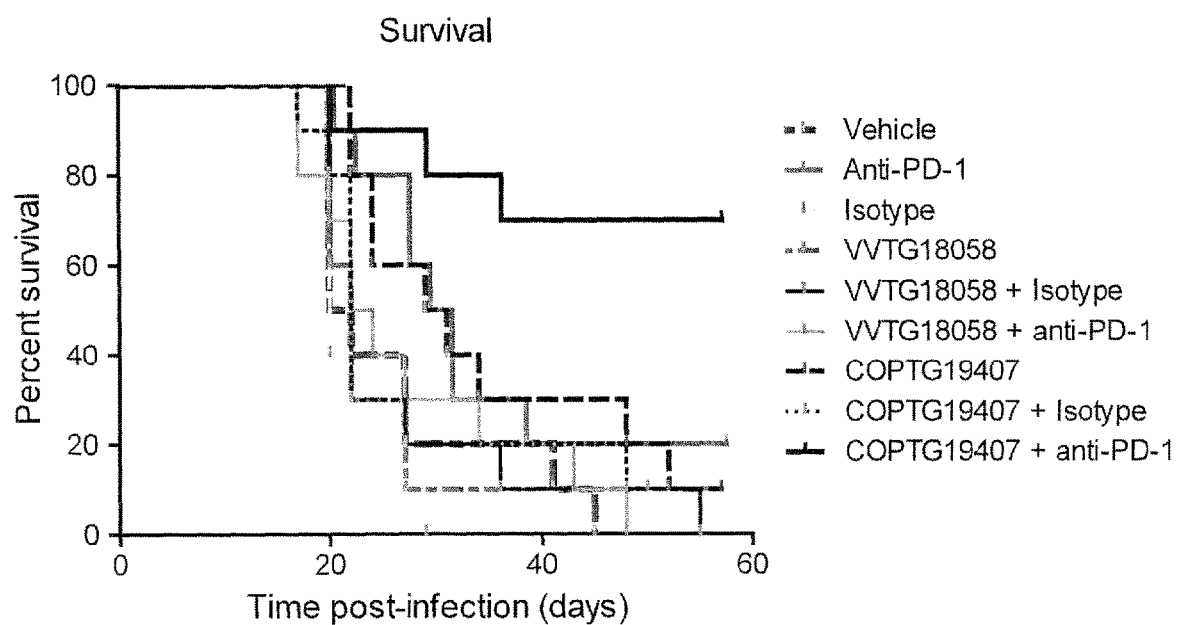
FIG. 37

A
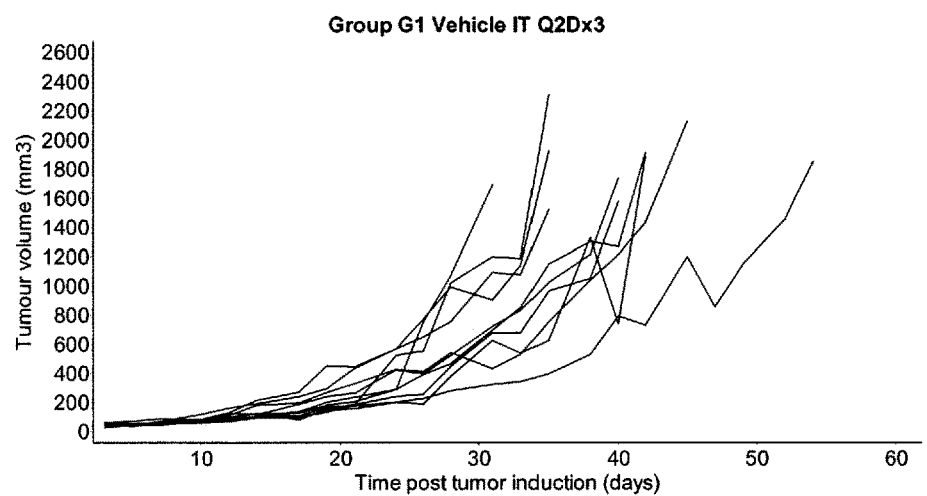
B
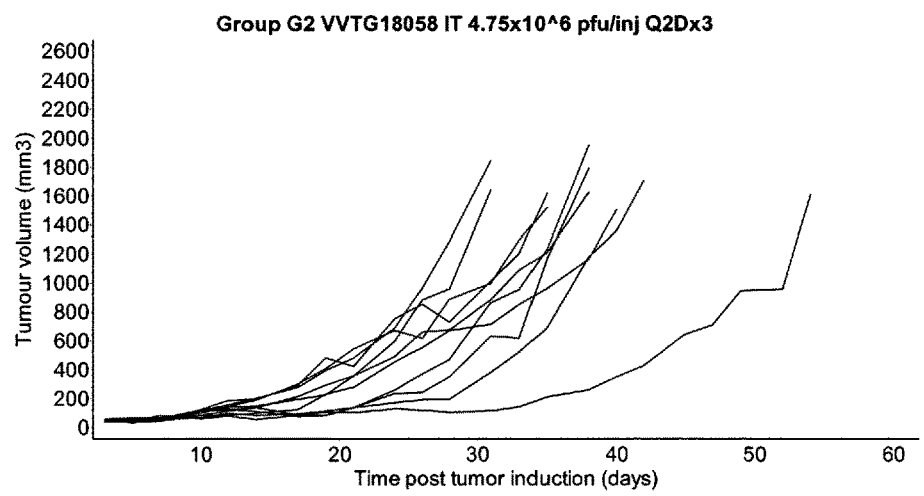
C
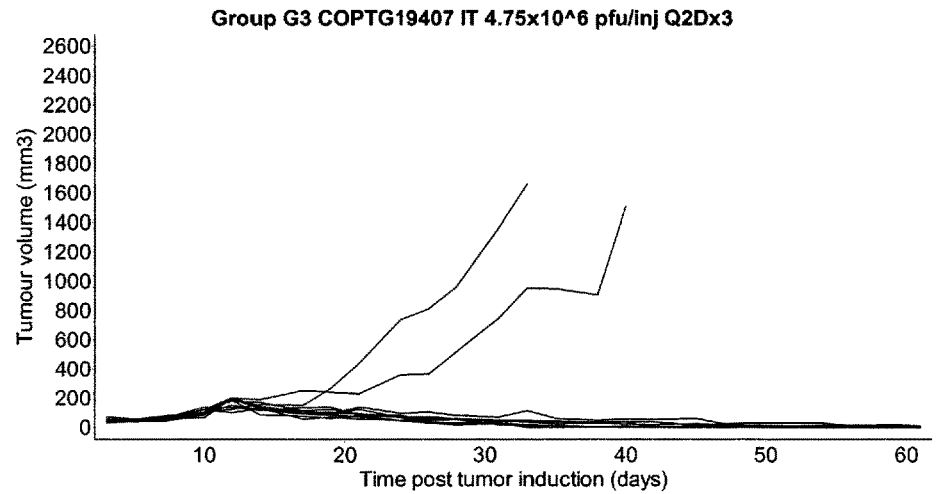
*Fig. 38*

D
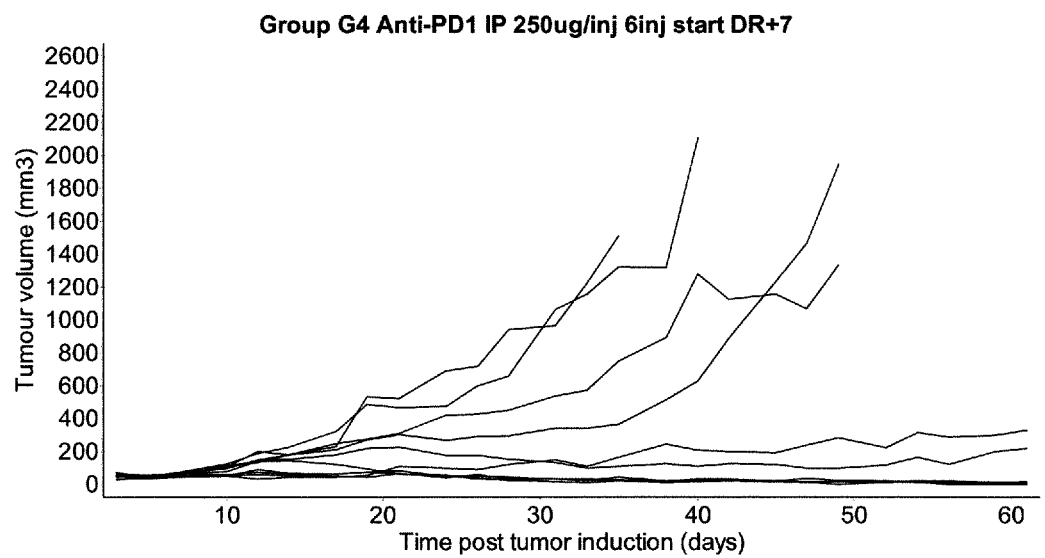
E
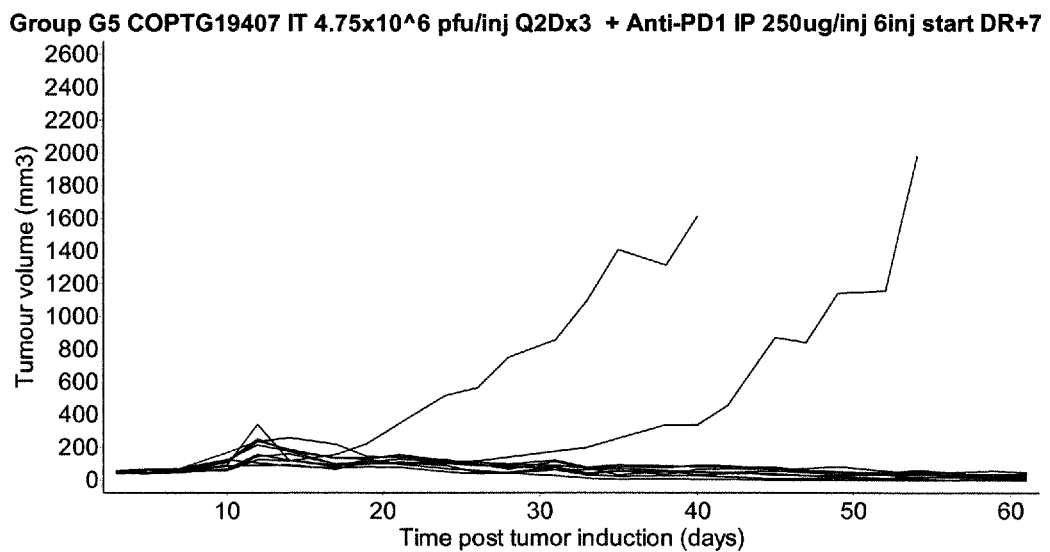
*Fig. 38, cont.*

A
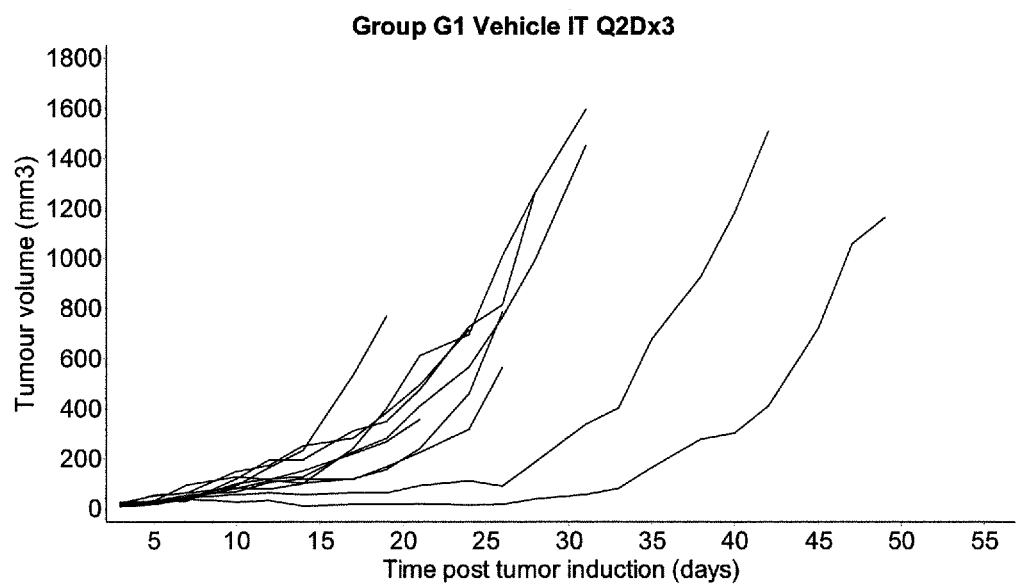
B
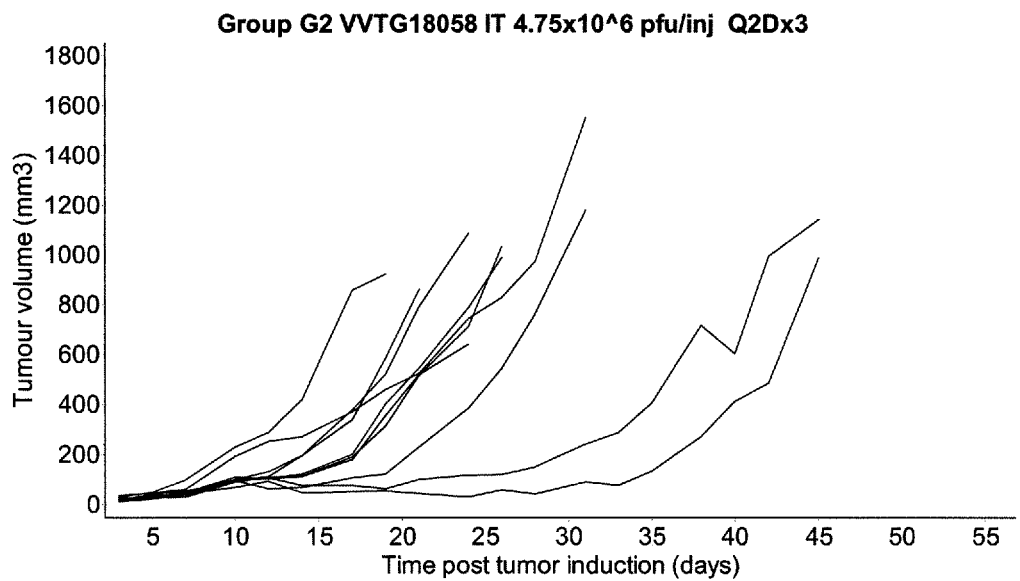
Fig. 40

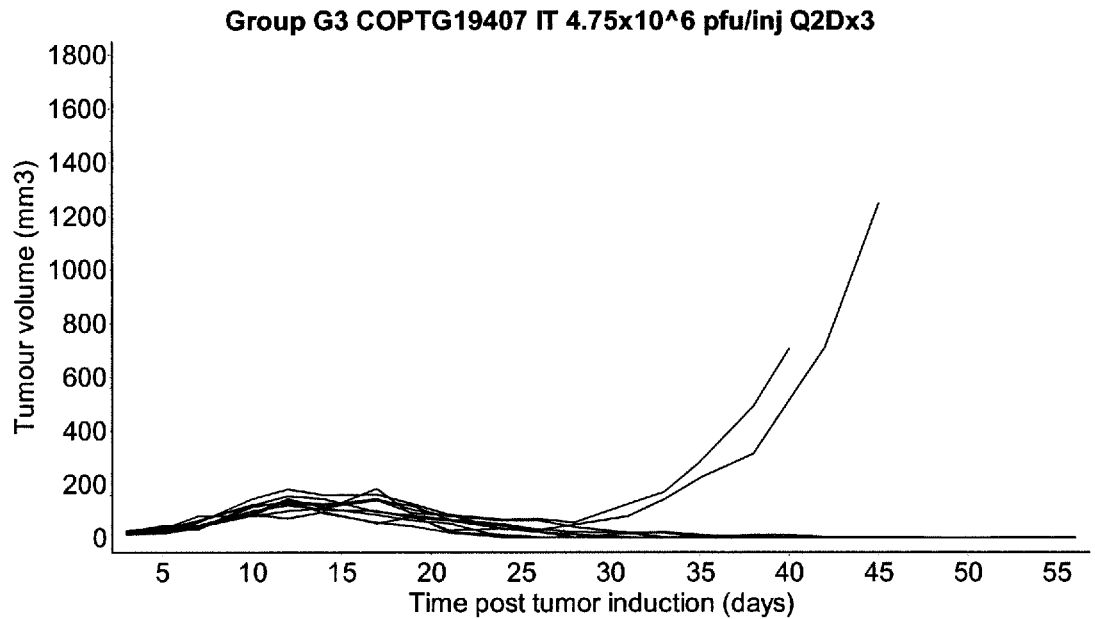
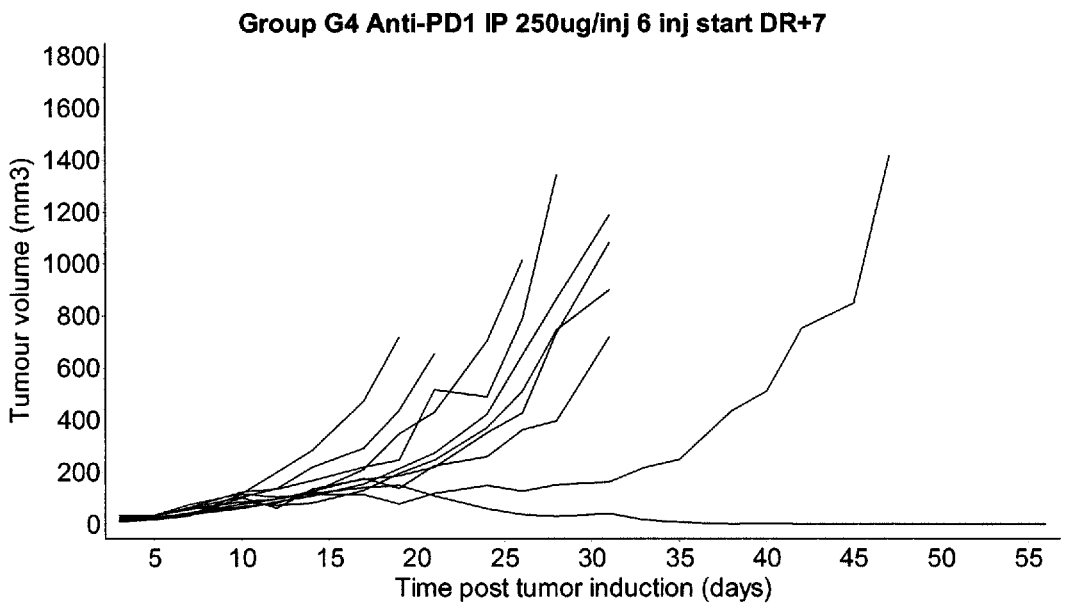
*Fig. 40, cont.*

E
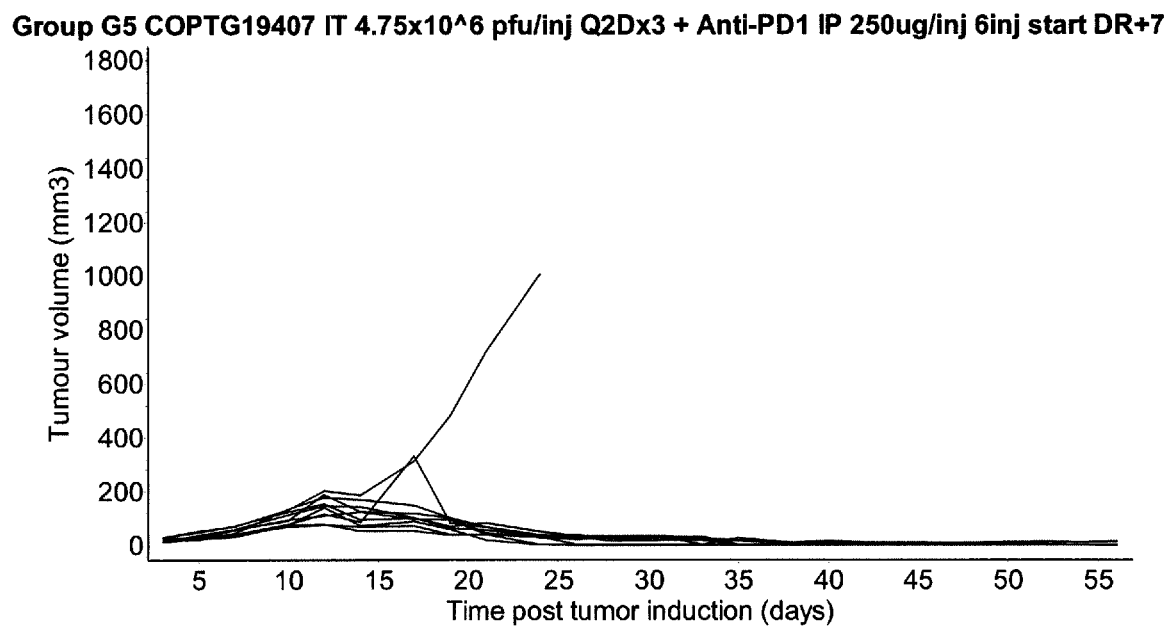
Fig. 40, cont.

ANTIBODIES AND NUCLEOTIDE SEQUENCES, AND USES THEREOF

This application is a national phase application under 35 U.S.C. § 371 of International Application No. PCT/EP2019/073488, filed Sep. 3, 2019, which claims priority to European Application No. 18192311.1, filed Sep. 3, 2018. The entire text of each of the above referenced disclosures is specifically incorporated herein by reference.

FIELD OF THE INVENTION

The present invention relates to novel anti-CTLA-4 antibody molecules, nucleotide sequences and expression vectors (e.g. oncolytic virus) encoding such antibody molecules to use thereof in cancer therapy. The novel antibodies have improved Treg depletion compared to ipilimumab.

BACKGROUND OF THE INVENTION

Cytotoxic T lymphocyte-associated antigen (CTLA-4 or CTLA4), also known as CD152, is a B7/CD28 family member that blocks T cell activation. CTLA-4 is expressed on activated T cells and transmits an inhibitory signal to T cells. It is homologous to the T cell co-stimulatory protein CD28, and both CTLA-4 and CD28 bind to CD80 (also denoted B7-1) and CD86 (also denoted B7-2). CTLA4 is also found in regulatory T cells (Tregs) and contributes to its inhibitory function. The CTLA-4 protein contains an extracellular V domain, a transmembrane domain, and a cytoplasmic tail.

Antibodies that block the interaction of CTLA-4 with its ligands B7.1 and B7.2 can enhance immune responses and have been shown to be capable of stimulating potent anti-tumour immunity (Korman et al 2006, Checkpoint blockade in cancer immunotherapy, *Adv Immunol*. 90:297-339).

Promising clinical results with immunomodulatory monoclonal antibodies (mAbs) have revived the belief that the immune system holds the key to controlling cancer. The classification of these mAb into checkpoint blockers (antagonists) or activators of co-stimulatory molecules (agonists) has recently come into question with the finding that examples of both types may combat tumours through depletion of suppressive regulatory T cells (Treg).

Immunomodulatory mAbs, such as ipilimumab and other anti-CTLA4 antibodies, have shown positive outcomes when trialled in difficult-to-treat malignancies, albeit in a minority of patients (Hodi, F. S., et al. 2010, *N Engl J Med* 363(8): 711-723; Beatty, G. L., et al. 2011, *Science* 331 (6024): 1612-1616; Brahmer, J. R., et al. 2012, *N Engl J Med* 366(26): 2455-2465; Topalian, S. L., et al. 2012 *N Engl J Med* 366(26): 2443-2454). These promising results have helped to reinvigorate the belief that the immune system can hold the key to controlling cancer. These mAbs were generated to target key molecular regulators on T cells or antigen-presenting cells (APCs) and to boost anticancer immunity through blockade of inhibitory signals (checkpoint blockers) or delivery of co-stimulatory signals (agonists). Recently this binary classification has come into question when the therapeutic activity of anti-CTLA4 antibodies, anti-GITR antibodies and anti-OX40 antibodies, which all target T cells, was found to involve deletion of suppressive CD4+ T regulatory cells dependent on co-engagement of activatory FcγRs (Bulliard, Jolicoeur et al. 2013, Marabelle, A., et al. 2013, *J Clin Invest* 123(6): 2447-2463; Simpson, T. R., et al. *J Exp Med* 210(9): 1695-1710).

A monoclonal CTLA-4 antibody, ipilimumab (YERVOY®; earlier denoted 10D1, BMS-734016, MDX 101, MDX-010, MDX-CTLA-4 and MDX-CTLA4), has been approved in several countries for the treatment of melanoma and is undergoing clinical trials for other indications (Weber 2008, Overcoming immunologic tolerance to melanoma: targeting CTLA-4 with ipilimumab (MDX-010) *Oncologist*, 13 (Suppl 4):16-25). Ipilimumab is a fully human anti-CTLA-4 monoclonal antibody (IgG1κ) produced in Chinese hamster ovary cells by recombinant DNA technology. It has 477202-00-9 and 6T8C155666. Ipilimumab is further defined in U.S. Pat. No. 9,789,182, which also sets out the sequences of ipilimumab's heavy and light chains (as SEQ ID NOs: 17 and 18, respectively), the sequences of the VH and/or VL regions (as SEQ ID NOs:19 and SEQ ID NO:20, respectively) and the CDR sequences (heavy chain CDR1, CDR2 and CDR3 as set forth in SEQ ID NOs:21, 22, and 23, and light chain CDR1, CDR2 and CDR3 as set forth in SEQ ID NOs: 24, 25, and 26).

A second fully human monoclonal anti-CTLA-4 antibody that has been tested in several clinical trials is tremelimumab (formerly ticilimumab, CP-675,206) (Ribas 2008, Overcoming immunologic tolerance to melanoma: targeting CTLA-4 with tremelimumab (CP-675,206) *Oncologist*, 13 (Suppl 4):10-5; Callahan et al 2010, Anti-CTLA-4 Antibody Therapy: Immune Monitoring During Clinical Development of a Novel Immunotherapy. *Semin Oncol*. 37(5): 473-484.; Blank et al 2015, Therapeutic use of anti-CTLA-4 antibodies. *International Immunology*, 27(1): 3-10).

Anti-CTLA-4 antibodies have been described in several patent applications and patents, including the following.

WO 93/00431 refers to a CTLA4 receptor protein, to a CTLA4Ig fusion protein, and to a method for regulation of cellular interactions using such a fusion protein or a monoclonal antibody.

WO 97/20574 refers to blockade of T lymphocyte downregulation associated with CTLA-4 signalling, and to a CTLA-4 blocking agent other than an antibody to the extracellular domain of CTLA-4 that increases the response of mammalian T cells to antigenic stimulus or decreases the growth of tumour cells in a mammalian host.

WO 00/37504 refers to human anti-CTLA-4 antibodies and use of such antibodies in treatment of cancer. WO 00/37504 further refers to the human monoclonal antibody tremelimumab, mentioned above, which is denoted 11.2.1 in that patent application. WO 01/14424 also refers to human antibodies that specifically bind to human CTLA-4, and to use thereof in treatment of human diseases and infections, such as cancer. WO 01/14424 further refers to the human monoclonal antibody ipilimumab, mentioned above and discussed further below, which is denoted 10D1 in that patent application.

SUMMARY OF THE INVENTION

The present invention relates to antibody molecules that specifically bind to CTLA-4, and have improved depleting effect on CTLA-4 positive cells compared to ipilimumab.

Furthermore, the present invention relates to antibody molecules that specifically bind to CTLA-4, which antibody molecules comprise the 6 CDRs having SEQ ID. NOs: 15, 16, 17, 10, 18 and 19 or the 6 CDRs having SEQ ID. NOs: 22, 23, 24, 10, 25 and 26.

Furthermore, the present invention relates to isolated nucleotide sequences encoding the above antibody molecules.

Furthermore, the present invention relates to plasmids comprising the above nucleotide sequences.

Furthermore, the present invention relates to viruses, such as oncolytic viruses, comprising the above nucleotide sequences or the above plasmids.

Furthermore, the present invention relates to cells, such as CAR T-cells, comprising the above nucleotide sequences or the above plasmids.

Furthermore, the present invention relates to the above antibody molecules, nucleotide sequences, plasmids and/or cells for use in medicine.

Furthermore, the present invention relates to the above antibody molecules, nucleotide sequences, plasmids, viruses and/or cells for use in the treatment of cancer.

Furthermore, the present invention relates to use of the above antibody molecules, nucleotide sequences, plasmids, viruses and/or cells for the manufacture of a pharmaceutical composition for use in the treatment of cancer.

Furthermore, the present invention relates to pharmaceutical compositions comprising at least one of the above antibody molecules, nucleotide sequences, plasmids, viruses and/or cells, and optionally a pharmaceutically-acceptable diluent, carrier or excipient.

Furthermore, the present invention relates to methods for treatment of cancer in a subject comprising administering to the subject a therapeutically effective amount of at least one of the above antibody molecules, nucleotide sequences, plasmids, viruses, cells and/or pharmaceutical compositions.

Furthermore, the present invention relates to an antibody molecule, an antibody molecule for use, an isolated nucleotide sequence, an isolated nucleotide sequence for use, a plasmid, a plasmid for use, a virus, a virus for use, a cell, a cell for use, a use, a pharmaceutical composition or a method of treatment as described herein with reference to the detailed description, examples and/or figures.

DETAILED DESCRIPTION OF THE INVENTION

CTLA-4 positive cells include regulatory T cells, Treg cells, Tregs or $T_{regs}$, (formerly known as suppressor T cells, sometimes also called suppressive regulatory T cells) which is a subpopulation of T cells capable of suppressing other immune cells in normal and pathological immune settings. Tregs are CD4 positive cells (CD4+ cells). There are other CD4+ T cells that are not Tregs; however, Tregs can be separated from non-Treg CD4+ cells in that Tregs also are FOXP3 positive (FOXP3+) while the non-Treg CD4+ cells are FOXP3 negative (FOXP3−).

Like ipilimumab, the anti-CTLA-4 antibody molecules described herein act, at least in part, by depleting CTLA-4 positive cells, such as Tregs. Further, like ipilimumab, the anti-CTLA-4 antibody molecules described herein block CTLA-4 interactions with B7.1 and B7.2. Thus, these antibodies can consequently help overcome CTLA-4 induced suppressive effects on effector T cell proliferation.

By depletion of Tregs, or Treg depletion, we refer herein to depletion, deletion or elimination of Tregs through physical clearance of cells. In particular, we refer to depletion of intratumoural Tregs. Depletion of Tregs may be achieved through ADCC, i.e. antibody-dependent cell-mediated cytotoxicity or antibody-dependent cellular cytotoxicity, and/or ADCP, i.e. antibody dependent cellular phagocytosis. This means that when an antibody molecule as described herein is administered to a subject, such as a human, it binds specifically to CTLA-4 expressed on the surface of Tregs, and this binding results in depletion of the Tregs. In some embodiments, the CTLA-4 is preferentially expressed on tumour infiltrating lymphocytes in the tumour microenvironment or on tumour cells.

ADCC is an immune mechanism through which Fc receptor-bearing effector cells can recognize and kill antibody-coated target cells expressing tumour-derived antigens, i.e. in the present case, CTLA-4, on their surface. ADCP is a similar mechanism, although it results in the target cells being killed through phagocytosis instead of cytotoxicity.

Antibodies are well known to those skilled in the art of immunology and molecular biology. Typically, an antibody comprises two heavy (H) chains and two light (L) chains. Herein, we sometimes refer to this complete antibody molecule as a full-size or full-length antibody. The antibody's heavy chain comprises one variable domain (VH) and three constant domains (CH1, CH2 and CH3), and the antibody's molecule light chain comprises one variable domain (VL) and one constant domain (CL). The variable domains (sometimes collectively referred to as the Fv region) bind to the antibody's target, or antigen. Each variable domain comprises three loops, referred to as complementary determining regions (CDRs), which are responsible for target binding. The constant domains are not involved directly in binding an antibody to an antigen, but exhibit various effector functions. Depending on the amino acid sequence of the constant region of their heavy chains, antibodies or immunoglobulins can be assigned to different classes. There are five major classes of immunoglobulins: IgA, IgD, IgE, IgG and IgM, and in humans several of these are further divided into subclasses (isotypes), e.g., IgG1, IgG2, IgG3, and IgG4; IgA1 and IgA2. Another part of an antibody is the Fc domain (otherwise known as the fragment crystallisable domain), which comprises two of the constant domains of each of the antibody's heavy chains. The Fc domain is responsible for interactions between the antibody and Fc receptor.

Fc receptors are membrane proteins which are often found on the cell surface of cells of the immune system (i.e. Fc receptors are found on the target cell membrane—otherwise known as the plasma membrane or cytoplasmic membrane). The role of Fc receptors is to bind antibodies via the Fc domain, and to internalize the antibody into the cell. In the immune system, this can result in antibody-mediated phagocytosis and antibody-dependent cell-mediated cytotoxicity.

The term antibody molecule, as used herein, encompasses full-length or full-size antibodies as well as functional fragments of full-length antibodies and derivatives of such antibody molecules.

Functional fragments of a full-size antibody have the same antigen binding characteristics as the corresponding full-size antibody and include either the same variable domains (i.e. the VH and VL sequences) and/or the same CDR sequences as the corresponding full-size antibody. That the functional fragment has the same antigen binding characteristics as the corresponding full-size antibody means that it binds to the same epitope on the target as the full-size antibody. Such a functional fragment may correspond to the Fv part of a full-size antibody. Alternatively, such a fragment may be a Fab, also denoted F(ab), which is a monovalent antigen-binding fragment that does not contain a Fc part, or a F(ab')$_2$, which is an divalent antigen-binding fragment that contains two antigen-binding Fab parts linked together by disulfide bonds or a F(ab'), i.e. a monovalent-variant of a F(ab')$_2$. Such a fragment may also be single chain variable fragment (scFv).

A functional fragment does not always contain all six CDRs of a corresponding full-size antibody. It is appreciated that molecules containing three or fewer CDR regions (in some cases, even just a single CDR or a part thereof) are capable of retaining the antigen-binding activity of the antibody from which the CDR(s) are derived. For example, in Gao et al., 1994, *J. Biol. Chem.*, 269: 32389-93 it is described that a whole VL chain (including all three CDRs) has a high affinity for its substrate.

Molecules containing two CDR regions have been described, for example, by Vaughan & Sollazzo 2001, *Combinatorial Chemistry & High Throughput Screening*, 4: 417-430. On page 418 (right column—3 Our Strategy for Design) a minibody including only the H1 and H2 CDR hypervariable regions interspersed within framework regions is described. The minibody is described as being capable of binding to a target. Pessi et al., 1993, *Nature*, 362: 367-9 and Bianchi et al., 1994, *J. Mol. Biol.*, 236: 649-59 are referenced by Vaughan & Sollazzo and describe the H1 and H2 minibody and its properties in more detail. In Qiu et al., 2007, *Nature Biotechnology*, 25:921-9 it is demonstrated that a molecule consisting of two linked CDRs are capable of binding antigen. Quiocho 1993, *Nature*, 362: 293-4 provides a summary of "minibody" technology. Ladner 2007, *Nature Biotechnology*, 25:875-7 comments that molecules containing two CDRs are capable of retaining antigen-binding activity.

Antibody molecules containing a single CDR region are described, for example, in Laune et al., 1997, *JBC*, 272: 30937-44, in which it is demonstrated that a range of hexapeptides derived from a CDR display antigen-binding activity and it is noted that synthetic peptides of a complete, single, CDR display strong binding activity. In Monnet et al., 1999, *JBC*, 274: 3789-96 it is shown that a range of 12-mer peptides and associated framework regions have antigen-binding activity and it is commented on that a CDR3-like peptide alone is capable of binding antigen. In Heap et al., 2005, *J. Gen. Virol.*, 86: 1791-1800 it is reported that a "micro-antibody" (a molecule containing a single CDR) is capable of binding antigen and it is shown that a cyclic peptide from an anti-HIV antibody has antigen-binding activity and function. In Nicaise et al., 2004, *Protein Science*, 13:1882-91 it is shown that a single CDR can confer antigen-binding activity and affinity for its lysozyme antigen.

Thus, antibody molecules having five, four, three or fewer CDRs are capable of retaining the antigen binding properties of the full-length antibodies from which they are derived.

The antibody molecule may also be a derivative of a full-length antibody or a fragment of such an antibody. The derivative has the same antigen binding characteristics as the corresponding full-size antibody in the sense that it binds to the same epitope on the target as the full-size antibody.

Thus, by the term "antibody molecule", as used herein, we include all types of antibody molecules and functional fragments thereof and derivatives thereof, including: monoclonal antibodies, polyclonal antibodies, synthetic antibodies, recombinantly produced antibodies, multi-specific antibodies, bi-specific antibodies, human antibodies, humanized antibodies, chimeric antibodies, single chain antibodies, variable fragments (Fvs), single-chain variable fragments (scFv fragments) including divalent single-chain variable fragments (di-scFvs) and disulfide-linked variable fragments, Fab fragments, F(ab')₂ fragments, Fab' fragments, antibody heavy chains, antibody light chains, homo-dimers of antibody heavy chains, homo-dimers of antibody light chains, heterodimers of antibody heavy chains, heterodimers of antibody light chains, antigen binding functional fragments of such homo- and heterodimers.

Further, the term "antibody molecule", as used herein, includes all classes of antibody molecules and functional fragments, including: IgG, IgG1, IgG2, IgG3, IgG4, IgA, IgM, IgD, and IgE.

In some embodiments, the antibody is a human IgG1. The skilled person is aware that the mouse IgG2a and human IgG1 productively engage with activatory Fc gamma receptors and share the ability to activate deletion of target cells through activation of activatory Fc gamma receptor bearing immune cells (e.g. macrophages and NK cells) by e.g. ADCP and ADCC. As such, whereas the mouse IgG2a is the preferred isotype for deletion in the mouse, human IgG1 is a preferred isotype for deletion in human. Conversely, it is known that optimal co-stimulation of TNFR superfamily agonist receptors e.g. 4-1BB, OX40, TNFRII, CD40 depends on antibody engagement of the inhibitory FcγRII. In the mouse the IgG1 isotype, which binds preferentially to inhibitory Fc gamma receptor (FcγRIIB) and only weakly to activatory Fc gamma receptors, is known to be optimal for costimulatory activity of TNFR-superfamily targeting mAb. While no direct equivalent of the mouse IgG1 isotype has been described in man, antibodies may be engineered to show a similarly enhanced binding to inhibitory over activatory human Fc gamma receptors. Such engineered TNFR-superfamily targeting antibodies also have improved co-stimulatory activity in vivo, in transgenic mice engineered to express human activatory and inhibitory Fc gamma receptors (Dahan et al, 2016, Therapeutic Activity of Agonistic, Human Anti-CD40 Monoclonal Antibodies Requires Selective FcγR Engagement. *Cancer Cell.* 29(6):820-31).

As outlined above, different types and forms of antibody molecules are included in the invention, and would be known to the person skilled in immunology. It is well known that antibodies used for therapeutic purposes are often modified with additional components which modify the properties of the antibody molecule.

Accordingly, we include that an antibody molecule of the invention or an antibody molecule used in accordance with the invention (for example, a monoclonal antibody molecule, and/or polyclonal antibody molecule, and/or bi-specific antibody molecule) comprises a detectable moiety and/or a cytotoxic moiety.

By "detectable moiety", we include one or more from the group comprising of: an enzyme; a radioactive atom; a fluorescent moiety; a chemiluminescent moiety; a bioluminescent moiety. The detectable moiety allows the antibody molecule to be visualised in vitro, and/or in vivo, and/or ex vivo.

By "cytotoxic moiety", we include a radioactive moiety, and/or enzyme, for example wherein the enzyme is a caspase, and/or toxin, for example wherein the toxin is a bacterial toxin or a venom; wherein the cytotoxic moiety is capable of inducing cell lysis.

We further include that the antibody molecule may be in an isolated form and/or purified form, and/or may be PEGylated.

As discussed above, the CDRs of an antibody bind to the antibody target. The assignment of amino acids to each CDR described herein is in accordance with the definitions according to Kabat E A et al. 1991, In "Sequences of Proteins of Immulogical Interest" Fifth Edition, NIH Publication No. 91-3242, pp xv-xvii.

As the skilled person would be aware, other methods also exist for assigning amino acids to each CDR. For example, the International ImMunoGeneTics information system (IMGT(R))) (world-wide-web at imgt.org and Lefranc and Lefranc "The Immunoglobulin FactsBook" published by Academic Press, 2001).

In a further embodiment, the antibody molecule of the present invention or used according to the invention is an antibody molecule that is capable of competing with the specific antibodies described herein, such as the antibody molecules comprising SEQ ID. NOs: 15, 16, 17, 10, 18 and 19 or SEQ ID. NOs: 22, 23, 24, 10, 25 and 26.

By "capable of competing for" we mean that the competing antibody is capable of inhibiting or otherwise interfering, at least in part, with the binding of an antibody molecule as defined herein to the specific target.

For example, such a competing antibody molecule may be capable of inhibiting the binding of an antibody molecule described herein by at least about 10%; for example at least about 20%, or at least about 30%, at least about 40%, at least about 50%, at least about 60%, at least about 70%, at least about 80%, at least about 90%, at least about 95%, at least about 100% and/or inhibiting the ability of the antibody described herein to prevent or reduce binding to the specific target by at least about 10%; for example at least about 20%, at least about 30%, at least about 40%, at least about 50%, at least about 60%, at least about 70%, at least about 80%, at least about 90%, at least about 95%, or at least about 100%.

Competitive binding may be determined by methods well known to those skilled in the art, such as Enzyme-linked immunosorbent assay (ELISA).

ELISA assays can be used to evaluate epitope-modifying or blocking antibodies. Additional methods suitable for identifying competing antibodies are disclosed in *Antibodies: A Laboratory Manual*, Harlow & Lane, which is incorporated herein by reference (for example, see pages 567 to 569, 574 to 576, 583 and 590 to 612, 1988, CSHL, NY, ISBN 0-87969-314-2).

It is well known that an antibody specifically binds a defined target molecule or antigen, and that this means that the antibody preferentially and selectively binds its target and not a molecule which is not a target.

The target CTLA-4 of the antibodies according to the present invention, or of the antibodies used in accordance with the invention, are expressed on the surface of cells, i.e. they are cell surface antigen, which would include an epitope (otherwise known in this context as a cell surface epitope) for the antibody. Cell surface antigen and epitope are terms that would be readily understood by one skilled in immunology or cell biology.

By "cell surface antigen", we include that the cell surface antigen or at least the epitope thereof to which the antibody molecule described herein, is exposed on the extracellular side of the cell membrane.

Methods of assessing protein binding are known to the person skilled in biochemistry and immunology. It would be appreciated by the skilled person that those methods could be used to assess binding of an antibody to a target and/or binding of the Fc domain of an antibody to an Fc receptor; as well as the relative strength, or the specificity, or the inhibition, or prevention, or reduction in those interactions. Examples of methods that may be used to assess protein binding are, for example, immunoassays, BIAcore, western blots, radioimmunoassay (RIA) and enzyme-linked immunosorbent assays (ELISAs) (See Fundamental Immunology Second Edition, Raven Press, New York at pages 332-336 (1989) for a discussion regarding antibody specificity).

Accordingly, herein both an "antibody molecule that specifically binds CTLA-4" and an "anti-CTLA-4 antibody molecule" refers to an antibody molecule that specifically binds the target CTLA-4 but does not bind to non-target, or binds to a non-target more weakly (such as with a lower affinity) than the target.

In some embodiments, the antibody molecule that specifically binds CTLA-4 (or the anti-CTLA-4 antibody molecule) refers to an antibody molecule that specifically binds to the extracellular domain of CTLA-4.

In some embodiments, the antibody molecule that specifically binds CTLA-4 (or the anti-CTLA-4 antibody molecule) does not cross react with CD28. In some embodiments, the antibody molecule that specifically binds CTLA-4 (or the anti-CTLA-4 antibody molecule) blocks the binding of CTLA-4 to CD80 and/or CD86, thereby inhibiting CLTA-4 signalling.

We also include the meaning that the antibody specifically binds to the target CTLA-4 at least two-fold more strongly, or at least five-fold more strongly, or at least 10-fold more strongly, or at least 20-fold more strongly, or at least 50-fold more strongly, or at least 100-fold more strongly, or at least 200-fold more strongly, or at least 500-fold more strongly, or at least than about 1000-fold more strongly than to a non-target.

Additionally, we include the meaning that the antibody specifically binds to the target CTLA-4 if it binds to the target with a $K_d$ of at least about $10^{-1}$ $K_d$, or at least about $10^{-2}$ $K_d$, or at least about $10^{-3}$ $K_d$, or at least about $10^{-4}$ $K_d$, or at least about $10^{-5}$ $K_d$, or at least about $10^{-6}$ $K_d$, or at least about $10^{-7}$ $K_d$, or at least about $10^{-8}$ $K_d$, or at least about $10^{-9}$ $K_d$, or at least about $10^{-10}$ $K_d$, or at least about $10^{-11}$ $K_d$, or at least about $10^{-12}$ $K_d$, or at least about $10^{-13}$ $K_d$, or at least about $10^{14}$ $K_d$, or at least about $10^{-15}$ $K_d$.

As mentioned above, the antibody molecules that specifically bind to CTLA-4 (or the anti-CTLA-4 antibody molecules) described herein has an improved depleting effect on CTLA-4 positive cells compared to ipilimumab.

That the antibody molecules have a depleting effect on CTLA-4 positive cells means that upon administration to a subject, such as a human, such an antibody binds specifically to CTLA-4 expressed on the surface of CTLA-4 positive cells, and this binding results in depletion of such cells.

In some embodiments, the CTLA-4 positive cells are CD4 positive (CD4+) cells, i.e. cells that express CD4.

In some embodiments, the CTLA-4 positive cells are both CD4 positive and FOXP3 positive, i.e. expressing both CD4 and FOXP3. These cells are Tregs. CD8 positive T cells also express CTLA-4, but Tregs express significantly higher levels of CTLA-4 than CD8 positive T cells. This makes Tregs more susceptible to depletion compared to lower expressing CD8+ cells.

In some situations, the CTLA-4 is preferentially expressed on immune cells in the tumour microenvironment (tumour infiltrating cells, TILS).

Thus, in a tumour microenvironment, the Tregs will be the cells that have the highest expression of CTLA-4, resulting in the antibody molecules that specifically bind to CTLA-4 (or the anti-CTLA-4 antibody molecules) having a Treg depleting effect. This is discussed in more detail below, e-g. in Example 4 and in connection with FIG. 13.

In some embodiments, CTLA-4 positive cells will be Tregs in a solid tumour. Such Tregs will have very high expression of CTLA-4, and therefore administration of an antibody molecules that specifically binds to CTLA-4, will preferentially result in depletion of such Tregs.

As mentioned above, the anti-CTLA-4 antibody molecules described herein are Treg depleting antibody molecules, which means that upon administration to a subject, such as a human, such an antibody molecule binds specifically to CTLA-4 expressed on the surface of Tregs, and this binding results in depletion of Tregs.

To decide whether an antibody molecule is an antibody molecule that has improved depleting effect on CTLA-4 positive cells compared to ipilimumab as referred to herein, it is possible to use an in vitro antibody-dependent cellular cytotoxicity (ADCC) assay or an in vivo test in a PBMC-NOG/SCID model.

The in vitro ADCC test which is performed using an NK-92 cell line stably transfected to express the CD16-158V allele together with GFP, wherein the ADCC test comprises the following consecutive seven steps:
1) CTLA-4 positive cells, CD4 positive cells or Tregs as target cells are isolated from peripheral blood of healthy donors. This isolation may be done using a CD4+ T cell isolation kit, such as a commercial kit from Miltenyi Biotec.
2) The target cells are then stimulated, e.g. for 48 hours, with CD3/CD28, for example using CD3/CD28 Dynabeads® and rhIL-2, such as 50 ng/ml rhIL-2. The stimulation may be done at 37° C.
3) The target cells are then pre-incubated with the antibody molecule to be tested, e.g. at 10 μg/ml for 30 min at 4° C., and are then mixed with NK cells.
4) The target cells are then incubated for an appropriate time, such as 4 hours, in RPMI 1640+GlutaMAX medium containing HEPES buffer, sodium pyruvate and FBS low IgG. The RPMI 1640+GlutaMAX medium may containing 10 mM HEPES buffer, 1 mM sodium pyruvate and 10% FBS low IgG, and the effector:target cell ratio may be 2:1.
5) Lysis is determined by flow cytometry.
6) Steps 1-5 are repeated, or performed in parallel, with ipilimumab used instead of the tested antibody molecule in step 3.
7) The results of the lysis for the tested antibody molecule are compared to the results of the lysis for ipilimumab. An improved lysis for the tested antibody molecule compared to ipilimumab demonstrates that the tested antibody molecule has improved depleting effect on CTLA-4 positive cells, CD4 positive cells or Tregs, respectively, depending on which target cells were used.

In some embodiments, the improved depleting effect in step 7) above is a significantly improved depleting effect.

This assay is demonstrated in more detail below in Example 4, in combination with FIG. 12.

The in vivo test is based on the combined use of PBMC mice and NOG/SCID mice, which is herein called a PBMC-NOG/SCID model. Both PBMC mice and NOG/SCID mice are well-known models. The in vivo test in the PBMC-NOG/SCID model comprises the following consecutive nine steps:
1) Human PBMCs (peripheral blood mononuclear cells) are isolated, washed and resuspended in sterile PBS. In some embodiments, the PBMCs are resuspended in PBS at 75×10$^6$ cells/ml.
2) NOG mice are injected i.v. (intravenously) with an appropriate amount, such as 200 μl, of the cell suspension from step 1). If 200 μl are injected, this corresponds to 15×10$^6$ cells/mouse.
3) A suitable time, such as 2 weeks, after injection, the spleens from the NOG mice are isolated and rendered into a single cell suspension. Optionally, a small sample from the single cell suspension is taken to determine the expression of CTLA-4 on human T cells by FACS, in order to confirm the CTLA-4 expression.
4) The cell suspension from step 3) is resuspended in sterile PBS. In some embodiments, the cess suspension is resuspended in sterile PBS at 50×10$^6$ cells/ml. If the optional CTLA-4 expression determination is included in step 3, the rest of the cell suspension is then resuspended in step 4.
5) SCID mice are injected i.p. (intraperitoneally) with an appropriate amount, such as 200 μl, of the suspension from step 4. If 200 μl are injected, this corresponds to 10×10$^6$ cells/mouse.
6) A suitable time, such as 1 hour, after the injection in step 5) the SCID mice are treated with an appropriate amount, such as 10 mg/kg, of either the antibody molecule to be tested, ipilimumab or an isotype control monoclonal antibody.
7) The intraperitoneal fluid of the treated SCID mice is collected a suitable time, such as 24 hours, after the treatment in step 6).
8) Human T cell subsets are identified and quantified by FACS using following markers: CD45, CD4, CD8, CD25 and/or CD127.
9) The results from identification and quantification of the T cell subsets from the mice treated with the tested antibody molecule is compared to the results from identification and quantification of the T cell subsets from the mice treated with ipilimumab and to the results from identification and quantification of the T cell subsets from the mice treated with isotype control monoclonal antibody. A lower number of CTLA-4 positive cells in the intraperitoneal fluid from mice treated with the antibody molecule to be tested compared to the number of CTLA-4 positive cells in the intraperitoneal fluid from mice treated with ipilimumab demonstrates that the antibody molecule has improved depleting effect on CTLA-4 positive cells compared to ipilimumab. A lower number of CD4 positive cells in the intraperitoneal fluid from mice treated with the antibody molecule to be tested compared to the number of CD4 positive cells in the intraperitoneal fluid from mice treated with ipilimumab demonstrates that the antibody molecule has improved depleting effect on CD4 positive cells compared to ipilimumab. A lower number of Tregs in the intraperitoneal fluid from mice treated with the antibody molecule to be tested compared to the number of Tregs in the intraperitoneal fluid from mice treated with ipilimumab demonstrates that the antibody molecule has improved depleting effect on Tregs compared to ipilimumab.

In this in vivo test, it is in some embodiments of most interest to look at the Treg depletion in step 7.

This assay is demonstrated in more detail below in Example 4, in combination with FIG. 14.

Treg depletion may also be assessed in an antibody-dependent cellular phagocytosis (ADCP) assay, as known to the skilled person.

In some embodiments, the antibody molecules have similar blocking effect on CTLA-4 interactions with B7.1 and B7.2 ligands compared to Yervoy. This may be assessed by ELISA (as shown in FIG. 10) or in a more functional assay where anti-CTLA-4 antibodies enhance the IL-2 production by T cells in response to stimulation of PBMCs with SEB.

In some embodiments, the anti-CTLA-4 antibody molecule is a human antibody molecule.

In some embodiments, the anti-CTLA-4 antibody molecule is a humanized antibody molecule.

In some embodiments, the anti-CTLA-4 antibody molecule is an antibody molecule of human origin, meaning that it originates from a human antibody molecule which then has been modified.

In some embodiments, the anti-CTLA-4 antibody molecule is a human IgG1 antibody.

In some embodiments, the anti-CTLA-4 antibody is an antibody in the form of a human IgG1 antibody showing improved binding to one or several activatory Fc receptors and/or being engineered for improved binding to one or several activatory Fc receptors; accordingly, in some embodiments, the anti-CTLA-4 antibody is an Fc-engineered human IgG1 antibody.

In some embodiments, the anti-CTLA-4 antibody is a murine or a humanized murine IgG2a antibody.

In some embodiments, the anti-CTLA-4 antibody is a murine antibody that is cross-reactive with human CTLA-4.

In some embodiments, the anti-CTLA-4 antibody is a monoclonal antibody.

In some embodiments, the anti-CTLA-4 antibody is a polyclonal antibody.

In some embodiments, the anti-CTLA-4 antibody molecule is an antibody molecule comprising one of the three alternative VH-CDR1 sequences, one of the three alternative VH-CDR2 sequences, one of the two alternative VH-CDR3 sequences, one of the two VL-CDR1 sequences, one of the two VL-CDR2 sequences, and/or one of the two alternative VL-CDR3 sequences presented in Table 1 below.

In some embodiments, the anti-CTLA-4 antibody molecule is selected from the group consisting of antibody molecules comprising 1-6 of the CDRs selected from the group consisting of SEQ ID. Nos: 3, 6, 8, 10, 12 and 14.

In some embodiments, the anti-CTLA-4 antibody molecule is selected from the group consisting of antibody molecules comprising the CDRs having SEQ ID. Nos: 3, 6, 8, 10, 12 and 14.

In some embodiments, the anti-CTLA-4 antibody molecule is selected from the group consisting of antibody molecules comprising 1-6 of the CDRs, VH-CDR1, VH-CDR2, VH-CDR3, VL-CDR1, and VL-CDR3,
wherein VH-CDR1, if present, is selected from the group consisting of SEQ ID. Nos: 15, 22, 29 and 35;
wherein VH-CDR2, if present, is selected from the group consisting of SEQ ID. Nos: 16, 23, 30, and 36;
wherein VH-CDR3, if present, is selected from the group consisting of SEQ ID. Nos: 17, 24, 31 and 37;
wherein VL-CDR1, if present, is selected from the group consisting of SEQ ID. Nos: 10 and 38;
wherein VL-CDR2, if present, is selected from the group consisting of SEQ ID. Nos: 18, 25, 32 and 39;
wherein VL-CDR3, if present, is selected from the group consisting of SEQ ID. Nos: 19, 26 and 40.

In some embodiments, the anti-CTLA-4 antibody molecule is an antibody molecule selected from the group consisting of antibody molecules comprising 6 CDRs selected from the group consisting of:
SEQ ID. NOs: 15, 16, 17, 10, 18 and 19;
SEQ ID. NOs: 22, 23, 24, 10, 25 and 26;
SEQ ID. NOs: 29, 30, 31, 10, 32 and 26; and
SEQ ID. NOs: 35, 36, 37, 38, 39 and 40.

In some embodiments, the anti-CTLA-4 antibody molecule is an antibody molecule comprising the 6 CDRs having SEQ ID. NOs: 15, 16, 17, 10, 18 and 19.

In some embodiments, the anti-CTLA-4 antibody molecule is an antibody molecule comprising the 6 CDRs having SEQ ID. NOs: 22, 23, 24, 10, 25 and 26.

In some embodiments, the anti-CTLA-4 antibody molecule is an antibody molecule selected from the group consisting of antibody molecules comprising a VH selected from the group consisting of SEQ ID. NOs: 20, 27, 33 and 41.

In some embodiments, the anti-CTLA-4 antibody molecule is an antibody molecule selected from the group consisting of antibody molecules comprising a VL selected from the group consisting of SEQ ID. NOs: 21, 28, 34 and 42.

In some embodiments, the anti-CTLA-4 antibody molecule is an antibody molecule selected from the group consisting of antibody molecules comprising a VH and a VL selected from the group consisting of: SEQ ID. Nos: 20-21, 27-28, 33-34 and 41-42.

In some embodiments, the anti-CTLA-4 antibody molecule comprises a VH having sequence SEQ ID. No: 20 and a VL having sequence SEQ ID. No: 21.

In some embodiments, the anti-CTLA-4 antibody molecule comprises a VH having sequence SEQ ID. No: 27 and a VL having sequence SEQ ID. No: 28.

TABLE 1

General CDR sequences of antibodies disclosed herein

| Relevant part of antibody | Sequence | Explanation of unidentified amino acid residues | SEQ. ID. NO |
|---|---|---|---|
| VH-CDR1 alternative 1 | $FX_1X_2YX_3MX_4WX_5R\ QAPG$ | $X_1$ = S or K; $X_2$ = D, S or A; $X_3$ = Y, S or A; $X_4$ = S or N; and $X_5$ = V or I | 1 |
| VH-CDR1 alternative 2 | $FSX_1YX_2MX_3WVRQ\ APG$ | $X_1$ = D or S; $X_2$ = Y, S or A; and $X_3$ = S or N | 2 |
| VH-CDR3 alternative 3 | $FSX_1YX_2MX_3WVRQ\ APG$ | $X_1$ = D or S; $X_2$ = Y or S; and $X_3$ = S or N | 3 |
| VH-CDR2, alternative 1 | $SX_1ISX_2X_3X_4X_5X_6X_7X_8X_9ADSVKGR$ | $X_1$ = G or A; $X_2$ = W, G or N; $X_3$ = S or T; $X_4$ = S or G; | 4 |

TABLE 1-continued

General CDR sequences of antibodies disclosed herein

| Relevant part of antibody | Sequence | Explanation of unidentified amino acid residues | SEQ. ID. NO |
|---|---|---|---|
| | | $X_5$ = R or G; $X_6$ = D, S or Y; $X_7$ = K, T or I; $X_8$ = G, Y, H or D; $X_9$ = Y or F | |
| VH-CDR2, alternative 2 | $SX_1ISX_2X_3X_4X_5X_6X_7X_8YADSVKGR$ | $X_1$ = G or A; $X_2$ = T, G or N; $X_3$ = S or T; $X_4$ = S or G; $X_5$ = R or G; $X_6$ = D, S or Y; $X_7$ = K, T or I; $X_8$ = G, Y, H or D | 5 |
| VH-CDR2, alternative 3 | $SX_1ISX_2X_3X_4X_5X_6X_7\ YADSVKGR$ | $X_1$ = G or A; $X_2$ = W or G; $X_3$ = S or G; $X_4$ = R or G; $X_5$ = D or S; $X_6$ = K or T; $X_7$ = G or Y, H or D | 6 |
| VH-CDR3 alternative 1 | $X_1X_2X_3X_4X_5X_6X_7X_8X_9X_{10}X_{11}X_{12}X_{13}X_{14}X_{15}$ | $X_1$ = T or A; $X_2$ = T or R; $X_3$ = D, Y or L; $X_4$ = L, R, S, or G; $X_5$ = A, V, S or Y; $X_6$ = R, E, G or S; $X_7$ = Y, M, L or G; $X_8$ = N, H, Y or none; $X_9$ = Q, D or none; $X_{10}$ = W, A, D or none; $X_{11}$ = L, F, R or none; $X_{12}$ = A, D, G or none; $X_{13}$ = D, I, M or none; $X_{14}$ = D or none; and $X_{15}$ = V or none | 7 |
| VH-CDR3 alternative 2 | $X1X_2DX_3X_4X_5X_6X_7X_8X_9X_{10}X_{11}X_{12}X_{13}$ | $X_1$ = T or A; $X_2$ = T or R;; $X_3$ = L or R; $X_4$ = A or V; $X_5$ = R or E; $X_6$ = Y or M; $X_7$ = N or none; $X_8$ = Q or none; $X_9$ = W or none; $X_{10}$ = L, or none; $X_{11}$ = A, or none; $X_{12}$ = D or none | 8 |
| VL-CDR1 alternative 1 | $CX_1GSSSNIGX_2X_3YX_4X_5X_6$ | $X_1$ = T or S; $X_2$ = A or S; $X_3$ = G or N; $X_4$ = D or V; $X_5$ = V or Y; $X_6$ = H or none | 9 |
| VL-CDR1 alternative 2 | CTGSSSNIGAGYDVH | | 10 |
| VL-CDR2 alternative 1 | $X_1NX_2X_3RPS$ | $X_1$ = G, R, or D; $X_2$ = D, N, or S; and $X_3$ = N, Q or K | 11 |
| VL-CDR2 alternative 2 | $X_1NX_2X_3RPS$ | $X_1$ = G or R; $X_2$ = D or N; and $X_3$ = N or Q | 12 |
| VL-CDR3 alternative 1 | $CX_1X_2X_3DX_4SLX_5G\ X_6VX_7$ | $X_1$ = A or Q; $X_2$ = V, A or S; $X_3$ = W or Y; $X_4$ = D or S; | 13 |

TABLE 1-continued

General CDR sequences of antibodies disclosed herein

| Relevant part of antibody | Sequence | Explanation of unidentified amino acid residues | SEQ. ID. NO |
|---|---|---|---|
| | | $X_5$ = N or S; $X_6$ = V, W or P; and $X_7$ = V or none | |
| VL-CDR3 alternative 2 | CAX$_1$WDDSLNG X$_2$V | $X_1$ = V or A; and $X_2$ = V or W | 14 |

TABLE 2

Specific anti-CTLA-4 antibody molecules; the CDR sequences are marked in bold in the full VH and VL sequences

| Antibody clone | Region | Sequence | SEQ. ID. NO: |
|---|---|---|---|
| 4-E03 | VH-CDR1 | FSDYYMSWVR QAPG | 15 |
| | VH-CDR2 | SGISWSSRDK GYADSVKGR | 16 |
| | VH-CDR3 | TTDLARY | 17 |
| | VL-CDR1 | CTGSSSNIGA GYDVH | 10 |
| | VL-CDR2 | GNDNRPS | 18 |
| | VL-CDR3 | CAVWDDSLNG VV | 19 |
| | VH | EVQLLESGGG LVQPGGSLRL SCAASGFTFS DYYMSWVRQA PGKGLEWVSG ISWSSRDKGY ADSVKGRFTI SRDNSKNTLY LQMNSLRAED TAVYYCTTDL ARYWGQGTLV TVSS | 20 |
| | VL | QSVLTQPPSA SGTPGQRVTI SCTGSSSNIG AGYDVHWYQQ LPGTAPKLLI YGNDNRPSGV PDRFSGSKSG TSASLAISGL RSEDEADYYC AVWDDSLNGV VFGGGTKLTV LG | 21 |
| | human immune_ globulin G1 (IgG1) light chain (LC) | MGWSCIILFLVATATGVHSQSVLTQPPSASGTPGQRVTISCTG SSSNIGAGYDVHWYQQLPGTAPKLLIYGNDNRPSGVPDRFSGS KSGTSASLAISGLRSEDEADYYCAVWDDSLNGVVFGGGTKLTV LGQPKAAPSVTLFPPSSEELQANKATLVCLISDFYPGAVTVAW KADSSPVKAGVETTTPSKQSNNKYAASSYLSLTPEQWKSHRSY SCQVTHEGSTVEKTVAPTECS | 53 |
| | human IgG1 heavy chain (HC) | MGWSCIILFLVATATGVHSEVQLLESGGGLVQPGGSLRLSCAA SGFTFSDYYMSWVRQAPGKGLEWVSGISWSSRDKGYADSVKGR FTISRDNSKNTLYLQMNSLRAEDTAVYYCTTDLARYWGQGTLV TVSSASTKGPSVFPLAPSSKSTSGGTAALGCLVKDYFPEPVTV SWNSGALTSGVHTFPAVLQSSGLYSLSSVVTVPSSSLGTQTYI CNVNHKPSNTKVDKKVEPKSCDKTHTCPPCPAPELLGGPSVFL FPPKPKDTLMISRTPEVTCVVVDVSHEDPEVKFNWYVDGVEVH NAKTKPREEQYNSTYRVVSVLTVLHQDWLNGKEYKCKVSNKAL PAPIEKTISKAKGQPREPQVYTLPPSRDELTKNQVSLTCLVKG FYPSDIAVEWESNGQPENNYKTTPPVLDSDGSFFLYSKLTVDK SRWQQGNVFSCSVMHEALHNHYTQKSLSLSPGK | 54 |
| 5-B07 | VH-CDR1 | FSSYSMNWVRQ APG | 22 |
| | VH-CDR2 | SAISGSGGST YYADSVKGR | 23 |
| | VH-CDR3 | ARDRVEMNQW LAD | 24 |
| | VL-CDR1 | CTGSSSNIGA GYDVH | 10 |
| | VL-CDR2 | RNNQRPS | 25 |
| | VL-CDR3 | CAAWDDSLNG WV | 26 |
| | VH | EVQLLESGGG LVQPGGSLRL SCAASGFTFS SYSMNWVRQA PGKGLEWVSA ISGSGGSTYY ADSVKGRFTI SRDNSKNTLY LQMNSLRAED TAVYYCARDR VEMNQWLADW GQGTLVTVSS | 27 |
| | VL | QSVLTQPPSA SGTPGQRVTI SCTGSSSNIG AGYDVHWYQQ LPGTAPKLLI YRNNQRPSGV PDRFSGSKSG TSASLAISGL RSEDEADYYC AAWDDSLNGW VFGGGTKLTV LG | 28 |
| | murine immuno- globulin (IgG2a) light chain (LC) | MGWSCIILFLVATATGVHSQSVLTQPPSASGTPGQRVTISCTG SSSNIGAGYDVHWYQQLPGTAPKLLIYRNNQRPSGVPDRFSGS KSGTSASLAISGLRSEDEADYYCAAWDDSLNGWVFGGGTKLTV LGQPKSSPSVTLFPPSSEELETNKATLVCTITDFYPGVVTVDW KVDGTPVTQGMETTQPSKQSNNKYMASSYLTLTARAWERHSSY SCQVTHEGHTVEKSLSRADCS | 62 |
| | murine immuno- globulin (IgG2a) heavy chain (HC) | MGWSCIILFLVATATGVHSEVQLLESGGGLVQPGGSLRLSCAA SGFTFSSYSMNWVRQAPGKGLEWVSAISGSGGSTYYADSVKGR FTISRDNSKNTLYLQMNSLRAEDTAVYYCARDRVEMNQWLADW GQGTLVTVSSAKTTAPSVYPLAPVCGDTTGSSVTLGCLVKGYF PEPVTLTWNSGSLSSGVHTFPAVLQSDLYTLSSSVTVTSSTWP SQSITCNVAHPASSTKVDKKIEPRGPTIKPCPPCKCPAPNLLG GPSVFIFPPKIKDVLMISLSPIVTCVVVDSEDDPDVQISWFV NNVEVHTAQTQTHREDYNSTLRVVSALPIQHQDWMSGKEFKCK | 63 |

TABLE 2-continued

Specific anti-CTLA-4 antibody molecules; the CDR sequences are marked in bold in the full VH and VL sequences

| Antibody clone | Region | Sequence | SEQ. ID. NO: |
|---|---|---|---|
| | | VNNKDLPAPIERTISKPKGSVRAPQVYVLPPPEEEMTKKQVTL TCMVTDFMPEDIYVEWTNNGKTELNYKNTEPVLDSDGSYFMYS KLRVEKKNWVERNSYSCSVVHEGLHNHHTTKSFSRTPGK | |
| 2-006 | VH-CDR1 | FSSYAMSWVRQ APG | 29 |
| | VH-CDR2 | SGISGSGGYI HYADSVKGR | 30 |
| | VH-CDR3 | ATYSSGLHDA FDI | 31 |
| | VL-CDR1 | CTGSSSNIGA GYDVH | 10 |
| | VL-CDR2 | DNNKRPS | 32 |
| | VL-CDR3 | CAAWDDSLNG WV | 26 |
| | VH | EVQLLESGGG LVQPGGSLRL SCAASGTFS SYAMSWVRQA PGKGLEWVSG ISGSGGYIHY ADSVKGRFTI SRDNSKNTLY LQMNSLRAED TAVYYCATYS SGLHDAFDIW GQGTLVTVSS | 33 |
| | VL | QSVLTQPPSA SGTPGQRVTI SCTGSSSNIG AGYDVHWYQQ LPGTAPKLLI YDNNKRPSGV PDRFSGSKSG TSASLAISGL RSEDEADYYC AAWDDSLNGW VFGGGTKLTV LG | 34 |
| 2-F09 | VH-CDR1 | FKAYSMSWIR QAPG | 35 |
| | VH-CDR2 | SGISNTGGST DFADSVKGR | 36 |
| | VH-CDR3 | ARLGYSGYDD RGMDV | 37 |
| | VL-CDR1 | CSGSSSNIGS NYVY | 38 |
| | VL-CDR2 | GNSNRPS | 39 |
| | VL-CDR3 | CQSYDSSLSG PVV | 40 |
| | VH | EVQLLESGGG LVQPGGSLRL SCAASGTFK AYSMSWIRQA PGKGLEWVSG ISNTGGSTDF ADSVKGRPTI SRDNSKNTLY LQMNSLRAED TAMYYCARLG YSGYDDRGMD VWGQGTLVTV SS | 41 |
| | VL | QSVLTQPPSA SGTPGQRVTI SCSGSSSNIG SNYVYWYQQL PGTAPKLLIY GNSNRPSGVP DRFSGSKSGT SASLAISGLR SEDEADYYCQ SYDSSLSGPV VFGGGTKLTV LG | 42 |

In some embodiments, the anti-CTLA-4 antibody molecules described herein may also comprise one or both of the constant regions presented in Table 3 below.

TABLE 3

Sequences of constant regions of antibodies disclosed herein

| Region | Sequence | SEQ. ID. NO: |
|---|---|---|
| CH | ASTKGPSVFPLAPSSKSTSGGTAALGCLVKDYF PEPVTVSWNSGALTSGVHTFPAVLQSSGLYSLS SVVTVPSSSLGTQTYICNVNHKPSNTKVDKKVE PKSCDKTHTCPPCPAPELLGGPSVFLFPPKPKD TLMISRTPEVTCVVVDVSHEDPEVKFNWYVDGV EVHNAKTKPREEQYNSTYRVVSVLTVLHQDWLN GKEYKCKVSNKALPAPIEKTISKAKGQPREPQV | 43 |

TABLE 3-continued

Sequences of constant regions of antibodies disclosed herein

| Region | Sequence | SEQ. ID. NO: |
|---|---|---|
| | YTLPPSRDELTKNQVSLTCLVKGFYPSDIAVEW ESNGQPENNYKTTPPVLDSDGSFFLYSKLTVDK SRWQQGNVFSCSVMHEALHNHYTQKSLSLSPGK | |
| CL | QPKAAPSVTLFPPSSEELQANKATLVCLISDFY PGAVTVAWKADSSPVKAGVETTTPSKQSNNKYA ASSYLSLTPEQWKSHRSYSCQVTHEGSTVEKTV APTECS | 44 |

In some embodiments, the anti-CTLA-4 antibody molecule is a molecule encoded by one of the nucleotide sequences presented in Table 4 below.

TABLE 4

Specific nucleotide sequences encoding anti-CTLA-4 antibody molecules

| Clone | Encoding | Sequence | SEQ. ID. NO: |
|---|---|---|---|
| 4-E03 γ1 heavy chain | 4-E03 VH | GAGGTGCAGCTGTTGGAGTCTGGGGGAGGCTTGGTACAG CCTGGGGGGTCCCTGAGACTCTCCTGTGCAGCCTCTGGA TTCACCTTCAGTGACTACTACATGAGCTGGGTCCGCCAG GCTCCCGGGAAGGGGCTGGAGTGGGTCTCAGGCATTAGT TGGAGTAGTCGTGACAAAGGCTATGCGGACTCTGTGAAG GGCCGTTTCACCATCTCCAGAGACAATTCCAAGAACACG CTGTATCTGCAAATGAACAGCCTGAGAGCCGAGGACACT GCCGTGTATTACTGTACCACAGATCTCGCTAGGTACTGG GGCCAGGGTACACTGGTCACCGTGAGCTCAGCCTCCACC AAGGGCCCATCGGTCTTCCCCCTGGCACCCTCCTCCAAG AGCACCTCTGGGGGCACAGCGGCCCTGGGCTGCCTGGTC AAGGACTACTTCCCCGAACCGGTGACGGTGTCGTGGAAC | 45 |

TABLE 4-continued

Specific nucleotide sequences encoding anti-CTLA-4 antibody molecules

| Clone | | Encoding Sequence | SEQ. ID. NO: |
|---|---|---|---|
| | | TCAGGCGCCCTGACCAGCGGCGTGCACACCTTCCCGGCT<br>GTCCTACAGTCCTCAGGACTCTACTCCCTCAGCAGCGTG<br>GTGACCGTGCCCTCCAGCAGCTTGGGCACCCAGACCTAC<br>ATCTGCAACGTGAATCACAAGCCCAGCAACACCAAGGTG<br>GACAAGAAAGTTGAGCCCAAATCTTGTGACAAAACTCAC<br>ACATGCCCACCGTGCCCAGCACCTGAACTCCTGGGGGGA<br>CCGTCAGTCTTCCTCTTCCCCCCAAAACCCAAGGACACC<br>CTCATGATCTCCCGGACCCCTGAGGTCACATGCGTGGTG<br>GTGGACGTGAGCCACGAAGACCCTGAGGTCAAGTTCAAC<br>TGGTACGTGGACGGCGTGGAGGTGCATAATGCCAAGACA<br>AAGCCGCGGGAGGAGCAGTACAACAGCACGTACCGTGTG<br>GTCAGCGTCCTCACCGTCCTGCACCAGGACTGGCTGAAT<br>GGCAAGGAGTACAAGTGCAAGGTCTCCAACAAAGCCCTC<br>CCAGCCCCCATCGAGAAAACCATCTCCAAAGCCAAAGGG<br>CAGCCCCGAGAACCACAGGTGTACACCCTGCCCCCATCC<br>CGGGATGAGCTGACCAAGAACCAGGTCAGCCTGACCTGC<br>CTGGTCAAAGGCTTCTATCCCAGCGACATCGCCGTGGAG<br>TGGGAGAGCAATGGGCAGCCGGAGAACAACTACAAGACC<br>ACGCCTCCCGTGCTGGACTCCGACGGCTCCTTCTTCCTC<br>TACAGCAAGCTCACCGTGGACAAGAGCAGGTGGCAGCAG<br>GGGAACGTCTTCTCATGCTCCGTGATGCATGAGGCTCTG<br>CACAACCACTACACGCAGAAGAGCCTCTCCCTGTCTCCG<br>GGTAAATGA | |
| 4-E03 λ<br>light chain | 4-E03<br>VL | CAGTCTGTGCTGACTCAGCCACCCTCAGCGTCTGGGACC<br>CCCGGGCAGAGGGTCACCATCTCCTGCACTGGGAGCAGC<br>TCCAACATCGGGGCAGGTTATGATGTACACTGGTATCAG<br>CAGCTCCCAGGAACGGCCCCCAAACTCCTCATCTATGGT<br>AATGATAACCGGCCCTCAGGGGTCCCTGACCGATTCTCT<br>GGCTCCAAGTCTGGCACCTCAGCCTCCCTGGCCATCAGT<br>GGGCTCCGGTCCGAGGATGAGGCTGATTATTACTGTGCA<br>GTATGGGATGACAGCCTGAATGGTGTGGTATTCGGCGGA<br>GGAACCAAGCTGACGGTCCTAGGTCAGCCCAAGGCTGCC<br>CCCTCGGTCACTCTGTTCCCGCCCTCCTCTGAGGAGCTT<br>CAAGCCAACAAGGCCACACTGGTGTGTCTCATAAGTGAC<br>TTCTACCCGGGAGCCGTGACAGTGGCCTGGAAGGCAGAT<br>AGCAGCCCCGTCAAGGCGGGAGTGGAGACCACCACACCC<br>TCCAAACAAAGCAACAACAAGTACGCGGCCAGCAGCTAT<br>CTGAGCCTGACGCCTGAGCAGTGGAAGTCCCACAGAAGC<br>TACAGCTGCCAGGTCACGCATGAAGGGAGCACCGTGGAG<br>AAGACAGTGGCCCCTACAGAATGTTCATGA | 46 |
| 5-B07 γ1<br>heavy chain | 5-B07<br>VH | GAGGTGCAGCTGTTGGAGTCTGGGGGAGGCTTGGTACAG<br>CCTGGGGGGTCCCTGAGACTCTCCTGTGCAGCCTCTGGA<br>TTCACCTTCAGTAGCTATAGCATGAACTGGGTCCGCCAG<br>GCTCCAGGGAAGGGGCTGGAGTGGGTCTCAGCTATTAGT<br>GGTAGTGGTGGTAGCACATACTACGCAGACTCCGTGAAG<br>GGCCGGTTCACCATCTCCAGAGACAATTCCAAGAACACG<br>CTGTATCTGCAAATGAACAGCCTGAGAGCCGAGGACACT<br>GCCGTGTATTACTGTGCGAGAGATCGGGTAGAGATGAAC<br>CAGTGGCTGGCCGACTGGGGCCAGGGTACACTGGTCACC<br>GTGAGCTCAGCCTCCACCAAGGGCCCATCGGTCTTCCCC<br>CTGGCACCCTCCTCCAAGAGCACCTCTGGGGGCACAGCG<br>GCCCTGGGCTGCCTGGTCAAGGACTACTTCCCCGAACCG<br>GTGACGGTGTCGTGGAACTCAGGCGCCCTGACCAGCGGC<br>GTGCACACCTTCCCGGCTGTCCTACAGTCCTCAGGACTC<br>TACTCCCTCAGCAGCGTGGTGACCGTGCCCTCCAGCAGC<br>TTGGGCACCCAGACCTACATCTGCAACGTGAATCACAAG<br>CCCAGCAACACCAAGGTGGACAAGAAAGTTGAGCCCAAA<br>TCTTGTGACAAAACTCACACATGCCCACCGTGCCCAGCA<br>CCTGAACTCCTGGGGGGACCGTCAGTCTTCCTCTTCCCC<br>CCAAAACCCAAGGACACCCTCATGATCTCCCGGACCCCT<br>GAGGTCACATGCGTGGTGGTGGACGTGAGCCACGAAGAC<br>CCTGAGGTCAAGTTCAACTGGTACGTGGACGGCGTGGAG<br>GTGCATAATGCCAAGACAAAGCCGCGGGAGGAGCAGTAC<br>AACAGCACGTACCGTGTGGTCAGCGTCCTCACCGTCCTG<br>CACCAGGACTGGCTGAATGGCAAGGAGTACAAGTGCAAG<br>GTCTCCAACAAAGCCCTCCCAGCCCCCATCGAGAAAACC<br>ATCTCCAAAGCCAAAGGGCAGCCCCGAGAACCACAGGTG<br>TACACCCTGCCCCCATCCCGGGATGAGCTGACCAAGAAC<br>CAGGTCAGCCTGACCTGCCTGGTCAAAGGCTTCTATCCC<br>AGCGACATCGCCGTGGAGTGGGAGAGCAATGGGCAGCCG<br>GAGAACAACTACAAGACCACGCCTCCCGTGCTGGACTCC | 47 |

TABLE 4-continued

Specific nucleotide sequences encoding anti-CTLA-4 antibody molecules

| Clone | Encoding | Sequence | SEQ. ID. NO: |
|---|---|---|---|
| | | GACGGCTCCTTCTTCCTCTACAGCAAGCTCACCGTGGAC<br>AAGAGCAGGTGGCAGCAGGGGAACGTCTTCTCATGCTCC<br>GTGATGCATGAGGCTCTGCACAACCACTACACGCAGAAG<br>AGCCTCTCCCTGTCTCCGGGTAAATGA | |
| 5-B07 λ<br>light chain | 5-B07<br>VL | CAGTCTGTGCTGACTCAGCCACCCTCAGCGTCTGGGACC<br>CCCGGGCAGAGGGTCACCATCTCCTGCACTGGGAGCAGC<br>TCCAACATCGGGGCAGGTTATGATGTACACTGGTATCAG<br>CAGCTCCCAGGAACGGCCCCCAAACTCCTCATCTATAGG<br>AATAATCAGCGGCCCTCAGGGGTCCCTGACCGATTCTCT<br>GGCTCCAAGTCTGGCACCTCAGCCTCCCTGGCCATCAGT<br>GGGCTCCGGTCCGAGGATGAGGCTGATTATTACTGTGCA<br>GCATGGGATGACAGCCTGAATGGTTGGGTGTTCGGCGGA<br>GGAACCAAGCTGACGGTCCTAGGTCAGCCCAAGGCTGCC<br>CCCTCGGTCACTCTGTTCCCGCCCTCCTCTGAGGAGCTT<br>CAAGCCAACAAGGCCACACTGGTGTGTCTCATAAGTGAC<br>TTCTACCCGGGAGCCGTGACAGTGGCCTGGAAGGCAGAT<br>AGCAGCCCCGTCAAGGCGGAGTGGAGACCACCACACCC<br>TCCAAACAAAGCAACAACAAGTACGCGGCCAGCAGCTAT<br>CTGAGCCTGACGCCTGAGCAGTGGAAGTCCCACAGAAGC<br>TACAGCTGCCAGGTCACGCATGAAGGGAGCACCGTGGAG<br>AAGACAGTGGCCCCTACAGAATGTTCATGA | 48 |
| 2-C06 γ1<br>heavy chain | 2-C06<br>VH | GAGGTGCAGCTGTTGGAGTCTGGGGGAGGCTTGGTACAG<br>CCTGGGGGGTCCCTGAGACTCTCCTGTGCAGCCTCTGGA<br>TTCACCTTTAGCAGCTATGCCATGAGCTGGGTCCGCCAG<br>GCTCCAGGGAAGGGGCTGGAGTGGGTCTCAGGTATTAGT<br>GGCAGCGGTGGGTACATACACTATGCAGACTCCGTGAAG<br>GGCCGGTTCACCATCTCCAGAGACAATTCCAAGAACACG<br>CTGTATCTGCAAATGAACAGCCTGAGAGCCGAGGACACT<br>GCCGTGTATTACTGTGCGACCTATAGCAGTGGCCTGCAT<br>GATGCTTTTGATATCTGGGGCCAGGGTACACTGGTCACC<br>GTGAGCTCAGCCTCCACCAAGGGCCCATCGGTCTTCCCC<br>CTGGCACCCTCCTCCAAGAGCACCTCTGGGGGCACAGCG<br>GCCCTGGGCTGCCTGGTCAAGGACTACTTCCCCGAACCG<br>GTGACGGTGTCGTGGAACTCAGGCGCCCTGACCAGCGGC<br>GTGCACACCTTCCCGGCTGTCCTACAGTCCTCAGGACTC<br>TACTCCCTCAGCAGCGTGGTGACCGTGCCCTCCAGCAGC<br>TTGGGCACCCAGACCTACATCTGCAACGTGAATCACAAG<br>CCCAGCAACACCAAGGTGGACAAGAAAGTTGAGCCCAAA<br>TCTTGTGACAAAACTCACACATGCCCACCGTGCCCAGCA<br>CCTGAACTCCTGGGGGGACCGTCAGTCTTCCTCTTCCCC<br>CCAAAACCCAAGGACACCCTCATGATCTCCCGGACCCCT<br>GAGGTCACATGCGTGGTGGTGGACGTGAGCCACGAAGAC<br>CCTGAGGTCAAGTTCAACTGGTACGTGGACGGCGTGGAG<br>GTGCATAATGCCAAGACAAAGCCGCGGGAGGAGCAGTAC<br>AACAGCACGTACCGTGTGGTCAGCGTCCTCACCGTCCTG<br>CACCAGGACTGGCTGAATGGCAAGGAGTACAAGTGCAAG<br>GTCTCCAACAAAGCCCTCCCAGCCCCCATCGAGAAAACC<br>ATCTCCAAAGCCAAAGGGCAGCCCCGAGAACCACAGGTG<br>TACACCCTGCCCCCATCCCGGGATGAGCTGACCAAGAAC<br>CAGGTCAGCCTGACCTGCCTGGTCAAAGGCTTCTATCCC<br>AGCGACATCGCCGTGGAGTGGGAGAGCAATGGGCAGCCG<br>GAGAACAACTACAAGACCACGCCTCCCGTGCTGGACTCC<br>GACGGCTCCTTCTTCCTCTACAGCAAGCTCACCGTGGAC<br>AAGAGCAGGTGGCAGCAGGGGAACGTCTTCTCATGCTCC<br>GTGATGCATGAGGCTCTGCACAACCACTACACGCAGAAG<br>AGCCTCTCCCTGTCTCCGGGTAAATGA | 49 |
| 2-C06 λ<br>light chain | 2-C06<br>VL | CAGTCTGTGCTGACTCAGCCACCCTCAGCGTCTGGGACC<br>CCCGGGCAGAGGGTCACCATCTCCTGCACTGGGAGCAGC<br>TCCAACATCGGGGCAGGTTATGATGTACACTGGTATCAG<br>CAGCTCCCAGGAACGGCCCCCAAACTCCTCATCTATGAC<br>AATAATAAGCGACCCTCAGGGGTCCCTGACCGATTCTCT<br>GGCTCCAAGTCTGGCACCTCAGCCTCCCTGGCCATCAGT<br>GGGCTCCGGTCCGAGGATGAGGCTGATTATTACTGTGCA<br>GCATGGGATGACAGCCTGAATGGTTGGGTGTTCGGCGGA<br>GGAACCAAGCTGACGGTCCTAGGTCAGCCCAAGGCTGCC<br>CCCTCGGTCACTCTGTTCCCGCCCTCCTCTGAGGAGCTT<br>CAAGCCAACAAGGCCACACTGGTGTGTCTCATAAGTGAC<br>TTCTACCCGGGAGCCGTGACAGTGGCCTGGAAGGCAGAT<br>AGCAGCCCCGTCAAGGCGGAGTGGAGACCACCACACCC<br>TCCAAACAAAGCAACAACAAGTACGCGGCCAGCAGCTAT<br>CTGAGCCTGACGCCTGAGCAGTGGAAGTCCCACAGAAGC<br>TACAGCTGCCAGGTCACGCATGAAGGGAGCACCGTGGAG<br>AAGACAGTGGCCCCTACAGAATGTTCATGA | 50 |

TABLE 4-continued

Specific nucleotide sequences encoding anti-CTLA-4 antibody molecules

| Clone | | Encoding Sequence | SEQ. ID. NO: |
|---|---|---|---|
| 2-F09 γ1 heavy chain | 2-F09 VH | GAGGTGCAGCTGTTGGAGTCTGGGGGAGGCTTGGTACAG CCTGGGGGGTCCCTGAGACTCTCCTGTGCAGCCTCTGGA TTCACCTTCAAAGCCTATAGCATGAGCTGGATCCGCCAG GCTCCAGGGAAGGGGCTGGAGTGGGTCTCAGGTATCAGT AACACGGGAGGTAGCACAGACTTCGCAGACTCCGTGAAG GGCCGGTTCACCATCTCCAGAGACAATTCCAAGAACACG CTGTATCTGCAAATGAACAGCCTGAGAGCCGAGGACACT GCCATGTATTACTGTGCGAGATTGGGATATAGTGGCTAC GACGACCGTGGTATGGACGTCTGGGGCCAAGGTACACTG GTCACCGTGAGCTCAGCCTCCACCAAGGGCCCATCGGTC TTCCCCCTGGCACCCTCCTCCAAGAGCACCTCTGGGGGC ACAGCGGCCCTGGGCTGCCTGGTCAAGGACTACTTCCCC GAACCGGTGACGGTGTCGTGGAACTCAGGCGCCCTGACC AGCGGCGTGCACACCTTCCCGGCTGTCCTACAGTCCTCA GGACTCTACTCCCTCAGCAGCGTGGTGACCGTGCCCTCC AGCAGCTTGGGCACCCAGACCTACATCTGCAACGTGAAT CACAAGCCCAGCAACACCAAGGTGGACAAGAAAGTTGAG CCCAAATCTTGTGACAAAACTCACACATGCCCACCGTGC CCAGCACCTGAACTCCTGGGGGGACCGTCAGTCTTCCTC TTCCCCCCAAAACCCAAGGACACCCTCATGATCTCCCGG ACCCCTGAGGTCACATGCGTGGTGGTGGACGTGAGCCAC GAAGACCCTGAGGTCAAGTTCAACTGGTACGTGGACGGC GTGGAGGTGCATAATGCCAAGACAAAGCCGCGGGAGGAG CAGTACAACAGCACGTACCGTGTGGTCAGCGTCCTCACC GTCCTGCACCAGGACTGGCTGAATGGCAAGGAGTACAAG TGCAAGGTCTCCAACAAAGCCCTCCCAGCCCCCATCGAG AAAACCATCTCCAAAGCCAAAGGGCAGCCCCGAGAACCA CAGGTGTACACCCTGCCCCCATCCCGGGATGAGCTGACC AAGAACCAGGTCAGCCTGACCTGCCTGGTCAAAGGCTTC TATCCCAGCGACATCGCCGTGGAGTGGGAGAGCAATGGG CAGCCGGAGAACAACTACAAGACCACGCCTCCCGTGCTG GACTCCGACGGCTCCTTCTTCCTCTACAGCAAGCTCACC GTGGACAAGAGCAGGTGGCAGCAGGGGAACGTCTTCTCA TGCTCCGTGATGCATGAGGCTCTGCACAACCACTACACG CAGAAGAGCCTCTCCCTGTCTCCGGGTAAATGA | 51 |
| 2-F09 λ light chain | 2-F09 VL | CAGTCTGTGCTGACTCAGCCACCCTCAGCGTCTGGGACC CCCGGGCAGAGGGTCACCATCTCTTGTTCTGGAAGCAGC TCCAACATCGGAAGTAATTATGTGTACTGGTATCAGCAG CTCCCAGGAACGGCCCCCAAACTCCTCATCTATGGTAAC AGCAATCGGCCCTCAGGGGTCCCTGACCGATTCTCTGGC TCCAAGTCTGGCACCTCAGCCTCCCTGGCCATCAGTGGG CTCCGGTCCGAGGATGAGGCTGATTATTACTGCCAGTCC TATGACAGCAGCCTGAGTGGTCCTGTGGTATTCGGCGGA GGAACCAAGCTGACGGTCCTAGGTCAGCCCAAGGCTGCC CCCTCGGTCACTCTGTTCCCGCCCTCCTCTGAGGAGCTT CAAGCCAACAAGGCCACACTGGTGTGTCTCATAAGTGAC TTCTACCCGGGAGCCGTGACAGTGGCCTGGAAGGCAGAT AGCAGCCCCGTCAAGGCGGGAGTGGAGACCACCACACCC TCCAAACAAAGCAACAACAAGTACGCGGCCAGCAGCTAT CTGAGCCTGACGCCTGAGCAGTGGAAGTCCCACAGAAGC TACAGCTGCCAGGTCACGCATGAAGGGAGCACCGTGGAG AAGACAGTGGCCCCTACAGAATGTTCATGA | 52 |

In some embodiments, it is advantageous that the antibody molecule binds both to human CTLA-4 (hCTLA-4) and to cynomolgus monkey CTLA-4 (cmCTLA-4 or cyno CTLA-4). Cross-reactivity with CTLA-4 expressed on cells in cynomolgus monkey, also called crab-eating macaque or *Macaca fascicularis*, may be advantageous since this enables testing of the antibody molecule in monkey without having to use a surrogate antibody, which particular focus on tolerability.

In some embodiments, it is advantageous that the antibody molecule binds both to human CTLA-4 (hCTLA-4) and to murine CTLA-4 (mCTLA-4). This may be advantageous since this enables testing of the antibody molecule in mice, with particular focus on effect and pharmacodynamics, without having to use a surrogate antibody.

In some embodiments, the antibody molecule binds to all three hCTLA-4, cmCTLA-4 and mCTLA-4.

In some embodiments, it is necessary to use a surrogate antibody to test an antibody molecule's functional activity in relevant in vivo models in mice. To ensure the comparability between the antibody molecule's effect in humans and the in vivo results for the surrogate antibody in mice, it is essential to select a functionally equivalent surrogate antibody having the same in vitro characteristics as the human antibody molecule.

In some embodiments, the antibody molecule does not bind human CD28.

It would be known to the person skilled in medicine, that medicines can be modified with different additives, for example to change the rate in which the medicine is absorbed by the body; and can be modified in different forms, for example to allow for a particular administration route to the body.

Accordingly, we include that the antibody molecules, nucleotide sequences, plasmids, viruses and/or cells described herein may be combined with a pharmaceutically acceptable excipient, carrier, diluent, vehicle and/or adjuvant into a pharmaceutical composition. In this context, the term pharmaceutical composition can be used interchangeably with the terms pharmaceutical preparation, pharmaceutical formulation, therapeutic composition, therapeutic preparation, therapeutic formulation and therapeutic entity.

The pharmaceutical compositions described herein may comprise, or in some embodiments consist of, antibody molecules, nucleotide sequences, plasmids, viruses or cells.

The pharmaceutical compositions described herein may in some embodiments consist of or comprise plasmids comprising nucleotide sequences encoding the above described antibody molecules or comprising the above described nucleotide sequences.

In some embodiments, the pharmaceutical compositions may comprise nucleotide sequences encoding parts of or a complete antibody molecule described herein integrated in a cell or viral genome or in a viriome. The pharmaceutical composition may then comprise a cell or a virus as a delivery vehicle for an antibody of the invention (or a delivery vehicle for a nucleotide sequence encoding an antibody of the invention). For example, in an embodiment, the virus may be in the form of a therapeutic oncolytic virus comprising nucleotide sequences encoding at least one of the antibody molecules described herein. In some embodiments, such an oncolytic virus comprises nucleotide sequences encoding a full-length human IgG antibody. In some embodiments, such an oncolytic virus comprises nucleotide sequences encoding an scFv, Fab or F(ab')$_2$ antibody molecule.

As described in the accompanying claims, in an embodiment the invention relates to a virus comprising a nucleotide sequence of the invention or a plasmid of the invention. Preferably, the virus is an oncolytic virus, such as a therapeutic oncolytic virus. As used herein, the term "oncolytic" refers to the capacity of a virus of selectively replicating in dividing cells (e.g. a proliferative cell such as a cancer cell) with the aim of slowing the growth and/or lysing said dividing cell, either in vitro or in vivo, while showing no or minimal replication in non-dividing (e.g. normal or healthy) cells. "Replication" (or any form of replication such as "replicate" and "replicating", etc.) means duplication of a virus that can occur at the level of nucleic acid or, preferably, at the level of infectious viral particle. Such an oncolytic virus can be obtained from any member of virus identified at present time. It may be a native virus that is naturally oncolytic or may be engineered by modifying one or more viral genes so-as to increase tumour selectivity and/or preferential replication in dividing cells, such as those involved in DNA replication, nucleic acid metabolism, host tropism, surface attachment, virulence, lysis and spread (see for example Wong et al., 2010, Viruses 2: 78-106). One may also envisage placing one or more viral gene(s) under the control of event or tissue-specific regulatory elements (e.g. promoter). Exemplary oncolytic viruses include without limitation reovirus, Seneca Valley virus (SW), vesicular stomatitis virus (VSV), Newcastle disease virus (NDV), herpes simplex virus (HSV), morbillivirus, adenovirus, poxvirus, retrovirus, measles virus, foamy virus, alpha virus, lentivirus, influenza virus, Sinbis virus, myxoma virus, rhabdovirus, picornavirus, coxsackievirus, parvovirus or the like. Such viruses are known to those skilled in the arts of medicine and virology.

In some embodiments, such an oncolytic virus is obtained from a herpes virus. The Herpesviridae are a large family of DNA viruses that all share a common structure and are composed of relatively large double-stranded, linear DNA genomes encoding 100-200 genes encapsidated within an icosahedral capsid which is enveloped in a lipid bilayer membrane. Although the oncolytic herpes virus can be derived from different types of HSV, particularly preferred are HSV1 and HSV2. The herpes virus may be genetically modified so-as to restrict viral replication in tumours or reduce its cytotoxicity in non-dividing cells. For example, any viral gene involved in nucleic acid metabolism may be inactivated, such as thymidine kinase (Martuza et al., 1991, Science 252: 854-6), ribonucleotide reductase (RR) (Mineta et al., 1994, Cancer Res. 54: 3363-66), or uracil-N-glycosylase (Pyles et al., 1994, J. Virol. 68: 4963-72). Another aspect involves viral mutants with defects in the function of genes encoding virulence factors such as the ICP34.5 gene (Chambers et al., 1995, Proc. Natl. Acad. Sci. USA 92: 1411-5). Representative examples of oncolytic herpes virus include NV1020 (e.g. Geevarghese et al., 2010, Hum. Gene Ther. 21(9): 1119-28) and T-VEC (Harrington et al., 2015, Expert Rev. Anticancer Ther. 15(12):1389-1403).

In some embodiments, such an oncolytic virus is obtained from an adenovirus. Methods are available in the art to engineer oncolytic adenoviruses. An advantageous strategy includes the replacement of viral promoters with tumour-selective promoters or modifications of the E1 adenoviral gene product(s) to inactivate its/their binding function with p53 or retinoblastoma (Rb) protein that are altered in tumour cells. In the natural context, the adenovirus E1B55 kDa gene cooperates with another adenoviral product to inactivate p53 (p53 is frequently dysregulated in cancer cells), thus preventing apoptosis. Representative examples of oncolytic adenoviruses include ONYX-015 (e.g. Khuri et al., 2000, Nat. Med 6(8): 879-85) and H101 also named Oncorine (Xia et al., 2004, Ai Zheng 23(12): 1666-70).

In some embodiments, such an oncolytic virus is a poxvirus. As used herein the term "poxvirus" refers to a virus belonging to the Poxviridae family, with a specific preference for a poxvirus belonging to the Chordopoxviridae subfamily and more preferably to the Orthopoxvirus genus. Vaccinia virus, cowpox virus, canarypox virus, ectromelia virus, myxoma virus are particularly appropriate in the context of the invention. Genomic sequences of such poxviruses are available in the art and specialized databases (e.g. Genbank under accession number NC_006998, NC_003663 or AF482758.2, NC_005309, NC_004105, NC_001132 respectively).

In specific and preferred embodiments, such an oncolytic poxvirus is an oncolytic vaccinia virus. Vaccinia viruses are members of the poxvirus family characterized by a 200 kb double-stranded DNA genome that encodes numerous viral enzymes and factors that enable the virus to replicate independently from the host cell machinery. The majority of vaccinia virus particles is intracellular (IMV for intracellular mature virion) with a single lipid envelop and remains in the cytosol of infected cells until lysis. The other infectious form is a double enveloped particle (EEV for extracellular enveloped virion) that buds out from the infected cell without lysing it. Although it can derive from any vaccinia virus strain, Elstree, Wyeth, Copenhagen, Lister and Western Reserve strains are particularly preferred. The gene nomenclature used herein is that of Copenhagen vaccinia strain unless otherwise indicated. However, correspondence between Copenhagen and other vaccinia strains are generally available in the literature.

Preferably, such an oncolytic vaccinia virus is modified by altering one or more viral gene(s). Said modification(s) preferably lead(s) to the absence of synthesis or the synthesis of a defective viral protein unable to ensure the activity of the protein produced under normal conditions by the unmodified gene. Exemplary modifications are disclosed in the literature with the goal of altering viral genes involved in DNA metabolism, host virulence, IFN pathway (e.g. Guse et al., 2011, Expert Opinion Biol. Ther. 11(5): 595-608) and the like. Modifications for altering a viral locus encompass deletion, mutation and/or substitution of one or more nucleotide(s) (contiguous or not) within the viral gene or its regulatory elements. Modification(s) can be made by a number of ways known to those skilled in the art using conventional recombinant techniques.

More preferably, such an oncolytic vaccinia virus is modified by altering the thymidine kinase-encoding gene (locus J2R). The thymidine kinase (TK) enzyme is involved in the synthesis of deoxyribonucleotides. TK is needed for viral replication in normal cells as these cells have generally low concentration of nucleotides whereas it is dispensable in dividing cells which contain high nucleotide concentration.

Alternatively to or in combination, such an oncolytic vaccinia virus is modified by altering at least one gene or both genes encoding ribonucleotide reductase (RR). In the natural context, this enzyme catalyses the reduction of ribonucleotides to deoxyribonucleotides that represents a crucial step in DNA biosynthesis. The viral enzyme is similar in subunit structure to the mammalian enzyme, being composed of two heterologous subunits, designed R1 and R2 encoded respectively by the I4L and F4L locus. In the context of the invention, either the I4L gene (encoding the R1 large subunit) or the F4L gene (encoding the R2 small subunit) or both may be inactivated (e.g. as described in WO2009/065546 and Foloppe et al., 2008, Gene Ther., 15: 1361-71). Sequences for the J2R, I4L and F4L genes and their locations in the genome of various poxviruses are available in public databases.

In some embodiments, such an oncolytic virus comprises nucleotide sequences encoding amino acid sequence having at least 80% identity with a sequence set out in table 2 above. In some embodiments, such an oncolytic virus comprises an amino acid sequence having at least 85% identity with a sequence set out in table 2 above. In some embodiments, such an oncolytic virus comprises an amino acid sequence having at least 90% identity with a sequence set out in table 2 above. In some embodiments, such an oncolytic virus comprises an amino acid sequence having at least 95% identity with a sequence set out in table 2 above.

In some embodiments, such an oncolytic virus comprises nucleotide sequences encoding SEQ. ID. NO: 20 and ID. NO: 21. In some embodiments, such an oncolytic virus comprises nucleotide sequences encoding SEQ. ID. NO: 27 and ID. NO: 28. In some embodiments, such a oncolytic virus comprises nucleotide sequences encoding SEQ. ID. NO: 33 and ID. NO: 34. In some embodiments, such a oncolytic virus comprises nucleotide sequences encoding SEQ. ID. NO: 41 and ID. NO: 42.

In some embodiments, such an oncolytic virus comprises nucleotide sequences having at least 80% identity with a sequence set out in table 4 above. In some embodiments, such an oncolytic virus comprises nucleotide sequences having at least 85% identity with a sequence set out in table 4 above. In some embodiments, such an oncolytic virus comprises nucleotide sequences having at least 90% identity with a sequence set out in table 4 above. In some embodiments, such an oncolytic virus comprises nucleotide sequences having at least 95% identity with a sequence set out in table 4 above.

In some embodiments, such a oncolytic virus comprises SEQ. ID. NO: 45 and 46. In some embodiments, such a oncolytic virus comprises SEQ. ID. NO: 47 and 48. In some embodiments, such a oncolytic virus comprises SEQ. ID. NO: 49 and 50. In some embodiments, such a oncolytic virus comprises SEQ. ID. NO: 51 and 52.

Some oncolytic viruses have capacity to host large enough DNA insertions to accommodate integration of full-length human antibody sequences. Attenuated Vaccinia viruses and Herpes Simplex Viruses are examples of therapeutic oncolytic viruses whose genome is sufficiently large to permit integration of full-length IgG antibody sequences (Chan, W. M. et al 2014 Annu Rev Virol 1(1): 119-141; Bommareddy, P. K., et al. 2018 Nat Rev Immunol 18(8): 498-513). Full-length IgG antibodies have successfully been integrated into oncolytic Vaccinia virus, resulting in expression and extracellular release (production) of full-length IgG antibodies upon infection of virus-susceptible host cells e.g. cancer cells (Kleinpeter, P., et al. 2016, Oncoimmunology 5(10): e1220467). Adenoviruses can also be engineered to encode full-length IgG antibodies that are functionally produced and secreted upon cellular infection (Marino, N., et al. 2017 J Clin Invest 123(6): 2447-2463).

In a preferred embodiment, such an oncolytic virus is a poxvirus (e.g. a vaccinia virus) defective for TK activity (resulting from alteration of the J2R locus) or defective for both TK and RR activities (resulting from alteration of both the J2R locus and at least one of the RR-encoding I4L and/or F4L locus) and comprising (a) nucleotide sequences encoding SEQ. ID. NO: 20 and ID. NO: 21 or (b) nucleotide sequences encoding SEQ. ID. NO: 27 and ID. NO: 28 or (c) nucleotide sequences encoding SEQ. ID. NO: 33 and ID. NO: 34 or (d) nucleotide sequences encoding SEQ. ID. NO: 41 and ID. NO: 42.

When appropriate, it may be advantageous that the nucleotide sequence(s) inserted in the oncolytic virus described herein include(s) additional regulatory elements to facilitate expression, trafficking and biological activity. For example, a signal peptide may be included for facilitating secretion outside the producer cell (e.g. infected cell). The signal peptide is typically inserted at the N-terminus of the encoded polypeptide immediately after the Met initiator. The choice of signal peptides is wide and is accessible to persons skilled in the art. For example, signal peptides originating from another immunoglobin (e.g. a heavy chain IgG) can be used in the context of the invention to allow secretion of the anti-CTLA4 antibody described herein outside the producer cell. For illustrative purposes, one may refer to SEQ ID NO: 53 and SEQ ID NO:54 comprising the light chain and the heavy chain of the 4-E03 antibody described herein equipped with IgG-originating peptide signals.

A particularly preferred oncolytic virus is a vaccinia virus (e.g. Copenhagen strain) defective for both TK and RR activities (resulting from alteration of both the J2R locus and the I4L loci) and comprising nucleotide sequences encoding SEQ. ID. NO: 20 and SEQ ID. NO: 21 or SEQ. ID. NO: 53 and SEQ ID. NO: 54.

In some embodiments, such an oncolytic virus may further comprise additional nucleotide sequence(s) of therapeutic interest such as nucleotide sequence(s) encoding immunomodulatory polypeptide(s) (i.e. a polypeptide involved in stimulating an immune response either directly or indirectly). Representative examples of suitable immunomodulatory polypeptides include, without any limitation, cytokines and chemokines with a specific preference for granulocyte macrophage colony stimulating factor (GM-CSF) and particularly human, non-human primate or murine GM-CSF. The additional nucleotide sequence may be easily obtained by standard molecular biology techniques (e.g. PCR amplification, cDNA cloning, chemical synthesis) using sequence data accessible in the art and the information provided herein. A particularly preferred oncolytic virus is a vaccinia virus (e.g. Copenhagen strain) defective for both TK and RR activities (resulting from alteration of both the J2R locus and the I4L loci) and comprising nucleotide sequences encoding SEQ. ID. NO: 20 and ID. NO: 21 or SEQ. ID. NO: 53 and SEQ ID. NO: 54 and a nucleotide sequence encoding a GM-CSF, with a specific preference for a human GM-CSF (e.g. having SEQ ID NO: 55 or SEQ ID NO: 56) or a murine GM-CSF (e.g. having SEQ ID NO: 57 or SEQ ID NO: 58).

In addition, the nucleotide sequences to be inserted in such an oncolytic virus can be optimized for providing high level expression in a particular host cell or subject by modifying one or more codon(s). Further to optimization of the codon usage, various modifications may also be envisaged so as to prevent clustering of rare, non-optimal codons being present in concentrated areas and/or to suppress or modify "negative" sequence elements which are expected to negatively influence expression levels. Such negative sequence elements include without limitation the regions having very high (>80%) or very low (<30%) GC content; AT-rich or GC-rich sequence stretches; unstable direct or inverted repeat sequences; R A secondary structures; and/or internal cryptic regulatory elements such as internal TATA-boxes, chi-sites, ribosome entry sites, and/or splicing donor/acceptor sites.

In some embodiments, the nucleotide sequence(s) are placed under the control of suitable regulatory elements for their proper expression in a host cell or subject. As used herein, the term "regulatory elements" refers to any element that allows, contributes or modulates the expression of the encoding nucleotide sequence(s) in a given host cell or subject, including their replication, duplication, transcription, splicing, translation, stability and/or transport in or outside the expressing cell. It will be appreciated by those skilled in the art that the choice of the regulatory elements can depend on such factors as the nucleotide sequence itself, the virus into which it is inserted, the host cell or subject, the level of expression desired, etc. The promoter is of special importance. In the context of the invention, it can be constitutive directing expression of the nucleotide sequence that it controls in many types of host cells or specific to certain host cells or regulated in response to specific events or exogenous factors (e.g. by temperature, nutrient additive, hormone, etc.) or according to the phase of a viral cycle (e.g. late or early). Promoters adapted to virus-mediated expression are known in the art. Representative examples for expression by an oncolytic poxvirus include without limitation the vaccinia p7.5K, pH5.R, p11K7.5, TK, p28, p11, pB2R, pA35R, K1L and pSE/L promoters (Erbs et al., 2008, Cancer Gene Ther. 15(1): 18-28; Orubu et al. 2012, PloS One 7: e40167), early/late chimeric promoters and synthetic promoters (Chakrabarti et al., 1997, Biotechniques 23: 1094-7; Hammond et al, 1997, J. Virol Methods 66: 135-8; and Kumar and Boyle, 1990, Virology 179: 151-8). In preferred embodiments, the nucleotide sequences of the light and heavy chains of the antibody described herein are respectively placed under the control of promoters having the same transcriptional strength, and preferably under the control of the same promoter (e.g. p7.5K such as the one described in SEQ ID NO: 59 or pH5.R such as the one described in SEQ ID NO: 60) to obtain a similar level of expression for both chains and therefore an optimal assembly of the antibody as a hetero-tetrameric protein (i.e. to avoid excess of non-associated chain). The additional nucleotide sequence (e.g. encoding GM-CSF) can be placed under a different promoter (e.g. pSE/L such as the one described in SEQ ID NO: 61).

Insertion of the nucleotide sequence(s) (possibly equipped with appropriate regulatory elements) in genome of such an oncolytic virus is made by conventional means, either using appropriate restriction enzymes or, preferably by homologous recombination. The nucleotide sequence(s) can independently be inserted at any location of the viral genome. Various sites of insertion may be considered, e.g. in a non-essential viral gene, in an intergenic region, or in a non-coding portion of the genome of such an oncolytic virus. J2R locus and/or I4L locus is particularly appropriate for an oncolytic virus being a poxvirus (e.g. a oncolytic vaccinia virus). Upon insertion of the nucleotide sequence(s) into the viral genome, the viral locus at the insertion site may be deleted at least partially. In one embodiment, this deletion or partial deletion may result in suppressed expression of the viral gene product encoded by the entirely or partially deleted locus resulting in a defective virus for said virus function. A particularly preferred oncolytic virus is a TK and/or RR defective vaccinia virus comprising the cassette encoding the heavy chain inserted at the J2R locus and the cassette encoding the light chain inserted at the I4L locus. The cassette encoding the additional GM-CSF-encoding nucleotide sequence can be inserted in another location of the virus genome or in J2R or I4L locus, with a preference for insertion at the I4L locus.

The present invention also provides a method for generating such an oncolytic virus described herein, and particularly an oncolytic poxvirus, into a suitable host cell (producer cell). In some embodiments, such a method comprises one or more step(s) of homologous recombination between a virus genome and a transfer plasmid comprising the nucleotide sequence(s) to be inserted (possibly with regulatory elements) flanked in 5' and 3' with viral sequences respectively present upstream and downstream the insertion site. Said transfer plasmid can be generated and introduced into the host cell by routine techniques (e.g. by transfection). The virus genome can be introduced into the host cell by infection. The size of each flanking viral sequence may vary from at least 100 bp and at most 1500 bp on each side of the nucleotide sequence (preferably from 200 to 550 bp and more preferably from 250 to 500 bp). Homologous recombination permitting to generate such an oncolytic virus is preferably carried out in cultured cell lines (e.g. HeLa, Vero) or in chicken embryonic fibroblasts (CEF) cells obtained from embryonated eggs.

In some embodiments, the identification of the oncolytic virus having incorporated the anti-CTLA4 encoding nucleotide sequences and possibly the additional nucleotide sequence (e.g. GM-CSF) may be facilitated by the use of a selection and/or a detectable gene. In preferred embodiments, the transfer plasmid further comprises a selection marker with a specific preference for the GPT gene (encoding a guanine phosphoribosyl transferase) permitting growth in a selective medium (e.g. in the presence of mycophenolic acid, xanthine and hypoxanthine) or a detectable gene encoding a detectable gene product such as GFP, e-GFP or mCherry. In addition, the use of an endonuclease capable of providing a double-stranded break in said selection or detectable gene may also be considered. Said endonuclease may be in the form of a protein or expressed by an expression vector.

Once generated, such an oncolytic virus can be amplified into a suitable host cell using conventional techniques including culturing the transfected or infected host cell under suitable conditions so as to allow the production and recovery of infectious particles.

The present invention also relates to a method for producing the oncolytic virus described herein. Preferably said method comprises the steps of a) preparing a producer cell line, b) transfecting or infecting the prepared producer cell line with the oncolytic virus, c) culturing the transfected or infected producer cell line under suitable conditions so as to allow the production of the virus, d) recovering the produced virus from the culture of said producer cell line and optionally e) purifying said recovered virus.

In some embodiments, the producer cell is selected from the group consisting of mammalian (e.g. human or non-human) cells such as HeLa cells (e.g. ATCC-CRM-CCL-2™ or ATCC-CCL-2.2™), HER96, PER-C6 (Fallaux et al., 1998, Human Gene Ther. 9: 1909-17), hamster cell lines such as BHK-21 (ATCC CCL-10) etc. and avian cells such as those described in WO2005/042728, WO2006/108846, WO2008/129058, WO2010/130756, WO2012/001075 as well as a primary chicken embryo fibroblast (CEF) prepared from chicken embryos obtained from fertilized eggs. Producer cells are preferably cultured in an appropriate medium which can, if needed, be supplemented with serum and/or suitable growth factor(s) or not (e.g. a chemically defined medium preferably free from animal- or human-derived products). An appropriate medium may be easily selected by those skilled in the art depending on the producer cells. Such media are commercially available. Producer cells are preferably cultured at a temperature comprised between +30° C. and +38° C. (more preferably at approximately +37° C.) for between 1 and 8 days before infection. If needed, several passages of 1 to 8 days may be made in order to increase the total number of cells.

In step b), producer cells are infected by the oncolytic virus under appropriate conditions using an appropriate multiplicity of infection (MOI) to permit productive infection of producer cells. For illustrative purposes, an appropriate MOI ranges from $10^{-3}$ to 20, with a specific preference for a MOI comprises from 0.01 to 5 and more preferably 0.03 to 1. Infection step is carried out in a medium which may be the same as or different from the medium used for the culture of producer cells.

In step c), infected producer cells are then cultured under appropriate conditions well known to those skilled in the art until progeny virus particles is produced. Culture of infected producer cells is also preferably performed in a medium which may be the same as or different from the medium/media used for culture of producer cells and/or for infection step, at a temperature between +32° C. and +37° C., for 1 to 5 days.

In step d), the virus particles produced in step c) are collected from the culture supernatant and/or the producer cells. Recovery from producer cells may require a step allowing the disruption of the producer cell membrane to allow the liberation of the virus. The disruption of the producer cell membrane can be induced by various techniques well known to those skilled in the art, including but not limited to freeze/thaw, hypotonic lysis, sonication, microfluidization, high shear (also called high speed) homogenization or high-pressure homogenization.

The recovered oncolytic virus may be at least partially purified before being distributed in doses and used as described herein. A vast number of purification steps and methods is available in the art, including e.g. clarification, enzymatic treatment (e.g. endonuclease, protease, etc.), chromatographic and filtration steps. Appropriate methods are described in the art (see e.g. WO2007/147528; WO2008/138533, WO2009/100521, WO2010/130753, WO2013/022764).

In one embodiment, the present invention also provides a cell infected with the oncolytic virus described herein.

The invention also encompasses pharmaceutical compositions comprising a virus, such as an oncolytic virus, as discussed above, and a pharmaceutically acceptable diluent, vehicle and/or an adjuvant.

The pharmaceutical composition may in some embodiments be in the form of a CAR-T cell, carrying parts or the complete antibody sequences described herein as part of the sequence coding for its chimeric antigen T cell receptor.

The invention also encompasses pharmaceutical compositions comprising a CAR-T cell as discussed above and a pharmaceutically acceptable diluent, vehicle and/or an adjuvant.

The invention also comprises other therapeutic modalities, or "shapes" of drugs, such as antibody drug conjugates, fusion proteins etc, and pharmaceutical composition comprising such therapeutic modalities.

The antibody molecules, nucleotide sequences, plasmids, viruses, cells and/or pharmaceutical compositions described herein may be suitable for parenteral administration including aqueous and/or non-aqueous sterile injection solutions which may contain anti-oxidants, and/or buffers, and/or bacteriostats, and/or solutes which render the formulation isotonic with the blood of the intended recipient; and/or aqueous and/or non-aqueous sterile suspensions which may include suspending agents and/or thickening agents. The antibody molecules, nucleotide sequences, plasmids, cells and/or pharmaceutical compositions described herein may be presented in unit-dose or multi-dose containers, for example sealed ampoules and vials, and may be stored in a freeze-dried (i.e. lyophilised) condition requiring only the addition of the sterile liquid carrier, for example water for injections, immediately prior to use.

Extemporaneous injection solutions and suspensions may be prepared from sterile powders, and/or granules, and/or tablets of the kind previously described.

For parenteral administration to human patients, the daily dosage level of the anti-CTLA-4 antibody molecule will usually be from 1 mg/kg bodyweight of the patient to 20 mg/kg, or in some cases even up to 100 mg/kg administered in single or divided doses. Lower doses may be used in special circumstances, for example in combination with prolonged administration. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Typically, a pharmaceutical composition (or medicament) described herein comprising an antibody molecule will contain the anti-CTLA-4 antibody molecule at a concentration of between approximately 2 mg/ml and 150 mg/ml or between approximately 2 mg/ml and 200 mg/ml. In some embodiments, the pharmaceutical compositions will contain the anti-CTLA-4 antibody molecule at a concentration of 10 mg/ml.

Typically, a pharmaceutical composition (or medicament) will contain the oncolytic virus described herein at a concentration of between approximately $10^3$ to $10^{12}$ vp (viral particles), iu (infectious unit) or pfu (plaque-forming units) depending on the virus and quantitative technique. The quantity of pfu present in a sample can be determined by counting the number of plaques following infection of permissive cells (e.g. CEF or Vero cells) to obtain a plaque forming units (pfu) titer, the quantity of vp by measuring the A260 absorbance, and the quantity of iu by quantitative immunofluorescence, e.g. using anti-virus antibodies. As a general guidance, individual doses which are suitable for a pharmaceutical composition comprising an oncolytic poxvirus range from approximately $10^3$ to approximately $10^{10}$ pfu, advantageously from approximately $10^3$ pfu to approximately $10^9$ pfu, preferably from approximately $10^4$ pfu to approximately $10^8$ pfu; and more preferably from approximately $10^4$ pfu to approximately $10^7$ pfu.

Generally, in humans, oral or parenteral administration of the antibody molecules, nucleotide sequences, plasmids, viruses, cells and/or pharmaceutical compositions described herein is the preferred route, being the most convenient. For veterinary use, the antibody molecules, nucleotide sequences, plasmids, viruses, cells and/or pharmaceutical compositions described herein are administered as a suitably acceptable formulation in accordance with normal veterinary practice and the veterinary surgeon will determine the dosing regimen and route of administration which will be most appropriate for a particular animal. Thus, the present invention provides a pharmaceutical formulation comprising an amount of an antibody molecule, nucleotide sequences plasmid, virus and/or cell of the invention effective to treat various conditions (as described above and further below). Preferably, the antibody molecules, nucleotide sequences, plasmids, viruses, cells and/or pharmaceutical compositions described herein is adapted for delivery by a route selected from the group comprising: intravenous; intratumoral; intramuscular; subcutaneous. Administration can be in the form of a single injection or several repeated injections (e.g with the same or different doses, with the same or different routes, at the same or different sites of administration). For illustrative purposes, individual doses comprising approximately $10^4$, $5\times10^4$, $10^5$, $5\times10^5$, $10^6$, $5\times10^6$, $10^7$, $5\times10^7$, $10^8$, $5\times10^8$, $10^9$, $5\times10^9$ or $10^{10}$ pfu of an oncolytic poxvirus (e.g. the TK and RR-defective vaccinia virus described herein) are particularly suited for intratumoral administration.

The present invention also includes antibody molecules, nucleotide sequences, plasmids, viruses, cells and/or pharmaceutical compositions described herein comprising pharmaceutically acceptable acid or base addition salts of the polypeptide binding moieties of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others. Pharmaceutically acceptable base addition salts may also be used to produce pharmaceutically acceptable salt forms of the agents according to the present invention. The chemical bases that may be used as reagents to prepare pharmaceutically acceptable base salts of the present agents that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others. The antibody molecules, nucleotide sequences, plasmids, viruses and/or cells described herein may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. In one embodiment, the lyophilised (freeze dried) polypeptide binding moiety loses no more than about 20%, or no more than about 25%, or no more than about 30%, or no more than about 35%, or no more than about 40%, or no more than about 45%, or no more than about 50% of its activity (prior to lyophilisation) when re-hydrated.

In some embodiments, the viral composition is suitably buffered at a physiological or slightly basic pH (e.g. from approximately pH 7 to approximately pH 9 with a specific preference for a pH comprised between 7 and 8.5 and more particularly close to 8). It might be beneficial to also include in the viral composition a monovalent salt so as to ensure an appropriate osmotic pressure. Said monovalent salt may notably be selected from NaCl and KCl, preferably said monovalent salt is NaCl, preferably in a concentration of 10 to 500 mM (e.g 50 mM). A suitable viral composition comprises saccharose 50 g/L, NaCl 50 mM, Tris-HCl 10 mM and Sodium glutamate 10 mM, pH8. The composition may also be formulated so as to include a cryoprotectant for protecting the oncolytic virus at low storage temperature. Suitable cryoprotectants include without limitation sucrose (or saccharose), trehalose, maltose, lactose, mannitol, sorbitol and glycerol, preferably in a concentration of 0.5 to 20% (weight in g/volume in L, referred to as w/v) as well as high molecular weight polymers such as dextran or polyvinylpyrrolidone (PVP).

The anti-CTLA-4 antibody molecules, nucleotide sequences and pharmaceutical compositions described herein can be used use in the treatment of cancer in a subject.

We include that the subject could be mammalian or non-mammalian. Preferably, the mammalian subject is a human or is a non-mammalian, such as a horse, or a cow, or a sheep, or a pig, or a camel, or a dog, or a cat. Most preferably, the mammalian subject is a human.

By "exhibit", we include that the subject displays a cancer symptom and/or a cancer diagnostic marker, and/or the cancer symptom and/or a cancer diagnostic marker can be measured, and/or assessed, and/or quantified.

It would be readily apparent to the person skilled in medicine what the cancer symptoms and cancer diagnostic markers would be and how to measure and/or assess and/or quantify whether there is a reduction or increase in the severity of the cancer symptoms, or a reduction or increase in the cancer diagnostic markers; as well as how those cancer symptoms and/or cancer diagnostic markers could be used to form a prognosis for the cancer.

Cancer treatments are often administered as a course of treatment, which is to say that the therapeutic agent is administered over a period of time. The length of time of the course of treatment will depend on a number of factors, which could include the type of therapeutic agent being administered, the type of cancer being treated, the severity of the cancer being treated, and the age and health of the subject, amongst others reasons.

By "during the treatment", we include that the subject is currently receiving a course of treatment, and/or receiving a therapeutic agent, and/or receiving a course of a therapeutic agent.

In some embodiments the cancer to be treated in accordance with the present invention is a solid tumour.

In some embodiments, the cancer is selected from the group consisting of advanced solid tumour, melanoma and other malignant neoplasms of skin, synovial sarcoma, non-small cell lung cancer (NSCLC), small cell lung cancer (SCLC), bladder cancer, prostate cancer, mesothelioma, ovarian cancer, breast cancer, renal cell cancer, hepatocellular carcinoma, head and neck cancer, and colorectal cancer.

Each one of the above described cancers is well-known, and the symptoms and cancer diagnostic markers are well described, as are the therapeutic agents used to treat those cancers. Accordingly, the symptoms, cancer diagnostic markers, and therapeutic agents used to treat the above mentioned cancer types would be known to those skilled in medicine.

Clinical definitions of the diagnosis, prognosis and progression of a large number of cancers rely on certain classifications known as staging. Those staging systems act to collate a number of different cancer diagnostic markers and cancer symptoms to provide a summary of the diagnosis, and/or prognosis, and/or progression of the cancer. It would be known to the person skilled in oncology how to assess the diagnosis, and/or prognosis, and/or progression of the cancer using a staging system, and which cancer diagnostic markers and cancer symptoms should be used to do so.

By "cancer staging", we include the Rai staging, which includes stage 0, stage I, stage II, stage III and stage IV, and/or the Binet staging, which includes stage A, stage B and stage C, and/or the Ann Arbour staging, which includes stage I, stage II, stage III and stage IV.

It is known that cancer can cause abnormalities in the morphology of cells. These abnormalities often reproducibly occur in certain cancers, which means that examining these changes in morphology (otherwise known as histological examination) can be used in the diagnosis or prognosis of cancer. Techniques for visualizing samples to examine the morphology of cells, and preparing samples for visualization, are well known in the art; for example, light microscopy or confocal microscopy.

By "histological examination", we include the presence of small, mature lymphocyte, and/or the presence of small, mature lymphocytes with a narrow border of cytoplasm, the presence of small, mature lymphocytes with a dense nucleus lacking discernible nucleoli, and/or the presence of small, mature lymphocytes with a narrow border of cytoplasm, and with a dense nucleus lacking discernible nucleoli, and/or the presence of atypical cells, and/or cleaved cells, and/or prolymphocytes.

It is well known that cancer is a result of mutations in the DNA of the cell, which can lead to the cell avoiding cell death or uncontrollably proliferating. Therefore, examining these mutations (also known as cytogenetic examination) can be a useful tool for assessing the diagnosis and/or prognosis of a cancer. An example of this is the deletion of the chromosomal location 13q14.1 which is characteristic of chronic lymphocytic leukaemia. Techniques for examining mutations in cells are well known in the art; for example, fluorescence in situ hybridization (FISH).

By "cytogenetic examination", we include the examination of the DNA in a cell, and, in particular the chromosomes. Cytogenetic examination can be used to identify changes in DNA which may be associated with the presence of a refractory cancer and/or relapsed cancer. Such may include: deletions in the long arm of chromosome 13, and/or the deletion of chromosomal location 13q14.1, and/or trisomy of chromosome 12, and/or deletions in the long arm of chromosome 12, and/or deletions in the long arm of chromosome 11, and/or the deletion of 11q, and/or deletions in the long arm of chromosome 6, and/or the deletion of 6q, and/or deletions in the short arm of chromosome 17, and/or the deletion of 17p, and/or the t(11:14) translocation, and/or the (q13:q32) translocation, and/or antigen gene receptor rearrangements, and/or BCL2 rearrangements, and/or BCL6 rearrangements, and/or t(14:18) translocations, and/or t(11:14) translocations, and/or (q13:q32) translocations, and/or (3:v) translocations, and/or (8:14) translocations, and/or (8:v) translocations, and/or t(11:14) and (q13:q32) translocations.

It is known that subjects with cancer exhibit certain physical symptoms, which are often as a result of the burden of the cancer on the body. Those symptoms often reoccur in the same cancer, and so can be characteristic of the diagnosis, and/or prognosis, and/or progression of the disease. A person skilled in medicine would understand which physical symptoms are associated with which cancers, and how assessing those physical systems can correlate to the diagnosis, and/or prognosis, and/or progression of the disease. By "physical symptoms", we include hepatomegaly, and/or splenomegaly.

BRIEF DESCRIPTION OF THE DRAWINGS

In the examples below, reference is made to the following figures:

FIG. 1: Antibodies of the invention specifically bind CTLA-4
  The antibodies were shown by ELISA to bind to human and cynomolgous CTLA-4 but not human CD28 protein. Binding for 2-006 (FIG. 1A), 4-E-03 (FIG. 1B), 5-B07 (FIG. 1C) was compared to Yervoy (FIG. 1D).

FIG. 2: Dose-dependent binding of anti-CTLA-4 mAb to hCTLA-4-transfected cells
  Anti-CTLA-4 mAb (FIG. 2A-2D) show strong binding to CTLA-4-expressing 293T cells similar to Yervoy (FIG. 2E).

CD4+ T cells obtained from peripheral cynomologous blood were stimulated in vitro with CD3/CD28 dynabeads. Binding of anti-CTLA-4 mAb (solid lines, top row) was analysed by FACS and compared to Yervoy (dotted line, top row) and a commercial FACS antibody (bottom row).

Figure 6:
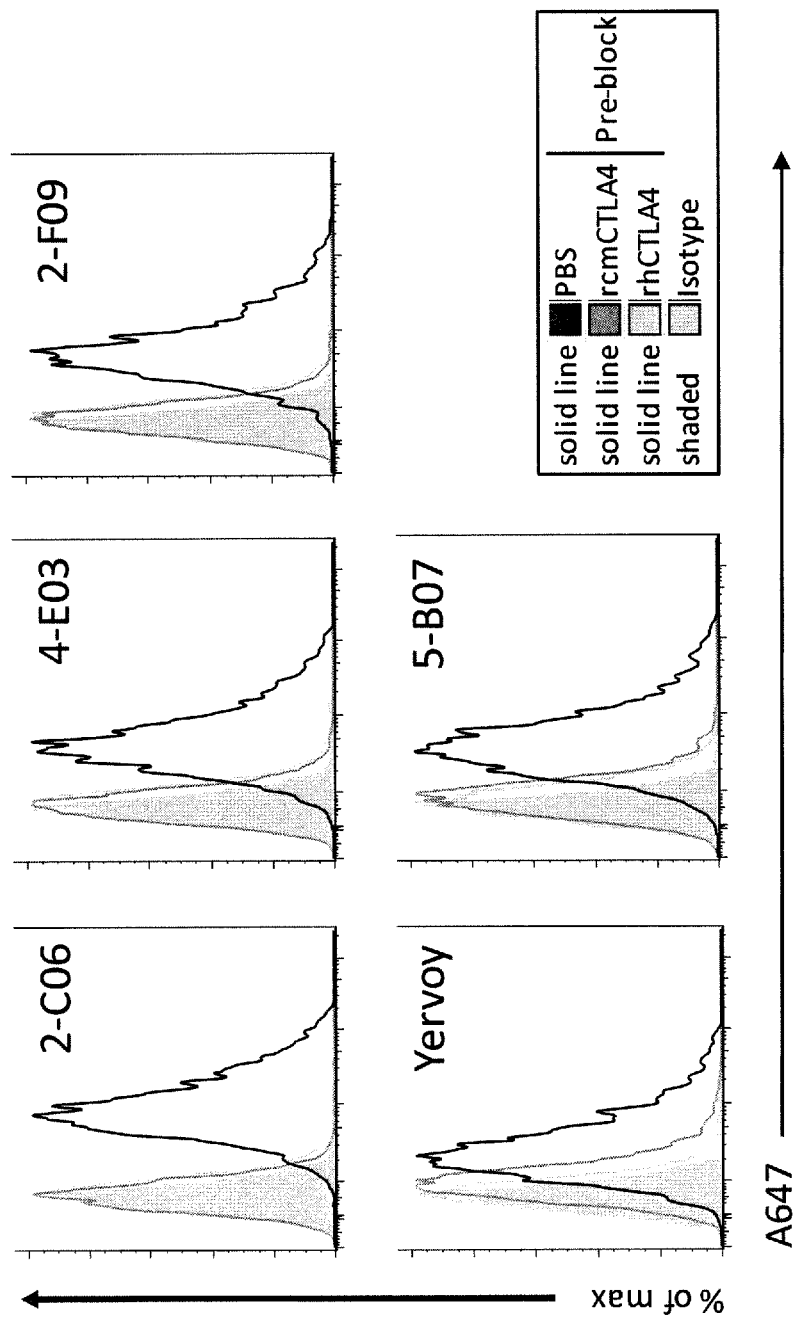

FIG. 6: Block of cell binding by human and cynomologous CTLA-4 protein

293T-CTLA-4 cells were stained with Alexa 647-labelled anti-CTLA-4 mAb (black line). Antibody binding was blocked by rhCTLA-4-Fc protein (light grey line) and rcmCTLA-4-Fc protein (dark grey line).

Figure 7:
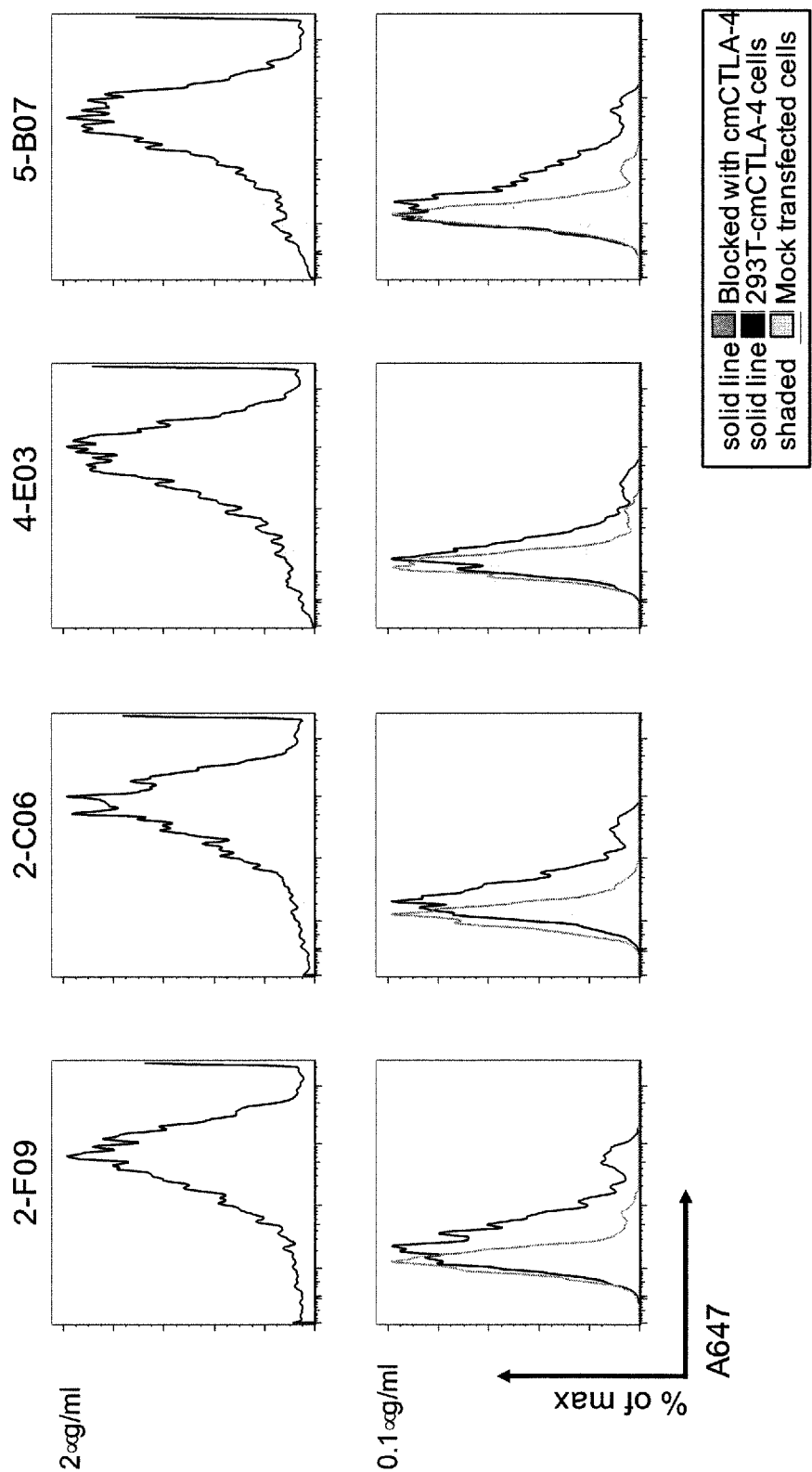

FIG. 7: Binding to 293T cells expressing cynomologous CTLA-4

293T cells were transiently transfected with cynomologous CTLA-4 and binding of anti-CTLA-4 mAb at different concentrations was analysed by FACS.

Figure 8:
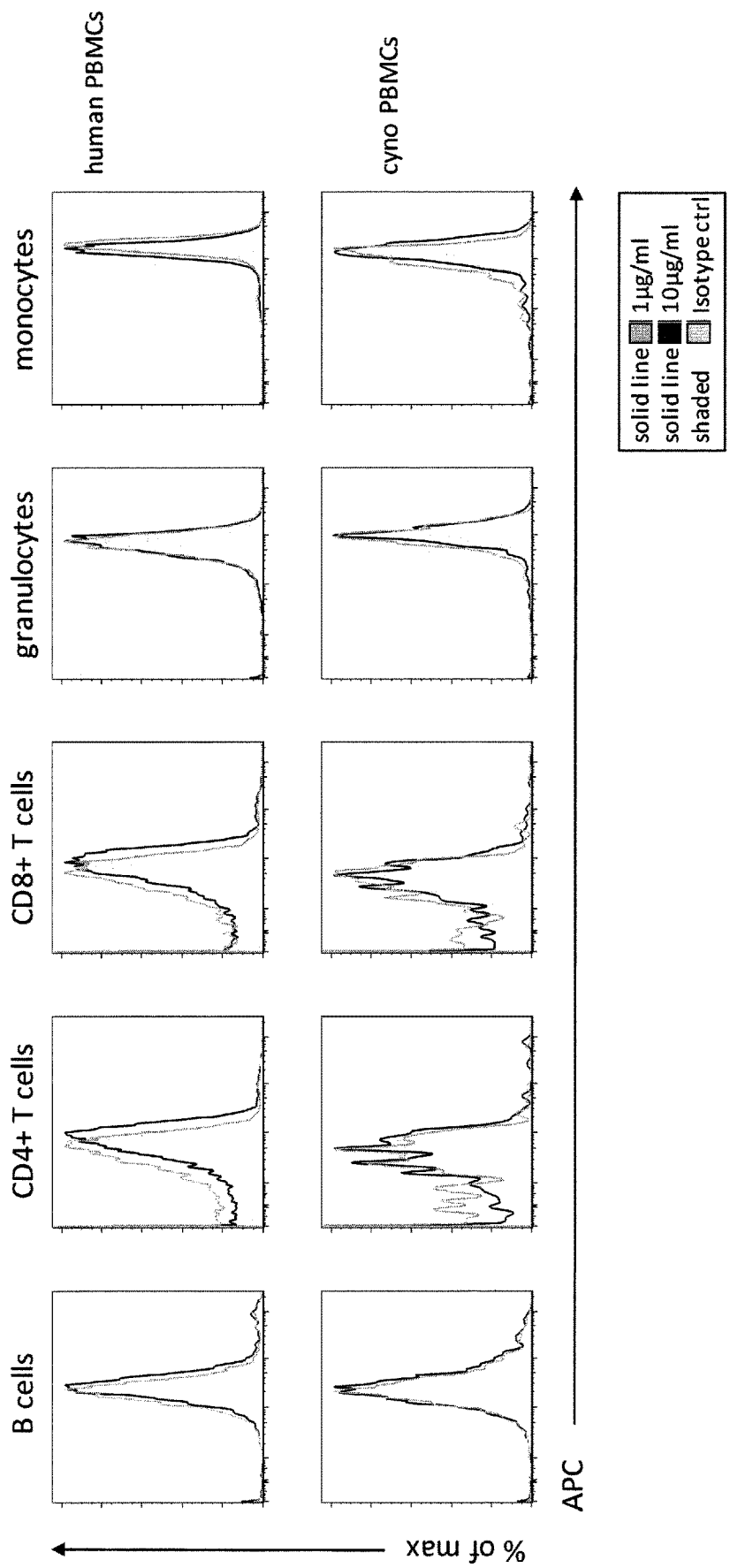

FIG. 8: Expected lack of binding to resting human/cynomologous PBMCs

4-E03—as well as 2-006, 5-B07 and 2-F09 (data not shown)—does not show any unspecific binding to different cell subsets in human (top row) and cynomologous (bottom row) PBMCs as analysed by FACS.

Figure 9:
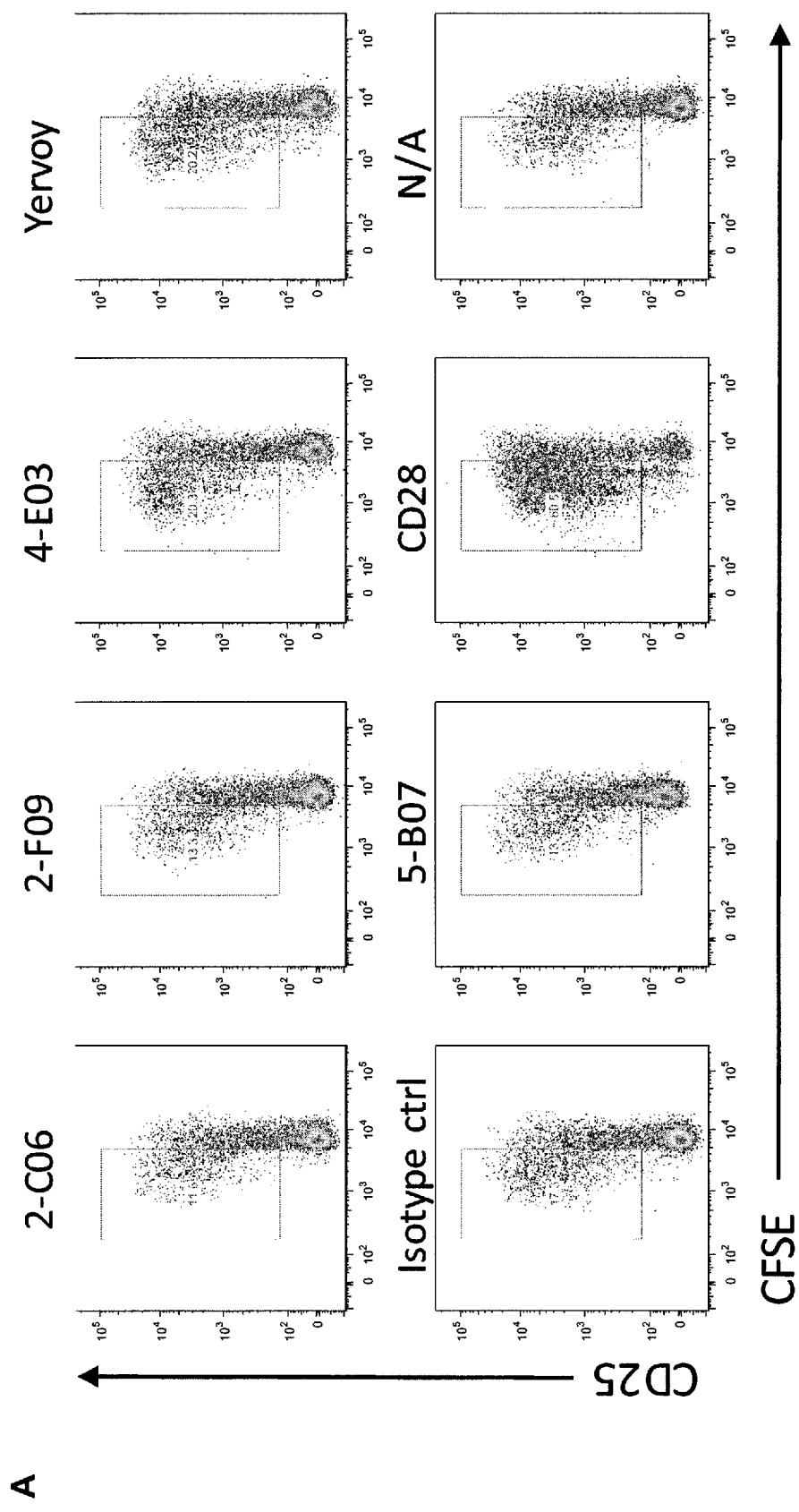

FIG. 9: Expected lack of direct agonistic activity

CFSE-labelled CD4+ T cells from healthy donors were stimulated with coated anti-CD3 plus soluble anti-CTLA-4 mAb or anti-CD28. % dividing cells (CFSElow CD25+ cells) were determined after 3 days by FACS. (A) FACS plots of one representative experiment (B) summarizing graph of 6 donors.

FIG. 10: CD80/CD86 blocking activity

Anti-CTLA-4 mAb block the binding of CD80 (FIG. 10A) and CD86 (FIG. 10B) to its ligand CTLA-4 as shown by ELISA.

Figure 11:
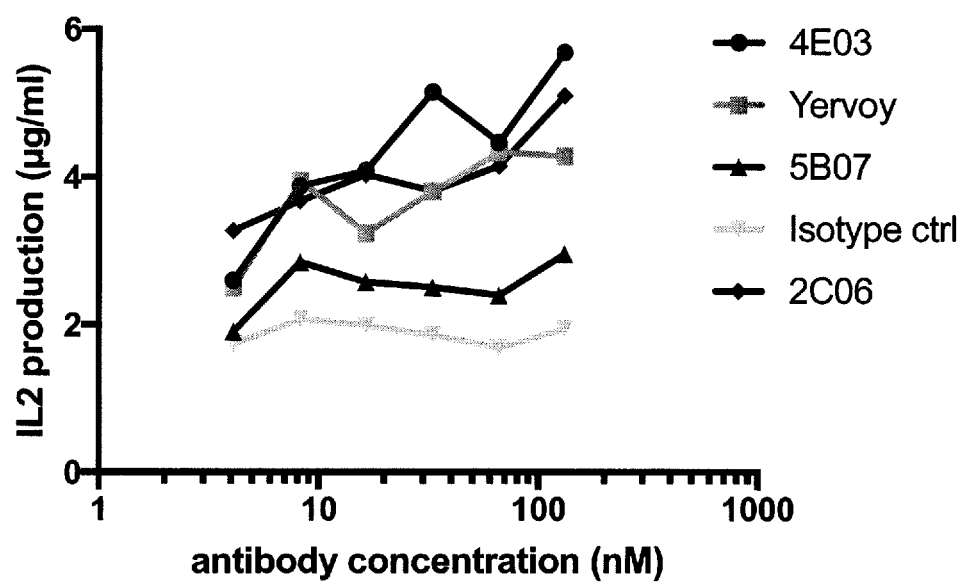

FIG. 11: Functional ligand block in vitro

PBMCs were stimulated with SEB plus titrating doses of anti-CTLA-4 antibodies. Amount of secreted IL-2 in the supernatant was determined by MSD. In this figure, 1 representative donor out of 6 is shown.

Figure 12:
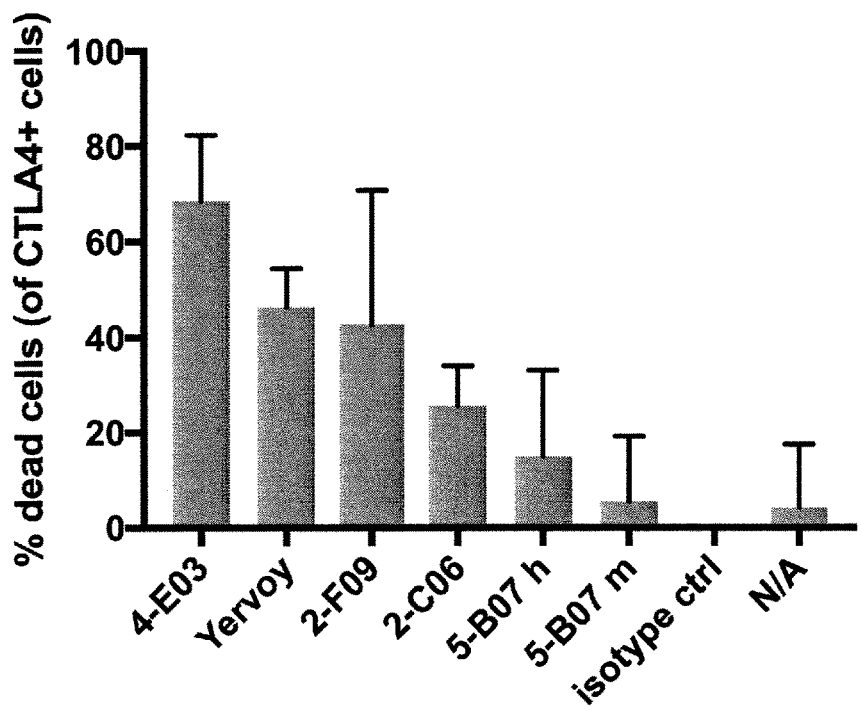

FIG. 12: ADCC assay on in vitro-activated CD4+ T cells

In vitro-activated CD4+ T cells from heathy donors pre-opsonized with anti-CTLA-4 mAbs at 10 µg/ml were co-cultured with NK cells (NK-92 cell line) at 2:1 ratio. ADCC activity was assessed by FACS as described below. The figure shows the mean+SD of 4-8 donors.

Figure 13:
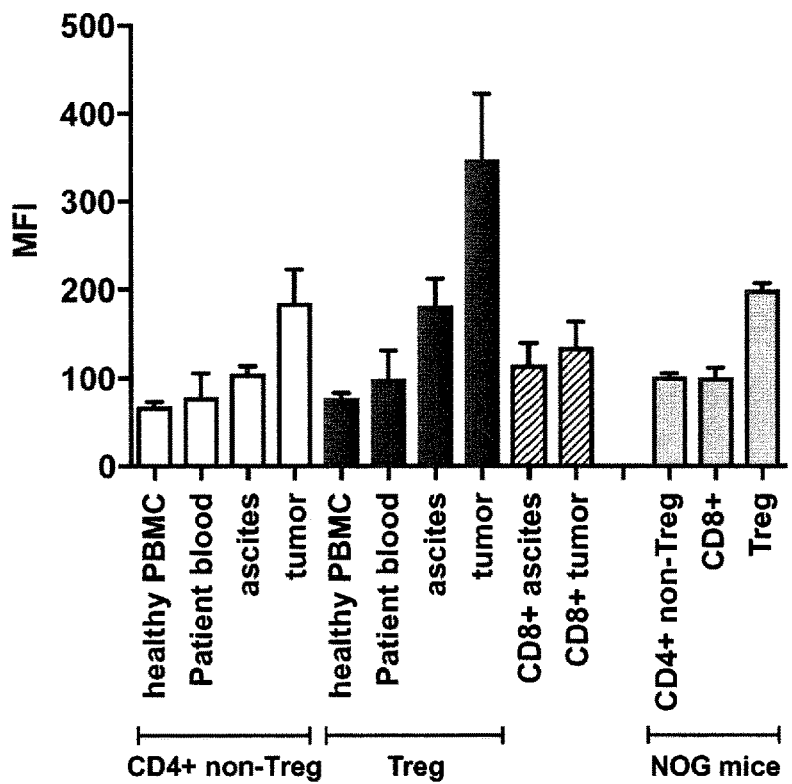

FIG. 13: CTLA-4 is highest expressed on tumour resident Treg cells.

Samples of freshly excised ovarian tumours and blood were obtained from patients at surgery. Ascites was collected from patients with different cancer indications. CTLA-expression on this patient material was compared to healthy PBMCs. Tumour samples were minced and digested. Peripheral blood mononuclear cells were separated by centrifugation. CTLA-4 expression was assessed on CD4+CD25+CD127− Treg cells, CD4+ non-Treg cells and CD8+ effector T cells by flow cytometry. Data represent individual patients/donors with n=12 for healthy PBMCs, n=20 for ascites, n=9 for tumour and n=5 for patient blood.

CTLA-4 expression was also analysed on human T cells which were activated in NOG mice in vivo and then isolated from the spleen of these mice (see FIG. 14).

FIG. 14: Anti-CTLA-4 mAb mediate Treg depletion in vivo.

Human PBMCs were injected i.v. into NOG mice. After approximately 2 weeks, spleens were taken and expression of CTLA-4 on human Treg cells and CD8+ T cells was analysed by FACS. Splenic cells isolated from NOG mice were transferred i.p. into SCID mice. 1 h later, mice were treated i.p. with CTLA-4 hIgG1 or control mAb. Intraperitoneal fluid was collected after 24 h and frequency of human T cell subsets (14A: Tregs and 14B: CD8+ T cells) was determined by flow cytometry.

FIG. 15: Table summarizing characteristics for anti-CTLA-4 antibodies

FIG. 16: FIG. 16: Characterization of mouse surrogate anti-CTLA-4 mAb

FIGS. 16A-B: Blocking ELISAs were performed with m5-B07 to evaluate ligand blocking characteristics. The antibody blocks the binding of FIG. 16A) CD80 and FIG. 16B) CD86 to its ligand CTLA-4 in a dose-dependent manner.

FIGS. 16C-D: 5-B07 in mouse IgG2a format mediated Treg depletion in CT26 tumor model. Balb/c mice were injected subcutaneously with $1 \times 10^6$ CT26 cells and treatment started at tumor size of ca 7×7 mm. After 3 injections of 10 mg/kg antibody, tumor single cell suspensions were analyzed for immune cell content by FACS. FIG. 16C: Ligand blocking surrogate antibody 5-B07 causes T reg depletion. This causes a shift in CD8+/Treg T cell ratio as depicted in FIG. 16D.

FIG. 17: Generation of COPTG19384 and COPTG19385

Schematic representation of COPTG19384 and COPTG19385 used in this study. COPTG19385 contains a deletion of J2R gene in TK locus replaced by the heavy chain of anti-CTLA-4 driven by p7.5K, and a deletion of I4L gene in RR locus replaced by the light chain of anti-CTLA-4 driven by p7.5K. COPTG19384 contains a deletion of J2R gene in TK locus replaced by the heavy chain of anti-CTLA-4 driven by p7.5K, and a deletion of I4L gene in RR locus replaced by the light chain of anti-CTLA-4 driven by p7.5K, and by GM-CSF driven by pSE/L.

FIG. 18: Expression analysis of 4-E03 monoclonal antibody in supernatant of CEF cells infected with COPTG19384

A) by Western Blot: CEF cells were infected at MOI 0.05 with COPTG19384 in triplicate. Cell supernatants were harvested after 48 h and were analysed by WB after an electrophoresis in non-reducing condition and using either an anti-Ig (left blot) or an anti-light chain (right blot) HRP conjugated antibody.

B) by ELISA: CEF cells were infected at MOI 0.05 with COPTG19384 in triplicate or VVTG17137. Cell supernatants were harvested after 48 h and were analysed by ELISA for detection of either 4-E03 monoclonal antibody.

Figure 19:
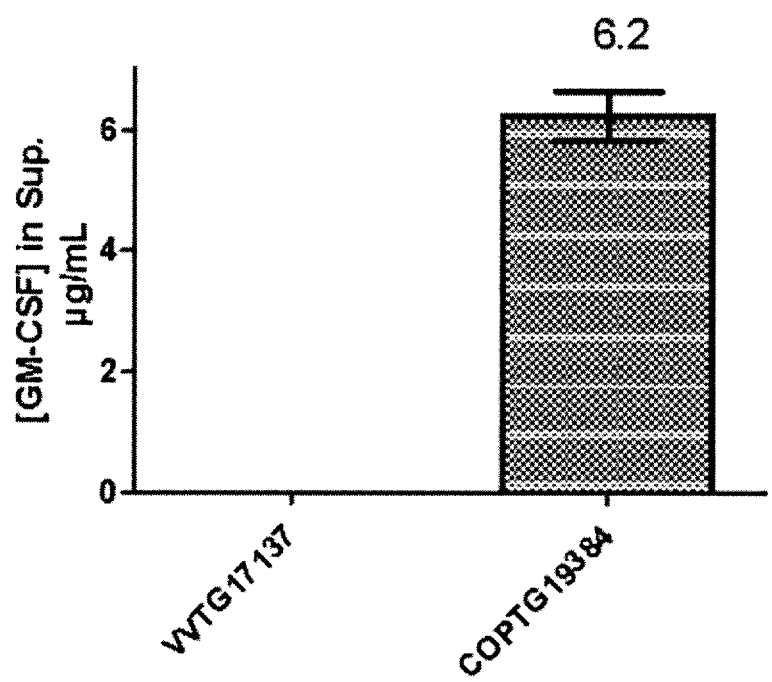

FIG. 19: Expression analysis of GM-CSF in supernatant of CEF cells infected with COPTG19384 by ELISA CEF cells were infected at MOI 0.05 with COPTG19384 primary research stock in triplicate or VVTG17137. Cell supernatants were harvested after 48 h and were analysed by ELISA for detection of GM-CSF.

FIG. 20: Replication studies of COP WT, COPTG19384 (two batches) and VVTG17137 (two batches) on normal and tumoral hepatocytes A) Replication rate on normal human hepatocytes.
B) Replication rate on malignant HepG2.
C) Therapeutic indexes calculated from the replication rates measured on HepG2 and hepatocytes.

Figure 21:
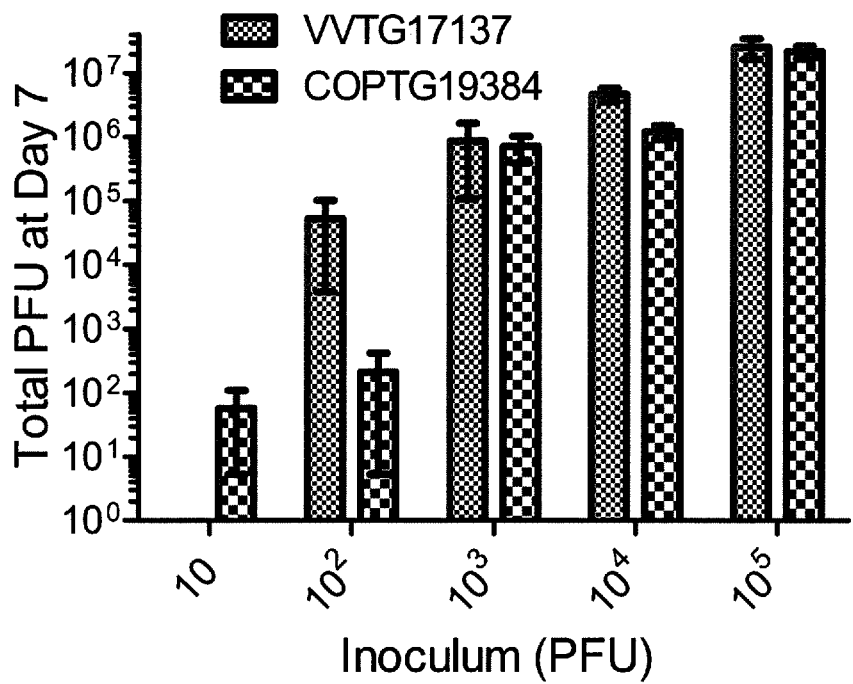

FIG. 21: Replication of COPTG19384 and VVTG17137 in reconstructed human skin
Replication of COPTG19384 and VVTG17137 were evaluated after 7 days and with inoculums varying from 10 to $10^5$ pfu. Results are the means and SEM of three measurements.

FIG. 22: Oncolytic activities of COPTG19384 and VVTG17137 in three human tumoral cell lines: MIA PaCa-2 (A), LoVo (B) and HepG2 (C)

Figure 23:
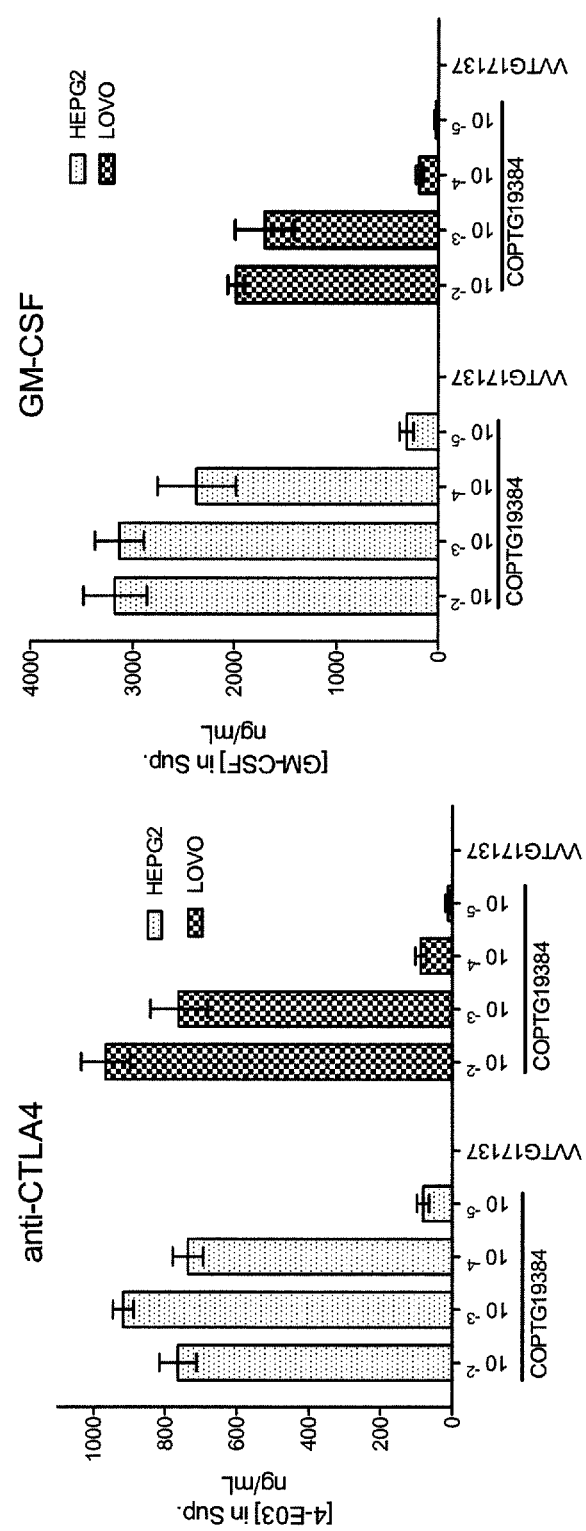

FIG. 23: Expression level of both 4-E03 monoclonal antibody and GM-CSF in (A) supernatants of infected HepG2 and LoVo and (B) supernatants of 5 different infected human tumoral cell lines
A) 4-E03 and GM-CSF expression levels were evaluated after 5 days of incubation, at MOI from $10^{-5}$ to $10^{-2}$ for COPTG19384 and at MOI of $10^{-2}$ for VVTG17137 used as negative control.
B) 4-E03 and GM-CSF expression levels were evaluated 48 hours after infection by COPTG19384 at MOI 0.05.

FIG. 24: Binding of different batches of 4-E03 to CTLA-4 protein
Binding of recombinantly produced 4-E03 by CHO (4-E03 research batch) or HEK (4-E03 tox batch) cells to (A) human and (B) cynomolgus recombinant protein was compared to the binding of 4-E03 purified from the supernatant of infected MIA PaCa-2 tumor cells (4-E03 TG) by ELISA.

FIG. 25: Binding of different batches of 4-E03 to CTLA-4 expressing cells
Binding of recombinantly produced 4-E03 by CHO (4-E03 research batch) or HEK (4-E03 tox batch) cells to (A) human and (B) cynomolgus CTLA-4 expressing cells was compared to the binding of 4-E03 purified from the supernatant of infected MIA PaCa-2 tumor cells (4-E03 TG) by flow cytometry.

Figure 26:
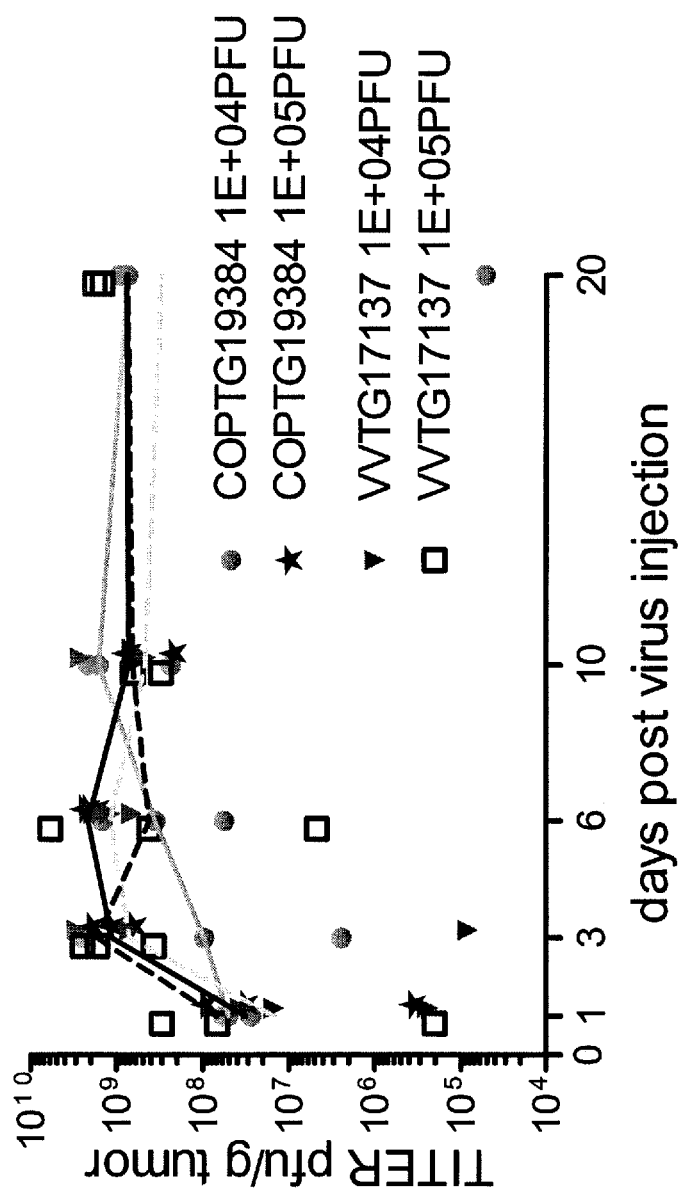

FIG. 26: Kinetic of virus accumulation in LoVo xenografted tumor
Kinetic of virus accumulation was evaluated in LoVo xenografted tumor after a single i.t. injection of either COPTG19384 or VVTG17137 at two different doses ($10^4$ or $10^5$ pfu). The solid or dashed lines represent the median of the three values determined at each time points.

FIG. 27: Kinetic of 4-E03 mAb and GM-CSF accumulation in LoVo xenografted tumor
A) Kinetic of 4-E03 mAb accumulation in LoVo xenografted tumor was evaluated after a single i.t. injection of either COPTG19384 or VVTG17137 at two different doses ($10^4$ or $10^5$ pfu) or after a single i.p. injection of 3 mg/kg of 4-E03 monoclonal antibody. The solid or dashed lines represent the median of the three values.
B) Kinetic of GM-CSF accumulation in LoVo xenografted tumor was evaluated after a single i.t. injection of either COPTG19384 at two different doses ($10^4$ or $10^5$ pfu) or VVTG17137 ($10^5$ pfu). The solid lines represent the median of the three values determined at each time points.

FIG. 28: Kinetic of 4-E03 mAb and GM-CSF concentrations in sera of LoVo xenografted mice
A) Kinetic of 4-E03 mAb concentrations in sera was evaluated after a single i.t. injection in LoVo xenografted tumor of either COPTG19384 or VVTG17137 at two different doses ($10^4$ or $10^5$ pfu) or after a single i.p. injection of 3 mg/kg of 4-E03 monoclonal antibody. The solid lines represent the median of the three values.
B) Kinetic of GM-CSF concentrations in sera after a single i.t. injection in LoVo xenografted tumor of either COPTG19384 at two different doses ($10^4$ or $10^5$ pfu) or VVTG17137 ($10^5$ pfu). The dashed lines represent the median of the three values determined at each time points.

Figure 29:
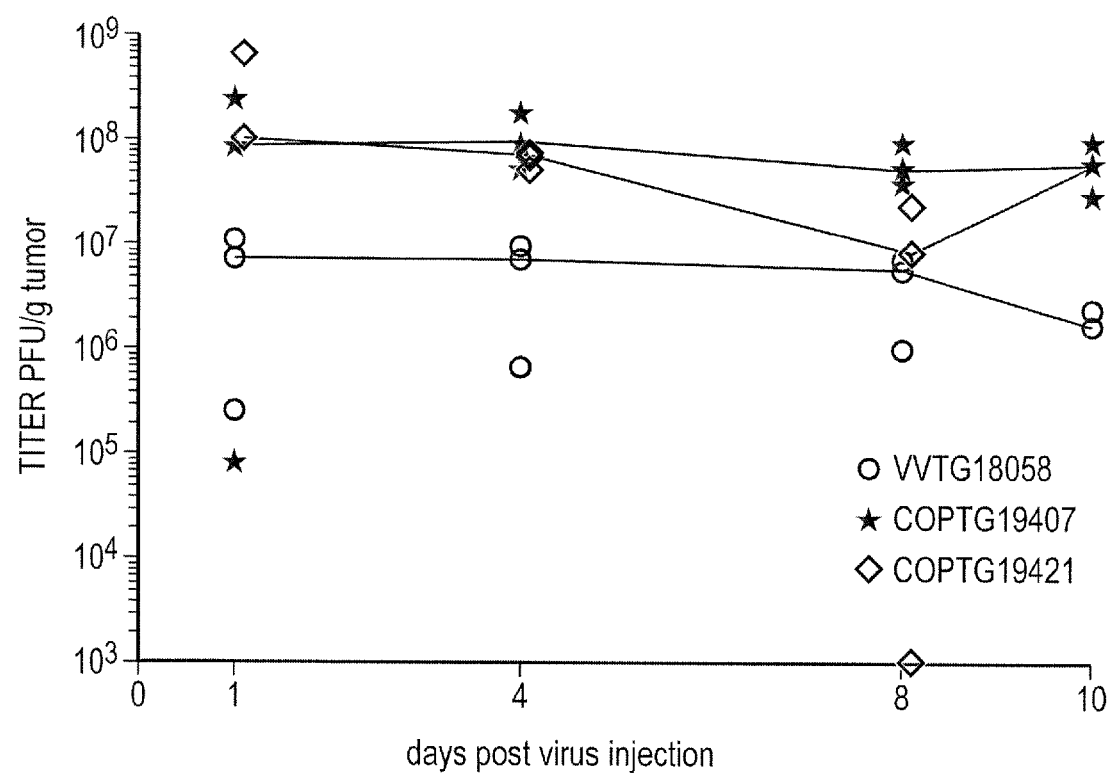

FIG. 29: Kinetic of virus accumulation in CT26 tumors
Kinetic of virus accumulation in CT26 tumors after three i.t. injections (at D0, D2 and D4) of either VVTG18058, COPTG19421 or COPTG19407 at $10^7$ pfu/injection.

FIG. 30: Kinetic of m5-B07 mAb and mGM-CSF accumulation in CT26 tumor
A) Kinetic of m5-B07 mAb concentrations in CT26 tumor during and after three i.t. injections of either VVTG18058, COPTG19421 or COPTG19407 ($10^7$ pfu/injection) or after a single i.p. injection of 3 mg/kg of m5-B07 monoclonal antibody. The solid lines represent the median of the three values.
B) Kinetic of mGM-CSF concentrations in CT26 tumor during and after three i.t. injections of either VVTG18058, COPTG19421 or COPTG19407 ($10^7$ pfu/injection) or after a single i.p. injection of 3 mg/kg of m5-B07 monoclonal antibody. The solid lines represent the median of the three values determined at each time points.

Figure 31:
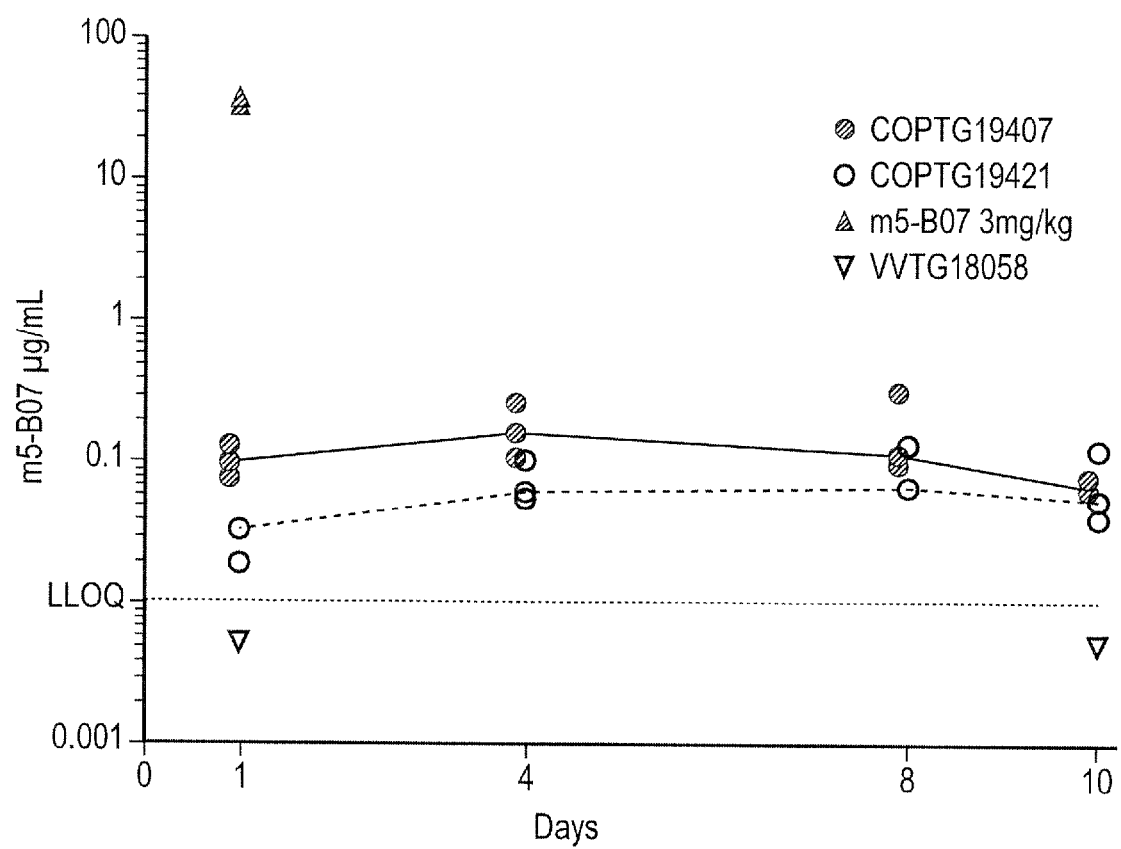

FIG. 31: Kinetic of m5-B07 mAb concentrations in sera of CT26 model
Kinetic of m5-B07 mAb concentrations in sera after three i.t. injections in CT26 tumor of either VVTG18058, COPTG19421 or COPTG19407 ($10^7$ pfu/injection) or after a single i.p. injection of 3 mg/kg of m5-B07 monoclonal antibody. The solid lines represent the median of the three values determined at each time points.

FIG. 32: Antitumoral activity in CT26 model: effect of COPTG19347+/−anti-PD1 on CT26 tumor growth (A) and mice survival (B)
CT26 cells were injected SC in BalB/c mice at D-7. COPTG19347 ($10^7$ pfu), VVTG18058 ($10^7$ pfu), VVTG18058 or buffer were injected IT, at D0, D2 and D4, possibly followed by the injection i.p. of 250 μg/mouse of anti-PD1 RMPI-14 at D7, D10, D14, D17 and D21.

Figure 33:
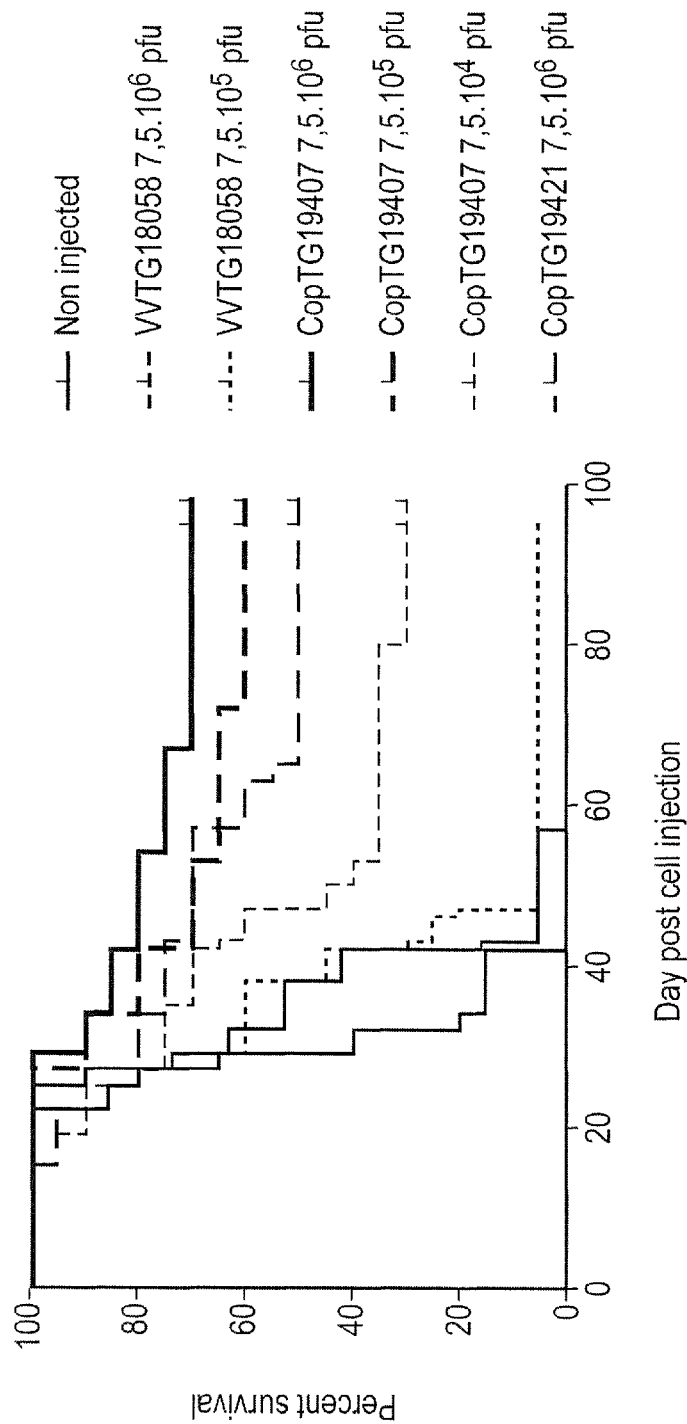

FIG. 33: Dose-effect evaluation in CT26 model (compilation of survival data observed after treatment of COPTG19407, COPTG19421 and VVTG18058)

FIG. 34: Anti-tumoral activity of COPTG19407 compared to VVTG18058 plus m5-B07 in CT26 tumor model
CT26 cells were injected s.c. into Balb/C mice. Treatment of the mice was started when tumors reached approx. 100 mm³. Mice were injected at D0, D2 and D5 with COPTG19407 ($8.5 \times 10^6$ pfu i.t.), VVTG18058 ($8.5 \times 10^6$ pfu i.t.), m5-B07 (10 mg/kg i.p.) or the combination of VVTG18058 ($8.5 \times 10^6$ pfu i.t.) plus m5-B07 (10 mg/kg i.p.). FIGS. 34A-D: Tumor growth and FIG. 34E: survival were followed over time.

FIG. 35: Individual tumor volume curves of BALB/c mice bearing subcutaneous A20 tumors.
A20 cells were injected s.c. into Balb/C mice. Treatment of the mice was started when tumors reached 80-100 mm³. Mice were injected at D0, D2 and D4 with vehicle (i.t), COPTG19407 ($4.75 \times 10^6$ pfu i.t.), VVTG18058 ($4.75 \times 10^6$ pfu i.t.), RMP1-14 (anti-mPD-1) (250 μg/mouse i.p.) or the combination of COPTG19407 ($4.75 \times 10^6$ pfu i.t.) plus RMP1-14 (250 μg/mouse i.p.).
A) Group 1 animals treated with vehicle
B) Group 2 animals treated with VVTG18058

C) Group 3 animals treated with COPTG19407
D) Group 4 animals treated with murine anti-PD1
E) Group 5 animals treated with COPTG19407 and murine anti-PD1

Figure 36:
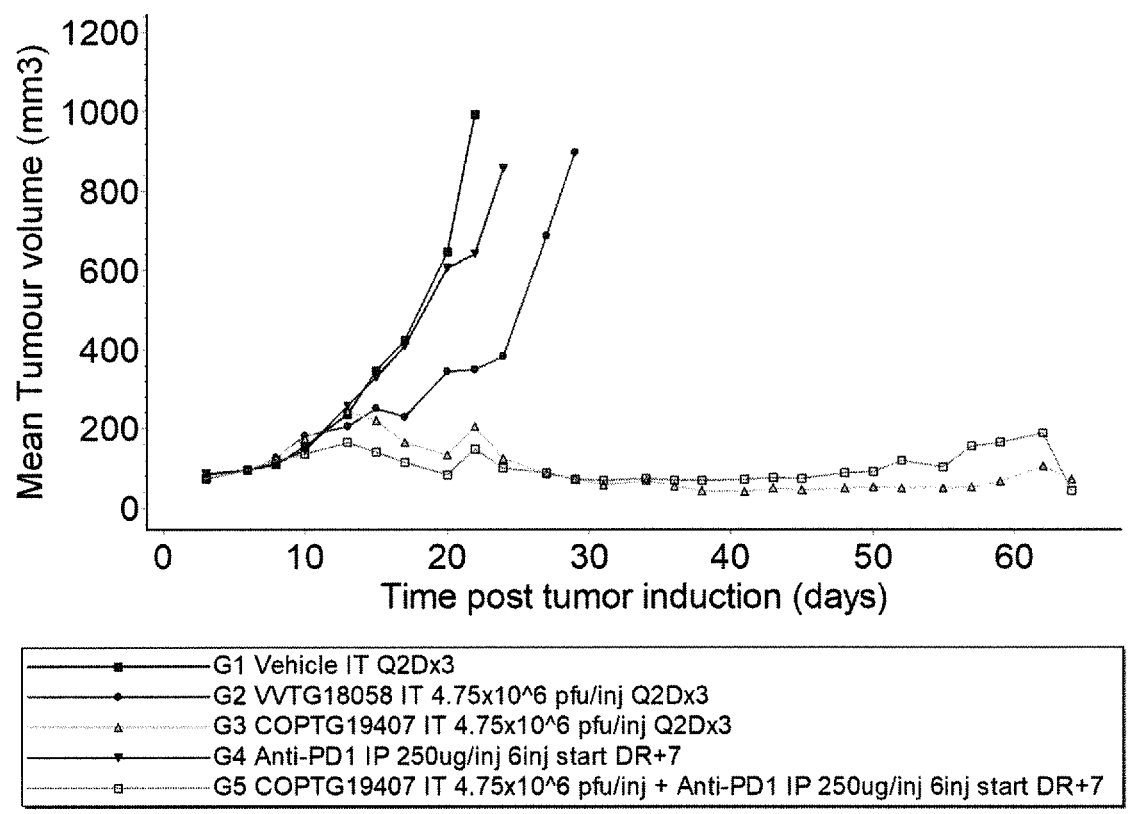

FIG. 36: Mean tumor volume curves of BALB/cN mice bearing subcutaneous A20 tumors.

Each point represents the mean of the recorded tumor volume per group. The tumor volumes of all animals were monitored over 64 days. Mice were treated with vehicle (group 1), VVTG18058 (group 2), COPTG19407 (group 3), the murine anti-PD1 antibody RMP1-14 (BioXCell) (group 4) and COPTG19407 and RMP1-14 (group 5). Animals were randomized on D7 and treated during the period D7 to D31. Last mice were sacrificed on D61.

FIG. 37: Antitumoral activity in A20 model: effect of COPTG19407+/−anti-PD1 on A20 tumor growth (A) and mice survival (B)

A20 cells were injected s.c. into Balb/C mice. Treatment of the mice was started when tumors reached 80-100 mm$^3$. Mice were treated with vehicle (i.t.) (group 1), anti-PD-1 (group 2), isotype (group 3), VVTG18058 ($10^5$ pfu i.t.) (group 4), VVTG18058 ($10^5$ pfu i.t.)+isotype (group 5), VVTG18058 ($10^5$ pfu i.t.)+anti-PD-1 (group 6), VVTG19407 ($10^5$ pfu i.t.) (group 7), VVTG19407 ($10^5$ pfu i.t.)+isotype (group 8) and VVTG19407 ($10^5$ pfu i.t.)+anti-PD-1 (group 9).

FIG. 38: Individual tumor volume curves of C57BL/6 mice bearing subcutaneous C38 tumors.

C38 cells were injected s.c. into C57bl/6 mice. Treatment of the mice was started when tumors reached 80-100 mm$^3$. Mice were injected at D0, D2 and D4 with vehicle (i.t), COPTG19407 ($4.75\times10^6$ pfu i.t.), VVTG18058 ($4.75\times10^6$ pfu i.t.), RMP1-14 (anti-mPD-1) (250 µg/mouse i.p.) or the combination of COPTG19407 ($4.75\times10^6$ pfu i.t.) plus RMP1-14 (250 µg/mouse i.p.).
A) Group 1 animals treated with vehicle
B) Group 2 animals treated with VVTG18058
C) Group 3 animals treated with COPTG19407
D) Group 4 animals treated with murine anti-PD1
E) Group 5 animals treated with COPTG19407 and murine anti-PD1

Figure 39:
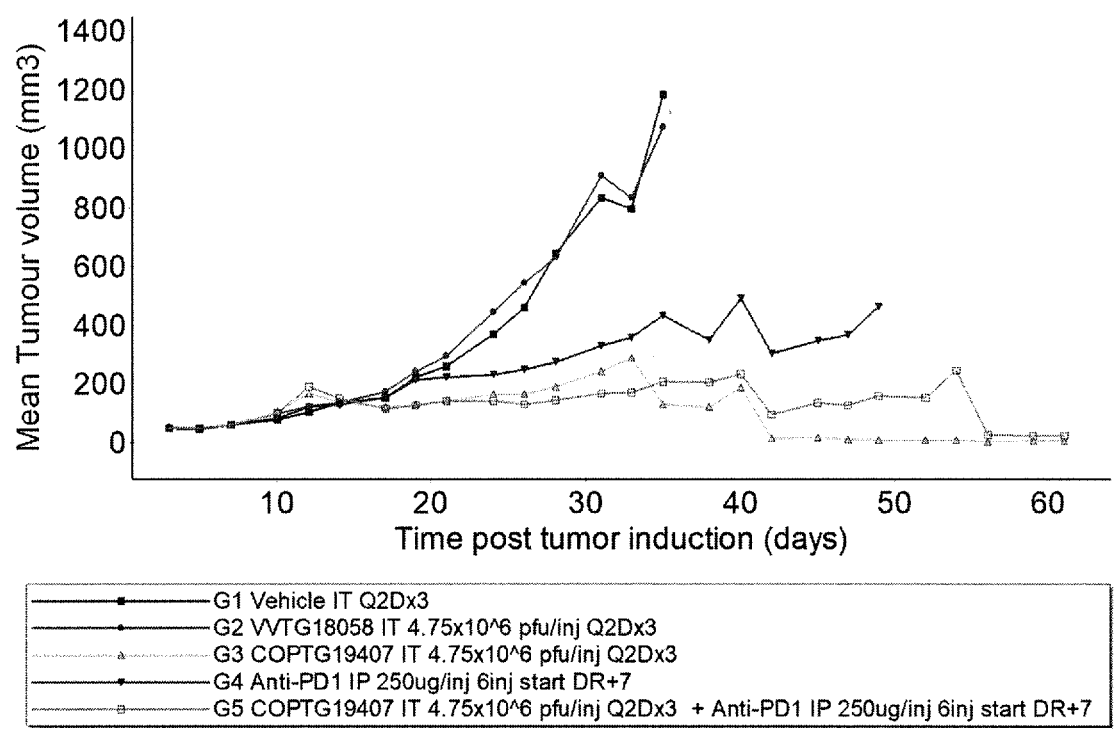

FIG. 39: Mean tumor volume curves of C57BL/6 mice bearing subcutaneous C38 tumors.

Each point represents the mean of the recorded tumor volume per group. The tumor volumes of all animals were monitored over 61 days. Mice were treated with vehicle (group 1), VVTG18058 (group 2), COPTG19407 (group 3), the murine anti-PD1 antibody RMP1-14 (BioXCell) (group 4) and COPTG19407 and RMP1-14 (group 5). Animals were randomized on D7 and treated during the period D7 to D31. Last mice were sacrificed on D61.

FIG. 40: Individual tumor volume curves of BALB/c mice bearing subcutaneous EMT6 tumors.

EMT6 cells were injected s.c. into Balb/C mice. Treatment of the mice was started when tumors reached 80-100 mm$^3$. Mice were injected at D0, D2 and D4 with vehicle (i.t), COPTG19407 ($4.75\times10^6$ pfu i.t.), VVTG18058 ($4.75\times10^6$ pfu i.t.), RMP1-14 (anti-mPD-1) (250 µg/mouse i.p.) or the combination of COPTG19407 ($4.75\times10^6$ pfu i.t.) plus RMP1-14 (250 µg/mouse i.p.).
A) Group 1 animals treated with vehicle
B) Group 2 animals treated with VVTG18058
C) Group 3 animals treated with COPTG19407
D) Group 4 animals treated with murine anti-PD1
E) Group 5 animals treated with COPTG19407 and murine anti-PD1

Figure 41:
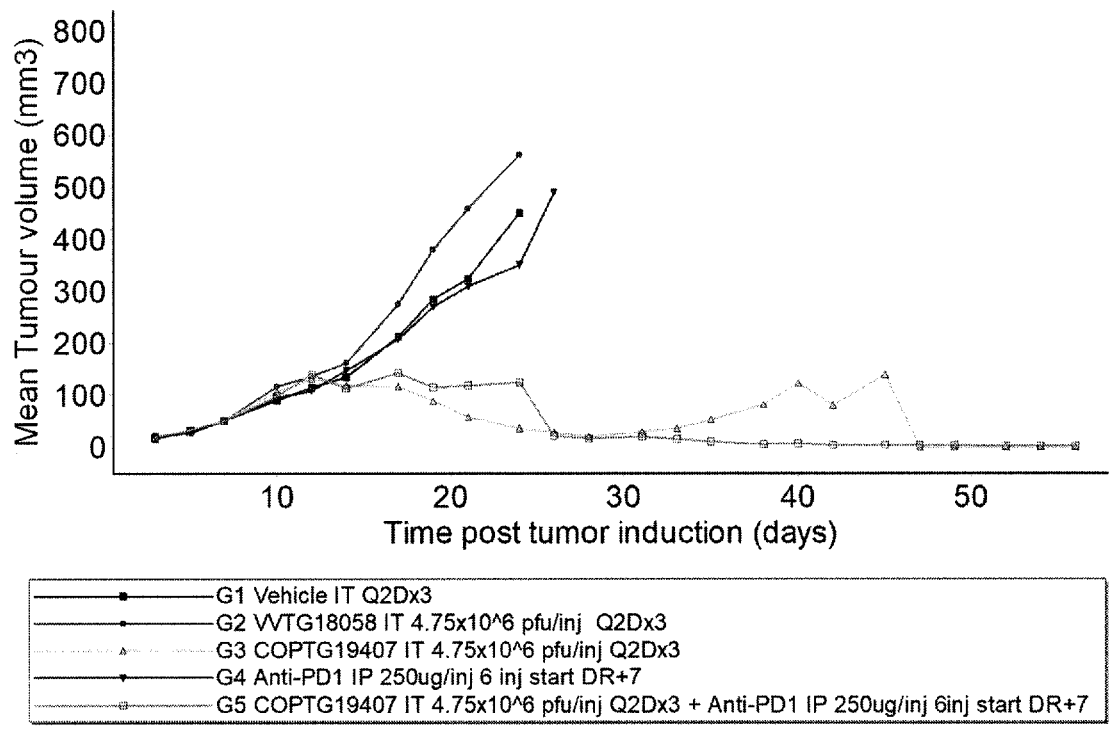

FIG. 41: Mean tumor volume curves of BALB/c mice bearing subcutaneous EMT6 tumors.

Each point represents the mean of the recorded tumor volume per group. The tumor volumes of all animals were monitored over 61 days. Mice were treated with vehicle (group 1), VVTG18058 (group 2), COPTG19407 (group 3), the murine anti-PD1 antibody RMP1-14 (BioXCell) (group 4) and COPTG19407 and RMP1-14 (group 5). Animals were randomized on D7 and treated during the period D7 to D31. Last mice were sacrificed on D56. Curves were stopped after the death of more than 20% of mice.

EXAMPLES

Specific, non-limiting examples which embody certain aspects of the invention will now be described. In the examples, rh protein denotes a human recombinant protein (e.g. rhIL-2 denotes human recombinant IL-2 protein) and rcm protein denotes a cynomologous recombinant protein (e.g. rcmCTLA4 denotes cynomologous recombinant CTLA-4 protein).

In addition to sequences mentioned above, some additional sequences are used in the examples, and these are set ut in Table 5 below.

TABLE 5

Additional sequences used in the examples

| 'dfj | Sequence | SEQ. ID. NO |
|---|---|---|
| Human GM-CSF without signal peptide | APARSPSPSTQPWEHVNAIQEARRLLNLSRDTAAEMNETVEVIEMF DLQEPTCLQTRLELYKQGLRGSLTKLKGPLTMMASHYKQHCPPTPE TSCATQTITFESFKENLKDFLLVIPFDCWEPVQE | 55 |
| Human GM-CSF with signal peptide | MWLQSLLLLGTVACSISAPARSPSPSTQPWEHVNAIQEARRLLNLS RDTAAEMNETVEVISEMFDLQEPTCLQTRLELYKQGLRGSLTKLKG PLTMMASHYKQHCPPTPETSCATQTITFESFKENLKDFLLVIPFDC WEPVQE | 56 |
| Murine GM-CSF without signal peptide | APTRSPITVTRPWKHVEAIKEALNLLDDMPVTLNEEVEVVSNEFSF KKLTCVQTRLKIFEQGLRGNFTKLKGALNMTASYYQTYCPPTPETD CETQVTTYADFIDSLKTFLTDIPFECKKPVQK | 57 |

TABLE 5-continued

Additional sequences used in the examples

| 'dfj | Sequence | SEQ. ID. NO |
|---|---|---|
| Murine GM-CSF with signal peptide | MWLQNLLFLGIVVYSLSAPTRSPITVTRPWKHVEAIKEALNLLDDM PVTLNEEVEVVSNEFSFKKLTCVQTRLKIFEQGLRGNFTKLKGALN MTASYYQTYCPPTPETDCETQVTTYADFIDSLKTFLTDIPFECKKP VQK | 58 |
| Promoter p7.5K | CCACCCACTTTTTATAGTAAGTTTTTCACCCATAAATAATAAATAC AATAATTAATTTCTCGTAAAAGTAGAAAATATATTCTAATTTATTG CACGGTAAGGAAGTAGAATCATAAAGAACAGT | 59 |
| Promoter pH5.4 | TTTATTCTATACTTAAAAAATGAAAATAAATACAAAGGTTCTTGAG GGTTGTGTTAAATTGAAAGCGAGAAATAATCATAAATTATTTCATT ATCGCGATATCCGTTAAGTTTG | 60 |
| Promoter pSE/L | AAAAATTGAAATTTTATTTTTTTTTTTGGAATATAAATA | 61 |

Example 1—Generation of CTLA-4 Specific Antibodies

Isolation of scFv Antibody Fragments

The n-CoDeR® scFv library (BioInvent; Söderlind E, et al Nat Biotechnol. 2000; 18(8):852-6) was used to isolate scFv antibody fragments recognizing human CTLA-4.

The phage library was used in three consecutive pannings against recombinant human protein. After phage incubation, the cells were washed to remove unbound phages. Binding phages were eluted with trypsin and amplified in E. coli. The resulting phage stock was converted to scFv format. E. coli was transformed with scFv bearing plasmids and individual scFv clones were expressed.

Identification of Unique CTLA-4 Binding scFv

Converted scFv from the third panning were assayed using a homogeneous FMAT analysis (Applied Biosystems, Carlsbad, CA, USA) for binding to transfected 293 FT cells expressing human CTLA-4 or a non-target protein.

Briefly, transfected cells were added to clear-bottom plates, together with the scFv-containing supernatant from expression plates (diluted 1:7), mouse anti-His Tag antibody (0.4 µg/ml; R&D Systems) and an APC-conjugated goat anti-mouse antibody (0.2 µg/ml; cat.no. 115-136-146, Jackson Immunoresearch). FMAT plates were incubated at room temperature (approximately 20-25° C.) for 9 h prior to reading. Target-specific bacterial clones were classified as actives and cherry picked into 96-well plate.

IgG Binding to CTLA-4 in ELISA 96-well plates (Lumitrac 600 LIA plate, Greiner) were coated overnight at 4° C. with recombinant human CTLA-4-Fc protein (R&D Systems) at 1 pmol/well, recombinant cynomologous (cm) CTLA-4-Fc protein (R&D Systems) at 1 pmol/well, recombinant mouse CTLA-4-Fc protein (R&D Systems) at 0.3 pmol/well, recombinant human CD28-Fc protein (R&D Systems) at 1 pmol/well or recombinant mouse CD28-Fc protein (R&D Systems) at 0.3 pmol/well. After washing, titrated doses of anti-CTLA-4 mAbs from 0 µg/ml to 0.06 ng/ml (66 nM to 0.3 pM) were allowed to bind for 1 hour. Plates were then washed again and bound antibodies were detected with an anti-human-F(ab)-HRP secondary antibody (Jackson ImmunoResearch) diluted in 50 ng/ml. Super Signal ELISA Pico (Thermo Scientific) was used as substrate and the plates were analysed using Tecan Ultra Microplate reader.

All antibodies were shown to bind to human and cynomologous CTLA-4 protein but not to human CD28 protein as assayed by ELISA. In addition, 5-B07 was shown to bind to mouse CTLA-4 but not mouse CD28 (see FIG. 1).

IgG Binding to CTLA-4-Expressing 293T Cells in Flow Cytometry

Converted IgG clones were analysed for binding to CTLA-4-expressing 293T cells (purchased from Crownbio). Cells were incubated with different concentrations (as indicated in FIG. 2) of anti-CTLA-4 mAb at 4° C. for 20 min prior to washing and staining with an APC-labelled goat anti-human secondary antibody (cat.no. 109-136-088, Jackson ImmunoResearch). Dead cells were excluded from analyses using Fixable Viability Dye eFluor780 (eBiosciences). Data acquisition was performed on a FACSVerse (BD Biosciences, Franklin Lakes, NJ) and analysed with FlowJo software (Tree Star, Ashland, OR).

The anti-CTLA-4 mAbs were shown to bind human CTLA-4-expressing 293T cells in a dose-dependent manner with a similar EC50 value as Yervoy (FIG. 2).

293T cells stably transfected with human CTLA-4, 293T cells transiently transfected with cynomologous CTLA-4, naive human or cynomologous PBMCs, in vitro-activated human or cyno CD4+ T cells were incubated with the concentrations of anti-CTLA-4 mAb indicated at 4° C. for 20 min prior to washing and staining with a APC-labelled anti-human secondary antibody (Jackson ImmunoResearch).

Example 2—Anti-CTLA-4 mAb Specifically Bind Human and Cynomologous CTLA-4-Expressing (Primary) Cells CTLA-4 Specific mAb Bind Primary Human and Cynomologous In Vitro-Activated CD4+ T Cells but not Naïve PBMCs Isolated from Healthy Donors PBMCs were isolated from buffy coats. Briefly, buffy were diluted 1:3 in PBS and were loaded onto Ficoll-Paque Plus (Amersham) cushions. Samples were centrifuged at 800×g for 20 min at 20° C. The upper, plasma-containing phase was removed and mononuclear cells were isolated from the distinct white band at the plasma/Ficoll interphase.

Human peripheral CD4+ T-cells were purified by negative selection using MACS CD4 T-cell isolation kit (Miltenyi Biotec). CD4+ T cells were activated in vitro with CD3/CD28 dynabeads (Life Technologies) plus 50 ng/ml rhIL-2 (R&D Systems) in R10 medium (RPMI containing 2 mM glutamine, 1 mM pyruvate, 100 IU/ml penicillin and streptomycin and 10% FBS (GIBCO by Life Technologies) for 3 days to upregulate CTLA-4 expression. Cynomologous CD4+ T cells were isolated using non-human CD4 microbeads (Miltenyi Biotec) and incubated with 50 ng/ml PMA (Sigma-Aldrich) and 100 ng/ml Ionomycin (Sigma-Aldrich) for 3 days.

Naive human or cynomologous PBMCs, in vitro-activated human or cyno CD4+ T cells were incubated with the indicated concentrations of anti-CTLA-4 mAb at 4° C. for 20 min prior to washing and staining with a APC-labelled anti-human secondary antibody (Jackson ImmunoResearch). Binding of anti-CTLA-4 mAb was analysed by FACS using a BD FACS Verse.

Figure 3:
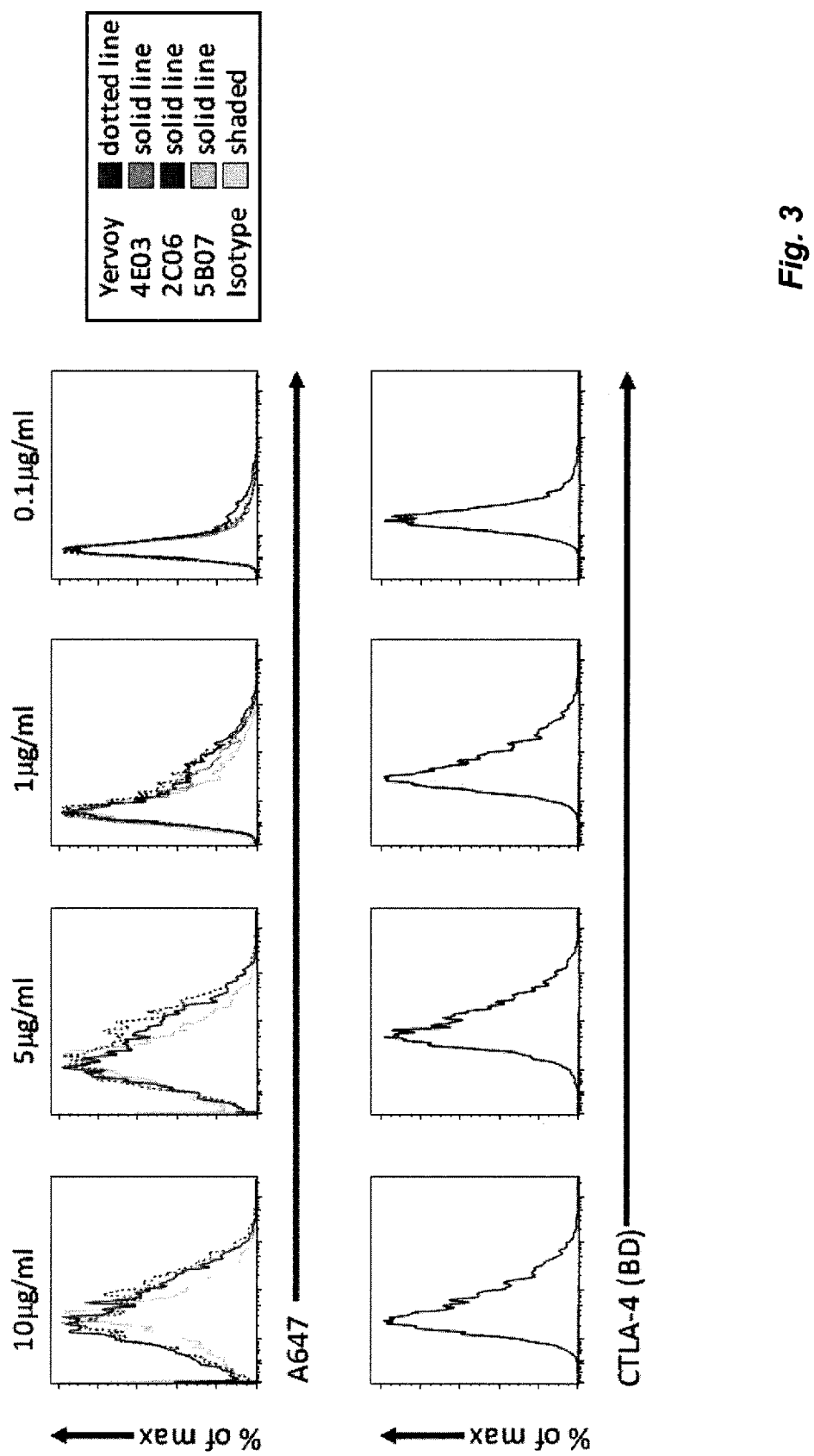
FIG. 3: Anti-CTLA-4 mAb bind to in vitro-activated human CD4+ T cells
  CD4+ T cells obtained from peripheral human blood were stimulated in vitro. Binding of anti-CTLA-4 mAb (solid lines, top row) was analysed by FACS and compared to Yervoy (dotted line, top row) and a commercial FACS antibody (bottom row).

The antibodies were shown to bind to in vitro-activated human (FIG. 3) and cynomologous (FIG. 5) CD4+ T cells but not to resting PBMCs (FIG. 8). The binding to endogenously CTLA-4 expressing T cells is similar to the staining with Yervoy (FIG. 3, upper row, dotted line) and a as a positive control a commercial anti-CTLA-4 FACS-antibody from BD Biosciences (clone BNI3; FIG. 3, bottom row).

Figure 4:
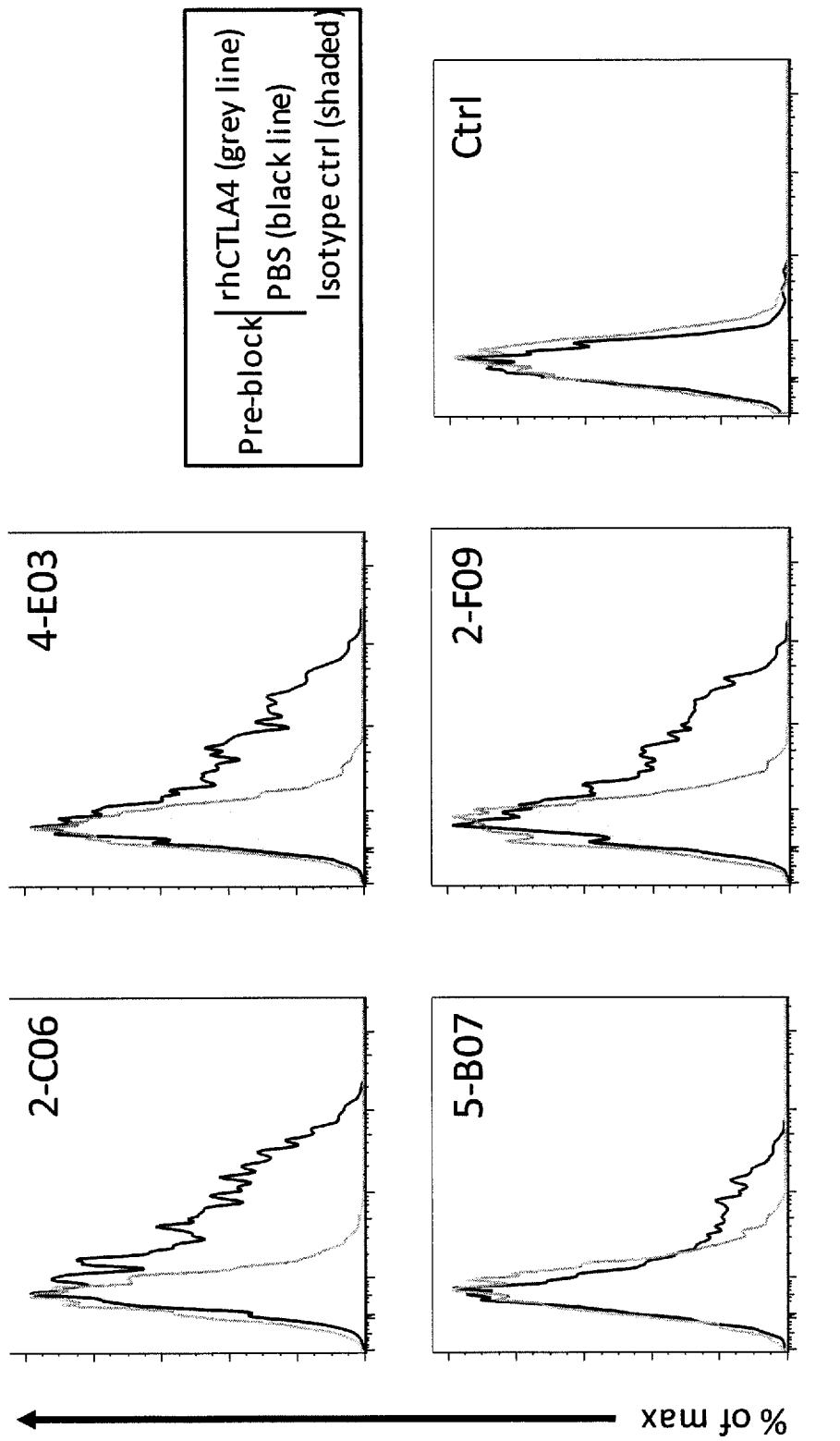
FIG. 4: Binding block on in vitro-activated CD4+ T cells
  Human in vitro-activated CD4+ T cells were stained with Alexa 647-labelled anti-CTLA-4 mAb (black line). Antibody binding was blocked by rhCTLA-4-Fc protein (grey line).

As shown in FIG. 4, the staining of human in vitro-activated CD4+ T cells (black line) can be completely blocked by rhCTLA-4-Fc (grey line) demonstrating the specificity of the antibodies. In this competitive binding assay, 2 μg/ml Alexa 647-labelled anti-CTLA-4 mAb was mixed with recombinant human CTLA-4-Fc protein (50 μg/ml) prior to incubation with CTLA-4 expressing cells. IgG binding was detected by FACS.

Transfected 293T Cells Expressing Human and Cynomologous CTLA-4 Confirm Cynocrossreactivity of the Tested Antibodies The cyno-crossreactivity of the antibodies was further confirmed on transfected CTLA-4 expressing 293T cells.

As demonstrated in FIG. 6, the binding of CTLA-4 specific antibodies to human CTLA-4 expressing transfected cells can be inhibited by human and cynomologous recombinant protein (both R&D Systems). The antibodies were also shown to bind to transfected cells expressing cynomologous CTLA-4 (FIG. 7, upper row). This binding can be blocked again by cynomologous recombinant protein (bottom row, grey line). The experiments were performed similar to the competitive assay described above in Example 2 in connection with FIG. 4.

Expected Lack of Direct Agonistic Activity

In vitro-proliferation assays were performed to exclude unanticipated direct agonistic activity (e.g. due to unspecific binding).

Human peripheral CD4+ T-cells were purified from healthy PBMCs by negative selection using MACS CD4 T-cell isolation kit (Miltenyi Biotec) and were thereafter labelled with CFSE (2 μM, Molecular Probes). Antibodies were cross-linked with F(ab')$_2$ goat anti-human IgG, Fcγ fragment specific or F(ab')$_2$ goat anti-mouse IgG, Fcγ fragment specific in a molar ratio IgG:F(ab')$_2$=1.5:1 for 1 h at RT. 1×10$^5$ purified human CD4+ T cells were stimulated with plate-bound anti-CD3 (0.5 μg/ml; clone UCHT1, R&D Systems) and 4 μg/ml of soluble, cross-linked anti-CTLA-4 or crosslinked anti-CD28 (clone CD28.2, BioLegend) for 72 hours at 37° C. Cells were washed and stained with a BV421-conjuagated anti-CD25 antibody (clone M-A251, BD Biosciences). The percentage of CD25+/CFSElow dividing cells was analysed by FACS.

FIG. 9 demonstrates that none of the tested anti-CTLA-4 mAb induces T cell proliferation in contrast to anti-CD28 stimulation.

Example 3—Anti-CTLA-4 mAb Block Ligand Binding of CD80/CD86

Ligand Blocking ELISA

The ligand blocking activity of anti-CTLA-4 IgGs was assessed by ELISA. To this end, recombinant human CTLA-4-Fc protein (R&D Systems) was coated to 96-well plates (Lumitrac 600 LIA plate, Greiner) at 1 pmol/well. After washing, titrated doses of anti-CTLA-4 mAbs were allowed to bind for 1 hour. His-tagged ligands were added at 200 nM and 100 nM, respectively (rhCD80 and rhCD86; R&D Systems) and the plates were further incubated for 15 minutes. After washing, bound ligand was detected with an HRP-labelled anti-His antibody (R&D Systems). Super Signal ELISA Pico (Thermo Scientific) was used as substrate and the plates were analysed using Tecan Ultra Microplate reader.

As shown in FIG. 10, anti-CTLA-4 antibodies tested show similar ligand blocking activity as Yervoy.

Functional Ligand Block In Vitro

For the SEB PBMC assay, total PBMCs from healthy donors were seeded on 96-well plates (1×10$^5$ cells/well) and stimulated with 1 μg/ml Staphylococcus enterotoxin B (SEB, Sigma Aldrich) in the presence of titrated doses of anti-CTLA-4 IgGs. IL-2 secretion was measured by MSD (Mesoscale) on day 3 according to manufactures' instructions.

The antibodies 4-E03 and 2-006 were shown to enhance IL-2 production and their potency was shown to be similar to that of Yervoy. In FIG. 11, one representative donor out of 6 is shown.

Example 4—Anti-CTLA-4 mAb Deplete CTLA-4 Expressing Cells In Vitro and In Vivo

Antibody Dependent Cellular Cytotoxicity (ADCC)

ADCC assays were performed using an NK-92 cell line stably transfected to express the CD16-158V allele together with GFP (purchased from Conkwest, San Diego, CA; Binyamin, L., et al., 2008, Blocking NK cell inhibitory self-recognition promotes antibody-dependent cellular cytotoxicity in a model of anti-lymphoma therapy. *Journal of immunology* 180, 6392-6401). CD4+ target T cells were isolated from peripheral blood of healthy donors using CD4+ T cell isolation kit (Miltenyi Biotec). Cells were stimulated for 48 hours with CD3/CD28 dynabeads (Life Technologies, Thermo Fisher) and 50 ng/ml rhIL-2 (R&D Systems) at 37° C. Target cells were pre-incubated with mAb at 10 μg/ml for 30 min at 4° C. prior to mixing with NK cells. The cells were incubated for 4 h in RPMI 1640+ GlutaMAX medium (Invitrogen) containing 10 mM HEPES buffer, 1 mM sodium Pyruvate and 10% FBS low IgG at a 2:1 effector:target cell ratio. Lysis was determined by flow cytometry. Briefly, at the end of the incubation, the cell suspension was stained with BV510-conjugated anti-CD4 (clone RPA-T4, BD Biosciences) together with 10 nM SYTOX Red dead cell stain (Invitrogen) or Fixable Viability Dye eFluor780 (eBioscience) for 20 min in the dark at 4° C. and the cells were then analysed using a FACSVerse (BD Biosciences).

4-E03 showed a significantly improved deletion of CTLA-4+ T cells in vitro compared to Yervoy (FIG. 12).

CTLA-4 Expression on Primary Patient Material

In order to validate the translational potential of the finding above on the depleting activity of anti-CTLA-4 mAb, the CTLA-4 expression was examined on primary patient material.

Ethical approval for the use of clinical samples was obtained by the Ethics Committee of Sickle University Hospital. Informed consent was provided in accordance with the Declaration of Helsinki. Samples were obtained through the Department of Gynocology and Department of Oncology at, Skånes University Hospital, Lund. Ascitic fluid was assessed as single cell suspensions that had been isolated. Tumour material was cut into small pieces and incubated in R10 with DNase I (Sigma Aldrich) and Liberase™ (Roche Diagnostics) for 20 min at 37° C. Remaining tissue was mechanically crashed and, together with the cell suspension, passed through a 70 μm cell strainer. Cells isolated from ascitic fluid and tumours were stained. To identify different T cell subsets following antibodies were used: CD4-BV510 (RPA-T4), CD25-BV421 (M-A251), anti-CD127-FITC (HIL-7R-M21), CTLA-4-PE (BNI3), CD8-PeCy7 (RPA-T8), CD3-APC (UCHT1), CD45-PercP-Cy5.5 (HI30), mouse IgG2a isotype, κ control-PE (G155-178; all from BD Biosciences). Data acquisition was performed using FACS-Verse and data analysed using FlowJo.

As shown in FIG. 13, CTLA-4 is highest expressed on intratumoral Treg cells which makes them a good target for depleting CTLA-4-specific antibodies.

PBMC-NOG/SCID Model

To confirm the in vitro findings on the depleting activity of the CTLA-4 specific antibodies, we analysed the depleting capacity of anti-CTLA-4 mAb in a PBMC-NOG/SCID model in vivo. The model is based on the well-established hu-PBMC-NOG model (Søndergaard H. et al., Clin Exp Immunol. 2013 May; 172(2):300-10. doi: 10.1111/cei.12051; Cox J H et al., PLoS One. 2013 Dec. 23; 8(12):e82944. doi: 10.1371/journal.pone.0082944. eCollection 2013) and was modified in-house as described below.

Mice were bred and maintained in local facilities in accordance with home office guidelines. Eight weeks-old female C.B. 17 scid (Bosma G C et al., Nature. 1983 Feb. 10; 301(5900):527-30) and NOG (NOD/Shi-scid/IL-2Rγ$^{null}$; Ito M et al, 2002, NOD/SCID/γ$_C^{null}$ mouse: an excellent recipient mouse model for engraftment of human cells. Blood 100(9):3175-3182) mice were supplied by Taconic (Bomholt, Denmark) and maintained in local animal facilities. For the PBMC-NOG/SCID (primary human xenograft) model, human PBMCs were isolated using Ficoll Paque PLUS and after washing the cells were resuspended in sterile PBS at $75 \times 10^6$ cells/ml. NOG mice were i.v. injected with 200 μl cell suspension corresponding to $15 \times 10^6$ cells/mouse. 2 weeks after injection, the spleens were isolated and rendered into a single cell suspension. Thereafter, a small sample was taken to determine the expression of CTLA-4 on human T cells by FACS. As indicated in FIG. 13, CTLA-4 is higher expressed on Treg cells compared to other T cells reflecting the situation in human patients. The majority of the cells was resuspended in sterile PBS at $50 \times 10^6$ cells/ml. SCID mice were injected i.p. with 200 μl of the suspension corresponding to $10 \times 10^6$ cells/mouse. 1 h later, mice were treated with 10 mg/kg of either anti-CTLA-4 hIgG1, Yervoy or isotype control mAb. The intraperitoneal fluid of the mice was collected after 24 h. Human T cell subsets were identified and quantified by FACS using following markers: CD45, CD4, CD8, CD25, CD127 (all from BD Biosciences).

All antibodies tested showed a similar or better Treg depleting activity than Yervoy. Other T cell populations, such as CD8+ effector T cells, were not affected (FIG. 14).

Example 5—the Selected Surrogate Antibody m5-B07 Shows the Same Functional Characteristics as 4-E03

In some of the examples, in particular the in vivo examples, the antibody clone 5-B07 in mIgG2a format has been used (also denoted m5-B07). This is a mouse antibody, which is a surrogate antibody to the human antibodies disclosed herein. It has been selected as a surrogate antibody since it binds murine CTLA-4 and thereby blocks ligand binding (FIG. 16A-B). Furthermore, it also shows Treg depleting activity (FIG. 16C-D).

Ligand Blocking ELISA

The ligand blocking activity of 5-B07 was assessed by ELISA. To this end, recombinant mouse CTLA-4-Fc protein (Sino Biological Inc.) was coated to 96-well plates (Lumitrac 600 LIA plate, Greiner) at 1 pmol/well. After washing, titrated doses of anti-CTLA-4 mAbs were allowed to bind for 1 hour. His-tagged ligands were added at 200 nM and 100 nM, respectively (rmCD80 and rmCD86; Sino Biological Inc.) and the plates were further incubated for 15 minutes. After washing, bound ligand was detected with an HRP-labelled anti-His antibody (R&D Systems). Super Signal ELISA Pico (Thermo Scientific) was used as substrate and the plates were analysed using Tecan Ultra Microplate reader.

As shown in FIG. 16, the antibody blocks the binding of (A) CD80 and (B) CD86 to its ligand CTLA-4.

Treg Depleting Activity In Vivo

The effects of CTLA-4 specific antibodies on the T cell subsets in the tumor in vivo was investigated in the CT26 tumor model as described below.

Mice were bred and maintained in local facilities in accordance with home office guidelines. Six to eight weeks-old female Balb/C were supplied by Taconic (Bomholt, Denmark) and maintained in local animal facilities. CT26 cells (ATCC) were grown in glutamax buffered RPMI, supplemented with 10% FCS. When cells were semi confluent they were detached with trypsin and resuspended in sterile PBS at $10 \times 10^6$ cells/ml. Mice were s.c. injected with 100 μl cell suspension corresponding to $1 \times 10^6$ cells/mouse. When the tumors reached approximately 7×7 mm, the mice were treated twice weekly i.p. with 10 mg/kg of the indicated antibodies as indicated in figures. After the third administration, tumors were dissected out, mechanically divided into small pieces and digested using a mixture of 100 μg/ml liberase (Roche) and 100 μg/ml Dnase (Sigma) in 37° C. for 2×5 min with Vortex in between. The cell suspension was then washed (400 g for 10 min) with PBS containing 10% FBS. Thereafter, the cells were resuspended in MACS buffer and stained with an antibody panel staining CD45, CD3, CD8, CD4 and CD25 (all from BD Biosciences). Before staining, the cells were blocked for unspecific binding using 100 μg/ml IVIG. Cells were analyzed using a FACS Verse (BD Biosciences). Mouse Treg cells were identified as CD45$^+$CD3$^+$CD4$^+$CD25$^+$ cells.

Figure 5:
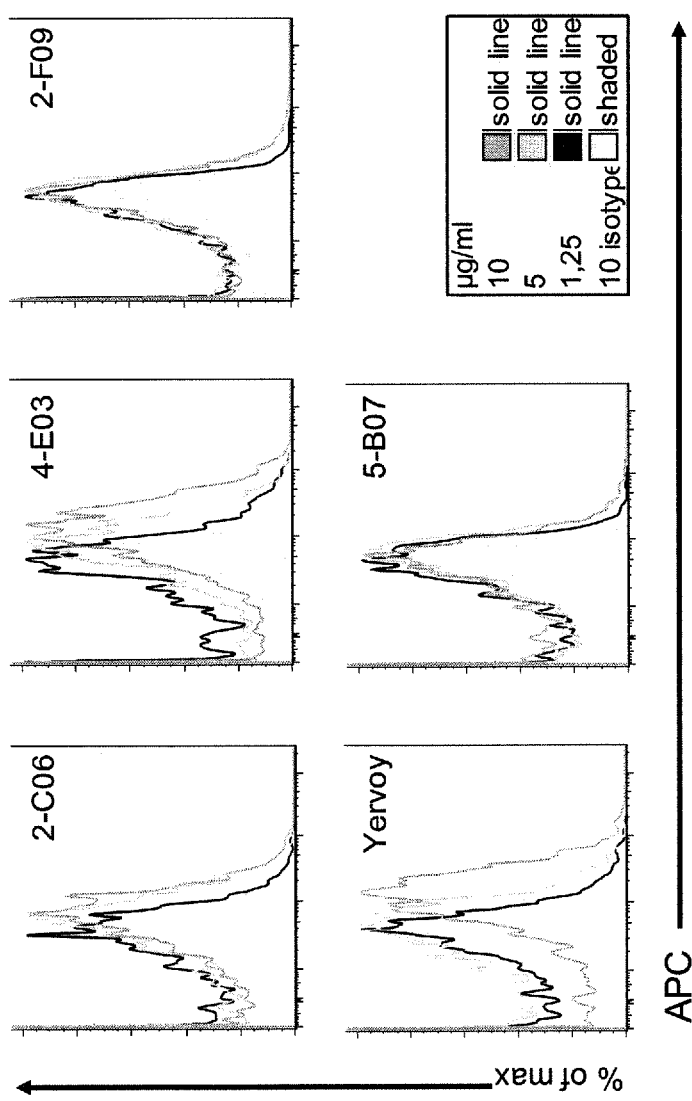
FIG. 5: Binding to in vitro-activated cynomologous CD4+ T cells

As shown in FIG. 16C, 5-B07 in mouse IgG2a format mediates Treg deletion in the tumor associated with D) increased CD8/Treg ratio compared to other CTLA-4 specific n-CoDeR antibodies and the well-described commercially available clone 9H10.

Example 6—Generation of a Virus Expressing Anti-CTLA4 mAb (COPTG19385) or Anti-CTLA4 mAb and GM-CSF (COPTG19384), Expression of Transgenes and Characterization of Genetic Stabilities COPTG19384 and COPTG19385 are vaccinia viruses (Copenhagen strain) encoding the monoclonal antibody anti-CTLA4 (4-E03). COPTG19384 further encodes the human GM-CSF. More particularly, COPTG19384 and COPTG19385 are both defective for thymidine kinase (TK, J2R locus) and ribonucleotide reductase (RR, I4L locus) activities. As illustrated in FIG. 17, the expression cassette encoding the 4-E03 heavy chain (HC; SEQ ID NO: 54) under the control of p7.5K promoter (SEQ ID NO: 59) was inserted at the J2R locus, and the expression cassette encoding the light chain (LC, SEQ ID NO: 53) of the 4-E03 IgG under the control of p7.5K promoter SEQ ID NO: 59) was placed at the I4L locus. For COPTG19384, the expression cassette encoding the human GM-CSF (SEQ ID NO: 56) under the control of pSE/L promoter (SEQ ID NO: 61) was also placed at the I4L locus.

The same promoter (p7.5K) was used to control the expression of HC and LC to obtain to same level of expression for both chains and therefore an optimal assembly of the antibody as a hetero-tetrameric protein (i.e. to avoid excess of non-associated chain). However, the same promoter for both chains of the antibody precludes from inserting them at the same locus (identical DNA sequences increase the risk of recombination and then elimination of transgenes). Therefore, the cassette encoding the 4-E03 HC was inserted at the J2R locus and the cassette encoding the 4-E03 LC at the I4L locus. The cassette encoding the GM-CSF transgene but under a different promoter (pSE/L) was also inserted into the I4L locus, like the antibody light chain.

Generation of COPTG19384

The vaccinia virus transfer plasmids, pTG19339 and pTG19341, were designed to allow insertion of nucleotide sequences by homologous recombination in J2R and in I4L loci of the vaccinia virus genome, respectively. They originate from the plasmid pUC18 into which were cloned the flanking sequences (BRG and BRD) surrounding the J2R (pTG19339) or I4L (pTG19341) locus. Each plasmid contains also the p7.5K promoter.

A synthetic fragment named "Fragment HC" of 1436 bp containing the HC gene of 4-E03 antibody was produced. A fragment "LC fragment" containing the LC gene of 4-E03 antibody and hGM-CSF gene under the control of the pSE/L was generated by a synthetic way and inserted in a plasmidic vector. The coding sequences were optimized for human codon usage, a Kozak sequence (ACC) was added before the ATG start codon and a transcriptional terminator (TTTTTNT) was added after the stop codon. Moreover, some patterns were excluded: TTTTTNT, GGGGG, CCCCC which are deleterious for expression in poxvirus.

The HC fragment was inserted in pTG19339 restricted with PvuII by homologous recombination, giving rise to pTG19367. The LC-carrying plasmid was restricted by SnaB1 and the resulting fragment "LC-GMCSF" was inserted by homologous recombination in pTG19341 restricted with PvuII, giving rise to pTG19384. In this plasmid, the expressions cassettes were inserted head to tail between recombination arms allowing homologous recombination in the I4L locus of vaccinia virus genome.

COPTG19384 was generated on chicken embryo fibroblast (CEF) by two successive homologous recombination for successive insertion in I4L and J2R loci and by using COPTG19156 as parental virus and the two transfer plasmids pTG19367 and pTG19384. CEF were isolated from 12 day-old embryonated SPF eggs (Charles River). The embryos were mechanically dilacerated, solubilized in a Tryple Select solution (Invitrogen) and cultured in a MBE (Eagle Based Medium; Gibco) supplemented with 5% FCS (Gibco) and 2 mM L-glutamine.

The homologous recombination between the transfer plasmids and parental vaccinia virus enables the generation of recombinant vaccinia viruses which have lost the GFP and the mCherry expression cassettes and gained the antibody and GM-CSF expression cassettes. COPTG19156 contains the expression cassette of the mCherry gene in its I4L locus and the expression cassette of the GFP gene in its J2R locus. The homologous recombination between the transfer plasmid pTG19367 and the parental COPTG19156 enables the generation of recombinant vaccinia viruses which have lost their GFP expression cassette and gained the 4-E03 heavy chain expression cassette and the selection was performed by isolation of red fluorescent plaques. This intermediary recombinant virus (COPTG19367) was used as parental virus for a second round of homologous recombination with pTG19384 as transfer plasmid for the generation of recombinant vaccinia viruses which have lost their mCherry expression cassette and gained the 4-E03 light chain and GM-CSF expression cassettes. The selection of COPTG19384 (FIG. 17) was performed by isolation of white non-fluorescent plaques.

The viral stock of COPTG19384 was amplified on CEFs in two F175 flasks to generate appropriate stocks of viruses which can be aliquoted and stored at −80° C. until use. Viral stock was titrated on CEF cells and infectious titers were expressed in pfu/mL and calculated with the following formula: number of lytic areas×dilution factor×4. For illustrative purposes, the produced viral stock titrated $6.8 \times 10^6$ pfu/mL. This stock was analyzed by PCR to verify the integrity of the expression cassettes and recombination arms using appropriate primer pairs. The stock was also analyzed by sequencing of both expression cassettes. Alignment of sequencing results showed 100% homology with the theoretical expected sequence. If needed, viral preparations were purified using conventional techniques (e.g. as described in WO2007/147528).

Generation of COPTG19385

The vaccinia virus transfer plasmids, pTG19339 and pTG19341, were designed to allow insertion of nucleotide sequences by homologous recombination in J2R and in I4L loci of the vaccinia virus genome, respectively. They originate from the plasmid pUC18 into which were cloned the flanking sequences (BRG and BRD) surrounding the J2R (pTG19339) or I4L (pTG19341) locus. Each plasmid contains also the p7.5K promoter.

A synthetic fragment named "Fragment HC" of 1436 bp containing the HC gene of 4-E03 antibody was produced. The coding sequences were optimized for human codon usage, a Kozak sequence (ACC) was added before the ATG start codon and a transcriptional terminator (TTTTTNT) was added after the stop codon. Moreover, some patterns were excluded: TTTTTNT, GGGGG, CCCCC which are deleterious for expression in poxvirus.

The HC fragment was inserted in pTG19339 restricted with PvuII by homologous recombination, giving rise to pTG19367.

The plasmid containing the expression cassette encoding only the 4-E03 light chain was obtained by elimination of the cassette encoding the hGM-CSF gene under the control of the pSE/L in the plasmid pTG19384 (described above). pTG19384 was restricted with NheI and XbaI (compatible cohesive ends) and was religated, giving rise to pTG19385.

COPTG19385 was generated on chicken embryo fibroblast (CEF) by two successive homologous recombination for successive insertion in J2R and I4L loci and by using COPTG19156 as parental virus and the two transfer plasmids pTG19367 and pTG19385. CEF were isolated from 12 day-old embryonated SPF eggs (Charles River). The embryos were mechanically dilacerated, solubilized in a Tryple Select solution (Invitrogen) and cultured in an MBE (Eagle Based Medium; Gibco) supplemented with 5% FCS (Gibco) and 2 mM L-glutamine.

The homologous recombination between the transfer plasmids and parental vaccinia virus enables the generation of recombinant vaccinia viruses which have lost the GFP and the mCherry expression cassettes and gained the antibody expression cassettes. COPTG19156 contains the expression cassette of the mCherry gene in its I4L locus and the expression cassette of the GFP gene in its J2R locus. The homologous recombination between the transfer plasmid pTG19367 and the parental COPTG19156 enables the generation of recombinant vaccinia viruses which have lost their GFP expression cassette and gained the 4-E03 heavy chain expression cassette and the selection was performed by isolation of red fluorescent plaques. This intermediary recombinant virus (COPTG19367) was used as parental virus for a second round of homologous recombination with pTG19385 as transfer plasmid for the generation of recombinant vaccinia viruses which have lost their mCherry expression cassette and gained the 4-E03 light chain expression cassette. The selection of COPTG19385 was performed by isolation of white non-fluorescent plaques.

The viral stock of COPTG19385 was amplified on CEFs in two F175 flasks to generate appropriate stocks of viruses which can be aliquoted and stored at −80° C. until use. Viral stock was titrated on CEF cells and infectious titers were expressed in pfu/mL and calculated with the following formula: number of lytic areas×dilution factor×4. For illustrative purposes, the produced viral stock titrated $1.04 \times 10^7$ pfu/mL. This stock was analyzed by PCR to verify the integrity of the expression cassettes and recombination arms using appropriate primer pairs. The stock was also analyzed by sequencing of both expression cassettes. Alignment of sequencing results showed 100% homology with the theoretical expected sequence. If needed, viral preparations were purified using conventional techniques (e.g. as described in WO2007/147528).

Expression of Transgenes

Virus-mediated expression of 4-E03 monoclonal antibody was evaluated in supernatants of CEF cells infected with COPTG19384 by Western Blot (WB) and compared to the recombinantly produced antibody (40 ng of 4-E03). WB allows to visualize the presence of non-functional molecules that do not bind the CTLA4 (e.g. molecules with incomplete chain assembly, aggregates). CEF cells were infected at MOI 0.05 with COPTG19384 viral stock in triplicate. Cell supernatants were harvested after 48 h and were analyzed by WB after an electrophoresis in non-reducing condition and using either an anti-Ig (left blot) or an anti-light chain (right blot) HRP conjugated antibody. The results illustrated in FIG. 18A indicate that the WB profile in non-reducing condition of the mAb produced by infected CEF is close to that of the purified 4-E03 with a similar apparent size between 100 to 150 kDa, indicating a correct chains-folding and assembly.

Quantification in supernatants of the functional secreted 4-E03 antibodies and GM-CSF was performed with ELISA. ELISA allowed to measure quantitively the amount of functional polypeptide produced in cell supernatants. VVTG17137 was used as a negative control. It is a vaccinia virus (Copenhagen strain) deleted in J2R and I4L loci encoding the suicide gene FCU1 (described in WO2009/065546).

For estimation of 4-E03 antibody, microplates were coated by an overnight incubation at 4° C. with 100 µL per well of CTLA4-Fc at 0.25 µg/mL. After incubation, the coating solution was discarded, blocking solution added and plates were incubated for 1 to 2 hours at RT before being washed. 4-E03 calibration standards (from 0.097 to 100 ng/mL), or samples (in triplicate) diluted in blocking solution were added to the wells and the plates were incubated for 2 hours at 37° C. before being washed. HRP conjugated antibody diluted in blocking solution was added to each well and plates were incubated 1 hour at 37° C. before being washed. After incubation with TMB solution 30 min at RT in darkness, $H_2SO_4$ 2 M (stop solution) was added to stop the enzymatic reaction. Absorbances were read at 450 nm on microplate reader. Absorbances were plotted versus antibody concentration of the calibration standard. As illustrated in FIG. 18B, functional 4-E03 mAb was produced in cells infected by COPTG19384, reaching concentrations close to 1 µg/mL.

Virus-mediated expression of GM-CSF was also evaluated in the same supernatants using Quantikine® ELISA (R&D Systems Ref SGM00). Briefly, this assay is using two anti-hGM-CSF antibodies. The first antibody used to capture the hGM-CSF in the samples was coated on the well surface of a 96-well plate. The second one is conjugated and added to the plate in solution to detect the captured hGM-CSF. The concentration of hGM-CSF in the sample is then calculated by interpolation from a calibration curve established with some purified hGM-CSF provided by the kit. As illustrated in FIG. 19, the level of expression of GM-CSF was around 6 µg/mL.

In conclusion, concentrations equal or above 1 µg/mL were detected for both transgenes indicating a satisfying level of expression.

Genetic Stability:

Genetic stability tests were performed after five passages of the virus on CEF in serum free medium at a multiplicity of infection (MOI) of $10^{-4}$. Passage P5 was diluted and inoculated on CEF cells in 60 mm culture dishes to obtain from 20 to 40 viral plaques per dish. One hundred viral plaques were isolated and sub-cultured. After one amplification cycle, isolated viral plaques were inoculated on CEF cells and tested by PCR and by ELISA. PCR analysis and expression of transgenes showed that more than 90% of clones have a correct profile. As the acceptance criteria for clinical development of a product is a genetic stability superior or equal to 90%, COPTG19384 was considered as genetically stable.

Example 7—In Vitro Characterization of COPTG19384

Replication Studies in Hepatocytes: Tumor-Selectivity of a Virus Expressing Anti-CTLA4 mAb and GM-CSF COPTG19384 carries two gene deletions encoding viral enzymes (TK and RR) involved in nucleotide metabolism. When functional, these enzymes allow the virus to replicate in cytoplasm of most of cells including the ones in resting state (i.e. with low nucleotide pool available). A host range study was performed in primary and malignant cells to verify that the insertion of the different transgenes in the J2R and I4L loci does not modify the host range selectivity. The replication of COPTG19384 was assessed on normal primary human cells (hepatocytes, prepared by Biopredic) and on tumoral cells from the same organ (HepG2 from hepatocarcinoma, ATCC® HB-8065™). Replication rates and therapeutic indexes were calculated and compared to those of both the wild type Copenhagen vaccinia (COP WT, virus without any deletion) as references for non-selective vaccinia virus and the recombinant double deleted VVTG17137 virus (deleted in J2R and 14L genes with the suicide FCU1 gene inserted in place of J2R), respectively. Two batches were assayed, a research batch (batch1) and a GMP-produced batch (batch 2). The replication rate was determined as the ratio of total infectious particles at the end of incubation/initial infectious particle (inoculum). The therapeutic index of each virus was determined as the ratio: replication rate on HepG2 cells/replication rate on hepatocytes. The higher the ratio the better the selectivity of the virus toward the tumoral cells.

Primary hepatocytes were grown in Basal Hepatic cell medium supplemented with 1.6% Additives for hepatocyte culture medium. HepG2 were seeded in 12 well plate at 4 E+05 cells/well and incubated for 24 H at 37° C. with 5% $CO_2$. Before infection the culture medium was removed and 70 pfu/well of virus in either PBS for hepatocytes or FCS-supplemented PBS for HepG2 were added to each well. The infected cells were incubated 30 min at 37° C. with 5% $CO_2$ and then 1.5 mL/well of culture medium were added. Plates were incubated at 37° C. with 5% $CO_2$ for 3 days and then stored at −80° C. Then, plates were thawed and wells sonicated 30 seconds with 40% of amplitude before titration on Vero cells.

Replication Rate in Normal Human Hepatocytes:

Normal hepatocytes were chosen to monitor the capacity of COPTG19384 in normal human cells as these primary cells can be obtained regularly directly from donors. In those cells, the COP WT spread well with a replication rate of more than 50,000 (FIG. 20A). In other words, each initial infection viral particle produced about 50,000 new viruses. In the case of the two recombinant double deleted viruses (i.e. VVTG17137 and COPTG19384), this replication rate was dramatically reduced to 5 to 15 according to the virus or batch of virus (FIG. 20A). This last result indicates that the attenuated replication toward normal cells brings along by the two deletions was conserved between VVTG17137 and COPTG19384.

Replication Rate in Tumoral Cells HepG2:

HepG2 cells were chosen to monitor the capacity of COPTG19384 to replicate in tumoral human cells as these cells are a malignant counterpart of normal hepatocytes. In those cells, the five viruses tested had a quite similar replication rate reaching about 100,000 new viruses whatever the initial virus tested (FIG. 20B). Therefore, the double deletion in both VVTG17137 and COPTG19384 and vectorization of transgenes did not impair their capacity to replicate in malignant cells.

Therapeutic Index:

As illustrated in FIG. 20C, the calculated index is only two for COP WT indicating a poor selectivity of the COP WT for the tumoral versus normal cells. In contrary, for both VVTG17137 and COPTG19384 (and for both lots of virus tested) this index varies from 8.2 E+03 to 1.8 E+04. This confirms that the two recombinant viruses have the same good selectivity toward tumoral versus normal cells.

These results demonstrated that COPTG19384 and VVTG17137 have a very similar replicative properties on both tumoral and healthy cells. Compared to COP WT, their replication on tumoral Hep G2 is similar whereas it is highly impaired on healthy hepatocytes. Therefore, the deletion of the two genes (J2R and 140 restricts the replication of the deleted virus to the multiplying cells (i.e. with high nucleotide pool) including the tumoral cells. Since the transgenes expression and the replication are tightly linked, COPTG19384 is an efficient vector for the selective delivery of therapeutic proteins into tumour.

Replication Assays on CEF and LoVo:

Replication of COPTG19384 was evaluated on CEF (producer cells) isolated from 11 or 12 day-old embryonated Specific Pathogens Free eggs (Charles Rivers) and on a tumoral human cell line (LoVo; ATCC® CCL-229™). CEF and LoVo cells were prepared in suspension and infected at MOI of $10^{-3}$ for CEF and $10^{-2}$ for LoVo (three wells per cells and per time point). After different times of incubation, Viral titration was done on Vero cells (CCL-81™). COPTG19384 replication was compared to the one of VVTG17137 as benchmark. The results show that the replication of COPTG19384 and VVTG17137 were similar in both CEF and LoVo (data not shown).

Replication Assays on Reconstructed Human Skin:

Replication of COPTG19384 was also evaluated on reconstructed human skin (T-Skin™/Human Full Thickness Skin Model). Thirty-six T-Skin™ samples obtained from (EPISKIN SA) were cultured in 6-well plates and maintained in fresh culture medium. VVTG17137 and COPTG19384 were distributed into each well (in triplicate) in order to obtain the attended final concentration (i.e. $10^1$ to $10^5$ pfu/well). A negative control corresponding of medium without virus was also tested (Mock). Plates were incubated at 37° C. with 5% $CO_2$ for 7 days and T-Skin™ samples were collected and cut in two pieces. Infectious titer was determined on one of the two pieces using Vero cells for virus titration. FIG. 21 shows that COPTG19384 replicates in reconstructed skin to the same extent as the benchmark VVTG17137 supporting the fact that the vectorization of both GM-CSF and 4-E03 mAb did not modify the replication behavior of the vaccinia virus on the human reconstructed skin.

Oncolytic Assay

Oncolytic activity is representative of the lytic activity of the tested viral samples on tumor cells. It was assessed by quantification of cell viability after 5 days of incubation on different tumor cell lines: the human colorectal adenocarcinoma cell line LoVo (ATCC® CCL-229™), the human pancreatic tumor cell line MIA PaCa-2 (ATCC® CCL-1420) and the human hepatocarcinoma cell line HepG2 (ATCC® HB-8065™). COPTG19384 oncolytic activities were compared to the ones of VVTG17137 as benchmark. A negative control corresponding of uninfected cells was also plated (Mock infected cells).

Cells were prepared, distributed in Eppendorf tubes (1.2× $10^6$ cells/tube) before being infected with the virus at a MOI of $10^{-6}$ to $10^{-2}$ and incubated 30 min at 37° C. Appropriate complete medium was added to Eppendorf tube and an aliquote of this suspension was added in each well (in triplicate) in 6-well plate containing 2 mL of appropriate complete medium. Plates were incubated at 37° C. with 5% $CO_2$ for 5 days and cell viability was determined on Vi-Cell counter. Results were expressed as a percentage of the cell viability of mock infected cells. The cell supernatants were also recovered for the determination of concentration of 4-E03 mAb and GM-CSF. FIG. 22 shows that the oncolytic activities of COPTG19384 and VVTG17137 are similar in the three tumoral cell lines assessed.

Level of Expression of Transgenes

The levels of expression of both 4-E03 monoclonal antibody and GM-CSF were measured by ELISA (as described in Example 6) in culture supernatants of HepG2 and LoVo cells recovered after oncolysis activity determination (5 day of infection at variable MOI).

The levels of expression of 4-E03 and GM-CSF were also measured by ELISA (see example 6) in supernatants of 5 cell lines cultured in the following conditions, respectively the human gastric carcinoma cell line Hs-746 T (ATCC® HTB- 135T™), the human ovarian tumor cell line SK-OV-3 (ATCC® HTB-77T™), the human pancreatic tumor cell line MIA PaCa-2 (ATCC® CCL-1420), the human colorectal adenocarcinoma cell line LoVo (ATCC® CCL-229™) and the human colorectal carcinoma cell line HCT 116 (ATCC® CCL-247T™). Each cell line was cultured (in triplicate) in 6-well plates ($10^6$ cells/well) and incubated at 37° C. with 5% $CO_2$ for 24 h before being infected at MOI 0.05. The cell supernatants were then recovered 48 h post infection for the determination of concentration of 4-E03 mAb and GM-CSF. As expected, the MOI, time post-infection and cell line are important parameters that impact the level of transgenes expression in supernatants of infected cells. FIG. 23A shows that a rather permissive to replication (HepG2) and a rather resistant (LoVo) tumoral cell line, when infected by COPTG19384, are able to produce in their culture supernatants approximately the same amount of 4-E03 mAb and GM-CSF. However, the maximum of expression for the HepG2 is reached at a MOI 10-fold lower than for the LoVo. Moreover, for the 5 tumoral cell lines tested, the expression of transgenes was above 0.1 and above 1 μg/mL for 4-E03 mAb and GM-CSF respectively (FIG. 23B). To be noted that the ELISA assay used to measure the concentration of 4-E03 mAb uses the antigen CTLA4 to capture the antibody. In other words, the antibodies measured by this assay are at least partially functional (i.e. recognizing their antigen, the other functions of the antibody are carried by the Fc part), Purification of 4-E03 mAb and Glycosylation Profile Analysis In order to produce a rather large quantity of 4-E03 mAb from infected cells, 15 F175 flasks containing ~4.7 $10^7$ Mia-PACA cells/flask were infected at MOI 0.01 with COPTG19384 and incubated 72 h. MIA Paca-2 cell culture supernatant (about 450 mL containing 670 μg of mAb 4-E03 as determined by ELISA) was harvested, pooled and clarified by centrifugation to remove most of the cell debris. Cleared supernatants were filtered on 0.2 μm filters and 2 mM EDTA (to inhibit putative metal proteases) and 20 mM Tris pH7.5 (to raise the pH) were added. The filtered supernatant was then passed through a protA Hitrap column (GE healthcare, ref 17-5079-01). The column was transferred and connected to Purifier FPLC (GE Healthcare) and purification program (THM/ProtA 1 mL injection loop frac bleu) was applied. The eluted fractions containing the mAb were loaded on NuPage Bis-Tris gels 4-12% (Thermo NP0323) after addition of Laemlli buffer (Biorad) containing or not beta-mercaptoethanol for reduction or not of the disulphide bonds of the mAb. The gel was stained with InstantBlue (Expedeon, ISB1L). Three fractions corresponding to the main peak of elution were pooled and, after dialysis against the formulation buffer, the antibody concentration was determined by absorbance at 280 nm. The final concentration of the purified mAb was 0.29 mg/mL.

The first characterization was an assessment of chains assembly by electrophoresis in reducing and non-reducing conditions. In non-reducing conditions the 2 light and 2 heavy chains assemble to form the native and functional antibody. It appeared that the purified 4-E03 from infected MIA PaCa-2 and the recombinantly produced 4-E03 have an undistinguishable electrophoresis profiles in both reducing and non-reducing conditions. In other words, the purified 4-E03 from infected MIA PaCa-2 has the expected ratio of light and heavy chains and is correctly assembled into 2 light and 2 heavy chains heterotetramer. The presence of this heterotetramer was also confirmed by mass spectrometry. The purified mAb was subject to mass spectrometry for glycosylation analysis. Briefly, the mAb was digested, or not, with IdeS protease that cleave specifically the IgG at the hinge (resulting in F(ab')$_2$ and Fc parts). The masses of the whole antibody or Fc parts that carry the N-glycosylation were determined and each mass was fitted with a theoretical mass calculated from the primary sequence of Fc and a glycosylation pattern. The glycosylation profile of 4-E03 mAb purified from infected MIA PaCa-2 was compared to the one of the recombinantly produced and purified 4-E03 and MabThera as benchmark for human IgG1 used in clinic. The results show that the glycosylation profiles of 4-E03 produced from infected MIA PaCa2 had a glycosylation profile different from the two antibody references with a majority of G0F (88%) whereas both recombinant 4-E03 and MabThera have a similar glycosylation profile with the typical G0F, G1F and G2F distribution. However, MIA PaCa-2 was suspected to be the cause of the low G1F and G2F species in the purified 4-E03 mAb due to a low level of Beta-1,4-Galactosyltransferase 1 transcript which could be the cause of the lack of galactosyl moiety (and therefore a lack of G1f and G2F) of the 4-E03 expressed in MIA PaCa-2.

The same type of purification followed by mass analysis was also performed from permeate recovered during the purification of the COPTG19384 produced on CEF. The results show that the glycosylation profiles of 4-E03 from infected CEF was very similar to the ones of MabThera or recombinant 4-E03. This latest result suggests that the glycosylation profile of the antibody is more impacted by the cell line used than by the infection itself.

4-E03 purified from the supernatant od infected MIA PaCa-2 cells (4-E03 TG) also exhibit the same binding characteristics as recombinantly produced 4-E03 by CHO (research batch) or HEK (tox batch) cells (FIGS. 24 and 25). This was demonstrated by ELISA (described in Example 1) to test the binding to recombinant (FIG. 24A) human and (FIG. 24B) cynomolgus CTLA-4 protein. A FACS analysis where the binding to (FIG. 25A) human and (FIG. 25B) cynomolgus CTLA-4 expressing cells was tested (see Example 1 and 2) confirmed similar cross-reactivity and binding affinities for the different 4-E03 batches.

GM-CSF Glycosylation and Disulphide Bonds Pattern

In order to investigate the glycosylation pattern and the presence of some disulphide bonds, different human tumoral cells line were infected by COPTG19384 and their supernatants were analysed by the same WB method. MIA-Paca-2, LoVo, HepG2 and HCT116 cells were infected at MOI 0.01 and incubated 72 h in culture medium without serum. The culture supernatants were harvested, clarified by centrifugation and then filtered on 0.2 μm filter. The supernatants were stored at −20° C. until analysis. They were treated by addition 8 μl of Rapid PNGase F Buffer 5× followed by an incubation at 75° C. for 5 minutes. One μL of PNGase F was then added (to remove N-glycans from glycoprotein) and the mixture incubated 30 minutes at 50° C. Twenty-five μL of samples were prepared by addition of 5 μL Laemmli buffer×4 with or without beta-mercaptoethanol (reducing and non-reducing conditions) before being submitted to western blotting. Immune complexes were detected using the Amersham ECL Prime Western Blotting and chemiluminescence was recorded with a Molecular Imager Chemi-DOC XRS (Biorad).

GM-CSF from infected HCT116, LoVo and MIA PaCa-2 displayed the same pattern of glycosylation whereas the GM-CSF produced by infected HepG2 migrated as a non-N-glycosylated molecule. These results indicate that the GM-CSF produced by the COPTG19384 infected human tumoral cells has the expected post-translational modifications (i.e. disulphide bonds and N-glycosylation). However, these modifications probably vary depending of the tumour cell lines used for infection and their specific metabolic status.

Example 8: Pharmacokinetics after Intratumoral Injections of COPTG19384

Kinetic of Expression in Tumor and Bloodstream of Anti-CTLA4 Antibodies, GM-CSF and Viruses after Intratumoral (i.t.) Injection of Vaccinia Viruses in a LoVo Xenografted Model.

Protocol $5 \times 10^6$ cells LoVo cells were implanted in right flank of Swiss nude mice (Charles River, France). After about two weeks when the tumours volume reached ~120 mm³, the mice were randomized and split in 6 groups of 15 animals.

Mice from group 1 received an i.t. administration of COPTG19384 at a dose of $1 \times 10^4$ pfu/mouse at D0 (first day of treatment).

Mice from group 2 received an i.t. administration of COPTG19384 at a dose of $1 \times 10^5$ pfu/mouse at D0.

Mice from group 3 received an i.t. administration of VVTG17137 at a dose of $1 \times 10^4$ pfu/mouse at D0.

Mice from group 4 received an i.t. administration of VVTG17137 at a dose of $1 \times 10^5$ pfu/mouse at D0.

Mice from group 5 received an intraperitoneal (i.p.) administration of 4-E03 at a dose of 3 mg/kg at D0.

Mice from group 6 received an i.p. administration of Ipilimumab (Yervoy) at a dose of 3 mg/kg at D0.

Tumour and blood from 3 animals were collected at days 1, 3, 6, 10 and 20. Tumors were weighted and homogenized for immediate processing. One quarter of the homogenized tumours was collected for virus titration and the remaining suspension was centrifuged and supernatants were stored at −20° C. until use. Blood was split in two parts: one was added to heparin tube (25 IU/100 µL of blood) for titration assay and frozen at −80° C. until analysis. Clarified sera were produced from the other part and stored at −20° C. until use. Virus titer was determined in tumor and blood samples by titration on Vero cells.

Kinetic of Virus Replication in LoVo Model:

In the LoVo model, where COPTG19384 was injected once at two doses ($1 \times 10^4$ or $1 \times 10^5$ pfu) the virus replication was monitored and compared to the one of VVTG17137 injected in same conditions. The results displayed in FIG. 26 show an important dispersion of the three values of virus titers measured for each time point. Anyway, the results show also that both viruses and at both doses replicate in the tumour and maintain a rather high titer/g of tumour from day 3 to up to 20 days after the injection. There is no obvious difference of virus titer, for a given time point, between the two doses of virus or between the two viruses used. Interestingly, all the blood samples were negative for virus detection excepted one sample (VVTG17137, dose: $1 \times 10^7$ pfu at Day 10) for which only 13 pfu/mL were detected (data not shown).

Together these results indicate that, after one i.t. injection of either $1 \times 10^4$ or $1 \times 10^5$ pfu, the virus' replication was maintained in LoVo tumours for at least 20 days with a barely detectable presence in the blood stream. It has to be noted that the LoVo xenografted model is very favourable to the virus replication as it uses permissive human tumour cells and Swiss nude mice that have a severely impaired immune system with, therefore, a limited anti-viral activity.

Kinetic of Transgenes Expression in LoVo Model:

As expected, the kinetic of transgenes expression in tumour followed kinetic of virus replication with a maximum concentration (Cmax) at days 6 or 10 for both 4-E03 mAb (FIG. 27A) and GM-CSF (FIG. 27B). In the case of the single injection of 4-E03 mAb (or Ipilimumab), the Cmax in tumour and blood were observed at the first time point (day 1) and the thereafter measured concentrations of mAb were in accordance with the pharmacokinetic of a human IgG1 in mouse (FIG. 28).

Moreover, the concentrations of 4-E03 into the tumour at Cmax and thereafter (i.e. from 6-10 to 20 days after injection) was around 10-fold higher following COPTG19384 treatment (for both doses) than after a single injection of 4-E03 mAb at a therapeutic dose of 3 mg/kg (FIG. 27A). In contrast, the concentration in blood of the mAb after COPTG19384 treatment was always inferior to those measured after i.p. injection of 3 mg/kg of 4-E03 (FIG. 28A). This result indicates that vectorization of mAb allows to reach high concentration into the tumour without exceeding or even reaching the blood concentration obtained at therapeutic dosing of mAb.

The kinetic of expression of GM-CSF after COPTG19384 treatment follows the one observed with 4-E03 (FIG. 27B). Interestingly, the levels of GM-CSF measured into the tumour are below the level of 4-E03 for the same samples, although in vitro LoVo infected by COPTG19384 express about two-fold more GM-CSF than 4-E03. The blood concentrations of GM-CSF were also very low compared to the 4-E03 ones (FIG. 28B). This result is in accordance with the in vivo half-life of GM-CSF that is very short compared to the one of a human IgG1.

These results indicate that the vectorized antibodies and GM-CSF are expressed mainly in the tumour after i.t. injection of COPTG19384 with a minimal systemic exposure. These results confirm that vectorization is particularly suitable for transgenes with toxicological (e.g. anti-CTLA4) or pharmacokinetic (e.g. GM-CSF) issues.

Kinetic of Expression in Tumor and Bloodstream of Anti-CTLA4 Antibodies, GM-CSF and Viruses after Intratumoral Injection of Vaccinia Viruses in a CT26 Syngenic Model Evaluation of the viral activities in the CT26 immuno-competent murine model requires the generation of several surrogate viruses encoding a murine anti-mCTLA4 with or without the murine GM-CSF:

COPTG19407 is a Vaccinia virus (Copenhagen strain) containing an expression cassette encoding the heavy chain of the murine m5-B07 IgG2 (SEQ ID NO: 63) under p7.5 promoter at the J2R locus, and an expression cassette encoding the light chain of the m5-B07 (SEQ ID NO: 62) under p7.5 promoter and murine GM-CSF (SEQ ID NO: 58) under pSE/L promoter at the I4L locus.

COPTG19421 is a Vaccinia virus (Copenhagen strain) containing an expression cassette encoding the m5-B07 heavy chain under p7.5 promoter at the J2R locus, and an expression cassette encoding the light chain of the m5-B07 under p7.5 promoter at the I4L locus.

VVTG18058, used as benchmark, is a Vaccinia virus (Copenhagen strain) deleted in J2R and I4L genes, without any transgene ("empty" virus).

These vaccinia viruses were generated as for the human counterparts by two successive homologous recombinations at J2R (TK) and then I4L (RR) loci following the process described in example 6. The ELISA method to quantify the m5-B07 antibody and mGM-CSF was similar to that described above (example 6, "expression of transgene" for 4-E03 and GM-CSF) except that murine CTLA4-Fc antigen was used to capture the murine antibody and Quantikine ELISA kit Mouse GM-CSF (R&D Systems) was used to quantify mGM-CSF. Oncolytic activity of these virus was also evaluated in various cell lines (one sarcoma: MCA205 and two colon carcinoma CT26 and MC38) and found similar to the one of VVTG18058 showing that vectorization of the murine antibody with or without the mGM-CSF did not impact the oncolytic abilities of the vaccinia virus (data not shown).

Protocol: CT26 cells ($2 \times 10^5$ cells) were implanted in right flank of Balb/c mice (Charles River, France). After about one week when the tumours volume reached 25-50 mm$^3$ the mice were randomized and split in 3 groups of 20 animals (groups 1 to 3) and one group 4 of 10 animals. Tumor and blood were collected and treated as described for the LoVo model except that they were collected at days 1, 4, 8 and 10 for the first 3 groups and day 1 for the group 4.

- Mice from group 1 received an i.t. administration of VVTG18058 at a dose of $1 \times 10^7$ pfu/mouse at D0, D2 and D4.
- Mice from group 2 received an i.t. administration of COPTG19407 at a dose of $1 \times 10^7$ pfu/mouse at D0, D2 and D4.
- Mice from group 3 received an i.t. administration of COPTG19421 at a dose of $1 \times 10^7$ pfu/mouse at D0, D2 and D4.
- Mice from group 4 received an i.p. administration of m5-1307 at a dose of 3 mg/kg at D0.

Kinetic of Virus Replication in CT26 Model:

In the CT26 model, where two surrogate viruses were injected thrice ($1 \times 10^7$ pfu/injection) the virus replication was monitored and compared to the one of VVTG18058 injected in the same conditions. The results displayed in FIG. 29 show, as for the LoVo model, an important dispersion of the three values of virus titers measured for each time point. However, the titers for the three viruses were maintained over the time and up to 10 days, indicating that the two transgenes did not impact the virus clearance or replication, at least in this window of time. No virus infectious particle was detected in any of the blood samples (data not shown).

Kinetic of Transgenes Expression in CT26 Model

Like for the LoVo model, the transgenes expression into the tumour mirrored the virus replication. In other words, the m5-B07 antibody (FIG. 30A) and mGM-CSF (FIG. 30B) were detected in the tumour at a rather constant level over the 10 days of the monitoring.

Figure 30A:
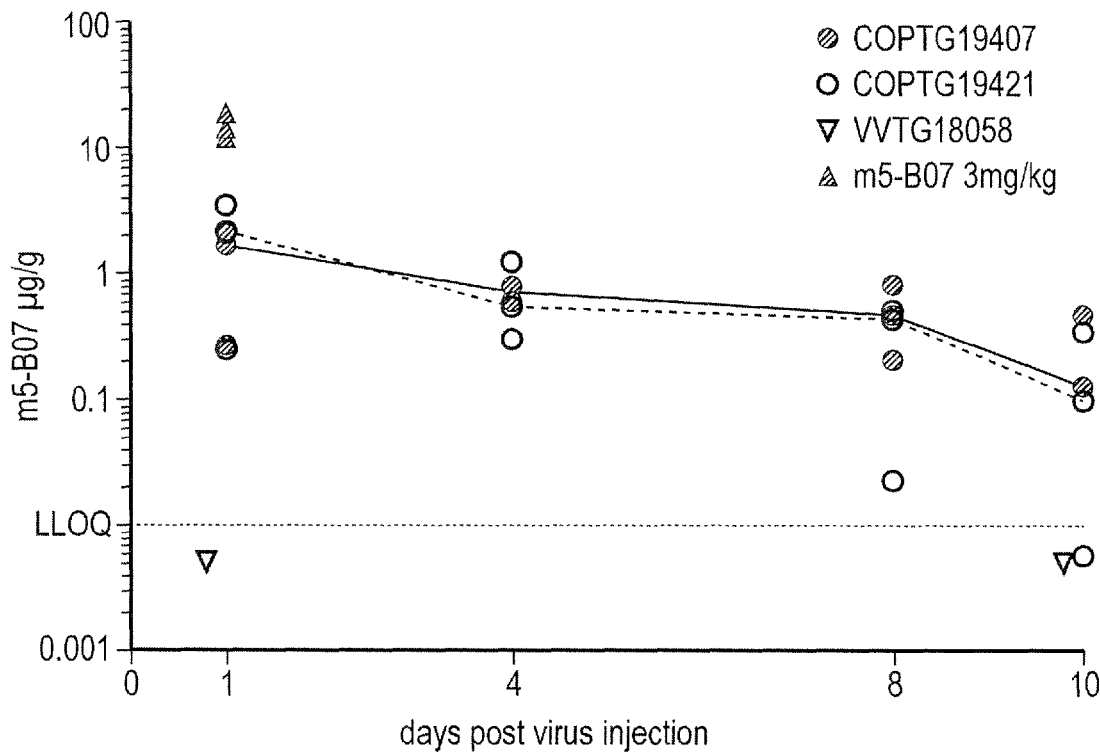

In the case of the monoclonal antibody, the Cmax reached after either COPTG19421 or COPTG19407 injections were about 10-fold lower than the Cmax observed with a single i.p. injection of the m5-B07 antibody at 3 mg/mL (FIG. 30A). In the serum, the difference was even more pronounced with a circulating concentration of m5-B07~100-fold lower after virus treatments versus m5-B07 injection at 3 mg/kg (FIG. 31).

Figure 30B:
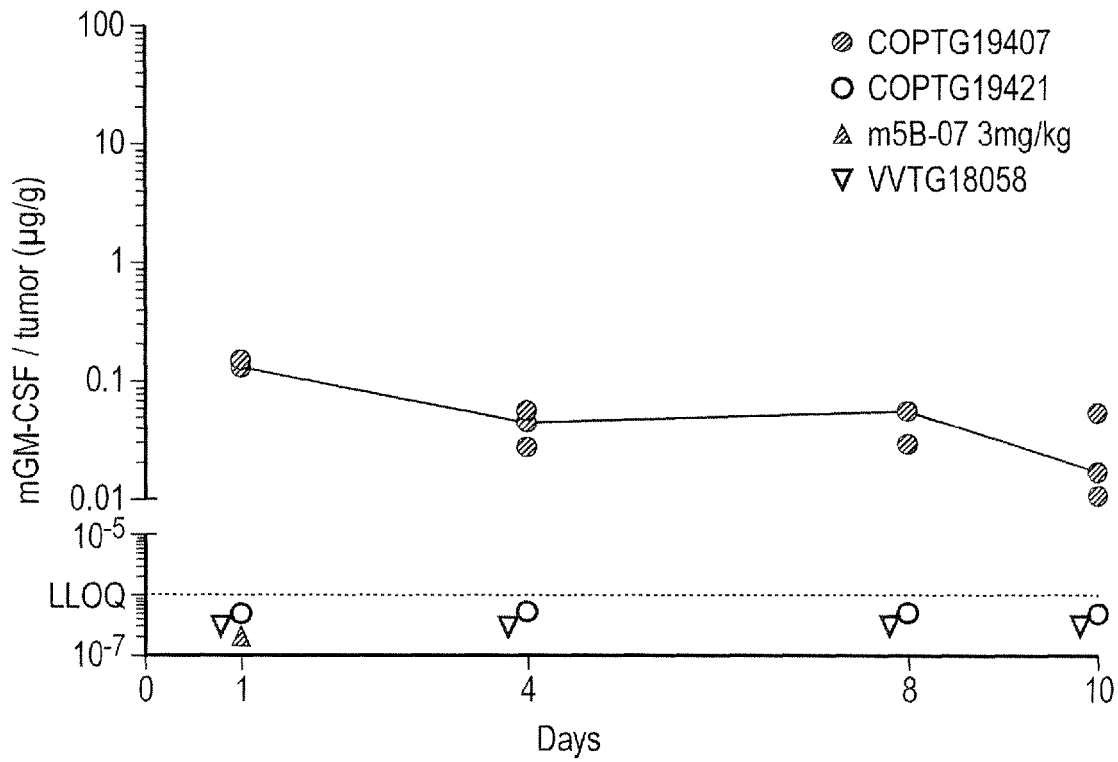

For GM-CSF, only the treatment by COPTG19407 yielded to measurable concentration of mGM-CSF in CT26 tumors indicating that the measured cytokine had a recombinant, rather than endogen, origin. Like in LoVo model, the mGM-CSF concentrations measured in tumour were lower than the ones of m5-B07 (FIG. 30B). Moreover, the mGM-CSF produced by the tumour was not detectable in any of sera sample probably due to a short half-life of the molecule that preclude any systemic accumulation.

Example 9: Antitumoral Activity Studies

COPTG19347 is a Vaccinia virus (Copenhagen strain) deleted in J2R and I4L genes and encoding a whole murine antibody (namely m5-B07, heavy and light chain) recognizing the murine CTLA4 antigen. COPTG19421 versus COPTG19347 expressed both m5-B07 but under different promoters: namely p7.5K and pH5.R respectively. Quantification of m5-B07 was assessed in supernatants of infected cells reaching about 1 μg/mL in infected CT26 at MOI $10^{-1}$ to about 4 μg/mL in infected MCA205 cells at MOI $10^{-2}$. The higher expression in MCA205 versus CT26 was observed also for mGM-CSF in the culture supernatant of cells infected by COPTG19407 (data not shown).

Antitumoral Activity in Mice Bearing CT26 Model in Combination with Anti-PD1 Protocol:

CT26 cells ($2 \times 10^5$ cells) were implanted in right flank of Balb/c mice (Charles River, France). When tumors reached a volume of 25-50 mm$^3$, the mice were randomized in five groups of ten animals. Briefly, the mice were treated by three i.t. administrations, 2 days apart, of virus followed of i.p. treatment of murine anti-PD1 (RMP1-14 BioXcell) twice a week for three weeks. More specifically,

- Mice from group 1 received vehicle;
- Mice from group 2 received an i.t. administration of $1 \times 10^7$ pfu of COPTG19347 at D0, D2 and D4;
- Mice from group 3 received an i.t. administration of $1 \times 10^7$ pfu of COPTG19347 at D0, D2 and D4 and i.p. intraperitoneal administration of 250 μg/mice of RMP1-14, at D7, D11, D14, D18 and D22;
- Mice from group 4 received an i.p. administration of 250 μg/mice of RMP1-14, at D7, D11, D14, D18 and D22;
- Mice from group 5 received an i.t. administration of $1 \times 10^7$ pfu of VVTG18058 at D0, D2 and D4.

Tumor dimensions were measured twice a week with calipers and their volumes calculated using the formula $(\pi/6)(\text{length} \times \text{width}^2)$. The animals were euthanized when their tumor volume reached 2000 mm$^3$.

Antitumoral Activities of COPTG19347 in CT26 Model

Figure 32A:
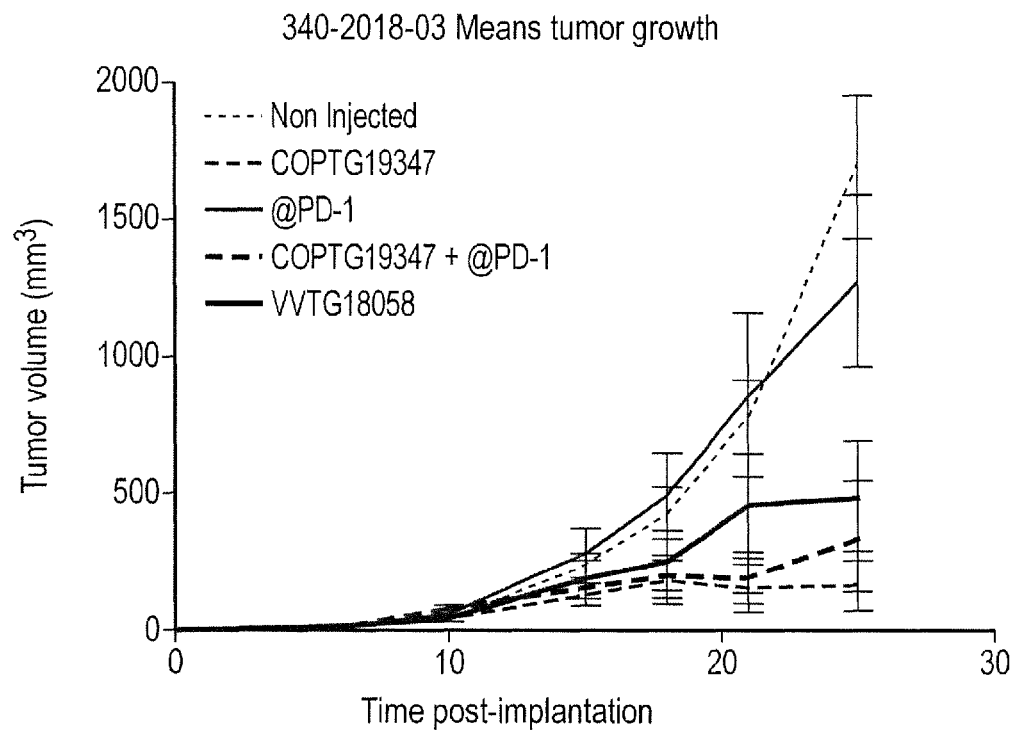
Figure 32B:
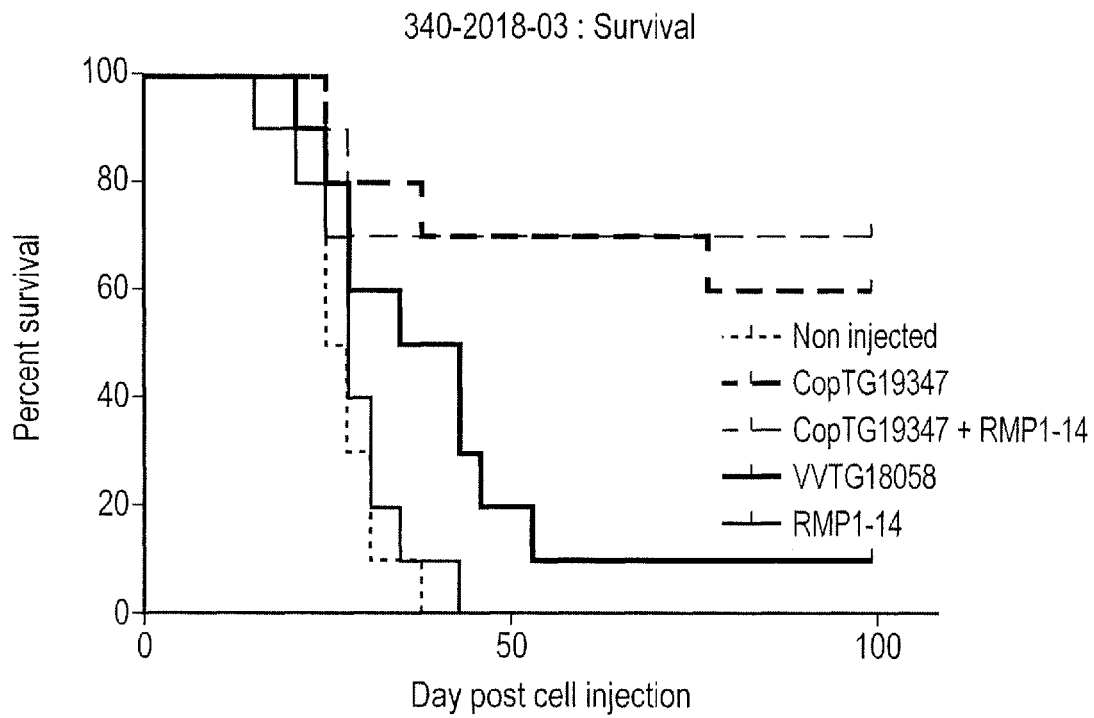

As illustrated in FIG. 32, COPTG19347 treatment yielded not only to tumour growth inhibition (FIG. 32A) but also to tumour regression that finally translate into tumour free mice that survive up to 100 days (FIG. 32B). Treatment with COPTG19347 yielded to 60% tumour free mice at day 100. The co-treatment with anti-PD-1 antibody did not improve significantly the tumour growth inhibition or the percentage of long surviving mice (about 70% tumour free mice at day 100). In comparison, RPMI-14 treatment did not provide any anti-tumor effect (same behavior as non-treated mice (all dead within the first 40 days) whereas VVTG18058 had a poor activity (about 10% tumour free mice at day 100).

Dose-Effect Evaluation in CT26 Model:

The three surrogate viruses were compared (different promoter to drive m5-B07 and with or without m-GM-CSF) and a dose escalation of COPTG19407 versus VVTG18058 was performed ($7.5 \times 10^4$, $7.5 \times 10^5$ or $7.5 \times 10^6$ pfu). The experimental conditions were exactly as the ones described above except that the co-treatment with anti-PD1 was omitted.

The results of two independent experiments demonstrated clearly that the three viruses tested COPTG19407, COPTG19421 and COPTG19347 had a strong anti-tumoral activity at the dose of $7.5 \times 10^6$ pfu. This confirm that neither the mGM-CSF encoded in COPTG19407 nor the use of a weakest promoter in COPTG19421 and COPTG19407 did impair the anti-tumoral activity of the armed viruses. At the highest dose tested (i.e. $7.5 \times 10^6$ pfu), the number of tumor free mice at 80 days were between 5/10 and 7/10 depending of the virus and of experiment versus 0/10 for the mice treated with the empty virus as summarized in the following Table.

TABLE 6

Effect of the surrogate viruses COPTG19407, COPTG19421 and COPTG19347 on the tumor growth after i.t. injections

| Virus name | TK locus | RR locus | Dose (pfu) | Number of tumor free mice at D 100 |
|---|---|---|---|---|
| COPTG19407 | p7.5K -HC* | p7.5K -LC*; pSE/L-GM-CSF | $7.5 \times 10^6$ | 7/10 |
| COPTG19421 | p7.5K -HC* | p7.5K -LC* | $7.5 \times 10^6$ | 5/10 |
| COPTG19347 | pH5.R -HC* | pH5.R -LC* | $7.5 \times 10^6$ | 7/10 |
| VVTG18058 | — | — | $7.5 \times 10^6$ | 0/10 |
| Mock | | | — | 0/10 |

*HC and LC stand for heavy and light chain of m5-B07 murine anti-mCTLA4 antibody respectively Moreover the dose escalation performed with both the "empty" virus (VVTG18058) and the COPTG19384 surrogate (COPTG19407) demonstrated that even at a relative low dose ($7.5 \times 10^4$ pfu) the antibody expressing virus had still some clear antitumoral activities with 4/10 and 2/10 tumor free mice at 80-98 days versus 0/10 for the treatment with VVTG18058 at the same low dose as shown in the following Table.

TABLE 7 effect of the dose of COPTG19407 or VVTG18058 on the tumor growth after i.t. injections

| Virus name | TK locus | RR locus | Dose (pfu) | Number of tumor free mice at D 100 |
|---|---|---|---|---|
| COPTG19407 | p7.5K -HC* | p7.5K -LC*; pSE/L-GM-CSF | $7.5 \times 10^6$ | 7/10 |
| | | | $7.5 \times 10^5$ | 8/10 |
| | | | $7.5 \times 10^4$ | 4/10 |
| VVTG18058 | — | — | $7.5 \times 10^6$ | 0/10 |
| | | | $7.5 \times 10^5$ | 0/10 |
| | | | $7.5 \times 10^4$ | 0/10 |

*HC and LC stand for heavy and light chain of m5-B07 murine anti-mCTLA4 antibody respectively A compilation of survival data (global survival plot compiled from two independent studies) are presented in FIG. 33. A statistical analysis, using logrank test, has been performed to figure out if there were significant differences between survival of each group.

Anti-Tumoral Activity of COPTG19407 Compared to the Combination of VVTG18058 Plus m5-B07

CT26 tumor-bearing mice were set up as described previously (Example 5). Briefly, CT26 cells were injected s.c. into Balb/C mice. The treatment of the mice was started when tumors reached approx. 100 mm³. Mice were then injected at D0, D2 and D5 with COPTG19407 ($8.5 \times 10^6$ pfu i.t.), VVTG18058 ($8.5 \times 10^6$ pfu i.t.), m5-B07 (10 mg/kg i.p.) or the combination of VVTG18058 ($8.5 \times 10^6$ pfu i.t.) plus m5-B07 (10 mg/kg i.p.). Tumor dimensions were then measured twice a week and mice were euthanized when tumors reached 2000 mm³. As shown in FIGS. 34A to 34D, tumor growth was significantly inhibited when mice were treated with the virus COPTG19407 expressing anti-CTLA-4 and GM-CSF whereas the combination of the unarmed virus plus anti-CTLA4 m5-B07 did not result in improved therapy compared to single agent use. In the groups treated with only m5-B07, only virus VVTG18058 or the combination of both m5-B07 and VVTG18058, only 20% of the mice survived after day 70 (FIG. 34E). In contrast, 90% of the mice survived more than 100 days after administration of COPTG19407 demonstrating the potency of the vectorization strategy.

Antitumoral Activity of VVTK RR-Encoding Anti-CTLA-4 and GM-CSF in Mice Bearing A20 Subcutaneous Murine B-Cell Lymphoma The A20 cell line is a BALB/c B cell lymphoma line derived from a spontaneous reticulum cell neoplasm found in an old BALB/cAnN mouse (ATCC TIB-208™).

Protocol (1):

Tumors were induced by subcutaneous injection of $5 \times 10^6$ of A20 cells into the right flank of female Balb/cN mice (Charles River, France). When tumors reached a mean volume of 95 mm³, 50 mice were randomized into 5 groups of ten animals.

Mice from group 1 received an i.t. administration of vehicle at D0, D2 and D4,

Mice from group 2 received an i.t. administration of VVTG18058 at a dose of $4.75 \times 10^6$ pfu at D0, D2 and D4, Mice from group 3 received an i.t. administration of COPTG19407 at a dose of $4.75 \times 10^6$ pfu at D0, D2 and D4, Mice from group 4 received an i.p. administration of anti-PD-1 antibody at a dose of 250 μg at D7, D10, D14, D17, D21 and D24, Mice from group 5 received an i.t. administration of COPTG19407 at a dose of $4.75 \times 10^6$ pfu at D0, D2 and D4 combined with an i.p. administration of anti-PD-1 antibody at a dose of 250 μg at D7, D10, D14, D17, D21 and D24.

Antitumoral Activity:

The tumor volumes of all animals was monitored throughout the study. The anti-tumoral activity of treatments is based on the evaluation of the criteria of tumor doubling time, tumor growth delay and tumor growth inhibition (T/C %).

Tumor doubling time was similar for Groups 1, 2 and 4 ranging from 5.14 days (Group 1) to 6.37 days (Group 2). For Group 3, the tumor doubling time could not be precisely calculated since the tumors did not grow exponentially indicating an increased efficacy of treatment, compared to Groups 1, 2 and 4. Similarly, tumor doubling time was calculated using only one animal in Group 5. 9 out of 10 mice in Group 3 had tumors which regressed on D15 and did not grow substantially in volume from D25 until the end of the study on D64. On D64, tumor volumes of these 9 mice ranged from 4 mm³ (technical limit of tumor detection) to 59.77 mm³. Similarly, in Group 5, tumors regressed in 9 mice following the start of treatment, to reach values ranging from 7.24 to 63.21 mm³ at the end of the study on D64. As it can be seen in FIG. 35 presenting the individual tumor volume curves of each group of treatment (Groups 1 to 5 corresponding to FIG. 35A to E), tumors did not grow in animals of groups 3 and 5 receiving COPTG19407 confirming the strong anti-tumor activity of the antibody-expressing virus with or without anti-PD1.

The tumor growth delay was calculated by estimating the time taken for tumors to reach a mean target volume of 300 mm³. The results were similar to those obtained with tumor doubling time, since this parameter could only be calculated for tumors that reached the target volume of 300 mm³, which was not the case for the majority of animals in Groups 3 and 5. Groups 1, 2 and 4 had mean tumor growth delays of 16, 21 and 17 days respectively which were not significantly different to each other. In addition, Groups 3 (n=2) had a mean tumor delay of 14 days, indicated that the tumors that did grow in this group, grew at the same rate as Groups 1, 2 and 4 however these tumors did actually regress in both animals. In comparison, the single tumor in Group 5 (n=1) which grew had a significantly (p≤0.0026) longer tumor growth delay than all other groups, of 43 days.

Tumor growth inhibition (T/C %) was calculated by comparing the median tumor volume of the vehicle treated Group 1 with the other treatment groups. Group 2 had an optimum T/C % of 34% on D22, indicating a transient marginal anti-tumoral activity but this value increased up to 71% by D31. Moderate anti-tumoral activity (10-30% T/C %) was observed in Group 4. In comparison, Groups 3 and 5 both showed marked anti-tumoral activity (T/C % less than 10%) from D27 to D31 (last calculable value of T/C %).

FIG. 36 illustrates the mean tumor volume curves on BALB/cN mice bearing subcutaneous A20 tumors demonstrating the dramatic effect of the anti-CTLA4 and Gm-CSF expressing virus COPTG19407 with or without anti-PD1 on tumor growth.

Protocol (2):

Tumors were induced by subcutaneous injection of $5 \times 10^6$ of A20 cells into the right flank of female BALB/cN mice. When tumors reached a mean volume of 80-100 mm$^3$, 90 animals were randomized into 9 groups of 10 animals.

Mice from group 1 received an i.t. administration of vehicle at D0, D2 and D4

Mice from group 2 received an i.p. administration of anti-PD-1 antibody at a dose of 250 µg/mouse/injection at D0, D4, D7, D10, D14 and D17

Mice from group 3 received an i.p. administration of isotype at a dose of 250 µg/mouse/injection at D0, D4, D7, D10, D14 and D17

Mice from group 4 received an i.t. administration of VVTG18058 at a dose of $1 \times 10^5$ pfu at D0, D2 and D4

Mice from group 5 received an i.t. administration of VVTG18058 at a dose of $1 \times 10^5$ pfu at D0, D2 and D4, and an i.p. administration of isotype at a dose of 250 µg/mouse/injection at D0, D4, D7, D10, D14 and D17

Mice from group 6 received an i.t. administration of VVTG18058 at a dose of $1 \times 10^5$ pfu at D0, D2 and D4 and an i.p. administration of anti-PD-1 antibody at a dose of 250 µg/mouse/injection at D0, D4, D7, D10, D14 and D17

Mice from group 7 received an i.t. administration of COPTG19407 at a dose of $1 \times 10^5$ pfu at D0, D2 and D4

Mice from group 8 received an i.t. administration of COPTG19407 at a dose of $1 \times 10^5$ pfu at D0, D2 and D4, combined with an i.p. administration of isotype at a dose of 250 µg/mouse/injection at D0, D4, D7, D10, D14, D17 and D24.

Mice from group 9 received an i.t. administration of COPTG19407 at a dose of $1 \times 10^5$ pfu at D0, D2 and D4, combined with an i.p. administration of anti-PD-1 antibody at a dose of 250 µg/mouse/injection at D0, D4, D7, D10, D14 and D17.

Antitumoral Activity:

The dose of COPTG19407 is suboptimal and demonstrated a mild antitumoral activity similar to the one of the anti-PD-1 treatment in terms of tumor volume and mice survival.

In contrast, the combination of COPTG19407 with anti-PD-1 showed an strong anti-tumoral activity resulting in a small tumor volume compared to the other groups as showed in FIG. 37A (approximately 290 mm$^3$ at Day 36 compared to approximatively 630 mm$^3$ and 750 mm$^3$ at day 24 for mice receiving anti-PD-1 alone or COPTG19407 alone respectively), and a much better survival of the animals as presented in FIG. 37B (7 animals still alive at Day 57 in group 9 versus only two or one in groups 2 or 7 respectively).

Antitumoral Activity Study of VVTK-RR-Encoding Anti-CTLA-4 and GM-CSF in Mice Bearing C38 Subcutaneous Colon Tumor Cells C38 is a murine colon adenocarcinoma originating from the American Type Culture Collection (ATCC CRL-2779™).

Protocol:

Tumors fragments (30-50 mg) were subcutaneously implanted into the right flank of female C57BL/6J mice (Janvier, France). When tumors reached a mean volume of approximately 60 mm$^3$, 50 animals were randomized into five groups of ten animals.

Mice from group 1 received an i.t. administration of vehicle at D0, D2 and D4,

Mice from group 2 received an i.t. administration of an VVTG18058 at a dose of $4.75 \times 10^6$ pfu at D0, D2 and D4, Mice from group 3 received an i.t. administration of COPTG19407 at a dose of $4.75 \times 10^6$ pfu at D0, D2 and D4, Mice from group 4 received an i.p. administration of the murine anti-PD-1 antibody at a dose of 250 µg at D7, D10, D14, D17, D21 and D24, Mice from group 5 received an i.t. administration of COPTG19407 at a dose of $4.75 \times 10^6$ pfu at D0, D2 and D4 combined with an i.p. administration of anti-PD-1 antibody at a dose of 250 µg at D7, D10, D14, D17, D21 and D24.

Antitumoral Activity:

As before, the tumor volumes of all animals was monitored throughout the study. Tumor doubling time was similar for Groups 1 and 2 at approximately 6.7 days. Group 4 (n=5) had a longer tumor doubling time (10.4 days) but there were no significant differences between groups. For Groups 3 and 5, the tumor doubling time was calculable but with fewer animals (n=2) since the majority of tumors on mice in these groups did not grow exponentially indicating an increased efficacy of treatment, compared to Groups 1, 2 and 4. As it can be seen from FIG. 38, 8 out of 10 mice in Group 3 had tumors which regressed from D15 and did not grow substantially in volume, with five mice having no detectable tumors at the end of the study on D61. Similarly, in Group 5, tumors regressed in 8 mice following the start of treatment, to reach values ranging from 0 (n=2) to 47.82 mm$^3$ at the end of the study on D61.

The tumor growth delay was calculated by estimating the time taken for tumors to reach a mean target volume of 300 mm$^3$. The results were similar to those obtained with tumor doubling time, since this parameter could only be calculated for tumors that reached the target volume of 300 mm$^3$, which was not the case for the majority of animals in Groups 3 and 5. There were no significant differences between groups. Groups 1, 2 and 4 (n=5) had mean tumor growth delays of 23 to 27 days respectively. In addition, Groups 3 (n=2) and 5 (n=3) had mean growth delays of 18 and 24 days, respectively. This indicated that the tumors that did grow in these two groups, grew at similar rates as those in Groups 1, 2 and 4.

Tumor growth inhibition (T/C %) was calculated by comparing the median tumor volume of the vehicle treated Group 1 with the other treatment groups. Group 2 did not show any tumor growth inhibition, since T/C % s remained above 100% for the duration of the study. In comparison, Groups 3, 4 and 5 all showed marked anti-tumoral activity (T/C % less than 10%) from D31 (Group 3 only) to D42 (last calculable value of T/C %). FIG. 39 illustrates the mean tumor volume curves of C57BL/6 mice bearing subcutaneous C38 tumors demonstrating the dramatic effect of the anti-CTLA4/GM-CSF expressing virus COPTG19407 with or without anti-PD1 on tumor growth.

Antitumoral Activity Study of VVTK-RR-Encoding Anti-CTLA-4 and GM-CSF in Mice Bearing EMT6 Subcutaneous Breast Tumor Cells EMT6 is a murine breast carcinoma originating from the ATTC (ATCC CRL-2755™)

Protocol:

Tumors were induced by subcutaneous injection of $1×10^6$ EMT6 cells in female BALB/cByJ mice (Charles River, France). When tumors reached a mean volume of approximately 51 mm$^3$, fifty mice were randomized by individual tumor volume into five groups of ten animals.

- Mice from group 1 received an i.t. administration of vehicle at D0, D2 and D4,
- Mice from group 2 received an i.t. administration of VVTG18058 at a dose of $4.75×10^6$ pfu at D0, D2 and D4,
- Mice from group 3 received an i.t. administration of COPTG19407 at a dose of $4.75×10^6$ pfu at D0, D2 and D4,
- Mice from group 4 received an i.p. administration of anti-PD-1 antibody at a dose of 250 µg at D7, D10, D14, D17, D21 and D24,
- Mice from group 5 received an i.t. administration of COPTG19407 at a dose of $4.75×10^6$ pfu at D0, D2 and D4 combined with an i.p. administration of anti-PD-1 antibody at a dose of 250 µg at D7, D10, D14, D17, D21 and D24.

The tumor volumes of all animals was monitored throughout the study by evaluating the criteria of tumor doubling time, tumor growth delay and tumor growth inhibition (T/C %).

Antitumoral Activity:

Tumor doubling time was similar for Groups 1, 2 and 4 at approximately 5.4 days. For Group 3, the tumor doubling time could not be calculated since the majority of tumors did not grow exponentially indicating an increased efficacy of treatment, compared to Groups 1, 2 and 4. A similar effect was observed in Group 5, where only one animal was used for the calculation of tumor doubling time. As can be seen on the graphs of individual tumor volume (FIG. 40), 8 out of 10 mice in Group 3 had tumors which regressed from D15 and did not grow substantially in volume, with seven mice having no detectable tumors at the end of the study on D61. Similarly, in Group 5, tumors regressed in 9 mice following the start of treatment, to reach values ranging from 0 (n=8) to 13.24 mm$^3$ at the end of the study on D56.

The tumor growth delay was calculated by estimating the time taken for tumors to reach a mean target volume of 200 mm$^3$. The results were similar to those obtained with tumor doubling time, since this parameter could only be calculated for tumors that reached the target volume of 200 mm$^3$, which was not the case for the majority of animals in Groups 3 and 5. Groups 1, 2 and 4 had mean tumor growth delays of approximately 19 days. In addition, Groups 3 and 5 (n=2 for both groups) had mean growth delays of 24 and 12 days, respectively. This indicated that the tumors that did grow in these two groups, grew at similar rates as those in Groups 1, 2 and 4. There were no significant differences between groups.

Tumor growth inhibition (T/C %) was calculated by comparing the median tumor volume of the vehicle treated Group 1 with the other treatment groups. Group 2 showed transient marginal tumor growth inhibition on D28 but increased to 79% on D31. Group 4 showed no anti-tumoral activity, with a T/C %>60% for the duration of the study. In comparison, Groups 3 and 5 both showed marked antitumoral activity (T/C % less than 10%) from D24 to D31 (last calculable value of T/C %).

FIG. 41 illustrates the mean tumor volume curves on BALB/cByJ mice bearing subcutaneous EMT6 tumors demonstrating the dramatic effect of the anti-CTLA4/GM-CSF expressing virus COPTG19407 with or without anti-PD1 on tumor growth.

CT26 Rechallenge

Balb/c mice challenged with CT26 tumor cells who survived after treatment with $10^4$, $10^5$ or $10^6$ pfu of COPTG19421 or $10^6$ pfu of COPTG19407 were rechallenged with CT26 tumor cells or challenged with Renca cells (renal adenocarcinoma cells: control), in order to study if a specific antitumoral immune response was raised.

TABLE 8

Effect of the rechallenge with CT26 tumor cells or challenge with Renca tumor cells on the number of tumor free mice

| Group | Tumor free/Total mice |
|---|---|
| CT26 control naïve | 0/5 |
| VVTG18058 $10^5$ + CT26 rechallenge | 0/1 |
| COPTG19421 $10^6$ + CT26 rechallenge | 3/3 |
| COPTG19421 $10^6$ + RenCa challenge | 0/2 |
| COPTG19407 $10^4$ + CT26 rechallenge | 1/1 |
| COPTG19407 $10^4$ + RenCa challenge | 0/1 |
| COPTG19407 $10^5$ + CT26 rechallenge | 1/2 |
| COPTG19407 $10^5$ + RenCa challenge | 0/2 |
| COPTG19407 $10^6$ + CT26 rechallenge | 2/4 |
| COPTG19407 $10^6$ + RenCa challenge | 0/3 |

Results presented in table 8 show that 0/8 mice having received COPTG19421 or COPTG19407 were tumor free after RenCa challenge, while 7/10 mice having received COPTG19421 or COPTG19407 were tumor free after CT26 rechallenge. This indicates that COPTG19421 and COPTG19407 raised a specific immune memory against CT26 cells.

The invention claimed is:

1. An antibody molecule that specifically binds to CTLA-4, wherein the antibody molecule comprises the 6 CDRs having VH-CDR1 of SEQ ID NO: 15, the VH-CDR2 of SEQ ID NO: 16, the VH-CDR3 of SEQ ID NO: 17, the VL-CDR1 of SEQ ID NO: 10, the VL-CDR2 of SEQ ID NO: 18, and the VL-CDR3 of SEQ ID NO: 19, or comprises the 6 CDRs having VH-CDR1 of SEQ ID NO: 22, the VH-CDR2 of SEQ ID NO: 23, the VH-CDR3 of SEQ ID NO: 24, the VL-CDR1 of SEQ ID NO: 10, the VL-CDR2 of SEQ ID NO: 25, and the VL-CDR3 of SEQ ID NO: 26.

2. The antibody molecule according to claim 1, which has improved depleting effect on CTLA-4 positive or CTLA-4 and CD4 positive cells compared to ipilimumab and/or which has improved depleting effect on Tregs compared to ipilimumab.

3. The antibody molecule according to claim 1, which is considered as having improved depleting effect on CTLA-4 positive cells, CD4 positive cells and/or Tregs compared to ipilimumab if it gives an improved depletion in:

(i) an in vitro ADCC test which is performed using an NK-92 cell line stably transfected to express the CD16-158V allele together with GFP, wherein the ADCC test comprises the following consecutive steps:

1) CTLA-4 positive cells, CD4 positive cells or Tregs as target cells are isolated from peripheral blood of healthy donors;
2) The target cells are then stimulated with CD3/CD28 and rhIL-2;
3) the target cells are then pre-incubated with the antibody molecule and are then mixed with NK cells;
4) The target cells are then incubated in RPMI 1640+ L-alanyl-L-glutamine dipeptide medium containing HEPES buffer, sodium pyruvate and FBS low IgG;
5) lysis is determined by flow cytometry;
6) steps 1-5 are repeated, or performed in parallel, with ipilimumab used instead of the antibody molecule in step 3; and
7) the results of the lysis for the antibody molecule are compared to the results of the lysis for ipilimumab, and an improved lysis for the antibody molecule compared to ipilimumab demonstrates that the antibody molecule has improved depleting effect on CTLA-4 positive cells, CD4 positive cells and/or Tregs; and/or (ii) an in vivo test in a PBMC-NOG/SCID model, wherein the in vivo test comprises the following consecutive steps:

1) Human PBMCs are isolated, washed and resuspended in sterile PBS;
2) NOG mice are injected intravenously (i.v.) with cell suspension from step 1);
3) the spleens from the NOG mice are isolated and rendered into a single cell suspension;
4) The cell suspension from step 3) is resuspended in sterile PBS;
5) SCID mice are injected intraperitoneally (i.p.) with suspension from step 4;
6) the SCID mice are then treated with either the antibody molecule, ipilimumab or an isotype control monoclonal antibody;
7) the intraperitoneal fluid of the treated SCID mice is collected;
8) human T cell subsets are identified and quantified by FACS using following markers: CD45, CD4, CD8, CD25, and/or CD127;
9) The results from identification and quantification of the T cell subsets from the mice treated with the antibody molecule is compared to the results from identification and quantification of the T cell subsets from the mice treated with ipilimumab and to the results from identification and quantification of the T cell subsets from the mice treated with isotype control monoclonal antibody, and a lower number of CTLA-4 positive cells, CD4 positive cells and/or Tregs in the intraperitoneal fluid from mice treated with the antibody molecule to be tested compared to the number of CTLA-4 positive cells, CD4 positive cells and/or Tregs in the intraperitoneal fluid from mice treated with ipilimumab demonstrates that the antibody molecule has improved depleting effect on CTLA-4 positive cells, CD4 positive cells and/or Tregs compared to ipilimumab.

4. The antibody molecule according to claim 1, wherein the antibody molecule comprises a variable heavy chain of SEQ ID NO: 20 and/or a variable light chain of SEQ ID NO: 21, or wherein the antibody comprises a variable heavy chain of SEQ ID NO: 27 and/or a variable light chain of SEQ ID NO: 28, or wherein the antibody molecule comprises the heavy chain constant region SEQ ID NO: 43 and/or the light chain constant region SEQ ID NO: 44.

5. The antibody molecule according to claim 1, wherein the antibody molecule is selected from the group consisting of a monoclonal antibody, a full-size antibody, a chimeric antibody, a single chain antibody, a Fab, a Fv, an scFv, a Fab', and a F(ab')$_2$.

6. The antibody molecule according to claim 1, which binds to human CTLA-4 (hCTLA-4) and/or to cynomolgus monkey CTLA-4 (cmCTLA-4) and/or to murine CTLA-4 (mCTLA-4), or which does not bind to human CD28.

7. The antibody molecule according to claim 1, wherein the antibody molecule is selected from the group consisting of a human IgG antibody, a humanized IgG antibody and an IgG antibody of human origin.

8. A pharmaceutical composition comprising or consisting of the antibody molecule as defined in claim 1, and optionally a pharmaceutically acceptable diluent, carrier, vehicle and/or excipient.

* * * * *

UNITED STATES PATENT AND TRADEMARK OFFICE
CERTIFICATE OF CORRECTION

| | | |
|---|---|---|
| PATENT NO. | : 12,291,569 B2 | Page 1 of 1 |
| APPLICATION NO. | : 17/272740 | |
| DATED | : May 6, 2025 | |
| INVENTOR(S) | : Frendéus et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1018 days.

Signed and Sealed this
Thirtieth Day of September, 2025

John A. Squires
*Director of the United States Patent and Trademark Office*

SEQUENCE LISTING

```
<160> NUMBER OF SEQ ID NOS: 63

<210> SEQ ID NO 1
<211> LENGTH: 14
<212> TYPE: PRT
<213> ORGANISM: Homo sapiens
<220> FEATURE:
<221> NAME/KEY: MISC_FEATURE
```

```
<222> LOCATION: (2)..(2)
<223> OTHER INFORMATION: X in position 2 is S or K
<220> FEATURE:
<221> NAME/KEY: MISC_FEATURE
<222> LOCATION: (3)..(3)
<223> OTHER INFORMATION: X in position 3 is D, S or A
<220> FEATURE:
<221> NAME/KEY: MISC_FEATURE
<222> LOCATION: (5)..(5)
<223> OTHER INFORMATION: X in position 5 is Y, S or A
<220> FEATURE:
<221> NAME/KEY: MISC_FEATURE
<222> LOCATION: (7)..(7)
<223> OTHER INFORMATION: X in position 7 is S or N
<220> FEATURE:
<221> NAME/KEY: MISC_FEATURE
<222> LOCATION: (9)..(9)
<223> OTHER INFORMATION: X in position 9 is V or I

<400> SEQUENCE: 1

Phe Xaa Xaa Tyr Xaa Met Xaa Trp Xaa Arg Gln Ala Pro Gly
1               5                   10

<210> SEQ ID NO 2
<211> LENGTH: 14
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X in position 3 is D or S
<220> FEATURE:
<221> NAME/KEY: MISC_FEATURE
<222> LOCATION: (5)..(5)
<223> OTHER INFORMATION: X in position 3 is Y, S or A
<220> FEATURE:
<221> NAME/KEY: MISC_FEATURE
<222> LOCATION: (7)..(7)
<223> OTHER INFORMATION: X in position 3 is S or N

<400> SEQUENCE: 2

Phe Ser Xaa Tyr Xaa Met Xaa Trp Val Arg Gln Ala Pro Gly
1               5                   10

<210> SEQ ID NO 3
<211> LENGTH: 14
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X in position 3 is D or S
<220> FEATURE:
<221> NAME/KEY: MISC_FEATURE
<222> LOCATION: (5)..(5)
<223> OTHER INFORMATION: X in position 5 is Y or S
<220> FEATURE:
<221> NAME/KEY: MISC_FEATURE
<222> LOCATION: (7)..(7)
<223> OTHER INFORMATION: X in position 5 is S or N

<400> SEQUENCE: 3

Phe Ser Xaa Tyr Xaa Met Xaa Trp Val Arg Gln Ala Pro Gly
1               5                   10

<210> SEQ ID NO 4
<211> LENGTH: 19
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X in position 2 is G or A
```

```
<220> FEATURE:
<221> NAME/KEY: MISC_FEATURE
<222> LOCATION: (5)..(5)
<223> OTHER INFORMATION: X in position 5 is W, G or N
<220> FEATURE:
<221> NAME/KEY: MISC_FEATURE
<222> LOCATION: (6)..(6)
<223> OTHER INFORMATION: X in position 6 is S or T
<220> FEATURE:
<221> NAME/KEY: MISC_FEATURE
<222> LOCATION: (7)..(7)
<223> OTHER INFORMATION: X in position 7 is S or G
<220> FEATURE:
<221> NAME/KEY: MISC_FEATURE
<222> LOCATION: (8)..(8)
<223> OTHER INFORMATION: X in position 8 is R or G
<220> FEATURE:
<221> NAME/KEY: MISC_FEATURE
<222> LOCATION: (9)..(9)
<223> OTHER INFORMATION: X in position 9 is D, S or Y
<220> FEATURE:
<221> NAME/KEY: MISC_FEATURE
<222> LOCATION: (10)..(10)
<223> OTHER INFORMATION: X in position 10 is K, T or I
<220> FEATURE:
<221> NAME/KEY: MISC_FEATURE
<222> LOCATION: (11)..(11)
<223> OTHER INFORMATION: X in position 11 is G, Y, H or D
<220> FEATURE:
<221> NAME/KEY: MISC_FEATURE
<222> LOCATION: (12)..(12)
<223> OTHER INFORMATION: X in position 12 is Y or F

<400> SEQUENCE: 4

Ser Xaa Ile Ser Xaa Xaa Xaa Xaa Xaa Xaa Xaa Ala Asp Ser Val
1               5                   10                  15

Lys Gly Arg

<210> SEQ ID NO 5
<211> LENGTH: 19
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X in position 2 is G or A
<220> FEATURE:
<221> NAME/KEY: MISC_FEATURE
<222> LOCATION: (5)..(5)
<223> OTHER INFORMATION: X in position 5 is W, G or N
<220> FEATURE:
<221> NAME/KEY: MISC_FEATURE
<222> LOCATION: (6)..(6)
<223> OTHER INFORMATION: X in position 6 is S or T
<220> FEATURE:
<221> NAME/KEY: MISC_FEATURE
<222> LOCATION: (7)..(7)
<223> OTHER INFORMATION: X in position 7 is S or G
<220> FEATURE:
<221> NAME/KEY: MISC_FEATURE
<222> LOCATION: (8)..(8)
<223> OTHER INFORMATION: X in position 8 is R or G
<220> FEATURE:
<221> NAME/KEY: MISC_FEATURE
<222> LOCATION: (9)..(9)
<223> OTHER INFORMATION: X in position 9 is D, S or Y
<220> FEATURE:
<221> NAME/KEY: MISC_FEATURE
<222> LOCATION: (10)..(10)
<223> OTHER INFORMATION: X in position 10 is K, T or I
<220> FEATURE:
<221> NAME/KEY: MISC_FEATURE
<222> LOCATION: (11)..(11)
<223> OTHER INFORMATION: X in position 11 is G, Y, H or D

<400> SEQUENCE: 5
```

```
Ser Xaa Ile Ser Xaa Xaa Xaa Xaa Xaa Xaa Tyr Ala Asp Ser Val
1               5                   10                  15

Lys Gly Arg

<210> SEQ ID NO 6
<211> LENGTH: 19
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X in position 2 is G or A
<220> FEATURE:
<221> NAME/KEY: MISC_FEATURE
<222> LOCATION: (5)..(5)
<223> OTHER INFORMATION: X in position 5 is W or G
<220> FEATURE:
<221> NAME/KEY: MISC_FEATURE
<222> LOCATION: (7)..(7)
<223> OTHER INFORMATION: X in position 7 is S or G
<220> FEATURE:
<221> NAME/KEY: MISC_FEATURE
<222> LOCATION: (8)..(8)
<223> OTHER INFORMATION: X in position 8 is R or G
<220> FEATURE:
<221> NAME/KEY: MISC_FEATURE
<222> LOCATION: (9)..(9)
<223> OTHER INFORMATION: X in position 9 is D or S
<220> FEATURE:
<221> NAME/KEY: MISC_FEATURE
<222> LOCATION: (10)..(10)
<223> OTHER INFORMATION: X in position 10 is K or T
<220> FEATURE:
<221> NAME/KEY: MISC_FEATURE
<222> LOCATION: (11)..(11)
<223> OTHER INFORMATION: X in position 11 is G or Y, H or D

<400> SEQUENCE: 6

Ser Xaa Ile Ser Xaa Ser Xaa Xaa Xaa Xaa Tyr Ala Asp Ser Val
1               5                   10                  15

Lys Gly Arg

<210> SEQ ID NO 7
<211> LENGTH: 15
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X in position 1 is T or A
<220> FEATURE:
<221> NAME/KEY: MISC_FEATURE
<222> LOCATION: (2)..(2)
<223> OTHER INFORMATION: X in position 2 is T or R
<220> FEATURE:
<221> NAME/KEY: MISC_FEATURE
<222> LOCATION: (3)..(3)
<223> OTHER INFORMATION: X in position 3 is D, Y or L
<220> FEATURE:
<221> NAME/KEY: MISC_FEATURE
<222> LOCATION: (4)..(4)
<223> OTHER INFORMATION: X in position 4 is L, R, S, or G
<220> FEATURE:
<221> NAME/KEY: MISC_FEATURE
<222> LOCATION: (5)..(5)
<223> OTHER INFORMATION: X in position 5 is A, V, S or Y
<220> FEATURE:
<221> NAME/KEY: MISC_FEATURE
<222> LOCATION: (6)..(6)
<223> OTHER INFORMATION: X in position 6 is R, E, G or S
<220> FEATURE:
<221> NAME/KEY: MISC_FEATURE
<222> LOCATION: (7)..(7)
```

```
<223> OTHER INFORMATION: X in position 6 is Y, M, L or G
<220> FEATURE:
<221> NAME/KEY: MISC_FEATURE
<222> LOCATION: (8)..(8)
<223> OTHER INFORMATION: X in position 8 is N, H, Y or none
<220> FEATURE:
<221> NAME/KEY: MISC_FEATURE
<222> LOCATION: (9)..(9)
<223> OTHER INFORMATION: X in position 9 is Q, D or none
<220> FEATURE:
<221> NAME/KEY: MISC_FEATURE
<222> LOCATION: (10)..(10)
<223> OTHER INFORMATION: X in position 10 is W, A, D or none
<220> FEATURE:
<221> NAME/KEY: MISC_FEATURE
<222> LOCATION: (11)..(11)
<223> OTHER INFORMATION: X in position 11 is L, F, R or none
<220> FEATURE:
<221> NAME/KEY: MISC_FEATURE
<222> LOCATION: (12)..(12)
<223> OTHER INFORMATION: X in position 12 is A, D, G or none
<220> FEATURE:
<221> NAME/KEY: MISC_FEATURE
<222> LOCATION: (13)..(13)
<223> OTHER INFORMATION: X in position 13 is D, I, M or none
<220> FEATURE:
<221> NAME/KEY: MISC_FEATURE
<222> LOCATION: (14)..(14)
<223> OTHER INFORMATION: X in position 14 is D or none
<220> FEATURE:
<221> NAME/KEY: MISC_FEATURE
<222> LOCATION: (15)..(15)
<223> OTHER INFORMATION: X in position 15 is V or none

<400> SEQUENCE: 7

Xaa Xaa Xaa Xaa Xaa Xaa Xaa Xaa Xaa Xaa Xaa Xaa Xaa Xaa Xaa
1               5                   10                  15

<210> SEQ ID NO 8
<211> LENGTH: 13
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X in position 1 is T or A
<220> FEATURE:
<221> NAME/KEY: MISC_FEATURE
<222> LOCATION: (2)..(2)
<223> OTHER INFORMATION: X in position 2 is T or R
<220> FEATURE:
<221> NAME/KEY: MISC_FEATURE
<222> LOCATION: (4)..(4)
<223> OTHER INFORMATION: X in position 4 is L or R
<220> FEATURE:
<221> NAME/KEY: MISC_FEATURE
<222> LOCATION: (5)..(5)
<223> OTHER INFORMATION: X in position 5 is A or V
<220> FEATURE:
<221> NAME/KEY: MISC_FEATURE
<222> LOCATION: (6)..(6)
<223> OTHER INFORMATION: X in position 6 is R or E
<220> FEATURE:
<221> NAME/KEY: MISC_FEATURE
<222> LOCATION: (7)..(7)
<223> OTHER INFORMATION: X in position 7 is Y or M
<220> FEATURE:
<221> NAME/KEY: MISC_FEATURE
<222> LOCATION: (8)..(8)
<223> OTHER INFORMATION: X in position 8 is N or none
<220> FEATURE:
<221> NAME/KEY: MISC_FEATURE
<222> LOCATION: (9)..(9)
<223> OTHER INFORMATION: X in position 9 is Q or none
<220> FEATURE:
<221> NAME/KEY: MISC_FEATURE
<222> LOCATION: (10)..(10)
```

```
<223> OTHER INFORMATION: X in position 10 is W or none
<220> FEATURE:
<221> NAME/KEY: MISC_FEATURE
<222> LOCATION: (11)..(11)
<223> OTHER INFORMATION: X in position 11 is L or none
<220> FEATURE:
<221> NAME/KEY: MISC_FEATURE
<222> LOCATION: (12)..(12)
<223> OTHER INFORMATION: X in position 12 is A or none
<220> FEATURE:
<221> NAME/KEY: MISC_FEATURE
<222> LOCATION: (13)..(13)
<223> OTHER INFORMATION: X in position 13 is D or none

<400> SEQUENCE: 8

Xaa Xaa Asp Xaa Xaa Xaa Xaa Xaa Xaa Xaa Xaa Xaa Xaa
1               5                   10

<210> SEQ ID NO 9
<211> LENGTH: 15
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X in position 2 is T or S
<220> FEATURE:
<221> NAME/KEY: MISC_FEATURE
<222> LOCATION: (10)..(10)
<223> OTHER INFORMATION: X in position 10 is A or S
<220> FEATURE:
<221> NAME/KEY: MISC_FEATURE
<222> LOCATION: (11)..(11)
<223> OTHER INFORMATION: X in position 11 is G or N
<220> FEATURE:
<221> NAME/KEY: MISC_FEATURE
<222> LOCATION: (13)..(13)
<223> OTHER INFORMATION: X in position 13 is D or V
<220> FEATURE:
<221> NAME/KEY: MISC_FEATURE
<222> LOCATION: (14)..(14)
<223> OTHER INFORMATION: X in position 14i s V or Y
<220> FEATURE:
<221> NAME/KEY: MISC_FEATURE
<222> LOCATION: (15)..(15)
<223> OTHER INFORMATION: X in position 15 i s H or none

<400> SEQUENCE: 9

Cys Xaa Gly Ser Ser Ser Asn Ile Gly Xaa Xaa Tyr Xaa Xaa Xaa
1               5                   10                  15

<210> SEQ ID NO 10
<211> LENGTH: 15
<212> TYPE: PRT
<213> ORGANISM: Homo sapiens

<400> SEQUENCE: 10

Cys Thr Gly Ser Ser Ser Asn Ile Gly Ala Gly Tyr Asp Val His
1               5                   10                  15

<210> SEQ ID NO 11
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X in position 1 is G, R, or D
<220> FEATURE:
<221> NAME/KEY: MISC_FEATURE
<222> LOCATION: (3)..(3)
<223> OTHER INFORMATION: X in position 3 is D, N, or S
<220> FEATURE:
```

```
<221> NAME/KEY: MISC_FEATURE
<222> LOCATION: (4)..(4)
<223> OTHER INFORMATION: X in position 4 is N, Q or K

<400> SEQUENCE: 11

Xaa Asn Xaa Xaa Arg Pro Ser
1               5

<210> SEQ ID NO 12
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: X in position 1 is G or R
<220> FEATURE:
<221> NAME/KEY: MISC_FEATURE
<222> LOCATION: (3)..(3)
<223> OTHER INFORMATION: X in position 3 is D or N
<220> FEATURE:
<221> NAME/KEY: MISC_FEATURE
<222> LOCATION: (4)..(4)
<223> OTHER INFORMATION: X in position 3 is N or Q

<400> SEQUENCE: 12

Xaa Asn Xaa Xaa Arg Pro Ser
1               5

<210> SEQ ID NO 13
<211> LENGTH: 13
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: X in position 2 is A or Q
<220> FEATURE:
<221> NAME/KEY: MISC_FEATURE
<222> LOCATION: (3)..(3)
<223> OTHER INFORMATION: X in position 3 is V, A or S
<220> FEATURE:
<221> NAME/KEY: MISC_FEATURE
<222> LOCATION: (4)..(4)
<223> OTHER INFORMATION: X in position 4 is W or Y
<220> FEATURE:
<221> NAME/KEY: MISC_FEATURE
<222> LOCATION: (6)..(6)
<223> OTHER INFORMATION: X in position 6 is D or S
<220> FEATURE:
<221> NAME/KEY: MISC_FEATURE
<222> LOCATION: (9)..(9)
<223> OTHER INFORMATION: X in position 9 is N or S
<220> FEATURE:
<221> NAME/KEY: MISC_FEATURE
<222> LOCATION: (11)..(11)
<223> OTHER INFORMATION: X in position 11 is V, W or P
<220> FEATURE:
<221> NAME/KEY: MISC_FEATURE
<222> LOCATION: (13)..(13)
<223> OTHER INFORMATION: X in position 13 is V or none

<400> SEQUENCE: 13

Cys Xaa Xaa Xaa Asp Xaa Ser Leu Xaa Gly Xaa Val Xaa
1               5                   10

<210> SEQ ID NO 14
<211> LENGTH: 12
<212> TYPE: PRT
<213> ORGANISM: Homo sapiens
<220> FEATURE:
<221> NAME/KEY: MISC_FEATURE
<222> LOCATION: (3)..(3)
```

```
<223> OTHER INFORMATION: X in position 3 is V or A
<220> FEATURE:
<221> NAME/KEY: MISC_FEATURE
<222> LOCATION: (11)..(11)
<223> OTHER INFORMATION: X in position 11 is V or W

<400> SEQUENCE: 14

Cys Ala Xaa Trp Asp Asp Ser Leu Asn Gly Xaa Val
1               5                   10

<210> SEQ ID NO 15
<211> LENGTH: 14
<212> TYPE: PRT
<213> ORGANISM: Homo sapiens

<400> SEQUENCE: 15

Phe Ser Asp Tyr Tyr Met Ser Trp Val Arg Gln Ala Pro Gly
1               5                   10

<210> SEQ ID NO 16
<211> LENGTH: 19
<212> TYPE: PRT
<213> ORGANISM: Homo sapiens

<400> SEQUENCE: 16

Ser Gly Ile Ser Trp Ser Ser Arg Asp Lys Gly Tyr Ala Asp Ser Val
1               5                   10                  15

Lys Gly Arg

<210> SEQ ID NO 17
<211> LENGTH: 7
<212> TYPE: PRT
<213> ORGANISM: Homo sapiens

<400> SEQUENCE: 17

Thr Thr Asp Leu Ala Arg Tyr
1               5

<210> SEQ ID NO 18
<211> LENGTH: 7
<212> TYPE: PRT
<213> ORGANISM: Homo sapiens

<400> SEQUENCE: 18

Gly Asn Asp Asn Arg Pro Ser
1               5

<210> SEQ ID NO 19
<211> LENGTH: 12
<212> TYPE: PRT
<213> ORGANISM: Homo sapiens

<400> SEQUENCE: 19

Cys Ala Val Trp Asp Asp Ser Leu Asn Gly Val Val
1               5                   10

<210> SEQ ID NO 20
<211> LENGTH: 114
<212> TYPE: PRT
<213> ORGANISM: Homo sapiens

<400> SEQUENCE: 20

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Ser Trp Ser Ser Arg Asp Lys Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Asp Leu Ala Arg Tyr Trp Gly Gln Gly Thr Leu Val Thr Val
                100                 105                 110

Ser Ser

<210> SEQ ID NO 21
<211> LENGTH: 112
<212> TYPE: PRT
<213> ORGANISM: Homo sapiens

<400> SEQUENCE: 21

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly Gly
            20                  25                  30

Tyr Asp Val His Trp Tyr Gln Gln Leu Pro Gly Thr Ala Pro Lys Leu
        35                  40                  45

Leu Ile Tyr Gly Asn Asp Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Val Trp Asp Asp Ser
                85                  90                  95

Leu Asn Gly Val Val Phe Gly Gly Gly Thr Lys Leu Thr Val Leu Gly
                100                 105                 110

<210> SEQ ID NO 22
<211> LENGTH: 14
<212> TYPE: PRT
<213> ORGANISM: Homo sapiens

<400> SEQUENCE: 22

Phe Ser Ser Tyr Ser Met Asn Trp Val Arg Gln Ala Pro Gly
1               5                   10

<210> SEQ ID NO 23
<211> LENGTH: 19
<212> TYPE: PRT
<213> ORGANISM: Homo sapiens

<400> SEQUENCE: 23

Ser Ala Ile Ser Gly Ser Gly Gly Ser Thr Tyr Tyr Ala Asp Ser Val
1               5                   10                  15

Lys Gly Arg

<210> SEQ ID NO 24
<211> LENGTH: 13
<212> TYPE: PRT
<213> ORGANISM: Homo sapiens
```

```
<400> SEQUENCE: 24

Ala Arg Asp Arg Val Glu Met Asn Gln Trp Leu Ala Asp
1               5                   10

<210> SEQ ID NO 25
<211> LENGTH: 7
<212> TYPE: PRT
<213> ORGANISM: Homo sapiens

<400> SEQUENCE: 25

Arg Asn Asn Gln Arg Pro Ser
1               5

<210> SEQ ID NO 26
<211> LENGTH: 12
<212> TYPE: PRT
<213> ORGANISM: Homo sapiens

<400> SEQUENCE: 26

Cys Ala Ala Trp Asp Asp Ser Leu Asn Gly Trp Val
1               5                   10

<210> SEQ ID NO 27
<211> LENGTH: 120
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Glu Met Asn Gln Trp Leu Ala Asp Trp Gly Gln
            100                 105                 110

Gly Thr Leu Val Thr Val Ser Ser
        115                 120

<210> SEQ ID NO 28
<211> LENGTH: 112
<212> TYPE: PRT
<213> ORGANISM: Homo sapiens

<400> SEQUENCE: 28

Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Arg Asn Asn Gln Arg Pro Ser Gly Val Pro Asp Arg Phe
    50                  55                  60
```

```
Ser Gly Ser Lys Ser Gly Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                 85                  90                  95

Leu Asn Gly Trp Val Phe Gly Gly Gly Thr Lys Leu Thr Val Leu Gly
            100                 105                 110
```

<210> SEQ ID NO 29  
<211> LENGTH: 14  
<212> TYPE: PRT  
<213> ORGANISM: Homo sapiens

<400> SEQUENCE: 29

```
Phe Ser Ser Tyr Ala Met Ser Trp Val Arg Gln Ala Pro Gly
 1               5                  10
```

<210> SEQ ID NO 30  
<211> LENGTH: 19  
<212> TYPE: PRT  
<213> ORGANISM: Homo sapiens

<400> SEQUENCE: 30

```
Ser Gly Ile Ser Gly Ser Gly Gly Tyr Ile His Tyr Ala Asp Ser Val
 1               5                  10                  15

Lys Gly Arg
```

<210> SEQ ID NO 31  
<211> LENGTH: 13  
<212> TYPE: PRT  
<213> ORGANISM: Homo sapiens

<400> SEQUENCE: 31

```
Ala Thr Tyr Ser Ser Gly Leu His Asp Ala Phe Asp Ile
 1               5                  10
```

<210> SEQ ID NO 32  
<211> LENGTH: 7  
<212> TYPE: PRT  
<213> ORGANISM: Homo sapiens

<400> SEQUENCE: 32

```
Asp Asn Asn Lys Arg Pro Ser
 1               5
```

<210> SEQ ID NO 33  
<211> LENGTH: 120  
<212> TYPE: PRT  
<213> ORGANISM: Homo sapiens

<400> SEQUENCE: 33

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Gly Ile Ser Gly Ser Gly Gly Tyr Ile His Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
```

```
                    85                  90                  95

Ala Thr Tyr Ser Ser Gly Leu His Asp Ala Phe Asp Ile Trp Gly Gln
                100                 105                 110

Gly Thr Leu Val Thr Val Ser Ser
            115                 120

<210> SEQ ID NO 34
<211> LENGTH: 112
<212> TYPE: PRT
<213> ORGANISM: Homo sapiens

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Asn Lys Arg Pro Ser Gly Val Pro Asp Arg Phe
        50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Ser
                85                  90                  95

Leu Asn Gly Trp Val Phe Gly Gly Gly Thr Lys Leu Thr Val Leu Gly
            100                 105                 110

<210> SEQ ID NO 35
<211> LENGTH: 14
<212> TYPE: PRT
<213> ORGANISM: Homo sapiens

<400> SEQUENCE: 35

Phe Lys Ala Tyr Ser Met Ser Trp Ile Arg Gln Ala Pro Gly
1               5                   10

<210> SEQ ID NO 36
<211> LENGTH: 19
<212> TYPE: PRT
<213> ORGANISM: Homo sapiens

<400> SEQUENCE: 36

Ser Gly Ile Ser Asn Thr Gly Gly Ser Thr Asp Phe Ala Asp Ser Val
1               5                   10                  15

Lys Gly Arg

<210> SEQ ID NO 37
<211> LENGTH: 15
<212> TYPE: PRT
<213> ORGANISM: Homo sapiens

<400> SEQUENCE: 37

Ala Arg Leu Gly Tyr Ser Gly Tyr Asp Asp Arg Gly Met Asp Val
1               5                   10                  15

<210> SEQ ID NO 38
<211> LENGTH: 14
<212> TYPE: PRT
<213> ORGANISM: Homo sapiens

<400> SEQUENCE: 38
```

Cys Ser Gly Ser Ser Ser Asn Ile Gly Ser Asn Tyr Val Tyr
1               5                   10

<210> SEQ ID NO 39
<211> LENGTH: 7
<212> TYPE: PRT
<213> ORGANISM: Homo sapiens

<400> SEQUENCE: 39

Gly Asn Ser Asn Arg Pro Ser
1               5

<210> SEQ ID NO 40
<211> LENGTH: 13
<212> TYPE: PRT
<213> ORGANISM: Homo sapiens

<400> SEQUENCE: 40

Cys Gln Ser Tyr Asp Ser Ser Leu Ser Gly Pro Val Val
1               5                   10

<210> SEQ ID NO 41
<211> LENGTH: 122
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Ala Tyr
            20                  25                  30

Ser Met Ser Trp Ile Arg Gln Ala Pro Gly Lys Gly Leu Glu Trp Val
        35                  40                  45

Ser Gly Ile Ser Asn Thr Gly Gly Ser Thr Asp Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Leu Gly Tyr Ser Gly Tyr Asp Asp Arg Gly Met Asp Val Trp
            100                 105                 110

Gly Gln Gly Thr Leu Val Thr Val Ser Ser
        115                 120

<210> SEQ ID NO 42
<211> LENGTH: 112
<212> TYPE: PRT
<213> ORGANISM: Homo sapiens

<400> SEQUENCE: 42

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg

```
                65                  70                  75                  80
Ser Glu Asp Glu Ala Asp Tyr Tyr Cys Gln Ser Tyr Asp Ser Ser Leu
                    85                  90                  95

Ser Gly Pro Val Val Phe Gly Gly Thr Lys Leu Thr Val Leu Gly
            100                 105                 110

<210> SEQ ID NO 43
<211> LENGTH: 330
<212> TYPE: PRT
<213> ORGANISM: Homo sapiens

<400> SEQUENCE: 43

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 44
<211> LENGTH: 105
<212> TYPE: PRT
<213> ORGANISM: Homo sapiens

<400> SEQUENCE: 44

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 45
<211> LENGTH: 1335
<212> TYPE: DNA
<213> ORGANISM: Homo sapiens

<400> SEQUENCE: 45
gaggtgcagc tgttggagtc tgggggaggc ttggtacagc ctggggggtc cctgagactc      60
tcctgtgcag cctctggatt caccttcagt gactactaca tgagctgggt ccgccaggct     120
cccgggaagg ggctggagtg ggtctcaggc attagttgga gtagtcgtga caaaggctat     180
gcggactctg tgaagggccg tttcaccatc tccagagaca attccaagaa cacgctgtat     240
ctgcaaatga acagcctgag agccgaggac actgccgtgt attactgtac cacagatctc     300
gctaggtact ggggccaggg tacactggtc accgtgagct cagcctccac caagggccca     360
tcggtcttcc ccctggcacc ctcctccaag agcacctctg gggcacagc ggccctgggc     420 tgcctggtca aggactactt ccccgaaccg gtgacggtgt cgtggaactc aggcgccctg     480
accagcggcg tgcacacctt cccggctgtc ctacagtcct caggactcta ctccctcagc     540
agcgtggtga ccgtgccctc agcagcttgg gcacccaga cctacatctg caacgtgaat     600
cacaagccca gcaacaccaa ggtggacaag aaagttgagc ccaaatcttg tgacaaaact     660
cacacatgcc caccgtgccc agcacctgaa ctcctggggg gaccgtcagt cttcctcttc     720
cccccaaaac ccaaggacac cctcatgatc tcccggaccc ctgaggtcac atgcgtggtg     780
gtggacgtga gccacgaaga ccctgaggtc aagttcaact ggtacgtgga cggcgtggag     840
gtgcataatg ccaagacaaa gccgcgggag gagcagtaca acagcacgta ccgtgtggtc     900
agcgtcctca ccgtcctgca ccaggactgg ctgaatggca aggagtacaa gtgcaaggtc     960
tccaacaaag ccctcccagc ccccatcgag aaaaccatct ccaaagccaa agggcagccc    1020
cgagaaccac aggtgtacac cctgccccca tcccgggatg agctgaccaa gaaccaggtc    1080
agcctgacct gcctggtcaa aggcttctat cccagcgaca tcgccgtgga gtgggagagc    1140
aatgggcagc cggagaacaa ctacaagacc acgcctcccg tgctggactc cgacggctcc    1200
ttcttcctct acagcaagct caccgtggac aagagcaggt ggcagcaggg gaacgtcttc    1260
tcatgctccg tgatgcatga ggctctgcac aaccactaca cgcagaagag cctctccctg    1320
tctccgggta aatga                                                     1335

<210> SEQ ID NO 46
<211> LENGTH: 654
<212> TYPE: DNA
<213> ORGANISM: Homo sapiens

<400> SEQUENCE: 46
cagtctgtgc tgactcagcc accctcagcg tctgggaccc ccgggcagag ggtcaccatc     60
tcctgcactg ggagcagctc caacatcggg gcaggttatg atgtacactg gtatcagcag    120
ctcccaggaa cggcccccaa actcctcatc tatggtaatg ataaccggcc ctcaggggtc    180
cctgaccgat tctctggctc caagtctggc acctcagcct ccctggccat cagtgggctc    240
cggtccgagg atgaggctga ttattactgt gcagtatggg atgacagcct gaatggtgtg    300
gtattcggcg gaggaaccaa gctgaccgtc ctaggtcagc ccaaggctgc cccctcggtc    360
actctgttcc cgccctcctc tgaggagctt caagccaaca ggccacact ggtgtgtctc     420 ataagtgact tctacccggg agccgtgaca gtggcctgga aggcagatag cagccccgtc    480
aaggcgggag tggagaccac cacaccctcc aaacaaagca caacaagta cgcggccagc    540 agctatctga gcctgacgcc tgagcagtgg aagtcccaca aagctacag ctgccaggtc     600 acgcatgaag ggagcaccgt ggagaagaca gtggccccta cagaatgttc atga          654

<210> SEQ ID NO 47
<211> LENGTH: 1353
<212> TYPE: DNA
<213> ORGANISM: Homo sapiens

<400> SEQUENCE: 47
gaggtgcagc tgttggagtc tgggggaggc ttggtacagc ctggggggtc cctgagactc     60
tcctgtgcag cctctggatt caccttcagt agctatagcc tgaactgggt ccgccaggct    120
ccagggaagg ggctggagtg gtctcagct attagtggta gtggtggtag cacatactac    180
gcagactccg tgaagggccg gttcaccatc tccagagaca attccaagaa cacgctgtat    240
ctgcaaatga acagcctgag agccgaggac actgccgtgt attactgtgc gagagatcgg    300
gtagagatga accagtggct ggccgactgg ggccagggta cactggtcac cgtgagctca    360
gcctccacca agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaaaactca cacatgccca ccgtgcccag cacctgaact cctgggggga    720
ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc   1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140

```
gccgtggagt gggagagcaa tgggcagccg gagaacaact acaagaccac gcctcccgtg      1200
ctggactccg acggctcctt cttcctctac agcaagctca ccgtggacaa gagcaggtgg      1260
cagcagggga acgtcttctc atgctccgtg atgcatgagg ctctgcacaa ccactacacg      1320
cagaagagcc tctccctgtc tccgggtaaa tga                                   1353
```

<210> SEQ ID NO 48
<211> LENGTH: 654
<212> TYPE: DNA
<213> ORGANISM: Homo sapiens

<400> SEQUENCE: 48

```
cagtctgtgc tgactcagcc accctcagcg tctgggaccc ccgggcagag ggtcaccatc        60
tcctgcactg ggagcagctc aacatcgggg gcaggttatg atgtacactg gtatcagcag       120
ctcccaggaa cggcccccaa actcctcatc tataggaata tcagcggcc ctcaggggtc        180 cctgaccgat tctctggctc caagtctggc acctcagcct ccctggccat cagtgggctc      240
cggtccgagg atgaggctga ttattactgt gcagcatggg atgacagcct gaatggttgg      300
gtgttcggcg gaggaaccaa gctgacggtc ctaggtcagc ccaaggctgc ccctcggtc       360 actctgttcc cgccctcctc tgaggagctt caagccaaca ggccacact ggtgtgtctc       420 ataagtgact ctacccgggg agccgtgaca gtggcctgga aggcagatag cagcccgtc      480 aaggcgggag tggagaccac cacaccctcc aaacaaagca caacaagta cgcggccagc       540 agctatctga gcctgacgcc tgagcagtgg aagtcccaca gaagctacag ctgccaggtc     600
acgcatgaag ggagcaccgt ggagaagaca gtggcccta cagaatgttc atga             654
```

<210> SEQ ID NO 49
<211> LENGTH: 1353
<212> TYPE: DNA
<213> ORGANISM: Homo sapiens

<400> SEQUENCE: 49

```
gaggtgcagc tgttggagtc tgggggaggc ttggtacagc ctgggggtc cctgagactc         60 tcctgtgcag cctctggatt cacctttagc agctatgcca tgagctgggt ccgccaggct       120
ccagggaagg ggctggagtg gtctcaggt attagtggca gcggtgggta catacactat       180
gcagactccg tgaagggccg gttcaccatc tccagagaca attccaagaa cacgctgtat      240
ctgcaaatga acagcctgag agccgaggac actgccgtgt attactgtgc gacctatagc      300
agtggcctgc atgatgcttt tgatatctgg ggccaggta cactggtcac cgtgagctca      360
gcctccacca agggcccatc ggtcttcccc ctggcaccct cctccaagag cacctctggg     420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca     540
ggactctact ccctcagcag cgtggtgacc gtgccctcca gcagcttggg cacccagacc     600
tacatctgca acgtgaatca caagcccagc aacaccaagg tggacaagaa agttgagccc     660
aaatcttgtg acaaaactca cacatgccca ccgtgcccag cacctgaact cctgggggga    720
ccgtcagtct tcctcttccc cccaaaaccc aaggacaccc tcatgatctc ccggaccct     780 gaggtcacat gcgtggtggt ggacgtgagc cacgaagacc ctgaggtcaa gttcaactgg     840
tacgtggacg gcgtggaggt gcataatgcc aagacaaagc cgcggagga gcagtacaac      900 agcacgtacc gtgtggtcag cgtcctcacc gtcctgcacc aggactggct gaatggcaag    960
```

```
gagtacaagt gcaaggtctc aacaaagcc ctcccagccc ccatcgagaa aaccatctcc   1020
aaagccaaag gcagccccg agaaccacag gtgtacaccc tgcccccatc ccgggatgag   1080
ctgaccaaga accaggtcag cctgacctgc ctggtcaaag gcttctatcc cagcgacatc   1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa tga                               1353
```

```
<210> SEQ ID NO 50
<211> LENGTH: 654
<212> TYPE: DNA
<213> ORGANISM: Homo sapiens

<400> SEQUENCE: 50
cagtctgtgc tgactcagcc accctcagcg tctgggaccc ccgggcagag ggtcaccatc    60
tcctgcactg ggagcagctc caacatcggg gcaggttatg atgtacactg gtatcagcag   120
ctcccaggaa cggcccccaa actcctcatc tatgacaata taagcgaccc ctcaggggtc   180
cctgaccgat tctctggctc caagtctggc acctcagcct ccctggccat cagtgggctc   240
cggtccgagg atgaggctga ttattactgt gcagcatggg atgacagcct gaatggttgg   300
gtgttcggcg gaggaaccaa gctgacggtc ctaggtcagc ccaaggctgc cccctcggtc   360
actctgttcc cgccctcctc tgaggagctt caagccaaca aggccacact ggtgtgtctc   420
ataagtgact tctacccggg agccgtgaca gtggcctgga aggcagatag cagccccgtc   480
aaggcgggag tggagaccac cacaccctcc aaacaaagca acaacaagta cgcggccagc   540
agctatctga gcctgacgcc tgagcagtgg aagtcccaca aagctacag ctgccaggtc   600 acgcatgaag ggagcaccgt ggagaagaca gtggccccta cagaatgttc atga         654
```

```
<210> SEQ ID NO 51
<211> LENGTH: 1359
<212> TYPE: DNA
<213> ORGANISM: Homo sapiens

<400> SEQUENCE: 51
gaggtgcagc tgttggagtc tgggggaggc ttggtacagc ctgggggggtc cctgagactc    60 tcctgtgcag cctctggatt caccttcaaa gcctatagca tgagctggat ccgccaggct   120
ccagggaagg ggctggagtg ggtctcaggt atcagtaaca cggagaggtag cacagacttc   180 gcagactccg tgaagggccg gttcaccatc tccagagaca attccaagaa cacgctgtat   240
ctgcaaatga acagcctgag agccgaggac actgccatgt attactgtgc cagattggga   300
tatagtggct acgacgaccg tggtatggac gtctgggggcc aagtacact ggtcaccgtg    360 agctcagcct ccaccaaggg cccatcggtc ttccccctgg caccctcctc caagagcacc   420
tctgggggca cagcggccct gggctgcctg gtcaaggact acttccccga accggtgacg   480
gtgtcgtgga actcaggcgc cctgaccagc ggcgtgcaca ccttcccggc tgtcctacag   540
tcctcaggac tctactccct cagcagcgtg gtgaccgtgc cctccagcag cttgggcacc   600
cagacctaca tctgcaacgt gaatcacaag cccagcaaca ccaaggtgga caagaaagtt   660
gagcccaaat cttgtgacaa aactcacaca tgcccaccgt gcccagcacc tgaactcctg   720
gggggaccgt cagtcttcct cttccccccca aaacccaagg acaccctcat gatctcccgg   780
acccctgagg tcacatgcgt ggtggtggac gtgagccacg aagaccctga ggtcaagttc   840
```

```
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcc cagcccccat cgagaaaacc   1020
atctccaaag ccaagggca gccccgagaa ccacaggtgt acaccctgcc cccatcccgg   1080
gatgagctga ccaagaacca ggtcagcctg acctgcctgg tcaaaggctt ctatcccagc   1140
gacatcgccg tggagtggga gagcaatggg cagccggaga caactacaa gaccacgcct   1200
cccgtgctgg actccgacgg ctccttcttc ctctacagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaatga                          1359
```

<210> SEQ ID NO 52
<211> LENGTH: 654
<212> TYPE: DNA
<213> ORGANISM: Homo sapiens

<400> SEQUENCE: 52

```
cagtctgtgc tgactcagcc accctcagcg tctgggaccc ccgggcagag ggtcaccatc     60
tcttgttctg gaagcagctc caacatcgga agtaattatg tgtactggta tcagcagctc    120
ccaggaacgg cccccaaact cctcatctat ggtaacagca atcggccctc aggggtccct    180
gaccgattct ctggctccaa gtctggcacc tcagcctccc tggccatcag tgggctccgg    240
tccgaggatg aggctgatta ttactgccag tcctatgaca gcagcctgag tggtcctgtg    300
gtattcggcg gaggaaccaa gctgacggtc ctaggtcagc ccaaggctgc ccctcggtc    360
actctgttcc cgcccctcc tgaggagctt caagccaaca aggccacact ggtgtgtctc    420
ataagtgact ctacccggg agccgtgaca gtggcctgga aggcagatag cagccccgtc    480
aaggcgggag tggagaccac cacaccctcc aaacaaagca acaacaagta cgcggccagc    540
agctatctga gcctgacgcc tgagcagtgg aagtcccaca aagctacag ctgccaggtc    600
acgcatgaag ggagcaccgt ggagaagaca gtggccccta cagaatgttc atga          654
```

<210> SEQ ID NO 53
<211> LENGTH: 236
<212> TYPE: PRT
<213> ORGANISM: Homo sapiens

<400> SEQUENCE: 53

```
Met Gly Trp Ser Cys Ile Ile Leu Phe Leu Val Ala Thr Ala Thr Gly
1               5                   10                  15

Val His Ser Gln Ser Val Leu Thr Gln Pro Pro Ser Ala Ser Gly Thr
            20                  25                  30

Pro Gly Gln Arg Val Thr Ile Ser Cys Thr Gly Ser Ser Ser Asn Ile
        35                  40                  45

Gly Ala Gly Tyr Asp Val His Trp Tyr Gln Gln Leu Pro Gly Thr Ala
    50                  55                  60

Pro Lys Leu Leu Ile Tyr Gly Asn Asp Asn Arg Pro Ser Gly Val Pro
65                  70                  75                  80

Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Val Trp
            100                 105                 110

Asp Asp Ser Leu Asn Gly Val Val Phe Gly Gly Gly Thr Lys Leu Thr
```

```
                115                 120                 125
Val Leu Gly Gln Pro Lys Ala Ala Pro Ser Val Thr Leu Phe Pro Pro
    130                 135                 140

Ser Ser Glu Glu Leu Gln Ala Asn Lys Ala Thr Leu Val Cys Leu Ile
145                 150                 155                 160

Ser Asp Phe Tyr Pro Gly Ala Val Thr Val Ala Trp Lys Ala Asp Ser
                165                 170                 175

Ser Pro Val Lys Ala Gly Val Glu Thr Thr Thr Pro Ser Lys Gln Ser
            180                 185                 190

Asn Asn Lys Tyr Ala Ala Ser Ser Tyr Leu Ser Leu Thr Pro Glu Gln
        195                 200                 205

Trp Lys Ser His Arg Ser Tyr Ser Cys Gln Val Thr His Glu Gly Ser
    210                 215                 220

Thr Val Glu Lys Thr Val Ala Pro Thr Glu Cys Ser
225                 230                 235

<210> SEQ ID NO 54
<211> LENGTH: 463
<212> TYPE: PRT
<213> ORGANISM: Homo sapiens

<400> SEQUENCE: 54

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Asp Tyr Tyr Met Ser Trp Val Arg Gln Ala Pro Gly Lys Gly Leu
    50                  55                  60

Glu Trp Val Ser Gly Ile Ser Trp Ser Arg Asp Lys Gly Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Thr Thr Asp Leu Ala Arg Tyr Trp Gly Gln Gly Thr Leu
        115                 120                 125

Val Thr Val Ser Ser Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
        195                 200                 205

Leu Gly Thr Gln Thr Tyr Ile Cys Asn Val Asn His Lys Pro Ser Asn
    210                 215                 220

Thr Lys Val Asp Lys Lys Val Glu Pro Lys Ser Cys Asp Lys Thr His
225                 230                 235                 240

Thr Cys Pro Pro Cys Pro Ala Pro Glu Leu Leu Gly Gly Pro Ser Val
                245                 250                 255
```

```
Phe Leu Phe Pro Pro Lys Pro Lys Asp Thr Leu Met Ile Ser Arg Thr
            260                 265                 270

Pro Glu Val Thr Cys Val Val Asp Val Ser His Glu Asp Pro Glu
        275                 280                 285

Val Lys Phe Asn Trp Tyr Val Asp Gly Val Glu Val His Asn Ala Lys
        290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Ala Leu Pro Ala Pro Ile Glu Lys Thr Ile
                340                 345                 350

Ser Lys Ala Lys Gly Gln Pro Arg Glu Pro Gln Val Tyr Thr Leu Pro
                355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Lys Leu Thr Val Asp Lys Ser Arg
                420                 425                 430

Trp Gln Gln Gly Asn Val Phe Ser Cys Ser Val Met His Glu Ala Leu
                435                 440                 445

His Asn His Tyr Thr Gln Lys Ser Leu Ser Leu Ser Pro Gly Lys
450                 455                 460

<210> SEQ ID NO 55
<211> LENGTH: 127
<212> TYPE: PRT
<213> ORGANISM: Homo sapiens

<400> SEQUENCE: 55

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
                20                  25                  30

Ala Ala Glu Met Asn Glu Thr Val Glu Val Ile Ser Glu Met Phe Asp
            35                  40                  45

Leu Gln Glu Pro Thr Cys Leu Gln Thr Arg Leu Glu Leu Tyr Lys Gln
        50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Thr Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 56
<211> LENGTH: 144
<212> TYPE: PRT
<213> ORGANISM: Homo sapiens

<400> SEQUENCE: 56
```

```
Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Thr Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140

<210> SEQ ID NO 57
<211> LENGTH: 124
<212> TYPE: PRT
<213> ORGANISM: Mus musculus

<400> SEQUENCE: 57

Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
            35                  40                  45

Leu Thr Cys Val Gln Thr Arg Leu Lys Ile Phe Glu Gln Gly Leu Arg
50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Val Gln Lys
            115                 120

<210> SEQ ID NO 58
<211> LENGTH: 141
<212> TYPE: PRT
<213> ORGANISM: Mus musculus

<400> SEQUENCE: 58

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
            35                  40                  45

Thr Leu Asn Glu Glu Val Glu Val Val Ser Asn Glu Phe Ser Phe Lys
50                  55                  60
```

```
Lys Leu Thr Cys Val Gln Thr Arg Leu Lys Ile Phe Glu Gln Gly Leu
 65                  70                  75                  80

Arg Gly Asn Phe Thr Lys Leu Lys Gly Ala Leu Asn Met Thr Ala Ser
                 85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Val Gln Lys
    130                 135                 140

<210> SEQ ID NO 59
<211> LENGTH: 124
<212> TYPE: DNA
<213> ORGANISM: Artificial Sequence
<220> FEATURE:
<223> OTHER INFORMATION: Promoter p7.5K

<400> SEQUENCE: 59
ccacccactt tttatagtaa gtttttcacc cataaataat aaatacaata attaatttct    60
cgtaaaagta gaaatatat tctaatttat tgcacggtaa ggaagtagaa tcataaagaa    120
cagt                                                                124

<210> SEQ ID NO 60
<211> LENGTH: 114
<212> TYPE: DNA
<213> ORGANISM: Artificial Sequence
<220> FEATURE:
<223> OTHER INFORMATION: Promoter pH5.R

<400> SEQUENCE: 60
tttattctat acttaaaaaa tgaaaataaa tacaaaggtt cttgagggtt gtgttaaatt    60
gaaagcgaga ataatcata aattatttca ttatcgcgat atccgttaag tttg           114

<210> SEQ ID NO 61
<211> LENGTH: 40
<212> TYPE: DNA
<213> ORGANISM: Artificial Sequence
<220> FEATURE:
<223> OTHER INFORMATION: Promoter pSE/L

<400> SEQUENCE: 61
aaaaattgaa attttatttt tttttttgg aatataaata                           40

<210> SEQ ID NO 62
<211> LENGTH: 236
<212> TYPE: PRT
<213> ORGANISM: Mus musculus

<400> SEQUENCE: 62

Met Gly Trp Ser Cys Ile Ile Leu Phe Leu Val Ala Thr Ala Thr Gly
  1               5                  10                  15

Val His Ser Gln Ser Val Leu Thr Gln Pro Pro Ser Ala Ser Gly Thr
             20                  25                  30

Pro Gly Gln Arg Val Thr Ile Ser Cys Thr Gly Ser Ser Ser Asn Ile
         35                  40                  45

Gly Ala Gly Tyr Asp Val His Trp Tyr Gln Gln Leu Pro Gly Thr Ala
     50                  55                  60

Pro Lys Leu Leu Ile Tyr Arg Asn Asn Gln Arg Pro Ser Gly Val Pro
 65                  70                  75                  80
```

```
Asp Arg Phe Ser Gly Ser Lys Ser Gly Thr Ser Ala Ser Leu Ala Ile
                85                  90                  95

Ser Gly Leu Arg Ser Glu Asp Glu Ala Asp Tyr Tyr Cys Ala Ala Trp
            100                 105                 110

Asp Asp Ser Leu Asn Gly Trp Val Phe Gly Gly Gly Thr Lys Leu Thr
            115                 120                 125

Val Leu Gly Gln Pro Lys Ser Ser Pro Ser Val Thr Leu Phe Pro Pro
130                 135                 140

Ser Ser Glu Glu Leu Glu Thr Asn Lys Ala Thr Leu Val Cys Thr Ile
145                 150                 155                 160

Thr Asp Phe Tyr Pro Gly Val Val Thr Val Asp Trp Lys Val Asp Gly
                165                 170                 175

Thr Pro Val Thr Gln Gly Met Glu Thr Thr Gln Pro Ser Lys Gln Ser
            180                 185                 190

Asn Asn Lys Tyr Met Ala Ser Ser Tyr Leu Thr Leu Thr Ala Arg Ala
            195                 200                 205

Trp Glu Arg His Ser Ser Tyr Ser Cys Gln Val Thr His Glu Gly His
        210                 215                 220

Thr Val Glu Lys Ser Leu Ser Arg Ala Asp Cys Ser
225                 230                 235

<210> SEQ ID NO 63
<211> LENGTH: 469
<212> TYPE: PRT
<213> ORGANISM: Mus musculus

<400> SEQUENCE: 63

Met Gly Trp Ser Cys Ile Ile Leu Phe Leu Val Ala Thr Ala Thr Gly
1               5                   10                  15

Val His Ser Glu Val Gln Leu Leu Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Ser Met Asn Trp Val Arg Gln Ala Pro Gly Lys Gly Leu
50                  55                  60

Glu Trp Val Ser Ala Ile Ser Gly Ser Gly Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Arg Val Glu Met Asn Gln Trp Leu Ala Asp
            115                 120                 125

Trp Gly Gln Gly Thr Leu Val Thr Val Ser Ser Ala Lys Thr Thr Ala
130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
            195                 200                 205

Val Thr Ser Ser Thr Trp Pro Ser Gln Ser Ile Thr Cys Asn Val Ala
```

```
                210                 215                 220
His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Asn Leu
                245                 250                 255

Leu Gly Gly Pro Ser Val Phe Ile Phe Pro Pro Lys Ile Lys Asp Val
                260                 265                 270

Leu Met Ile Ser Leu Ser Pro Ile Val Thr Cys Val Val Val Asp Val
            275                 280                 285

Ser Glu Asp Asp Pro Asp Val Gln Ile Ser Trp Phe Val Asn Asn Val
        290                 295                 300

Glu Val His Thr Ala Gln Thr Gln Thr His Arg Glu Asp Tyr Asn Ser
305                 310                 315                 320

Thr Leu Arg Val Val Ser Ala Leu Pro Ile Gln His Gln Asp Trp Met
                325                 330                 335

Ser Gly Lys Glu Phe Lys Cys Lys Val Asn Asn Lys Asp Leu Pro Ala
                340                 345                 350

Pro Ile Glu Arg Thr Ile Ser Lys Pro Lys Gly Ser Val Arg Ala Pro
            355                 360                 365

Gln Val Tyr Val Leu Pro Pro Pro Glu Glu Glu Met Thr Lys Lys Gln
        370                 375                 380

Val Thr Leu Thr Cys Met Val Thr Asp Phe Met Pro Glu Asp Ile Tyr
385                 390                 395                 400

Val Glu Trp Thr Asn Asn Gly Lys Thr Glu Leu Asn Tyr Lys Asn Thr
                405                 410                 415

Glu Pro Val Leu Asp Ser Asp Gly Ser Tyr Phe Met Tyr Ser Lys Leu
                420                 425                 430

Arg Val Glu Lys Lys Asn Trp Val Glu Arg Asn Ser Tyr Ser Cys Ser
            435                 440                 445

Val Val His Glu Gly Leu His Asn His His Thr Thr Lys Ser Phe Ser
        450                 455                 460

Arg Thr Pro Gly Lys
465
```